(12) United States Patent
Sasada et al.

(10) Patent No.: US 10,141,514 B2
(45) Date of Patent: Nov. 27, 2018

(54) COMPOSITION AND LIGHT EMITTING DEVICE USING THE SAME

(71) Applicant: Sumitomo Chemical Company, Limited, Tokyo (JP)

(72) Inventors: Toshiaki Sasada, Tsukuba (JP); Makoto Anryu, Osaka (JP); Seiichirou Yokoya, Tokyo (JP); Kohei Asada, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 15/303,920

(22) PCT Filed: Mar. 30, 2015

(86) PCT No.: PCT/JP2015/060680
§ 371 (c)(1),
(2) Date: Oct. 13, 2016

(87) PCT Pub. No.: WO2015/159744
PCT Pub. Date: Oct. 22, 2015

(65) Prior Publication Data
US 2017/0040542 A1    Feb. 9, 2017

(30) Foreign Application Priority Data

Apr. 18, 2014  (JP) .................................. 2014-086129
Dec. 25, 2014  (JP) .................................. 2014-261999

(51) Int. Cl.
*H01L 51/54* (2006.01)
*C09K 11/06* (2006.01)
(Continued)

(52) U.S. Cl.
CPC .......... *H01L 51/0043* (2013.01); *C07F 5/025* (2013.01); *C07F 15/0033* (2013.01); *C08G 61/122* (2013.01); *C08G 61/128* (2013.01); *C08L 65/00* (2013.01); *C09K 11/025* (2013.01); *C09K 11/06* (2013.01); *H01L 51/0035* (2013.01); *H01L 51/0039* (2013.01); *H01L 51/0085* (2013.01); *C08G 2261/124* (2013.01); *C08G 2261/135* (2013.01); *C08G 2261/148* (2013.01); *C08G 2261/1414* (2013.01); *C08G 2261/1424* (2013.01); *C08G 2261/1426* (2013.01); *C08G 2261/312* (2013.01); *C08G 2261/314* (2013.01); *C08G 2261/3142* (2013.01); *C08G 2261/3162* (2013.01); *C08G 2261/3221* (2013.01); *C08G 2261/411* (2013.01); *C08G 2261/512* (2013.01); *C08G 2261/514* (2013.01);
(Continued)

(58) Field of Classification Search
None
See application file for complete search history.

(56) References Cited

U.S. PATENT DOCUMENTS

2005/0031903 A1* 2/2005 Park et al. .......... C07F 15/0033
428/690
2006/0008670 A1* 1/2006 Lin et al. ............. C07D 231/12
428/690
(Continued)

FOREIGN PATENT DOCUMENTS

EP    2492988 A1    8/2012
EP    2530100 A1    12/2012
(Continued)

OTHER PUBLICATIONS

Office Action dated Jun. 2, 2015 in JP Application No. 2014-26199.
Extended European Search Report dated Sep. 11, 2017 in EP Application No. 15780028.5.
Office Action dated May 25, 2018 in EP Application No. 15780028.5.

*Primary Examiner* — Marie R. Yamnitzky
(74) *Attorney, Agent, or Firm* — Panitch Schwarze Belisario & Nadel LLP

(57) ABSTRACT

A composition is provided containing: a phosphorescent compound having an emission spectrum whose maximum peak wavelength is between 380 nm or more and less than 495 nm, having no dendron and represented by formula (1'); two or more phosphorescent compounds having an emission spectrum whose maximum peak wavelength is between 495 nm or more and less than 750 nm and having a dendron; and a compound represented by formula (H-1).

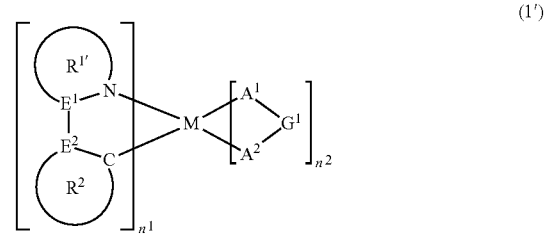

(1')

In formula (1') M represents an iridium atom or the like, $n^1$ represents an integer of 1 or more, $n^2$ represents an integer of 0 or more, $E^1$ and $E^2$ represent a carbon atom or the like, the ring $R^{1'}$ represents a diazole ring, the ring $R^2$ represents a 6-membered aromatic hydrocarbon ring or the like, and $A^1$-$G^1$-$A^2$ represents an anionic bidentate ligand.

12 Claims, No Drawings

(51) Int. Cl.
*H01L 51/00* (2006.01)
*C07F 15/00* (2006.01)
*C07F 5/02* (2006.01)
*C08L 65/00* (2006.01)
*C08G 61/12* (2006.01)
*C09K 11/02* (2006.01)
*H01L 51/50* (2006.01)

(52) U.S. Cl.
CPC . *C08G 2261/5242* (2013.01); *C08G 2261/76* (2013.01); *C08G 2261/95* (2013.01); *C09K 2211/1007* (2013.01); *C09K 2211/1029* (2013.01); *C09K 2211/1044* (2013.01); *C09K 2211/1059* (2013.01); *C09K 2211/185* (2013.01); *H01L 51/5016* (2013.01); *H01L 51/5056* (2013.01)

(56) References Cited

U.S. PATENT DOCUMENTS

| | | | |
|---|---|---|---|
| 2008/0100199 A1 | 5/2008 | Sekine et al. | |
| 2009/0167165 A1* | 7/2009 | Otsu et al. | C07D 209/86 313/504 |
| 2010/0231123 A1* | 9/2010 | Otsu et al. | C09K 11/06 313/504 |
| 2012/0199825 A1 | 8/2012 | Soga et al. | |
| 2012/0326140 A1 | 12/2012 | Fukushima et al. | |
| 2013/0193840 A1 | 8/2013 | Soga et al. | |
| 2013/0200349 A1 | 8/2013 | Soga et al. | |
| 2014/0175415 A1 | 6/2014 | Steudel et al. | |

FOREIGN PATENT DOCUMENTS

| | | | |
|---|---|---|---|
| EP | 2594607 A1 | 5/2013 |
| JP | 2005-93098 A | 4/2005 |
| JP | 2005-100881 A | 4/2005 |
| JP | 2006-188673 A | 7/2006 |
| JP | 2007-184348 A | 7/2007 |
| JP | 2008-174499 A | 7/2008 |
| JP | 2011-174062 A | 9/2011 |
| JP | 2012-36381 A | 2/2012 |
| JP | 2014-148663 A | 8/2014 |
| WO | 02066552 A1 | 8/2002 |
| WO | 03/103341 A1 | 12/2003 |
| WO | 2004020504 A1 | 3/2004 |
| WO | 2004101707 A1 | 11/2004 |
| WO | 2009/116414 A1 | 9/2009 |
| WO | 2011/049241 A1 | 4/2011 |
| WO | 2011141714 A1 | 11/2011 |
| WO | 2012153082 A1 | 11/2012 |

\* cited by examiner

COMPOSITION AND LIGHT EMITTING DEVICE USING THE SAME

CROSS-REFERENCE TO RELATED APPLICATION

This application is a Section 371 of International Application No. PCT/JP2015/060680, filed Mar. 30, 2015, which was published in the Japanese language on Oct. 22, 2015, under International Publication No. WO 2015/159744 A1, and the disclosure of which is incorporated herein by reference.

TECHNICAL FIELD

The present invention relates to a composition and a light emitting device using the same.

BACKGROUND ART

Light emitting devices such as an organic electroluminescent device (organic EL device) can be suitably used for applications of displays and the like because of high external quantum efficiency and low driving voltage, and are recently attracting attention.

As the material used in a light emitting layer of a light emitting device, for example, a composition comprising a polymer compound composed of a phenylene constitutional unit, a blue phosphorescent compound 1 represented by the following formula, a green phosphorescent compound 1 represented by the following formula and a red phosphorescent compound 1 represented by the following formula is proposed (Patent document 1). The blue phosphorescent compound 1 is a phosphorescent compound having a ligand skeleton constituted of a 6-membered aromatic heterocyclic ring and a 6-membered aromatic hydrocarbon ring, and the green phosphorescent compound 1 is a phosphorescent compound having no dendron.

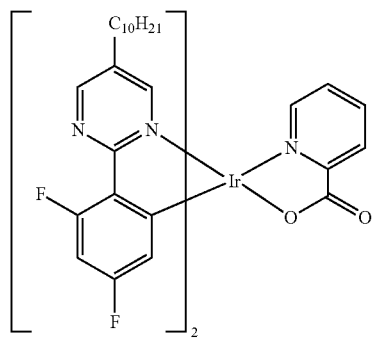

Blue Phosphorescent compound 1

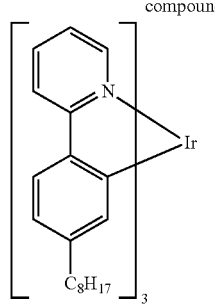

Green Phosphorescent compound 1

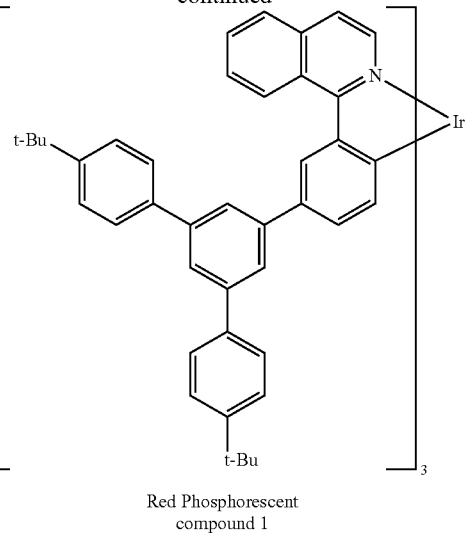

Red Phosphorescent compound 1

As the material used in a light emitting layer of a light emitting device, for example, a composition comprising a low molecular weight compound having a heterocyclic structure, a blue phosphorescent compound 2 represented by the following formula, a green phosphorescent compound 2 represented by the following formula and a red phosphorescent compound 2 represented by the following formula is proposed (Patent document 2). The green phosphorescent compound 2 and the red phosphorescent compound 2 are a phosphorescent compound having no dendron.

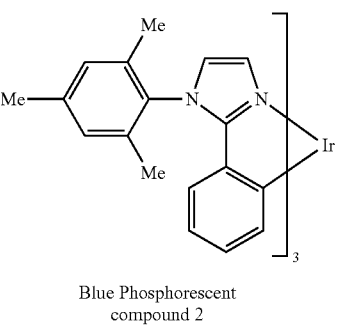

Blue Phosphorescent compound 2

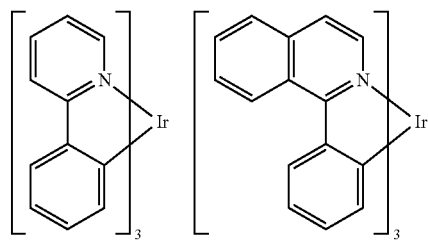

Green Phosphorescent compound 2     Red Phosphorescent compound 2

PRIOR ART DOCUMENT

Patent Document

Patent document 1: JP-A No. 2012-36381
Patent document 2: International Publication WO2009/116414

SUMMARY OF THE INVENTION

Problems to be Solved by the Invention

A light emitting device produced by using the above-described composition, however, had not necessarily sufficient external quantum efficiency.

Then, the present invention has an object of providing a composition which is useful for production of a light emitting device excellent in external quantum efficiency. Further, the present invention has an object of providing a light emitting device produced by using the composition.

Means for Solving the Problems

In a first aspect, the present invention provides a composition comprising
a phosphorescent compound having an emission spectrum the maximum peak wavelength of which is between 380 nm or more and less than 495 nm and having no dendron (B),
two or more phosphorescent compounds having an emission spectrum the maximum peak wavelength of which is between 495 nm or more and less than 750 nm and having a dendron (DGR), and
a compound represented by the formula (H-1),
wherein
the phosphorescent compound (B) is a phosphorescent compound represented by the formula (1), and
the phosphorescent compound (DGR) is a phosphorescent compound represented by the formula (2)
(hereinafter, referred to also as "first composition of the present invention".):

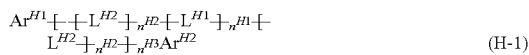

(H-1)

[wherein,
$Ar^{H1}$ and $Ar^{H2}$ each independently represent an aryl group or a monovalent heterocyclic group, and these groups each optionally have a substituent.

$n^{H1}$ and $n^{H2}$ each independently represent 0 or 1. When a plurality of $n^{H1}$ are present, they may be the same or different. The plurality of $n^{H2}$ may be the same or different.

$n^{H3}$ represents an integer of 0 or more.

$L^{H1}$ represents an arylene group, a divalent heterocyclic group or a group represented by $—[C(R^{H11})_2]n^{H11}—$, and these groups each optionally have a substituent. When a plurality of $L^{H1}$ are present, they may be the same or different.

$n^{H11}$ represents an integer of 1 to 10. $R^{H11}$ represents a hydrogen atom, an alkyl group, a cycloalkyl group, an alkoxy group, a cycloalkoxy group, an aryl group or a monovalent heterocyclic group, and these groups each optionally have a substituent. The plurality of $R^{H11}$ may be the same or different and may be combined together to form a ring together with the carbon atoms to which they are attached.

$L^{H2}$ represents a group represented by $—N(-L^{H21}-R^{H21})—$. When a plurality of $L^{H2}$ are present, they may be the same or different.

$L^{H21}$ represents a single bond, an arylene group or a divalent heterocyclic group, and these groups each optionally have a substituent. $R^{H21}$ represents a hydrogen atom, an alkyl group, a cycloalkyl group, an aryl group or a monovalent heterocyclic group, and these groups each optionally have a substituent.]

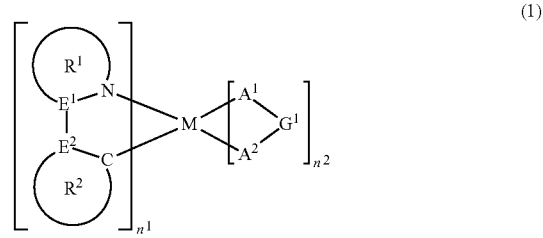

(1)

[wherein,
M represents a ruthenium atom, a rhodium atom, a palladium atom, an iridium atom or a platinum atom.

$n^1$ represents an integer of 1 or more, $n^2$ represents an integer of 0 or more, and $n^1+n^2$ is 2 or 3. $n^1+n^2$ is 3 when M is a ruthenium atom, a rhodium atom or an iridium atom, while $n^1+n^2$ is 2 when M is a palladium atom or a platinum atom.

$E^1$ and $E^2$ each independently represent a carbon atom or a nitrogen atom. At least one of $E^1$ and $E^2$ is a carbon atom.

The ring $R^1$ represents a 5-membered aromatic heterocyclic ring, and this ring optionally has a substituent. When a plurality of the substituents are present, they may be the same or different and may be combined together to form a ring together with the atoms to which they are attached. When a plurality of the rings $R^1$ are present, they may be the same or different.

The ring $R^2$ represents a 5-membered or 6-membered aromatic hydrocarbon ring or a 5-membered or 6-membered aromatic heterocyclic ring, and these rings each optionally have a substituent. When a plurality of the substituents are present, they may be the same or different and may be combined together to form a ring together with the atoms to which they are attached. When a plurality of the rings $R^2$ are present, they may be the same or different. $E^2$ is a carbon atom when the ring $R^2$ is a 6-membered aromatic heterocyclic ring.

The substituent which the ring $R^1$ optionally has and the substituent which the ring $R^2$ optionally has may be combined together to form a ring together with the atoms to which they are attached.

$A^1$-$G^1$-$A^2$ represents an anionic bidentate ligand. $A^1$ and $A^2$ each independently represent a carbon atom, an oxygen atom or a nitrogen atom, and these atoms may be an atom constituting a ring. $G^1$ represents a single bond or an atomic group constituting the bidentate ligand together with $A^1$ and $A^2$. When a plurality of $A^1$-$G^1$-$A^2$ are present, they may be the same or different.]

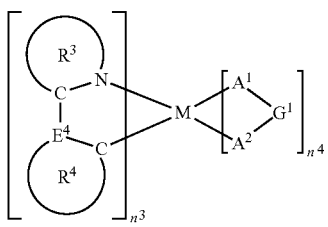

(2)

[wherein,

M represents a ruthenium atom, a rhodium atom, a palladium atom, an iridium atom or a platinum atom.

$n^3$ represents an integer of 1 or more, $n^4$ represents an integer of 0 or more, and $n^3+n^4$ is 2 or 3. $n^3+n^4$ is 3 when M is a ruthenium atom, a rhodium atom or an iridium atom, while $n^3+n^4$ is 2 when M is a palladium atom or a platinum atom.

$E^4$ represents a carbon atom or a nitrogen atom.

The ring $R^3$ represents a 6-membered aromatic heterocyclic ring, and this ring optionally has a substituent. When a plurality of the substituents are present, they may be the same or different and may be combined together to form a ring together with the atoms to which they are attached. When a plurality of the rings $R^3$ are present, they may be the same or different.

The ring $R^4$ represents a 5-membered or 6-membered aromatic hydrocarbon ring or a 5-membered or 6-membered aromatic heterocyclic ring, and these rings each optionally have a substituent. When a plurality of the substituents are present, they may be the same or different and may be combined together to form a ring together with the atoms to which they are attached. When a plurality of the rings $R^4$ are present, they may be the same or different. $E^4$ is a carbon atom when the ring $R^4$ is a 6-membered aromatic heterocyclic ring.

The substituent which the ring $R^3$ optionally has and the substituent which the ring $R^4$ optionally has may be combined together to form a ring together with the atoms to which they are attached.

At least one ring selected from the group consisting of the ring $R^3$ and the ring $R^4$ has a dendron.

$A^1$-$G^1$-$A^2$ represents an anionic bidentate ligand. $A^1$ and $A^2$ each independently represent a carbon atom, an oxygen atom or a nitrogen atom, and these atoms may be an atom constituting a ring. $G^1$ represents a single bond or an atomic group constituting the bidentate ligand together with $A^1$ and $A^2$. When a plurality of $A^1$-$G^1$-$A^2$ are present, they may be the same or different.].

In the first composition of the present invention, the phosphorescent compound represented by the formula (1) is preferably a phosphorescent compound represented by the formula (1'), because a light emitting device produced by using the first composition of the present invention is more excellent in external quantum efficiency:

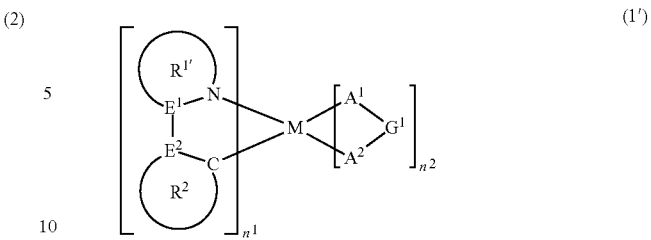

(1')

[wherein,

M, $n^1$, $n^2$, $E^1$, $E^2$, the ring $R^2$ and $A^1$-$G^1$-$A^2$ represent the same meaning as described above.

The ring $R^{1'}$ represents a diazole ring, and this diazole ring optionally has a substituent. When a plurality of the substituents are present, they may be the same or different and may be combined together to form a ring together with the atoms to which they are attached. When a plurality of the rings $R^{1'}$ are present, they may be the same or different.

The substituent which the ring $R^{1'}$ optionally has and the substituent which the ring $R^2$ optionally has may be combined together to form a ring together with the atoms to which they are attached.].

In a second aspect, the present invention provides a composition comprising a phosphorescent compound having an emission spectrum the maximum peak wavelength of which is between 380 nm or more and less than 495 nm and having no dendron (B), two or more phosphorescent compounds having an emission spectrum the maximum peak wavelength of which is between 495 nm or more and less than 750 nm and having a dendron (DGR), and a polymer compound comprising a constitutional unit represented by the formula (Y), wherein the phosphorescent compound (B) is a phosphorescent compound represented by the above-described formula (1), and the phosphorescent compound (DGR) is a phosphorescent compound represented by the above-described formula (2)

(hereinafter, referred to also as "second composition of the present invention".):

(Y)

[wherein, $Ar^{y1}$ represents an arylene group, a divalent heterocyclic group or a divalent group in which at least one arylene group and at least one divalent heterocyclic group are bonded directly to each other, and these groups each optionally have a substituent.].

In a third aspect, the present invention provides a light emitting device produced by using the above-described composition.

Effect of the Invention

The present invention can provide a composition which is useful for production of a light emitting device excellent in external quantum efficiency. Further, the present invention can provide a light emitting device produced by using the composition.

The light emitting device according to a preferred embodiment of the present invention (specifically, a light emitting device having a light emitting layer obtained by using the composition of the present invention and a hole transporting layer obtained by using a polymer compound of a hole transporting layer described later) is a light emitting device excellent also in luminance life.

MODES FOR CARRYING OUT THE INVENTION

Suitable embodiments of the present invention will be illustrated in detail below.

<Explanation of Common Term>

Terms commonly used in the present specification have the following meanings unless otherwise stated.

Me represents a methyl group, Et represents an ethyl group, Bu represents a butyl group, i-Pr represents an isopropyl group, and t-Bu represents a tert-butyl group.

A hydrogen atom may be a heavy hydrogen atom or a light hydrogen atom.

A solid line representing a bond to a central metal in a formula representing a metal complex denotes a covalent bond or a coordinate bond.

"Polymer compound" denotes a polymer having molecular weight distribution and having a polystyrene-equivalent number average molecular weight of $1\times10^3$ to $1\times10^8$.

A polymer compound may be any of a block copolymer, a random copolymer, an alternating copolymer and a graft copolymer, and may also be another embodiment.

An end group of a polymer compound is preferably a stable group because if a polymerization active group remains intact at the end, when the polymer compound is used for fabrication of a light emitting device, the light emitting property or luminance life possibly becomes lower. This end group is preferably a group having a conjugated bond to the main chain, and includes, for example, groups bonding to an aryl group or a monovalent heterocyclic group via a carbon-carbon bond.

"Low molecular weight compound" denotes a compound having no molecular weight distribution and having a molecular weight of $1\times10^4$ or less.

"Constitutional unit" denotes a unit structure found once or more in a polymer compound.

"Alkyl group" may be any of linear or branched. The number of carbon atoms of the linear alkyl group is, not including the number of carbon atoms of a substituent, usually 1 to 50, preferably 3 to 30, more preferably 4 to 20. The number of carbon atoms of the branched alkyl groups is, not including the number of carbon atoms of a substituent, usually 3 to 50, preferably 3 to 30, more preferably 4 to 20.

The alkyl group optionally has a substituent, and examples thereof include a methyl group, an ethyl group, a propyl group, an isopropyl group, a butyl group, an isobutyl group, a tert-butyl group, a pentyl group, an isoamyl group, a 2-ethylbutyl group, a hexyl group, a heptyl group, an octyl group, a 2-ethylhexyl group, a 3-propylheptyl group, a decyl group, a 3,7-dimethyloctyl group, a 2-ethyloctyl group, a 2-hexyl-decyl group and a dodecyl group, and groups obtained by substituting a hydrogen atom in these groups with a cycloalkyl group, an alkoxy group, a cycloalkoxy group, an aryl group, a fluorine atom or the like, and the alkyl group having a substituent includes a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-di-n-hexylphenyl) propyl group and a 6-ethyloxyhexyl group.

The number of carbon atoms of "Cycloalkyl group" is, not including the number of carbon atoms of a substituent, usually 3 to 50, preferably 3 to 30, more preferably 4 to 20.

The cycloalkyl group optionally has a substituent, and examples thereof include a cyclohexyl group, a cyclohexylmethyl group and a cyclohexylethyl group.

"Aryl group" denotes an atomic group remaining after removing from an aromatic hydrocarbon one hydrogen atom linked directly to a carbon atom constituting the ring. The number of carbon atoms of the aryl group is, not including the number of carbon atoms of a substituent, usually 6 to 60, preferably 6 to 20, more preferably 6 to 10.

The aryl group optionally has a substituent, and examples thereof include a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group, a 4-phenylphenyl group, and groups obtained by substituting a hydrogen atom in these groups with an alkyl group, a cycloalkyl group, an alkoxy group, a cycloalkoxy group, an aryl group, a fluorine atom or the like.

"Alkoxy group" may be any of linear or branched. The number of carbon atoms of the linear alkoxy group is, not including the number of carbon atoms of a substituent, usually 1 to 40, preferably 4 to 10. The number of carbon atoms of the branched alkoxy group is, not including the number of carbon atoms of a substituent, usually 3 to 40, preferably 4 to 10.

The alkoxy group optionally has a substituent, and examples thereof include a methoxy group, an ethoxy group, a propyloxy group, an isopropyloxy group, a butyloxy group, an isobutyloxy group, a tert-butyloxy group, a pentyloxy group, a hexyloxy group, a heptyloxy group, an octyloxy group, a 2-ethylhexyloxy group, a nonyloxy group, a decyloxy group, a 3,7-dimethyloctyloxy group and a lauryloxy group, and groups obtained by substituting a hydrogen atom in these groups with a cycloalkyl group, an alkoxy group, a cycloalkoxy group, an aryl group, a fluorine atom or the like.

The number of carbon atoms of "Cycloalkoxy group" is, not including the number of carbon atoms of a substituent, usually 3 to 40, preferably 4 to 10.

The cycloalkoxy group optionally has a substituent, and examples thereof include a cyclohexyloxy group.

The number of carbon atoms of "Aryloxy group" is, not including the number of carbon atoms of a substituent, usually 6 to 60, preferably 7 to 48.

The aryloxy group optionally has a substituent, and examples thereof include a phenoxy group, a 1-naphthyloxy group, a 2-naphthyloxy group, a 1-anthracenyloxy group, a 9-anthracenyloxy group, a 1-pyrenyloxy group, and groups obtained by substituting a hydrogen atom in these groups with an alkyl group, a cycloalkyl group, an alkoxy group, a cycloalkoxy group, a fluorine atom or the like.

"p-Valent heterocyclic group" (p represents an integer of 1 or more) denotes an atomic group remaining after removing from a heterocyclic compound p hydrogen atoms among hydrogen atoms directly linked to a carbon atom or a hetero atom constituting the ring. Of p-valent heterocyclic groups, "p-valent aromatic heterocyclic groups" as an atomic group remaining after removing from an aromatic heterocyclic compound p hydrogen atoms among hydrogen atoms directly linked to a carbon atom or a hetero atom constituting the ring are preferable.

"Aromatic heterocyclic compound" denotes a compound in which the heterocyclic ring itself shows aromaticity such as oxadiazole, thiadiazole, thiazole, oxazole, thiophene, pyrrole, phosphole, furan, pyridine, pyrazine, pyrimidine, triazine, pyridazine, quinoline, isoquinoline, carbazole, dibenzosilole and dibenzophosphole, and a compound in which an aromatic ring is condensed to the heterocyclic ring even if the heterocyclic ring itself shows no aromaticity such as phenoxazine, phenothiazine, dibenzoborole, dibenzosilole and benzopyran.

The number of carbon atoms of the monovalent heterocyclic group is, not including the number of carbon atoms of a substituent, usually 2 to 60, preferably 4 to 20.

The monovalent heterocyclic group optionally has a substituent, and examples thereof include a thienyl group, a pyrrolyl group, a furyl group, a pyridyl group, a piperidyl group, a quinolyl group, an isoquinolyl group, a pyrimidinyl group, a triazinyl group, and groups obtained by substituting a hydrogen atom in these groups with an alkyl group, a cycloalkyl group, an alkoxy group, a cycloalkoxy group or the like.

"Halogen atom" denotes a fluorine atom, a chlorine atom, a bromine atom or an iodine atom.

"Amino group" optionally has a substituent, and a substituted amino group is preferable. The substituent which an amino group has is preferably an alkyl group, a cycloalkyl group, an aryl group or a monovalent heterocyclic group.

The substituted amino group includes, for example, a dialkylamino group, a dicycloalkylamino group and a diarylamino group.

The amino group includes, for example, a dimethylamino group, a diethylamino group, a diphenylamino group, a bis(4-methylphenyl)amino group, a bis(4-tert-butylphenyl)amino group and a bis(3,5-di-tert-butylphenyl)amino group.

"Alkenyl group" may be any of linear or branched. The number of carbon atoms of the linear alkenyl group, not including the number of carbon atoms of the substituent, is usually 2 to 30, preferably 3 to 20. The number of carbon atoms of the branched alkenyl group, not including the number of carbon atoms of the substituent, is usually 3 to 30, preferably 4 to 20.

The number of carbon atoms of "Cycloalkenyl group", not including the number of carbon atoms of the substituent, is usually 3 to 30, preferably 4 to 20.

The alkenyl group and cycloalkenyl group each optionally have a substituent, and examples thereof include a vinyl group, a 1-propenyl group, a 2-propenyl group, a 2-butenyl group, a 3-butenyl group, a 3-pentenyl group, a 4-pentenyl group, a 1-hexenyl group, a 5-hexenyl group, a 7-octenyl group, and these groups having a substituent.

"Alkynyl group" may be any of linear or branched. The number of carbon atoms of the alkynyl group, not including the number of carbon atoms of the substituent, is usually 2 to 20, preferably 3 to 20. The number of carbon atoms of the branched alkynyl group, not including the number of carbon atoms of the substituent, is usually 4 to 30, preferably 4 to 20.

The number of carbon atoms of "Cycloalkynyl group", not including the number of carbon atoms of the substituent, is usually 4 to 30, preferably 4 to 20.

The alkynyl group and cycloalkynyl group each optionally have a substituent, and examples thereof include an ethynyl group, a 1-propynyl group, a 2-propynyl group, a 2-butynyl group, a 3-butynyl group, a 3-pentynyl group, a 4-pentynyl group, a 1-hexynyl group, a 5-hexynyl group, and these groups having a substituent.

"Arylene group" denotes an atomic group remaining after removing from an aromatic hydrocarbon two hydrogen atoms linked directly to carbon atoms constituting the ring. The number of carbon atoms of the arylene group is, not including the number of carbon atoms of a substituent, usually 6 to 60, preferably 6 to 30, more preferably 6 to 18.

The arylene group optionally has a substituent, and examples thereof include a phenylene group, a naphthalenediyl group, an anthracenediyl group, a phenanthrenediyl group, a dihydrophenanthrenediyl group, a naphthacenediyl group, a fluorenediyl group, a pyrenediyl group, a perylenediyl group, a chrysenediyl group, and these groups having a substituent, preferably, groups represented by the formulae (A-1) to (A-20). The arylene group includes groups obtained by linking a plurality of these groups.

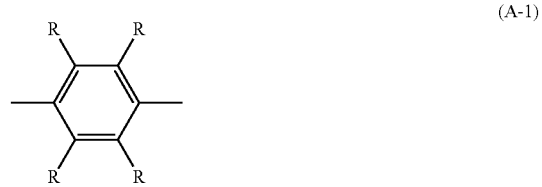

(A-1)

(A-2)

(A-3)

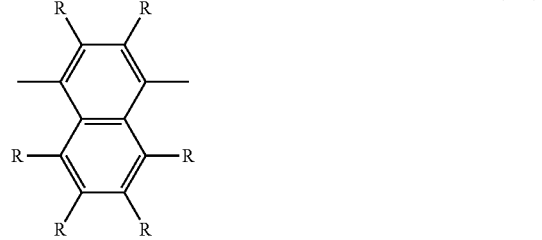

(A-4)

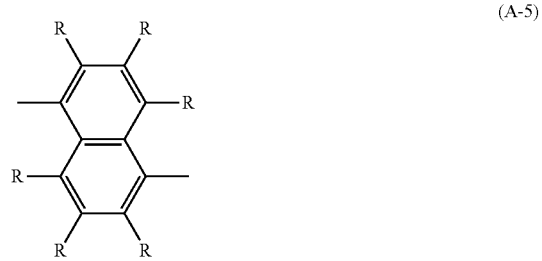

(A-5)

(A-6)

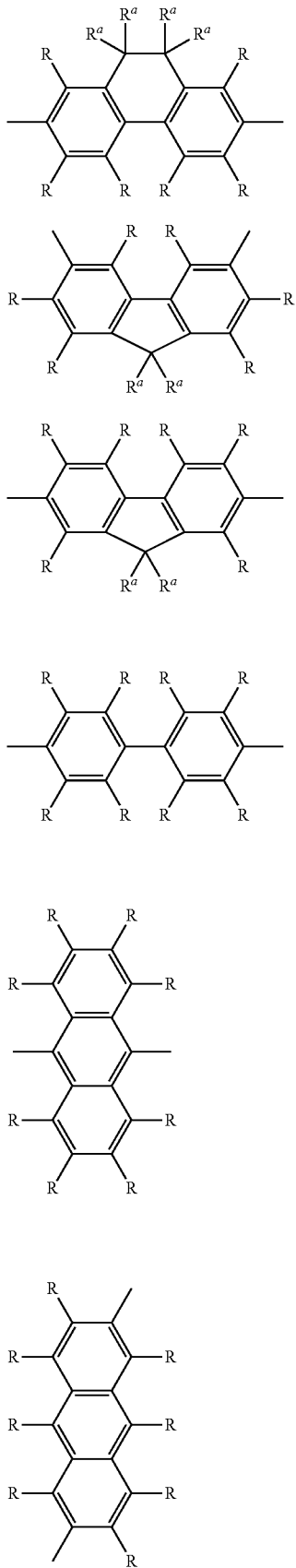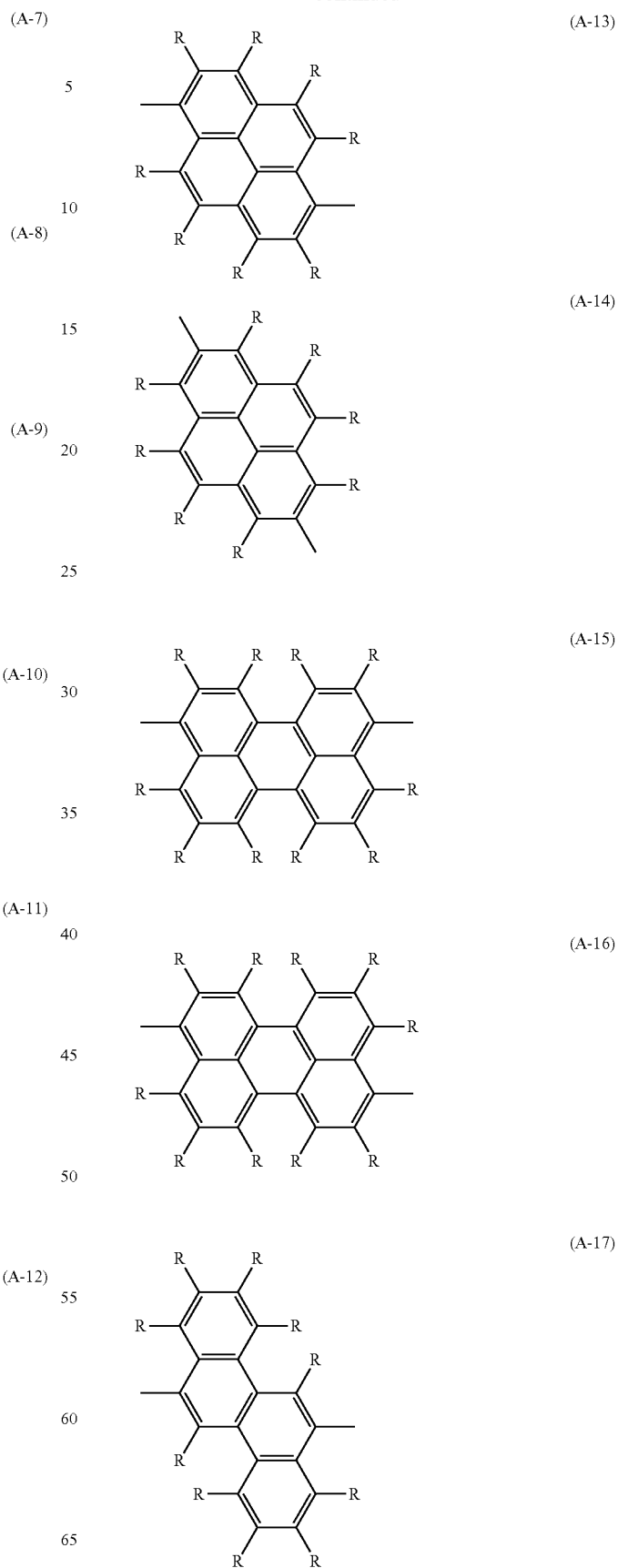

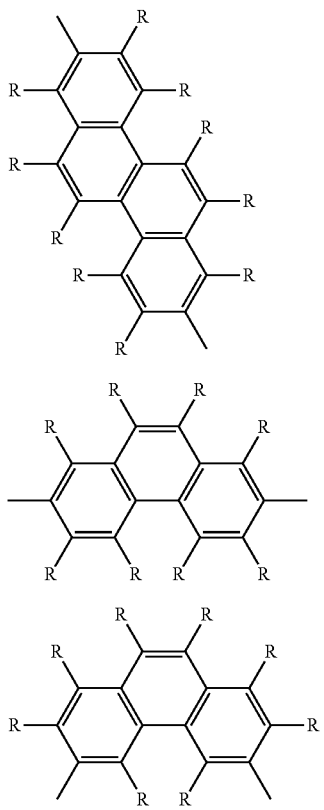

(A-18)

(A-19)

(A-20)

[wherein, R and $R^a$ each independently represent a hydrogen atom, an alkyl group, a cycloalkyl group, an aryl group or a monovalent heterocyclic group. The plurality of R and $R^a$ each may be the same or different, and groups $R^a$ may be combined together to form a ring together with the atoms to which they are attached.]

The number of carbon atoms of the divalent heterocyclic group is, not including the number of carbon atoms of a substituent, usually 2 to 60, preferably 3 to 20, more preferably 4 to 15.

The divalent heterocyclic group optionally has a substituent, and examples thereof include divalent groups obtained by removing from pyridine, diazabenzene, triazine, azanaphthalene, diazanaphthalene, carbazole, dibenzofuran, dibenzothiophene, dibenzosilole, phenoxazine, phenothiazine, acridine, dihydroacridine, furan, thiophene, azole, diazole and triazole two hydrogen atoms among hydrogen atoms linking directly to a carbon atom or a hetero atom constituting the ring, preferably groups represented by the formulae (AA-1) to (AA-34). The divalent heterocyclic group includes groups obtained by linking a plurality of these groups.

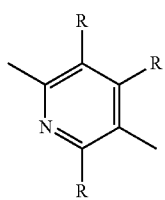

(AA-1)

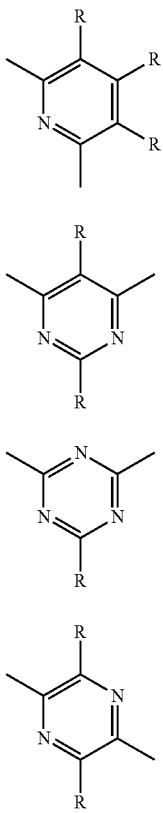

(AA-2)

(AA-3)

(AA-4)

(AA-5)

(AA-6)

(AA-7)

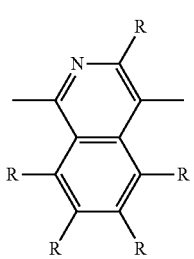

(AA-8)

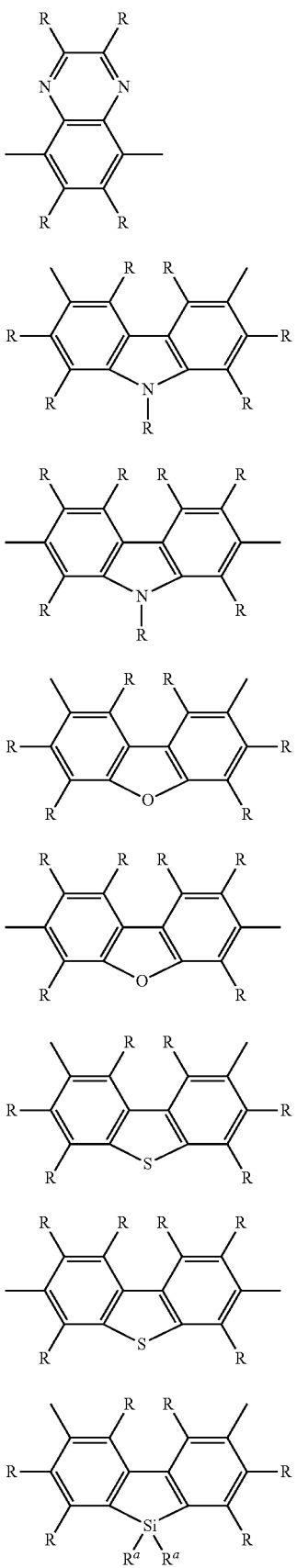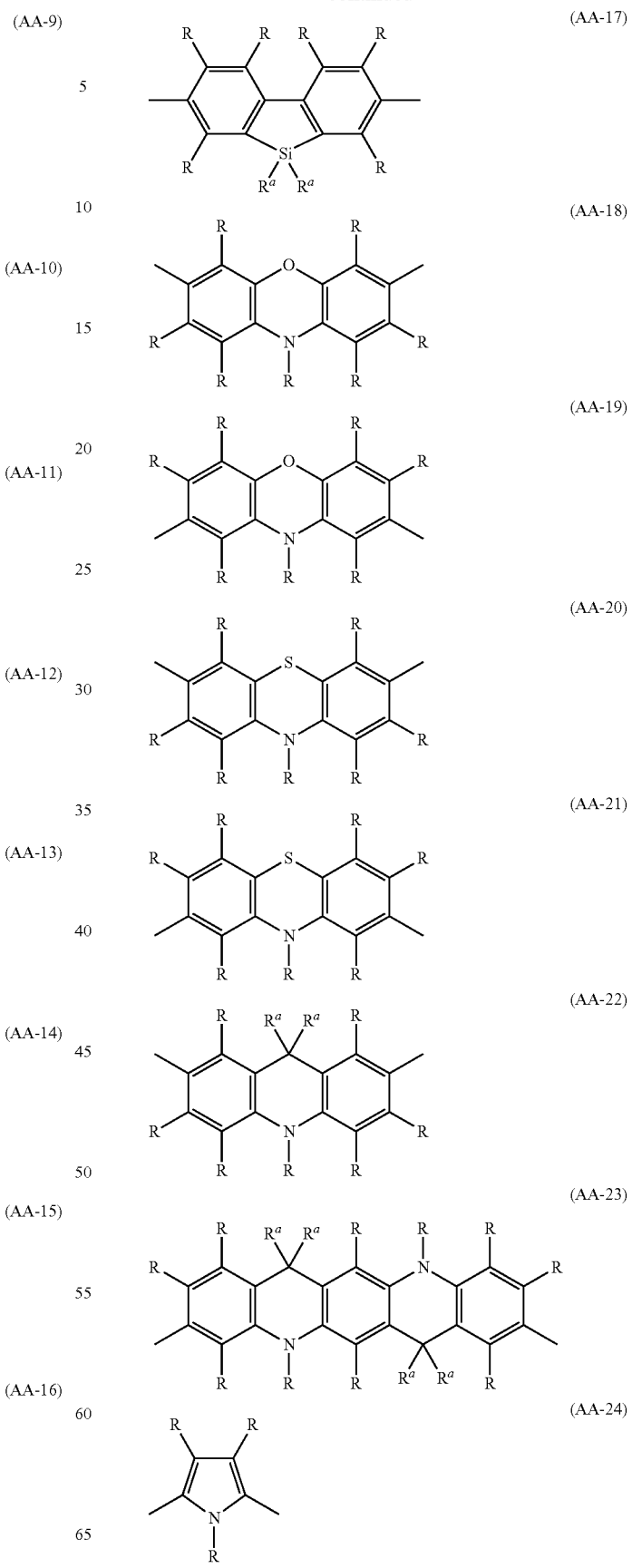

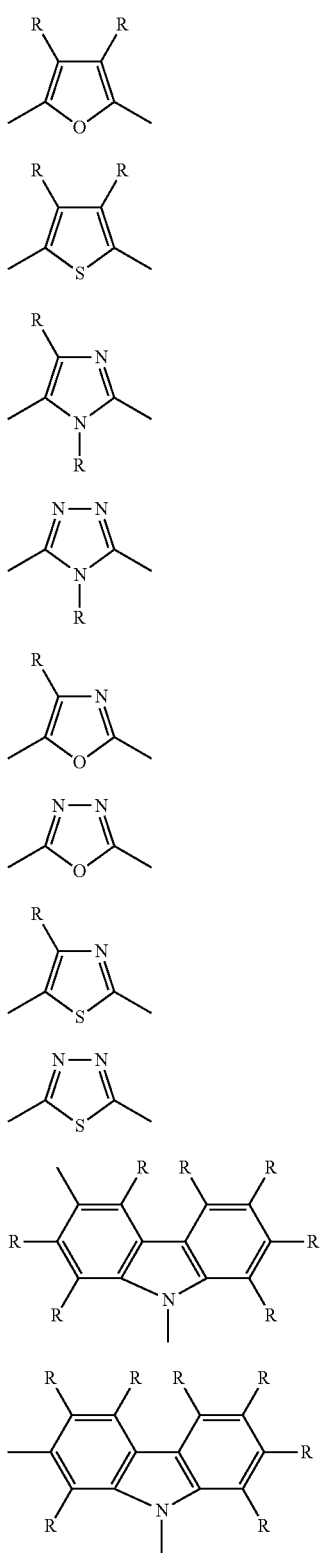

[wherein, R and R$^a$ represent the same meaning as described above.]

"Crosslinkable group" is a group capable of forming a new bond by being subjected to a heating treatment, an ultraviolet irradiation treatment, a radical reaction and the like, and the crosslinkable group is preferably any one of groups represented by the formulae (B-1) to (B-17). These groups each optionally have a substituent.

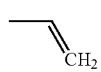 (B-1)

 (B-2)

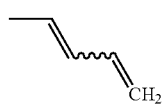 (B-3)

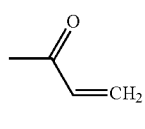 (B-4)

(B-5)

(B-6)

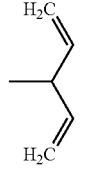 (B-7)

 (B-8)

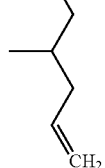 (B-9)

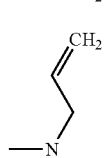 (B-10)

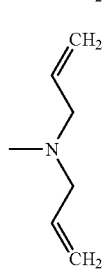 (B-11)

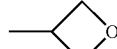 (B-12)

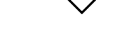

-continued

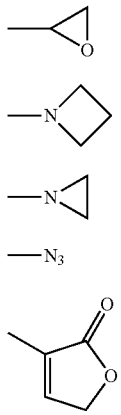

(B-13)

(B-14)

(B-15)

(B-16)

(B-17)

"Substituent" represents a halogen atom, a cyano group, an alkyl group, a cylcoalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group or a cycloalkynyl group. The substituent may be a crosslinkable group.

<Phosphorescent Compound>

"Phosphorescent compound" denotes a compound showing a phosphorescent property, preferably is a metal complex showing emission from the triplet excited state. This metal complex showing emission from the triplet excited state has a central metal atom and a ligand.

As the central metal atom, exemplified are metal atoms having an atomic number of 40 or more, showing a spin-orbital interaction with the complex, and capable of causing intersystem crossing between the singlet state and the triplet state. Exemplified as the metal atom are a ruthenium atom, a rhodium atom, a palladium atom, an iridium atom and a platinum atom.

As the ligand, exemplified are neutral or anionic monodentate ligands or neutral or anionic polydentate ligands forming at least one bond selected from the group consisting of a coordinate bond and a covalent bond between it and the central metal atom. As the bond between the central metal atom and the ligand, exemplified are a metal-nitrogen bond, a metal-carbon bond, a metal-oxygen bond, a metal-phosphorus bond, a metal-sulfur bond and a metal-halogen bond. The polydentate ligand denotes usually a bidentate or more and hexadentate or less ligand.

The phosphorescent compounds are available from Aldrich, Luminescence Technology Corp., American Dye Source and the like.

As the obtaining method other than the above-described means, known methods described in literatures such as "Journal of the American Chemical Society, Vol. 107, 1431-1432 (1985)", "Journal of the American Chemical Society, Vol. 106, 6647-6653 (1984)", International Publication WO 2011/024761, International Publication WO 2002/44189, JP-A No. 2006-188673 and the like can also be used to produce the phosphorescent compounds.

The emission spectrum maximum peak wavelength of the phosphorescent compound can be evaluated by dissolving the phosphorescent compound in an organic solvent such as xylene, toluene, chloroform, tetrahydrofuran and the like to prepare a dilute solution (about $1 \times 10^{-6}$ to $1 \times 10^{-3}$ wt %) and measuring the PL spectrum of the dilute solution at room temperature. The organic solvent for dissolving the phosphorescent compound is preferably xylene.

<Dendron>

"Dendron" is a group having a regular dendritic branched structure having a branching point at an atom or ring. The phosphorescent compound having a dendron as a partial structure (called a phosphorescent compound having a dendron in some cases) includes, for example, structures described in literatures such as International Publication WO 02/067343, JP-A No. 2003-231692, International Publication WO 2003/079736, International Publication WO 2006/097717 and the like.

The dendron is preferably a group represented by the formula (D-A) or (D-B), more preferably a group represented by the formula (D-A).

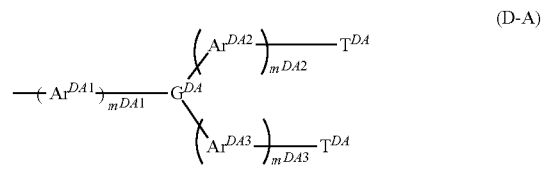

(D-A)

[wherein, $m^{DA1}$, $m^{DA2}$ and $m^{DA3}$ each independently represent an integer of 0 or more.

$G^{DA}$ represents a nitrogen atom, an aromatic hydrocarbon group or a heterocyclic group, and these groups each optionally have a substituent.

$Ar^{DA1}$, $Ar^{DA2}$ and $Ar^{DA3}$ each independently represent an arylene group or a divalent heterocyclic group, and these groups each optionally have a substituent. When a plurality of $Ar^{DA1}$, $Ar^{DA2}$ and $Ar^{DA3}$ are present, they may be the same or different at each occurrence.

$T^{DA}$ represents an aryl group or a monovalent heterocyclic group, and these groups each optionally have a substituent. The plurality of $R^{DA}$ may be the same or different.]

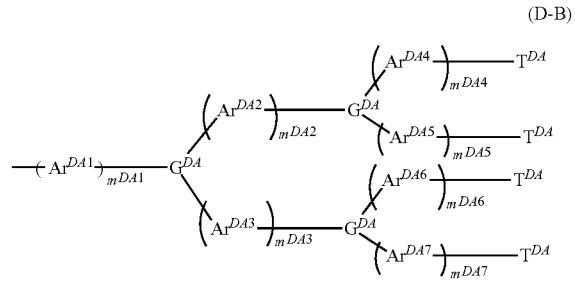

(D-B)

[wherein, $m^{DA1}$, $m^{DA2}$, $m^{DA3}$, $m^{DA4}$, $m^{DA5}$, $m^{DA6}$ and $m^{DA7}$ each independently represent an integer of 0 or more.

$G^{DA}$ represents a nitrogen atom, an aromatic hydrocarbon group or a heterocyclic group, and these groups each optionally have a substituent. The plurality of $G^{DA}$ may be the same or different.

$Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group, and these groups each optionally have a substituent. When a plurality of $Ar^{DA1}$, $Ar^{DA2}$, $Ar^{DA3}$, $Ar^{DA4}$, $Ar^{DA5}$, $Ar^{DA6}$ and $Ar^{DA7}$ are present, they may be the same or different at each occurrence.

$T^{DA}$ represents an aryl group or a monovalent heterocyclic group, and these groups each optionally have a substituent. The plurality of $R^{DA}$ may be the same or different.]

$m^{DA1}$, $m^{DA2}$, $m^{DA3}$, $m^{DA4}$, $m^{DA5}$, $m^{DA6}$ and $m^{DA7}$ represent usually an integer of 10 or less, preferably an integer of 5 or less, more preferably 0 or 1, further preferably 0.

It is preferable that $m^{DA2}$ and $m^{DA3}$ are the same integer.

It is preferable that $m^{DA4}$, $m^{DA5}$, $m^{DA6}$ and $m^{DA7}$ are the same integer.

It is more preferable that $m^{DA2}$, $m^{DA3}$, $m^{DA4}$, $m^{DA5}$, $m^{DA6}$ and $m^{DA7}$ are the same integer, and it is further preferable that $m^{DA1}$, $m^{DA2}$, $m^{DA3}$, $m^{DA4}$, $m^{DA5}$, $m^{DA6}$ and $m^{DA7}$ are the same integer.

$G^{DA}$ is preferably a group obtained by removing from a benzene ring, a pyridine ring, a pyrimidine ring, a triazine ring or a carbazole ring three hydrogen atoms linking directly to a carbon atom or a nitrogen atom constituting the ring unless otherwise stated, and these groups each optionally have a substituent.

The substituent which $G^{DA}$ optionally has is preferably an alkyl group, an cycloalkyl group, an alkoxy group, a cycloalkoxy group, an aryl group or a monovalent heterocyclic group.

$G^{DA}$ is preferably a group represented by the formula (GDA-11) to (GDA-15), and these groups each optionally have a substituent.

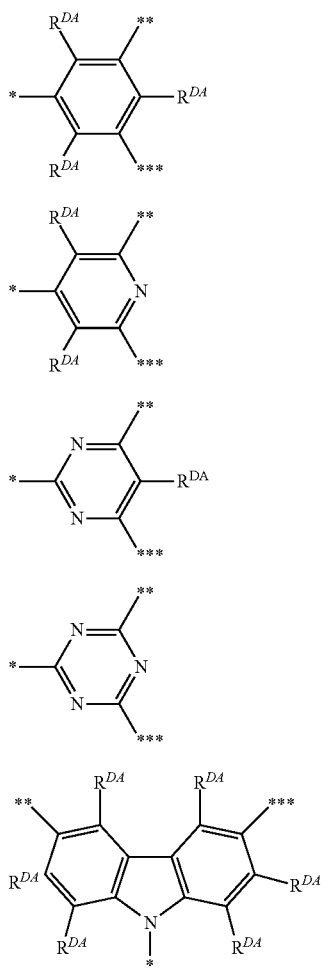

[wherein,

\* represents a linkage to $Ar^{DA1}$ in the formula (D-A), $Ar^{DA1}$ in the formula (D-B), $Ar^{DA2}$ in the formula (D-B) or $Ar^{DA3}$ in the formula (D-B).

\*\* represents a linkage to $Ar^{DA2}$ in the formula (D-A), $Ar^{DA2}$ in the formula (D-B), $Ar^{DA4}$ in the formula (D-B) or $Ar^{DA6}$ in the formula (D-B).

\*\*\* represents a linkage to $Ar^{DA3}$ in the formula (D-A), $Ar^{DA3}$ in the formula (D-B), $Ar^{DA5}$ in the formula (D-B) or $Ar^{DA7}$ in the formula (D-B).

$R^{DA}$ represents a hydrogen atom, an alkyl group, a cycloalkyl group, an alkoxy group, a cycloalkoxy group, an aryl group or a monovalent heterocyclic group, and these groups each optionally have a substituent. When a plurality of $R^{DA}$ are present, they may be the same or different.]

$R^{DA}$ is preferably a hydrogen atom, an alkyl group, a cycloalkyl group, an alkoxy group or a cycloalkoxy group, more preferably a hydrogen atom, an alkyl group or cycloalkyl group, and these groups each optionally have a substituent.

It is preferable that $Ar^{DA1}$, $Ar^{DA2}$, $Ar^{DA3}$, $Ar^{DA4}$, $Ar^{DA5}$, $Ar^{DA6}$ and $Ar^{DA7}$ are groups represented by the formulae (ArDA-1) to (ArDA-3).

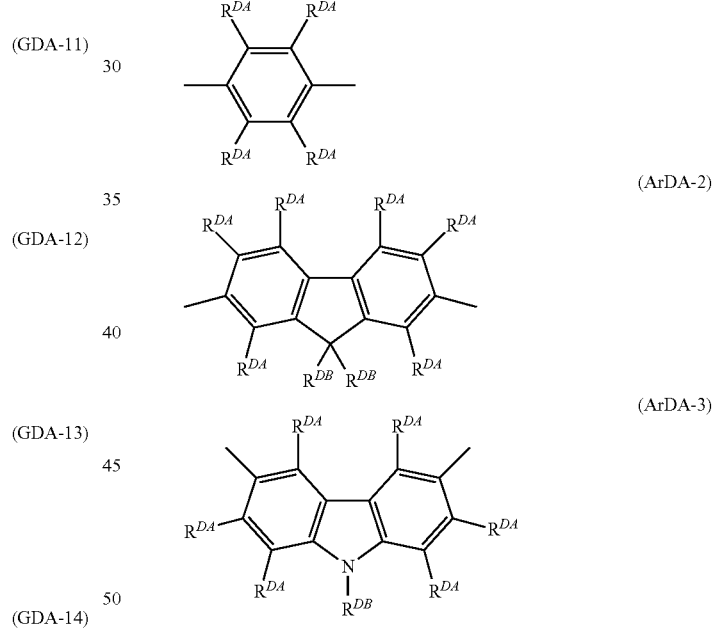

[wherein, $R^{DA}$ represents the same meaning as described above.

$R^{DB}$ represents a hydrogen atom, an alkyl group, a cycloalkyl group, an aryl group or a monovalent heterocyclic group, and these groups each optionally have a substituent. When a plurality of $R^{DB}$ are present, they may be the same or different.]

$R^{DB}$ is preferably an alkyl group, a cycloalkyl group, an aryl group or a monovalent heterocyclic group, more preferably an aryl group or a monovalent heterocyclic group, further preferably an aryl group, and these groups each optionally have a substituent.

$T^{DA}$ is preferably groups represented by the formulae (TDA-1) to (TDA-3).

(TDA-1)

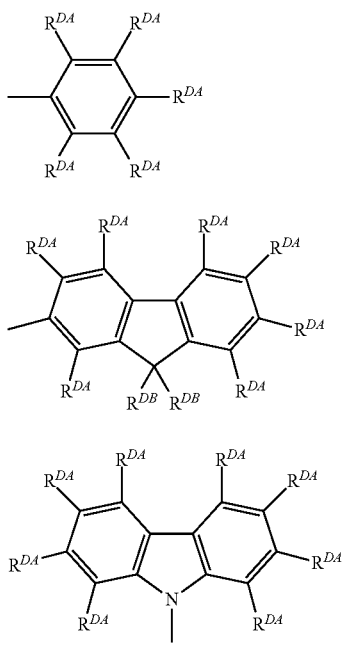

(TDA-2)

(TDA-3)

[wherein, $R^{DA}$ and $R^{DB}$ represent the same meaning described above.]

The group represented by the formula (D-A) is preferably a group represented by the formula (D-A1) to (D-A3).

(D-A1)

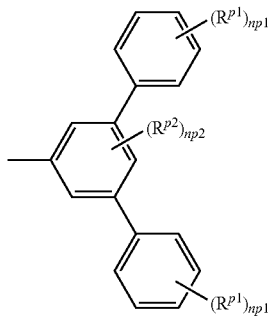

(D-A2)

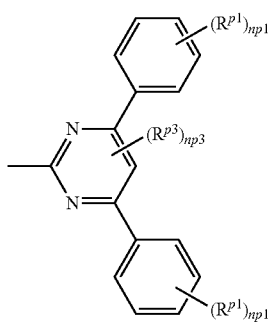

(D-A3)

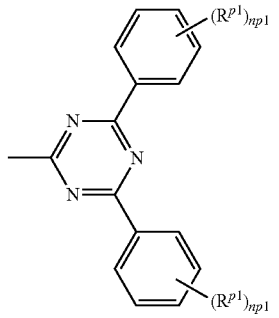

[wherein, $R^{p1}$, $R^{p2}$ and $R^{p3}$ each independently represent an alkyl group, a cycloalkyl group, an alkoxy group, a cycloalkoxy group or a halogen atom. When a plurality of $R^{p1}$ and $R^{p2}$ are present, they may be the same or different at each occurrence.

np1 represents an integer of 0 to 5, np2 represents an integer of 0 to 3, and np3 represents 0 or 1. The plurality of np1 may be the same or different.]

The group represented by the formula (D-B) is preferably a group represented by the formula (D-B1) to (D-B3).

(D-B1)

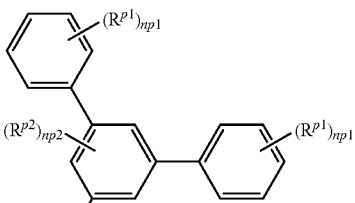

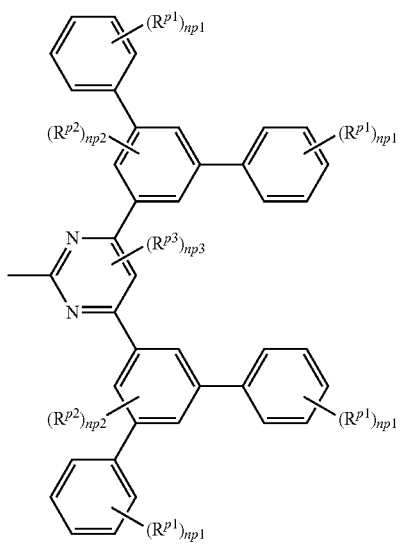

(D-B2)

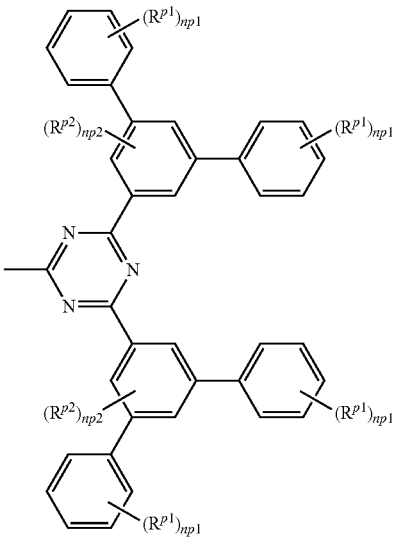

(D-B3)

[wherein, $R^{p1}$, $R^{p2}$ and $R^{p3}$ each independently represent an alkyl group, a cycloalkyl group, an alkoxy group, a cycloalkoxy group or a halogen atom. When a plurality of $R^{p1}$ and $R^{p2}$ are present, they may be the same or different at each occurrence.

np1 represents an integer of 0 to 5, np2 represents an integer of 0 to 3, and np3 represents 0 or 1. When a plurality of np1 and np2 are present, they may be the same or different at each occurrence.]

np1 is preferably 0 or 1, more preferably 1. np2 is preferably 0 or 1, more preferably 0. np3 is preferably 0.

$R^{p1}$, $R^{p2}$ and $R^{p3}$ are preferably an alkyl group or a cycloalkyl group.

As the dendron, groups represented by the formulae (D-A-1) to (D-A-20) and (D-B-1) to (D-B-8) are exemplified.

TABLE 1

| formula | $m^{DA1}$ | $Ar^{DA1}$ | $G^{DA}$ | $m^{DA2}$, $m^{DA3}$ | $Ar^{DA2}$, $Ar^{DA3}$ | $T^{DA}$ |
|---|---|---|---|---|---|---|
| (D-A-1) | 0 | — | [benzene-1,3,5-triyl] | 0 | — | [phenyl-$R^p$] |
| (D-A-2) | 1 | [1,4-phenylene] | [benzene-1,3,5-triyl] | 0 | — | [phenyl-$R^p$] |
| (D-A-3) | 1 | [2,6-dimethyl-1,4-phenylene with Me, Me] | [benzene-1,3,5-triyl] | 0 | — | [phenyl-$R^p$] |

TABLE 1-continued

| formula | $m^{DA1}$ | $Ar^{DA1}$ | $G^{DA}$ | $m^{DA2}, m^{DA3}$ | $Ar^{DA2}, Ar^{DA3}$ | $T^{DA}$ |
|---|---|---|---|---|---|---|
| (D-A-4) | 1 | 2,5-dimethylphenyl | 1,3-phenylene (*, **, ***) | 0 | — | phenyl-$R^p$ |
| (D-A-5) | 1 | 2,3-dimethylphenyl | 1,3-phenylene (*, **, ***) | 0 | — | phenyl-$R^p$ |
| (D-A-6) | 0 | — | carbazol-N-yl (2,7-substituted) | 0 | — | carbazole-$R^p$ |
| (D-A-7) | 1 | 1,4-phenylene | carbazol-N-yl (2,7-substituted) | 0 | — | carbazole-$R^p$ |
| (D-A-8) | 0 | — | nitrogen atom | 0 | — | phenyl-$R^p$ |

TABLE 2

| formula | $m^{DA1}$ | $Ar^{DA1}$ | $G^{DA}$ | $m^{DA2}, m^{DA3}$ | $Ar^{DA2}, Ar^{DA3}$ | $T^{DA}$ |
|---|---|---|---|---|---|---|
| (D-A-9) | 1 | 1,4-phenylene | nitrogen atom | 0 | — | phenyl-$R^p$ |
| (D-A-10) | 0 | — | pyridine-2,4,6-triyl (*, **, ***) | 0 | — | phenyl-$R^p$ |

TABLE 2-continued
| formula | $m^{DA1}$ | $Ar^{DA1}$ | $G^{DA}$ | $m^{DA2}, m^{DA3}$ | $Ar^{DA2}, Ar^{DA3}$ | $T^{DA}$ |
|---|---|---|---|---|---|---|
| (D-A-11) | 1 | 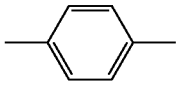 | 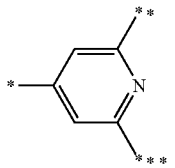 | 0 | — | 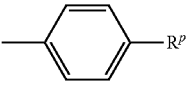 |
| (D-A-12) | 0 | — | 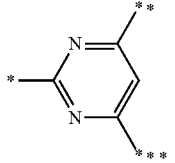 | 0 | — | 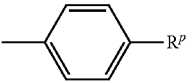 |
| (D-A-13) | 1 |  | 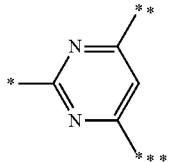 | 0 | — | 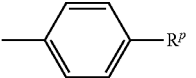 |
| (D-A-14) | 0 | — | 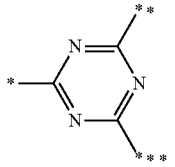 | 0 | — | 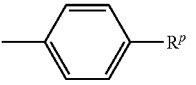 |
| (D-A-15) | 1 |  | 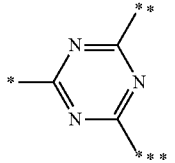 | 0 | — | 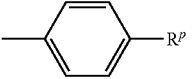 |
| (D-A-16) | 0 | — | 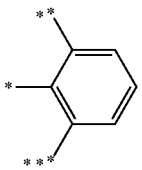 | 0 | — | 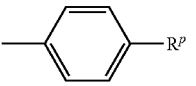 |
| (D-A-17) | 1 |  | 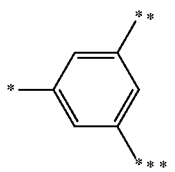 | 1 |  | 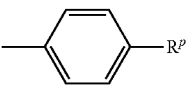 |

TABLE 2-continued
| formula | $m^{DA1}$ | $Ar^{DA1}$ | $G^{DA}$ | $m^{DA2}, m^{DA3}$ | $Ar^{DA2}, Ar^{DA3}$ | $T^{DA}$ |
|---|---|---|---|---|---|---|
| (D-A-18) | 1 | | nitrogen atom | 1 | | |
| (D-A-19) | 1 | | | 0 | — | |
| (D-A-20) | 1 | | | 0 | — | |
[wherein, *,  and * represent the same meaning as described above.]
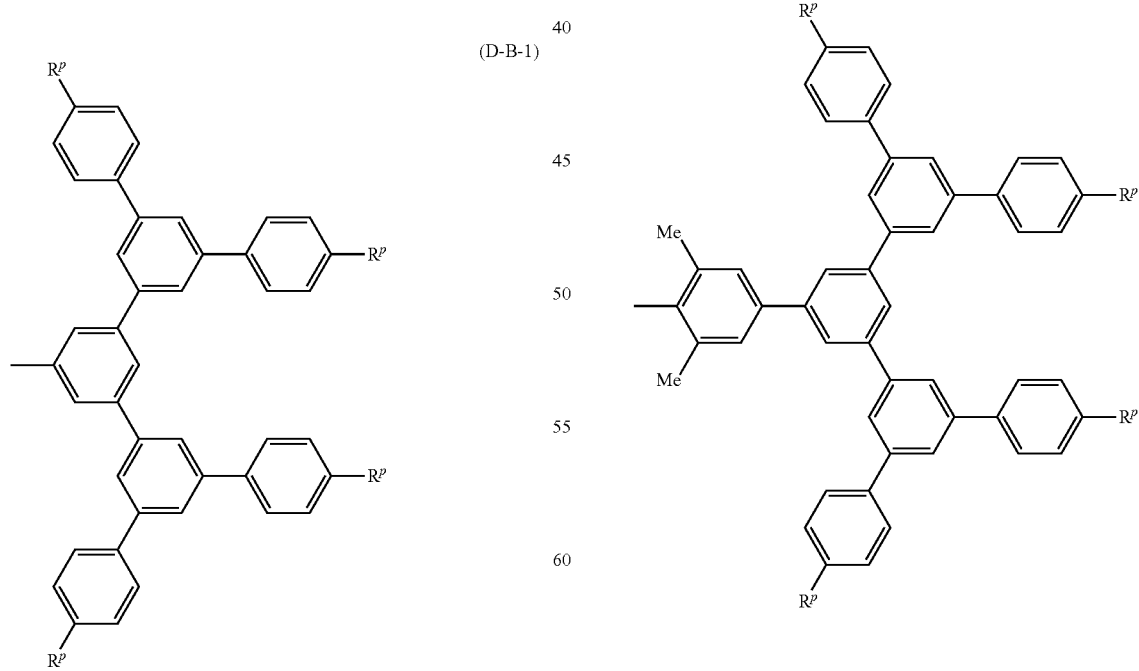

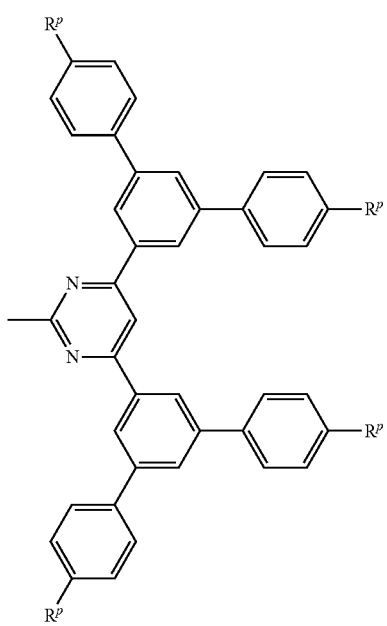
(D-B-3)
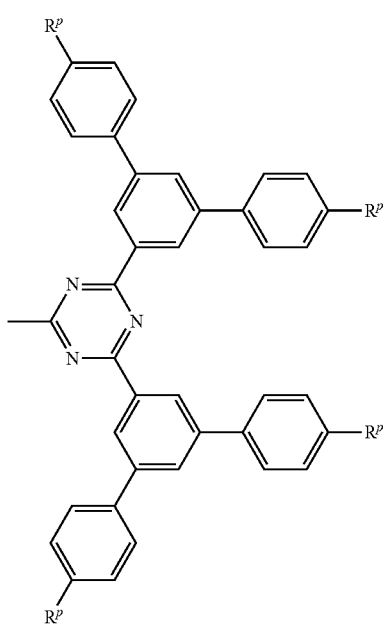
(D-B-4)
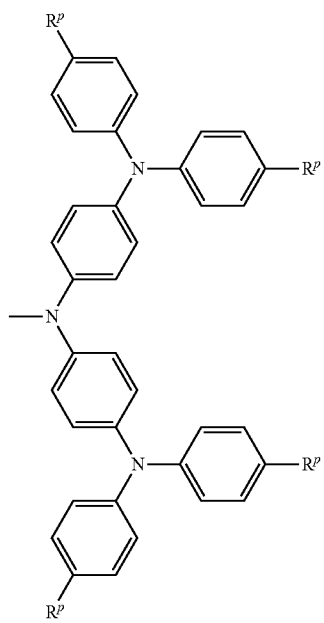
(D-B-5)
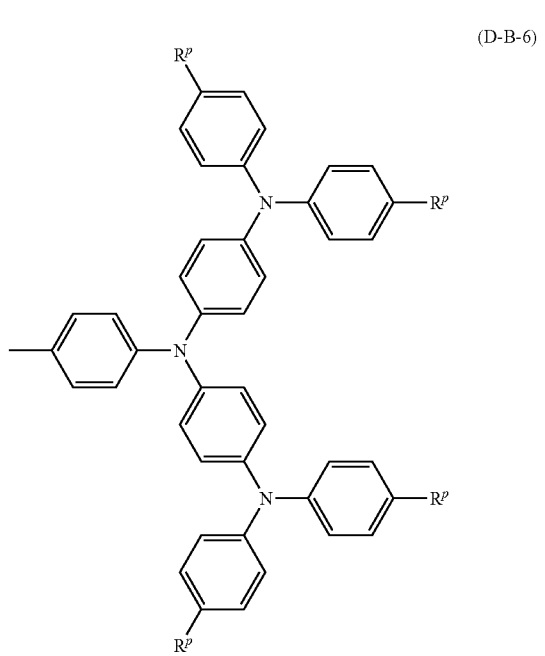
(D-B-6)

-continued (D-B-7)

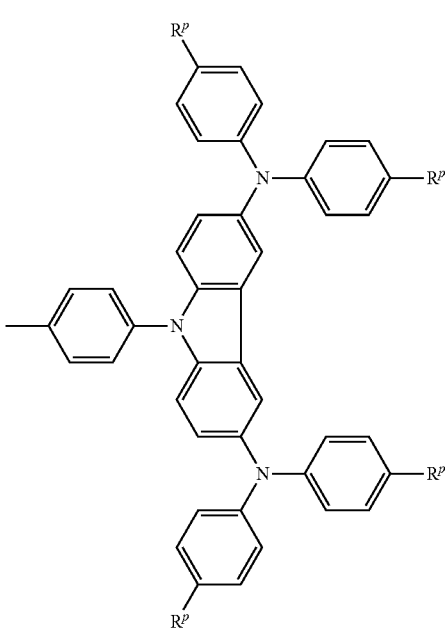

(D-B-8)

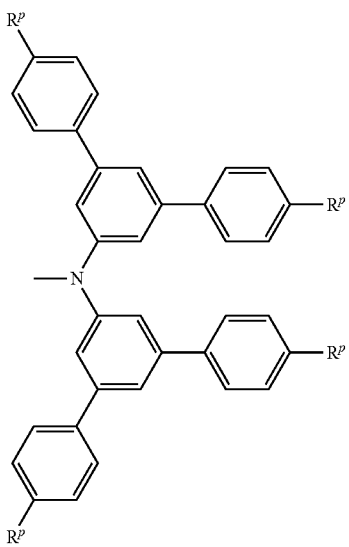

$R^p$ represents a hydrogen atom, an alkyl group, a cycloalkyl group, an alkoxy group or a cycloalkoxy group and these groups each optionally have a substituent, and $R^p$ is preferably a methyl group, a tert-butyl group, a hexyl group, a 2-ethylhexyl group, a group represented by the formula (Rp-1) or a 2-ethylhexyloxy group, more preferably a tert-butyl group or a group represented by the formula (Rp-1).

(Rp-1)

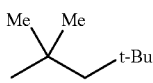

<Phosphorescent Compound (B)>

The phosphorescent compound (B) contained in the first composition and the second composition of the present invention is a phosphorescent compound having an emission spectrum the maximum peak wavelength of which is between 380 nm or more and less than 495 nm and having no dendron, and represented by the formula (1).

(1)

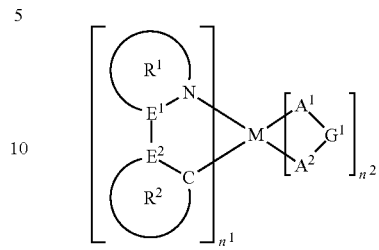

$E^1$ and $E^2$ are preferably a carbon atom.

M is preferably an iridium atom or a platinum atom, more preferably an iridium atom, because a light emitting device produced by using the composition of the present invention (the first or second composition of the present invention) is excellent in external quantum efficiency.

$n^1$ is preferably 2 or 3, more preferably 3 when M is a ruthenium atom, a rhodium atom or an iridium atom.

$n^1$ is preferably 2 when M is a palladium atom or a platinum atom.

The ring $R^1$ is preferably a 5-membered aromatic heterocyclic ring having 1 to 4 nitrogen atoms as a constitutional atom, more preferably a 5-membered aromatic heterocyclic ring having 2 to 3 nitrogen atoms as a constitutional atom, further preferably a diazole ring or a triazole ring, particularly preferably an imidazole ring or a triazole ring, and these rings each optionally have a substituent.

The ring $R^2$ is preferably a benzene ring, a naphthalene ring, a fluorene ring, a phenanthrene ring, a pyridine ring, a diazabenzene ring or a triazine ring, more preferably a benzene ring, a pyridine ring or a pyrimidine ring, further preferably a benzene ring, and these rings each optionally have a substituent.

The substituent which the ring $R^1$ and the ring $R^2$ optionally have is preferably an alkyl group, a cycloalkyl group, an aryl group, a monovalent heterocyclic group, an alkoxy group, a cycloalkoxy group, an aryloxy group or a fluorine atom, more preferably an alkyl group, a cycloalkyl group, an aryl group, a monovalent heterocyclic group or a fluorine atom, further preferably as alkyl group, an aryl group or a monovalent heterocyclic group, particularly preferably an alkyl group or an aryl group, and these groups each optionally further have a substituent. When a plurality of the substituents which the ring $R^1$ and the ring $R^2$ optionally have are present, they may be the same or different and may be combined together to form a ring together with the atoms to which they are attached.

The anionic bidentate ligand represented by $A^1$-$G^1$-$A^2$ includes, for example, ligands represented by the following formulae.

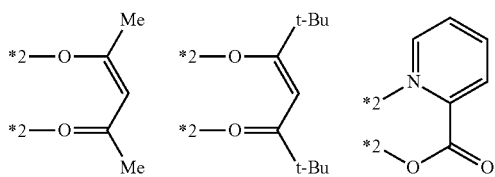

-continued

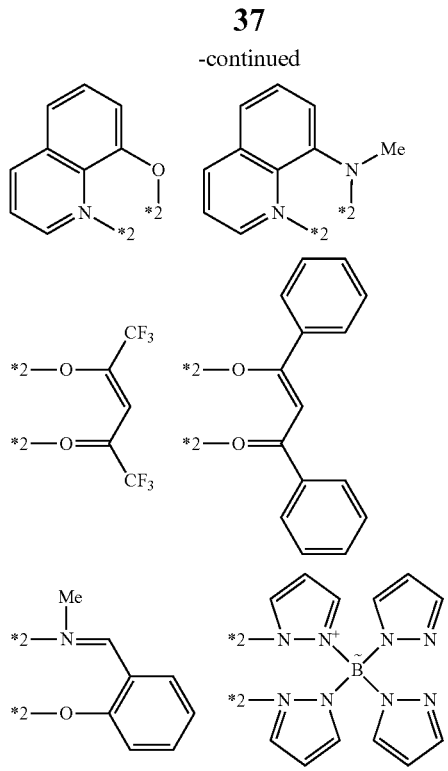

[wherein, *2 represents a site binding to M or M¹ described later.]

The anionic bidentate ligand represented by $A^1$-$G^1$-$A^2$ may be ligands represented by the following formulae. The anionic bidentate ligand represented by $A^1$-$G^1$-$A^2$ is different from the ligand of which number is defined by a subscript $n^1$.

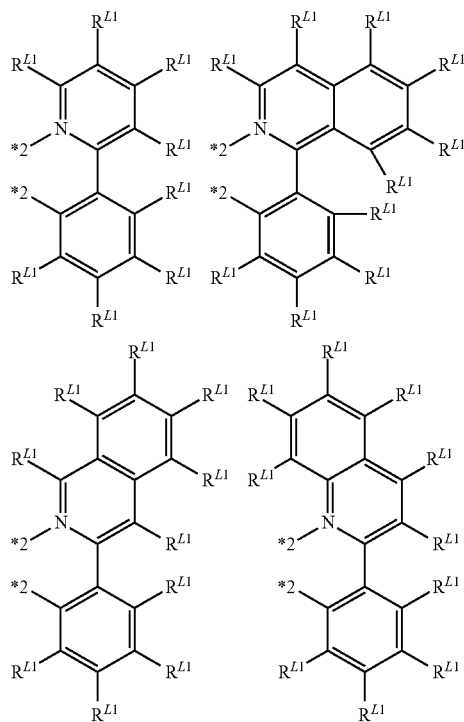

-continued

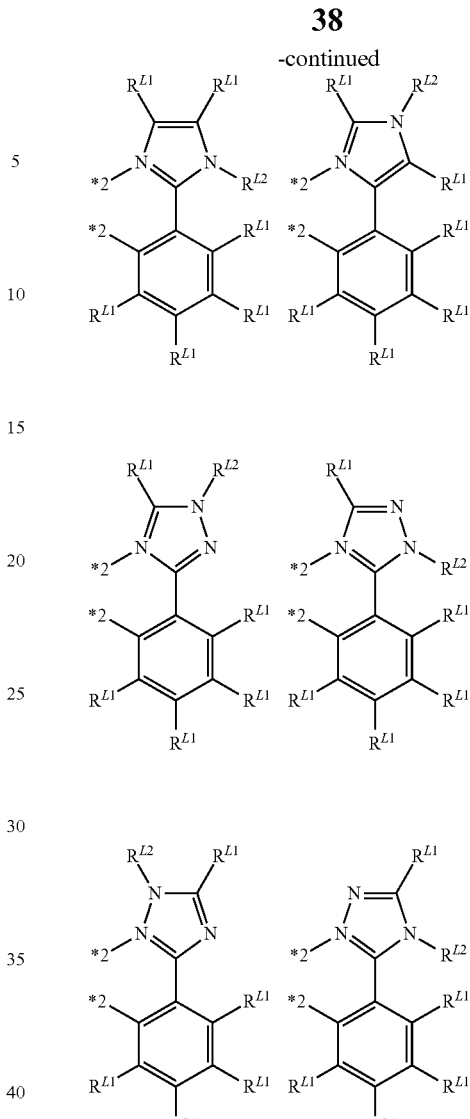

[wherein,
* represents the same meaning as described above.

$R^{L1}$ represents a hydrogen atom, an alkyl group, a cycloalkyl group, an aryl group, a monovalent heterocyclic group or a halogen atom, and these groups each optionally have a substituent. The plurality of $R^{L1}$ may be the same or different.

$R^{L2}$ represents an alkyl group, a cycloalkyl group, an aryl group, a monovalent heterocyclic group or a halogen atom, and these groups each optionally have a substituent.]

$R^{L1}$ is preferably a hydrogen atom, an alkyl group, an aryl group or a fluorine atom, and these groups each optionally have a substituent.

$R^{L2}$ is preferably an alkyl group or an aryl group, and these groups each optionally have a substituent.

In the first composition of the present invention, the phosphorescent compound represented by the formula (1) is preferably a phosphorescent compound represented by the formula (1'), because a light emitting device produced by using the first composition of the present invention is more excellent in external quantum efficiency.

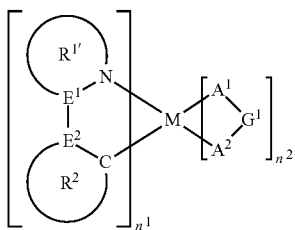

(1')

The ring $R^{1'}$ is preferably an imidazole ring, because a light emitting device produced by using the first composition of the present invention is more excellent in external quantum efficiency, and this imidazole ring optionally has a substituent.

The substituent which the ring $R^{1'}$ and the ring $R^2$ optionally have is preferably an alkyl group, a cycloalkyl group, an aryl group, a monovalent heterocyclic group, an alkoxy group, a cycloalkoxy group, an aryloxy group or a fluorine atom, more preferably an alkyl group, a cycloalkyl group, an aryl group, a monovalent heterocyclic group or a fluorine atom, further preferably an alkyl group, an aryl group or a monovalent heterocyclic group, particularly preferably an alkyl group or an aryl group, and these groups each optionally further have a substituent. When a plurality of the substituents which the ring $R^{1'}$ and the ring $R^2$ optionally have are present, they may be the same or different and may be combined together to form a ring together with the atoms to which they are attached.

The phosphorescent compound represented by the formula (1) is preferably a phosphorescent compound represented by the formula (1-A).

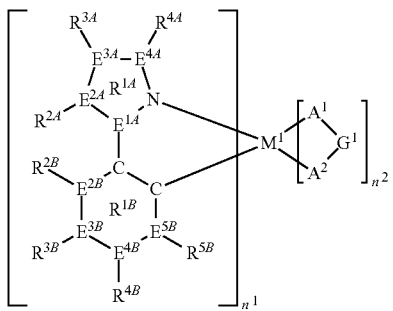

(1-A)

[wherein, $n^1$, $n^2$ and $A^1$-$G^1$-$A^2$ represent the same meaning as described above.

$M^1$ represents an iridium atom or a platinum atom.

$E^{1A}$, $E^{2A}$, $E^{3A}$, $E^{4A}$, $E^{2B}$, $E^{3B}$, $E^{4B}$ and $E^{5B}$ each independently represent a nitrogen atom or a carbon atom. When a plurality of $E^{1A}$, $E^{2A}$, $E^{3A}$, $E^{4A}$, $E^{2B}$, $E^{3B}$, $E^{4B}$ and $E^{5B}$ are present, they may be the same or different at each occurrence. $R^{2A}$, $R^{3A}$ and $R^{4A}$ may be either present or not present when $E^{2A}$, $E^{3A}$ and $E^{4A}$ are a nitrogen atom. $R^{2B}$, $R^{3B}$, $R^{4B}$ and $R^{5B}$ are not present when $E^{2B}$, $E^{3B}$, $E^{4B}$ and $E^{5B}$ are a nitrogen atom.

$R^{2A}$, $R^{3A}$, $R^{4A}$, $R^{2B}$, $R^{3B}$, $R^{4B}$ and $R^{5B}$ each independently represent a hydrogen atom, an alkyl group, a cycloalkyl group, an alkoxy group, a cycloalkoxy group, an aryl group, an aryloxy group, a monovalent heterocyclic group or a halogen atom, and these groups each optionally have a substituent. When a plurality of $R^{2A}$, $R^{3A}$, $R^{4A}$, $R^{2B}$, $R^{3B}$, $R^{4B}$ and $R^{5B}$ are present, they may be the same or different at each occurrence. $R^{2A}$ and $R^{3A}$, $R^{3A}$ and $R^{4A}$, $R^{2A}$ and $R^{2B}$, $R^{2B}$ and $R^{3B}$, $R^{3B}$ and $R^{4B}$, and $R^{4B}$ and $R^{5B}$ each may be combined together to form a ring together with the atoms to which they are attached.

The ring $R^{1A}$ represents a diazole ring or a triazole ring constituted of a nitrogen atom, $E^{1A}$, $E^{2A}$, $E^{3A}$ and $E^{4A}$.

The ring $R^{1B}$ represents a benzene ring, a pyridine ring or a pyrimidine ring constituted of two carbon atoms, $E^{2B}$, $E^{3B}$, $E^{4B}$ and $E^{5B}$.]

$M^1$ is preferably an iridium atom.

When the ring $R^{1A}$ is a diazole ring, it is preferable that $E^{2A}$ or $E^{3A}$ is a nitrogen atom, and it is more preferable that $E^{2A}$ is a nitrogen atom.

When the ring $R^{1A}$ is a triazole ring, it is preferable that any two of $E^{2A}$, $E^{3A}$ and $E^{4A}$ are a nitrogen atom, and it is more preferable that $E^{2A}$ and $E^{3A}$ are a nitrogen atom.

When $E^{2A}$ is a nitrogen atom and $R^{2A}$ is present, $R^{2A}$ is preferably an alkyl group, a cycloalkyl group, an aryl group or a monovalent heterocyclic group, more preferably an alkyl group or an aryl group, and these groups each optionally have a substituent.

When $E^{2A}$ is a carbon atom, $R^{2A}$ is preferably a hydrogen atom, an alkyl group, a cycloalkyl group, an aryl group or a monovalent heterocyclic group, more preferably a hydrogen atom, an alkyl group or an aryl group, further preferably a hydrogen atom or an alkyl group, and these groups each optionally have a substituent.

When $E^{3A}$ is a nitrogen atom and $R^{3A}$ is present, $R^{3A}$ is preferably an alkyl group, a cycloalkyl group, an aryl group or a monovalent heterocyclic group, more preferably an alkyl group or an aryl group, and these groups each optionally have a substituent.

When $E^{3A}$ is a carbon atom, $R^{3A}$ is preferably a hydrogen atom, an alkyl group, a cycloalkyl group, an aryl group or a monovalent heterocyclic group, more preferably a hydrogen atom, an alkyl group or an aryl group, further preferably a hydrogen atom or an alkyl group, and these groups each optionally have a substituent.

When $E^{4A}$ is a nitrogen atom and $R^{4A}$ is present, $R^{4A}$ is preferably an alkyl group, a cycloalkyl group, an aryl group or a monovalent heterocyclic group, more preferably an alkyl group or an aryl group, and these groups each optionally have a substituent.

When $E^{4A}$ is a carbon atom, $R^{4A}$ is preferably a hydrogen atom, an alkyl group, a cycloalkyl group, an aryl group or a monovalent heterocyclic group, more preferably a hydrogen atom, an alkyl group or an aryl group, further preferably a hydrogen atom or an alkyl group, and these groups each optionally have a substituent.

When the ring $R^{1B}$ is a pyridine ring, it is preferable that any one of $E^{3B}$, $E^{4B}$ and $E^{5B}$ is a nitrogen atom, and it is more preferable that $E^{3B}$ is a nitrogen atom.

When the ring $R^{1B}$ is a diazabenzene ring, it is preferable that $E^{2B}$ and $E^{4B}$, or $E^{3B}$ and $E^{5B}$ are a nitrogen atom, and it is more preferable that $E^{3B}$ and $E^{5B}$ are a nitrogen atom.

It is preferable that the ring $R^{1B}$ is a benzene ring.

$R^{2B}$, $R^{3B}$, $R^{4B}$ and $R^{5B}$ are preferably a hydrogen atom, an alkoxy group, a cycloalkoxy group, an alkyl group, a cycloalkyl group, an aryl group, a monovalent heterocyclic group or a fluorine atom, more preferably a hydrogen atom, an alkyl group, an aryl group or a monovalent heterocyclic group, further preferably a hydrogen atom, an alkyl group or an aryl group, and these groups each optionally have a substituent.

$R^{5B}$ is preferably a hydrogen atom or an alkyl group, more preferably a hydrogen atom.

In the first composition of the present invention, the phosphorescent compound represented by the formula (1') is preferably a phosphorescent compound represented by the formula (1'-A).

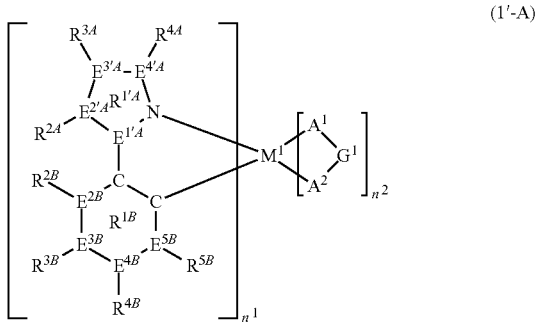

(1'-A)

[wherein, $n^1$, $n^2$, $A^1$-$G^1$-$A^2$, $M^1$, $E^{2B}$, $E^{3B}$, $E^{4B}$, $E^{5B}$, $R^{2A}$, $R^{3A}$, $R^{4A}$, $R^{2B}$, $R^{3B}$, $R^{4B}$, $R^{5B}$ and the ring $R^{1B}$ represent the same meaning as described above.

$E^{1'A}$, $E^{2'A}$, $E^{3'A}$ and $E^{4'A}$ each independently represent a nitrogen atom or a carbon atom. When a plurality of $E^{1'A}$, $E^{2'A}$, $E^{3'A}$ and $E^{4'A}$ are present, they may be the same or different at each occurrence. $R^{2A}$, $R^{3A}$ and $R^{4A}$ may be either present or not present when $E^{2'A}$, $E^{3'A}$ and $E^{4'A}$ are a nitrogen atom. One selected from the group consisting of $E^{1'A}$, $E^{2'A}$, $E^{3'A}$ and $E^{4'A}$ is a nitrogen atom, and the remaining three are a carbon atom.

The ring $R^{1'A}$ represents a diazole ring constituted of a nitrogen atom, $E^{1'A}$, $E^{2'A}$, $E^{3'A}$ and $E^{4'A}$.]

The ring $R^{1'A}$ is preferably an imidazole ring, because a light emitting device produced by using the first composition of the present invention is more excellent in external quantum efficiency.

In the ring $R^{1'A}$, it is preferable that $E^{2'A}$ or $E^{3'A}$ is a nitrogen atom, and it is more preferable that $E^{2'A}$ is a nitrogen atom.

When $E^{2'A}$ is a nitrogen atom and $R^{2A}$ is present, $R^{2A}$ is preferably an alkyl group, a cycloalkyl group, an aryl group or a monovalent heterocyclic group, more preferably an alkyl group or an aryl group, further preferably an aryl group, and these groups each optionally have a substituent.

When $E^{2'A}$ is a carbon atom, $R^{2A}$ is preferably a hydrogen atom, an alkyl group, a cycloalkyl group, an aryl group or a monovalent heterocyclic group, more preferably a hydrogen atom, an alkyl group or an aryl group, further preferably a hydrogen atom or an alkyl group, and these groups each optionally have a substituent.

When $E^{3'A}$ is a nitrogen atom and $R^{3A}$ is present, $R^{3A}$ is preferably an alkyl group, a cycloalkyl group, an aryl group or a monovalent heterocyclic group, more preferably an alkyl group or an aryl group, further preferably an aryl group, and these groups each optionally have a substituent.

When $E^{3'A}$ is a carbon atom, $R^{3A}$ is preferably a hydrogen atom, an alkyl group, a cycloalkyl group, an aryl group or a monovalent heterocyclic group, more preferably a hydrogen atom, an alkyl group or an aryl group, further preferably a hydrogen atom or an alkyl group, and these groups each optionally have a substituent.

When $E^{4'A}$ is a nitrogen atom and $R^{4A}$ is present, $R^{4A}$ is preferably an alkyl group, a cycloalkyl group, an aryl group or a monovalent heterocyclic group, more preferably an alkyl group or an aryl group, and these groups each optionally have a substituent.

When $E^{4'A}$ is a carbon atom, $R^{4A}$ is preferably a hydrogen atom, an alkyl group, a cycloalkyl group, an aryl group or a monovalent heterocyclic group, more preferably a hydrogen atom, an alkyl group or an aryl group, further preferably a hydrogen atom or an alkyl group, and these groups each optionally have a substituent.

The phosphorescent compound represented by the formula (1-A) is preferably a phosphorescent compound represented by the formula (1-A1) to (1-A4), more preferably a phosphorescent compound represented by the formula (1-A1) or the formula (1-A3), further preferably a phosphorescent compound represented by the formula (1-A1).

In the first composition of the present invention, the phosphorescent compound represented by the formula (1'-A) is preferably a phosphorescent compound represented by the formula (1-A3) or (1-A4), more preferably a phosphorescent compound represented by the formula (1-A3).

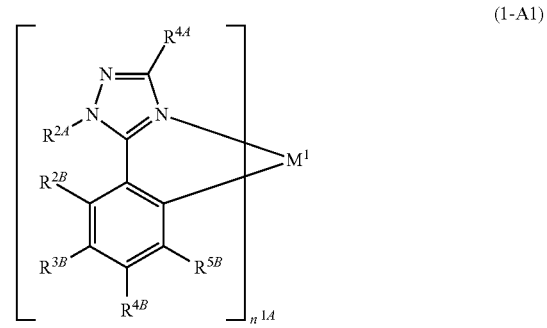

(1-A1)

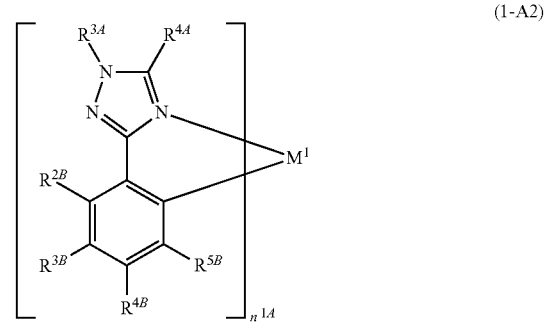

(1-A2)

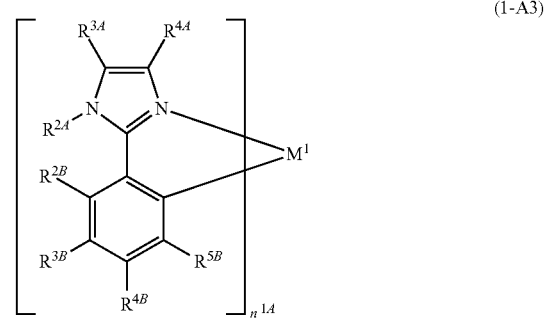

(1-A3)

-continued

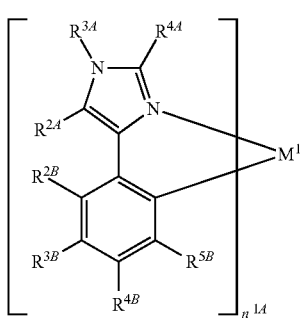

(1-A4)

[wherein, $M^1$, $R^{2A}$, $R^{3A}$, $R^{4A}$, $R^{2B}$, $R^{3B}$, $R^{4B}$ and $R^{5B}$ represent the same meaning as described above.

$n^{1A}$ represents an integer of 2 or 3, and $n^{1A}$ is 3 when $M^1$ is an iridium atom, while $n^{1A}$ is 2 when $M^1$ is a platinum atom.]

The phosphorescent compound represented by the formula (1-A1) includes, for example, phosphorescent compounds represented by the formulae (1-A1-1) to (1-A1-15), preferably phosphorescent compounds represented by the formulae (1-A1-1) to (1-A1-13).

TABLE 3

| formula | $M^1$ | $n^{1A}$ | $R^{2A}$ | $R^{4A}$ | $R^{2B}$ | $R^{3B}$ | $R^{4B}$ | $R^{5B}$ |
|---|---|---|---|---|---|---|---|---|
| (1-A1-1) | Ir | 3 | Me | $C_3H_7$ | H | H | H | H |
| (1-A1-2) | Ir | 3 | Me | $C_3H_7$ | H | H | F | H |
| (1-A1-3) | Ir | 3 | Me | $C_3H_7$ | H | H | $CF_3$ | H |
| (1-A1-4) | Ir | 3 | 2-Me-C$_6$H$_4$ | i-Pr | H | H | H | H |
| (1-A1-5) | Ir | 3 | 2,4-Me$_2$-C$_6$H$_3$ | $C_3H_7$ | H | H | H | H |
| (1-A1-6) | Ir | 3 | 2,3,5-Me$_3$-C$_6$H$_2$ | $C_3H_7$ | H | H | H | H |
| (1-A1-7) | Ir | 3 | 2,3,4,5,6-Me$_5$-C$_6$ | $C_3H_7$ | H | H | H | H |
| (1-A1-8) | Ir | 3 | 3,4,5-Me$_3$-biphenyl | $C_3H_7$ | H | H | H | H |
| (1-A1-9) | Ir | 3 | 3,5-(t-Bu)$_2$-C$_6$H$_3$ | $C_3H_7$ | H | H | H | H |

TABLE 3-continued

| formula | $M^1$ | $n^{1A}$ | $R^{2A}$ | $R^{4A}$ | $R^{2B}$ | $R^{3B}$ | $R^{4B}$ | $R^{5B}$ |
|---|---|---|---|---|---|---|---|---|
| (1-A1-10) | Ir | 3 | 4-C₆H₁₃-phenyl | Me | F | H | F | H |
| (1-A1-11) | Ir | 3 | Me | C₃H₇ | H | 4-t-Bu-phenyl | H | H |
| (1-A1-12) | Ir | 3 | Me | C₃H₇ | H | H | 4-C₆H₁₃-phenyl | H |
| (1-A1-13) | Ir | 3 | 4-C₆H₁₃-phenyl | C₃H₇ | H | 3,4,5-trimethylphenyl (Me, Me, Me) | H | H |
| (1-A1-14) | Pt | 2 | Me | C₃H₇ | H | H | H | H |
| (1-A1-15) | Pt | 2 | 3,4,5-trimethylphenyl (Me, Me, Me) | C₃H₇ | H | H | H | H |

The phosphorescent compound represented by the formula (1-A2) includes, for example, phosphorescent compounds represented by the formulae (1-A2-1) to (1-A2-15), preferably phosphorescent compounds represented by the formulae (1-A2-1) to (1-A2-13).

TABLE 4

| formula | $M^1$ | $n^{1A}$ | $R^{3A}$ | $R^{4A}$ | $R^{2B}$ | $R^{3B}$ | $R^{4B}$ | $R^{5B}$ |
|---|---|---|---|---|---|---|---|---|
| (1-A2-1) | Ir | 3 | Me | C₃H₇ | H | H | H | H |
| (1-A2-2) | Ir | 3 | Me | C₃H₇ | H | H | F | H |
| (1-A2-3) | Ir | 3 | Me | C₃H₇ | H | H | CF₃ | H |
| (1-A2-4) | Ir | 3 | 2-methylphenyl (Me) | i-Pr | H | H | H | H |
| (1-A2-5) | Ir | 3 | 3,4-dimethylphenyl (Me, Me) | C₃H₇ | H | H | H | H |
| (1-A2-6) | Ir | 3 | 3,4,5-trimethylphenyl (Me, Me, Me) | C₃H₇ | H | H | H | H |

TABLE 4-continued

| formula | M¹ | $n^{1A}$ | $R^{3A}$ | $R^{4A}$ | $R^{2B}$ | $R^{3B}$ | $R^{4B}$ | $R^{5B}$ |
|---|---|---|---|---|---|---|---|---|
| (1-A2-7) | Ir | 3 | pentamethylphenyl (Me,Me,Me,Me,Me) | $C_3H_7$ | H | H | H | H |
| (1-A2-8) | Ir | 3 | 3,4,5-trimethylbiphenyl (Me,Me,Me, with phenyl) | $C_3H_7$ | H | H | H | H |
| (1-A2-9) | Ir | 3 | 3,5-di-t-butylphenyl (t-Bu, t-Bu) | $C_3H_7$ | H | H | H | H |
| (1-A2-10) | Ir | 3 | 4-hexylphenyl ($C_6H_{13}$) | Me | F | H | F | H |
| (1-A2-11) | Ir | 3 | Me | $C_3H_7$ | H | 4-t-butylphenyl (t-Bu) | H | H |
| (1-A2-12) | Ir | 3 | Me | $C_3H_7$ | H | H | 4-hexylphenyl ($C_6H_{13}$) | H |
| (1-A2-13) | Ir | 3 | 4-hexylphenyl ($C_6H_{13}$) | $C_3H_7$ | H | 3,4,5-trimethylphenyl (Me,Me,Me) | H | H |
| (1-A2-14) | Pt | 2 | Me | $C_3H_7$ | H | H | H | H |
| (1-A2-15) | Pt | 2 | 3,4,5-trimethylphenyl (Me,Me,Me) | $C_3H_7$ | H | H | H | H |

The phosphorescent compound represented by the formula (1-A3) includes, for example, phosphorescent compounds represented by the formulae (1-A3-1) to (1-A3-19), preferably phosphorescent compounds represented by the formulae (1-A3-1) to (1-A3-17), more preferably phosphorescent compounds represented by the formulae (1-A3-5) to (1-A3-17).

TABLE 5

| formula | M¹ | $n^{1A}$ | $R^{2A}$ | $R^{3A}$ | $R^{4A}$ | $R^{2B}$ | $R^{3B}$ | $R^{4B}$ | $R^{5B}$ |
|---|---|---|---|---|---|---|---|---|---|
| (1-A3-1) | Ir | 3 | Me | H | H | H | H | H | H |
| (1-A3-2) | Ir | 3 | Me | H | H | H | H | F | H |

TABLE 5-continued

| formula | M¹ | n¹ᴬ | R²ᴬ | R³ᴬ | R⁴ᴬ | R²ᴮ | R³ᴮ | R⁴ᴮ | R⁵ᴮ |
|---|---|---|---|---|---|---|---|---|---|
| (1-A3-3) | Ir | 3 | Me | H | H | F | H | CF₃ | H |
| (1-A3-4) | Ir | 3 | Me | C₃H₇ | C₃H₇ | H | H | H | H |
| (1-A3-5) | Ir | 3 | 2-methylphenyl | H | H | H | H | H | H |
| (1-A3-6) | Ir | 3 | 2,5-dimethylphenyl | H | H | H | H | H | H |
| (1-A3-7) | Ir | 3 | 2,3,5-trimethylphenyl | Me | C₃H₇ | H | H | H | H |
| (1-A3-8) | Ir | 3 | 2,3-dimethyl-5-hexylphenyl | H | H | H | H | H | H |
| (1-A3-9) | Ir | 3 | 2,3-diisopropyl-5-hexylphenyl | H | H | H | H | H | H |
| (1-A3-10) | Ir | 3 | 3,5-di-t-butylphenyl | H | C₃H₇ | H | H | H | H |

TABLE 6

| formula | M¹ | n¹ᴬ | R²ᴬ | R³ᴬ | R⁴ᴬ | R²ᴮ | R³ᴮ | R⁴ᴮ | R⁵ᴮ |
|---|---|---|---|---|---|---|---|---|---|
| (1-A3-11) | Ir | 3 | pentamethylphenyl | i-Pr | H | H | H | H | H |

TABLE 6-continued

| formula | M¹ | n¹ᴬ | R²ᴬ | R³ᴬ | R⁴ᴬ | R²ᴮ | R³ᴮ | R⁴ᴮ | R⁵ᴮ |
|---|---|---|---|---|---|---|---|---|---|
| (1-A3-12) | Ir | 3 | 3,5-di(i-Pr)-4-methyl-biphenyl-yl | H | H | H | H | H | H |
| (1-A3-13) | Ir | 3 | 3,4,5-trimethyl-3',5'-dimethyl-biphenyl-yl | H | H | H | H | H | H |
| (1-A3-14) | Ir | 3 | 3,4,5-trimethyl-phenyl-C₆H₁₃ | H | H | H | H | Me | H |
| (1-A3-15) | Ir | 3 | 2,6-dimethylphenyl | H | H | H | H | F | H |
| (1-A3-16) | Ir | 3 | 3,4,5-trimethyl-phenyl-C₆H₁₃ | H | H | H | 4-t-Bu-phenyl | H | H |
| (1-A3-17) | Ir | 3 | 2,6-dimethylphenyl | C₃H₇ | C₃H₇ | H | H | 4-C₆H₁₃-phenyl | H |
| (1-A3-18) | Pt | 2 | Me | H | H | H | H | H | H |

TABLE 6-continued

| formula | $M^1$ | $n^{1A}$ | $R^{2A}$ | $R^{3A}$ | $R^{4A}$ | $R^{2B}$ | $R^{3B}$ | $R^{4B}$ | $R^{5B}$ |
|---|---|---|---|---|---|---|---|---|---|
| (1-A3-19) | Pt | 2 | 3,4,5-trimethylphenyl-C6H13 | H | H | H | H | H | H |

The phosphorescent compound represented by the formula (1-A4) includes, for example, phosphorescent compounds represented by the formulae (1-A4-1) to (1-A4-19), preferably phosphorescent compounds represented by the formulae (1-A4-1) to (1-A4-17), more preferably phosphorescent compounds represented by the formulae (1-A4-5) to (1-A4-17).

TABLE 7

| formula | $M^1$ | $n^{1A}$ | $R^{2A}$ | $R^{3A}$ | $R^{4A}$ | $R^{2B}$ | $R^{3B}$ | $R^{4B}$ | $R^{5B}$ |
|---|---|---|---|---|---|---|---|---|---|
| (1-A4-1) | Ir | 3 | Me | H | H | H | H | H | H |
| (1-A4-2) | Ir | 3 | Me | H | H | H | H | F | H |
| (1-A4-3) | Ir | 3 | Me | H | H | F | H | $CF_3$ | H |
| (1-A4-4) | Ir | 3 | Me | $C_3H_7$ | $C_3H_7$ | H | H | H | H |
| (1-A4-5) | Ir | 3 | 2-methylphenyl | H | H | H | H | H | H |
| (1-A4-6) | Ir | 3 | 3,4-dimethylphenyl | H | H | H | H | H | H |
| (1-A4-7) | Ir | 3 | 3,4,5-trimethylphenyl | Me | $C_3H_7$ | H | H | H | H |
| (1-A4-8) | Ir | 3 | 3,5-dimethyl-4-C6H13-phenyl | H | H | H | H | H | H |
| (1-A4-9) | Ir | 3 | 3,5-di-i-Pr-4-C6H13-phenyl | H | H | H | H | H | H |

TABLE 7-continued

| formula | M¹ | n¹ᴬ | R²ᴬ | R³ᴬ | R⁴ᴬ | R²ᴮ | R³ᴮ | R⁴ᴮ | R⁵ᴮ |
|---|---|---|---|---|---|---|---|---|---|
| (1-A4-10) | Ir | 3 | 3,5-di-t-Bu-phenyl | H | C₃H₇ | H | H | H | H |

TABLE 8

| formula | M¹ | n¹ᴬ | R²ᴬ | R³ᴬ | R⁴ᴬ | R²ᴮ | R³ᴮ | R⁴ᴮ | R⁵ᴮ |
|---|---|---|---|---|---|---|---|---|---|
| (1-A4-11) | Ir | 3 | pentamethylphenyl (2,3,4,5,6-Me₅) | i-Pr | H | H | H | H | H |
| (1-A4-12) | Ir | 3 | 3,5-di-i-Pr-4-Me-biphenyl-yl | H | H | H | H | H | H |
| (1-A4-13) | Ir | 3 | 3,4,5-tri-Me-3',5'-di-Me-biphenyl-yl | H | H | H | H | H | H |
| (1-A4-14) | Ir | 3 | 3,4,5-tri-Me-phenyl with C₆H₁₃ | H | H | H | H | Me | H |
| (1-A4-15) | Ir | 3 | 2,3-di-Me-phenyl | H | H | H | H | F | H |
| (1-A4-16) | Ir | 3 | 3,4,5-tri-Me-phenyl with C₆H₁₃ | H | H | H | 4-t-Bu-phenyl | H | H |
| (1-A4-17) | Ir | 3 | 2,3-di-Me-phenyl | C₃H₇ | C₃H₇ | H | H | 4-C₆H₁₃-phenyl | H |

TABLE 8-continued

| formula | $M^1$ | $n^{1A}$ | $R^{2A}$ | $R^{3A}$ | $R^{4A}$ | $R^{2B}$ | $R^{3B}$ | $R^{4B}$ | $R^{5B}$ |
|---|---|---|---|---|---|---|---|---|---|
| (1-A4-18) | Pt | 2 | Me | H | H | H | H | H | H |
| (1-A4-19) | Pt | 2 | (Me,Me,Me-C6H3-C6H13) | H | H | H | H | H | H |

The phosphorescent compound (B) includes, for example, phosphorescent compounds represented by the formulae (1-A1-1) to (1-A1-15), the formulae (1-A2-1) to (1-A2-15), the formulae (1-A3-1) to (1-A3-19), the formulae (1-A4-1) to (1-A4-19) and the formulae (1-A-1) to (1-A-11), preferably phosphorescent compounds represented by the formulae (1-A1-1) to (1-A1-13), the formulae (1-A2-1) to (1-A2-13), the formulae (1-A3-1) to (1-A3-17) or the formulae (1-A4-1) to (1-A4-17), more preferably phosphorescent compounds represented by the formulae (1-A1-1) to (1-A1-13) or the formulae (1-A3-1) to (1-A3-17).

In the first composition of the present invention, the phosphorescent compound (B) is preferably a phosphorescent compound represented by the formula (1-A3-1) to (1-A3-17) or the formula (1-A4-1) to (1-A4-17), more preferably a phosphorescent compound represented by the formula (1-A3-1) to (1-A3-17).

(1-A-1)

(1-A-2)

(1-A-3)

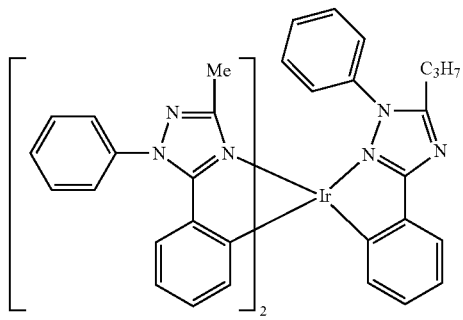
(1-A-4)

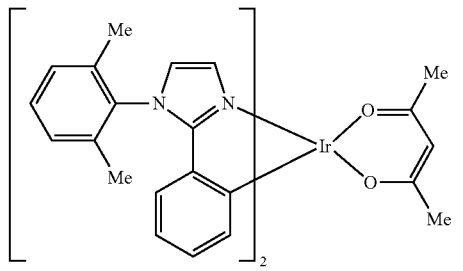
(1-A-5)

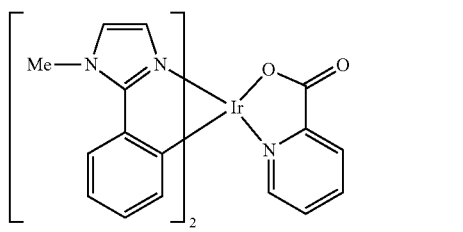
(1-A-6)

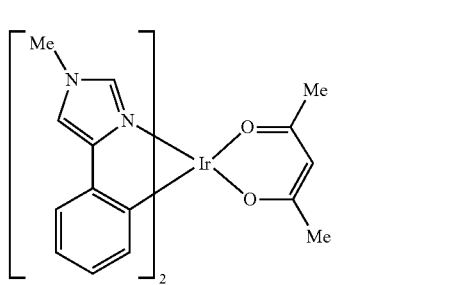
(1-A-7)

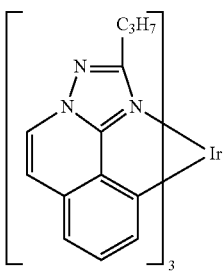
(1-A-8)

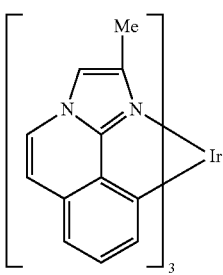
(1-A-9)

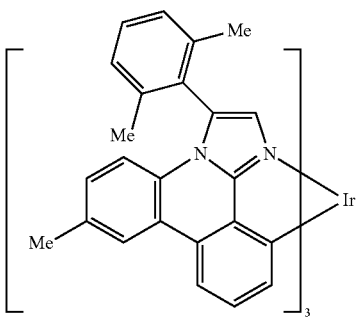
(1-A-10)

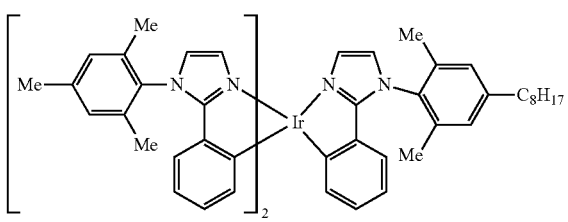
(1-A-11)

<Phosphorescent Compound (DGR)>

The two or more phosphorescent compounds (DGR) contained in the first composition and the second composition of the present invention are a phosphorescent compound having an emission spectrum, the maximum peak wavelength of which is between 495 nm or more and less than 750 nm and having a dendron, and represented by the formula (2).

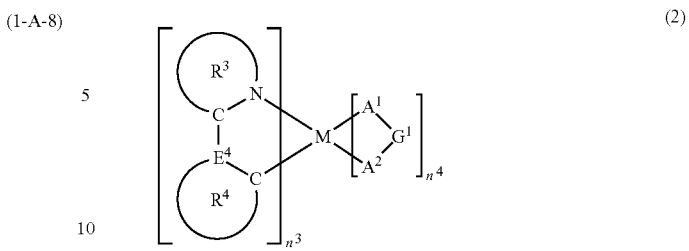
(2)

$E^4$ is preferably a carbon atom.

$n^3$ is preferably 2 or 3, more preferably 3 when M is a ruthenium atom, a rhodium atom or an iridium atom.

$n^3$ is preferably 2 when M is a palladium atom or a platinum atom.

The ring $R^3$ is a 6-membered aromatic heterocyclic ring, and substituents carried on this ring may be combined together to form a ring together with the atoms to which they are attached. The ring $R^3$ is preferably a 6-membered aromatic heterocyclic ring having 1 to 4 nitrogen atoms as a constitutional atom, more preferably a 6-membered aromatic heterocyclic ring having 1 to 2 nitrogen atoms as a constitutional atom, further preferably a pyridine ring, a diazabenzene ring, a quinoline ring or an isoquinoline ring, particularly preferably a pyridine ring, a quinoline ring or an isoquinoline ring, and these rings each optionally have a substituent.

The ring $R^4$ is a 5-membered or 6-membered aromatic hydrocarbon ring or a 5-membered or 6-membered aromatic heterocyclic ring, and substituents carried on these rings may be combined together to form a ring together with the atoms to which they are attached. The ring $R^4$ is preferably a benzene ring, a naphthalene ring, a fluorene ring, a phenanthrene ring, a pyridine ring, a diazabenzene ring, a pyrrole ring, a furan ring or a thiophene ring, more preferably a benzene ring, a naphthalene ring or a fluorene ring, further preferably a benzene ring, and these rings each optionally have a substituent.

"At least one ring selected from the group consisting of the ring $R^3$ and the ring $R^4$ has a dendron" means that a part or all of hydrogen atoms directly bonded to carbon atoms or hetero atoms constituting at least one ring among the plurality of rings present are substituted with a dendron. For example, when a plurality of the rings $R^3$ and the rings $R^4$ in the formula (2) are present (namely, $n^3$ is 2 or 3), it is permissible that at least one ring among the plurality of the rings $R^3$ and the plurality of the rings $R^4$ has a dendron.

The number of the dendron which at least one ring among the rings $R^3$ and the rings $R^4$ has is usually 1 to 5, and is preferably 1 to 3, more preferably 1 or 2, further preferably 1, because synthesis of a phosphorescent compound is easy.

When the dendron which at least one ring among the rings $R^3$ and the rings $R^4$ has is a group represented by the formula (D-A) or (D-B) and $m^{DA1}$ is an integer of 1 or more, $Ar^{DA1}$ bonded to the ring $R^3$ and/or the ring $R^4$ is preferably a phenylene group optionally having a substituent, more preferably a group represented by the formula (ArDA-1).

When the dendron which at least one ring among the rings $R^3$ and the rings $R^4$ has is a group represented by the formula (D-A) or (D-B) and $m^{DA1}$ is 0, $G^{DA1}$ bonded to the ring $R^3$ and/or the ring $R^4$ is preferably a group obtained by removing from a benzene ring or a triazine ring optionally having a substituent three hydrogen atoms bonded directly to carbon atoms constituting the ring, more preferably a group represented by the formula (GDA-11) or (GDA-14).

The dendron which at least one ring among the rings $R^3$ and the rings $R^4$ has is preferably a group represented by the formula (D-A1), (D-A3), (D-B1) or (D-B3), more preferably a group represented by the formula (D-A1) or (D-A3).

When M is a ruthenium atom, a rhodium atom or an iridium atom, the number of the dendron which a phosphorescent compound represented by the formula (2) has is usually 1 to 15, and is preferably 1 to 9, more preferably 2 to 6, because synthesis of a phosphorescent compound represented by the formula (2) is easy.

When M is a palladium atom or a platinum atom, the number of the dendron which a phosphorescent compound represented by the formula (2) has is usually 1 to 9, and is preferably 1 to 6, more preferably 2 to 4, because synthesis of a phosphorescent compound represented by the formula (2) is easy.

The substituent which the ring $R^3$ and the ring $R^4$ optionally have is preferably an alkyl group, a cycloalkyl group, an aryl group, a monovalent heterocyclic group, an alkoxy group, a cycloalkoxy group, an aryloxy group or a dendron, more preferably an alkyl group, a cycloalkyl group, an aryl group, a monovalent heterocyclic group or a dendron, further preferably an alkyl group, an aryl group or a dendron, and these groups each optionally further have a substituent. When a plurality of the substituents which the ring $R^3$ and the ring $R^4$ optionally have are present, they may be the same or different and may be combined together to form a ring together with the atoms to which they are attached.

The definition and examples of the anionic bidentate ligand represented by $A^1$-$G^1$-$A^2$ in the formula (2) are the same as the definition and examples of the anionic bidentate ligand represented by $A^1$-$G^1$-$A^2$ in the phosphorescent compound represented by the formula (1) described above. The anionic bidentate ligand represented by $A^1$-$G^1$-$A^2$ is different from the ligand of which number is defined by a subscript $n^3$.

The phosphorescent compound represented by the formula (2) is preferably a phosphorescent compound represented by the formula (2-A1) to (2-A5), more preferably a phosphorescent compound represented by the formula (2-A1), (2-A2) or (2-A5).

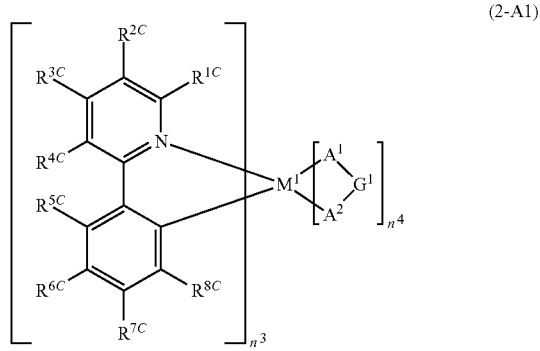

(2-A1)

[wherein, $M^1$, $A^1$-$G^1$-$A^2$, $n^3$ and $n^4$ represent the same meaning as described above.

$R^{1C}$, $R^{2C}$, $R^{3C}$, $R^{4C}$, $R^{5C}$, $R^{6C}$, $R^{7C}$ and $R^{8C}$ each independently represent a hydrogen atom, an alkyl group, a cycloalkyl group, an alkoxy group, a cycloalkoxy group, an aryl group, an aryloxy group, a monovalent heterocyclic group, a halogen atom or a dendron, and these groups each optionally have a substituent. When a plurality of $R^{1C}$, $R^{2C}$, $R^{3C}$, $R^{4C}$, $R^{5C}$, $R^{6C}$, $R^{7C}$ and $R^{8C}$ are present, they may be the same or different at each occurrence. $R^{1C}$ and $R^{2C}$, $R^{2C}$ and $R^{3C}$, $R^{3C}$ and $R^{4C}$, $R^{4C}$ and $R^{5C}$, $R^{5C}$ and $R^{6C}$, $R^{6C}$ and $R^{7C}$, and $R^{7C}$ and $R^{8C}$ each may be combined together to form a ring together with the carbon atoms to which they are attached.

At least one selected from the group consisting of $R^{1C}$, $R^{2C}$, $R^{3C}$, $R^{4C}$, $R^{5C}$, $R^{6C}$, $R^{7C}$ and $R^{8C}$ is a dendron.]

$R^{1C}$, $R^{2C}$, $R^{3C}$, $R^{4C}$, $R^{5C}$, $R^{6C}$, $R^{7C}$ and $R^{8C}$ are preferably a hydrogen atom, an alkyl group, a cycloalkyl group, an alkoxy group, a cycloalkoxy group, an aryl group, a monovalent heterocyclic group or a dendron, more preferably a hydrogen atom, an alkyl group, an aryl group, a monovalent heterocyclic group or a dendron, and these groups each optionally have a substituent.

At least one selected from the group consisting of $R^{1C}$, $R^{2C}$, $R^{3C}$, $R^{4C}$, $R^{5C}$, $R^{6C}$, $R^{7C}$ and $R^{8C}$ is a dendron, and when a plurality of $R^{1C}$, $R^{2C}$, $R^{3C}$, $R^{4C}$, $R^{5C}$, $R^{6C}$, $R^{7C}$ and $R^{8C}$ are present (namely, $n^3$ is 2 or 3), it is permissible that at least one of a plurality of $R^{1C}$, $R^{2C}$, $R^{3C}$, $R^{4C}$, $R^{5C}$, $R^{6C}$, $R^{7C}$ and $R^{8C}$ is a dendron.

The dendron is preferably a group represented by the formula (D-A1), (D-A3), (D-B1) or (D-B3), more preferably a group represented by the formula (D-A1) or (D-A3).

$R^{1C}$, $R^{4C}$, $R^{5C}$ and $R^{8C}$ are preferably a hydrogen atom, an alkyl group, a cycloalkyl group, an aryl group, a monovalent heterocyclic group, an alkoxy group or a cycloalkoxy group, more preferably a hydrogen atom, an alkyl group or an aryl group, further preferably a hydrogen atom or an alkyl group, particularly preferably a hydrogen atom, and these groups each optionally have a substituent.

$R^{2C}$, $R^{3C}$, $R^{6C}$ and $R^{7C}$ are preferably a hydrogen atom, an alkyl group, a cycloalkyl group, an aryl group, a monovalent heterocyclic group, an alkoxy group, a cycloalkoxy group or a dendron, more preferably a hydrogen atom, an alkyl group, an aryl group, a monovalent heterocyclic group or a dendron, further preferably a hydrogen atom or a dendron, and these groups each optionally have a substituent.

It is preferable that at least one selected from the group consisting of $R^{2C}$, $R^{3C}$, $R^{6C}$ and $R^{7C}$ is a dendron, and it is more preferable that $R^{2C}$ or $R^{6C}$ is a dendron.

The phosphorescent compound represented by the formula (2-A1) includes, for example, phosphorescent compounds represented by the formula (2-A1-1) to the formula (2-A1-27).

TABLE 9

| formula | $M^1$ | $n^3$ | $R^{1C}$, $R^{4C}$, $R^{5C}$, $R^{8C}$ | $R^{2C}$ | $R^{3C}$ | $R^{6C}$ | $R^{7C}$ | $n^4$ | $A^1$—$G^1$—$A^2$ |
|---|---|---|---|---|---|---|---|---|---|
| (2-A1-1) | Ir | 3 | H | H | H | formula (D-A-8) | H | 0 | — |
| (2-A1-2) | Ir | 3 | H | H | H | H | formula (D-A-8) | 0 | — |
| (2-A1-3) | Ir | 3 | H | H | H | formula (D-A-1) | H | 0 | — |

TABLE 9-continued

| formula | M¹ | n³ | R¹ᶜ, R⁴ᶜ, R⁵ᶜ, R⁸ᶜ | R²ᶜ | R³ᶜ | R⁶ᶜ | R⁷ᶜ | n⁴ | A¹—G¹—A² |
|---|---|---|---|---|---|---|---|---|---|
| (2-A1-4) | Ir | 3 | H | H | H | H | formula (D-A-1) | 0 | — |
| (2-A1-5) | Ir | 3 | H | formula (D-A-1) | H | H | H | 0 | — |
| (2-A1-6) | Ir | 3 | H | H | formula (D-A-1) | H | H | 0 | — |
| (2-A1-7) | Ir | 3 | H | formula (D-A-12) | H | H | H | 0 | — |
| (2-A1-8) | Ir | 3 | H | formula (D-A-14) | H | H | H | 0 | — |
| (2-A1-9) | Ir | 3 | H | H | formula (D-A-14) | H | H | 0 | — |
| (2-A1-10) | Ir | 3 | H | formula (D-A-14) | H | H | 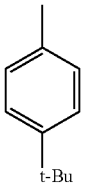 | 0 | — |
| (2-A1-11) | Ir | 3 | H | formula (D-A-14) | H | formula (D-A-1) | H | 0 | — |

TABLE 10

| formula | M¹ | n³ | R¹ᶜ, R⁴ᶜ, R⁵ᶜ, R⁸ᶜ | R²ᶜ | R³ᶜ | R⁶ᶜ | R⁷ᶜ | n⁴ | A¹-G¹-A² |
|---|---|---|---|---|---|---|---|---|---|
| (2-A1-12) | Ir | 3 | H | formula (D-A-14) | H | H | formula (D-A-1) | 0 | — |
| (2-A1-13) | Ir | 3 | H | formula (D-A-14) | H | formula (D-A-9) | H | 0 | — |
| (2-A1-14) | Ir | 3 | H | H | formula (D-A-9) | H | formula (D-A-8) | 0 | — |
| (2-A1-15) | Ir | 3 | H | H | H | formula (D-A-19) | H | 0 | — |
| (2-A1-16) | Ir | 3 | H | H | H | formula (D-B-1) | H | 0 | — |
| (2-A1-17) | Ir | 3 | H | formula (D-B-1) | H | H | H | 0 | — |
| (2-A1-18) | Ir | 3 | H | formula (D-B-4) | H | H | H | 0 | — |
| (2-A1-19) | Ir | 3 | H | formula (D-B-4) | H | formula (D-B-6) | H | 0 | — |
| (2-A1-20) | Pt | 2 | H | H | H | formula (D-A-1) | H | 0 | — |
| (2-A1-21) | Pt | 2 | H | formula (D-A-1) | H | H | H | 0 | — |
| (2-A1-22) | Pt | 2 | H | formula (D-A-14) | H | H | H | 0 | — |
| (2-A1-23) | Pt | 2 | H | formula (D-A-14) | H | formula (D-A-9) | H | 0 | — |

TABLE 11

| formula | M¹ | n³ | R¹ᶜ, R⁴ᶜ, R⁵ᶜ, R⁸ᶜ | R²ᶜ | R³ᶜ | R⁶ᶜ | R⁷ᶜ | n⁴ | A¹—G¹—A² |
|---|---|---|---|---|---|---|---|---|---|
| (2-A1-24) | Ir | 2 | H | H | H | formula (D-A-1) | H | 1 | 2-methylphenyl-(N-methylpyridinium) with t-Bu |
| (2-A1-25) | Ir | 2 | H | H | H | formula (D-A-1) | H | 1 | N-methylpyridinium-methylphenyl-phenyl-t-Bu |
| (2-A1-26) | Ir | 2 | H | H | H | formula (D-A-1) | H | 1 | N-methylisoquinolinium-methylphenyl-phenyl-t-Bu |
| (2-A1-27) | Ir | 2 | H | formula (D-A-14) | H | H | H | 1 | N-methylisoquinolinium-methylphenyl |

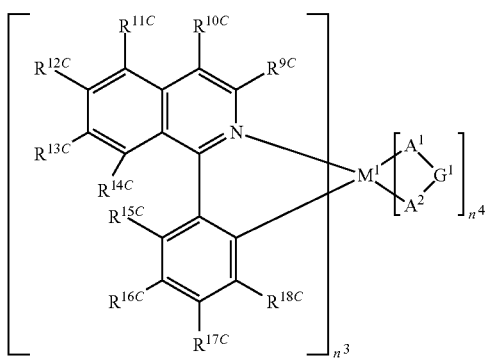

(2-A2)

[wherein, $M^1$, $A^1$-$G^1$-$A^2$, $n^3$ and $n^4$ represent the same meaning as described above.

$R^{3C}$, $R^{10C}$, $R^{11C}$, $R^{12C}$, $R^{13C}$, $R^{14C}$, $R^{15C}$, $R^{16C}$, $R^{17C}$ and $R^{18C}$ each independently represent a hydrogen atom, an alkyl group, a cycloalkyl group, an alkoxy group, a cycloalkoxy group, an aryl group, an aryloxy group, a monovalent heterocyclic group, a halogen atom, or a dendron, and these groups each optionally have a substituent. When a plurality of $R^{9C}$, $R^{10C}$, $R^{11C}$, $R^{12C}$, $R^{13C}$, $R^{14C}$, $R^{15C}$, $R^{16C}$, $R^{17C}$ and $R^{18C}$ are present, they may be the same or different at each occurrence. $R^{9C}$ and $R^{10C}$, $R^{10C}$ and $R^{11C}$, $R^{11C}$ and $R^{12C}$, $R^{12C}$ and $R^{13C}$, $R^{13C}$ and $R^{14C}$, $R^{14C}$ and $R^{15C}$, $R^{15C}$ and $R^{16C}$, $R^{16C}$ and $R^{17C}$, and $R^{17C}$ and $R^{18C}$ each may be combined together to form a ring together with the carbon atoms to which they are attached.

At least one selected from the group consisting of $R^{9C}$, $R^{10C}$, $R^{11C}$, $R^{12C}$, $R^{13C}$, $R^{14C}$, $R^{15C}$, $R^{16C}$, $R^{17C}$ and $R^{18C}$ is a dendron.]

$R^{9C}$, $R^{10C}$, $R^{11C}$, $R^{12C}$, $R^{13C}$, $R^{14C}$, $R^{15C}$, $R^{16C}$, $R^{17C}$ and $R^{18C}$ are preferably a hydrogen atom, an alkyl group, a cycloalkyl group, an alkoxy group, a cycloalkoxy group, an aryl group, a monovalent heterocyclic group or a dendron, more preferably a hydrogen atom, an alkyl group, an aryl group, a monovalent heterocyclic group or a dendron, and these groups each optionally have a substituent.

At least one selected from the group consisting of $R^{9C}$, $R^{10C}$, $R^{11C}$, $R^{12C}$, $R^{13C}$, $R^{14C}$, $R^{15C}$, $R^{16C}$, $R^{17C}$ and $R^{18C}$ is a dendron, and when a plurality of $R^{9C}$, $R^{10C}$, $R^{11C}$, $R^{12C}$, $R^{13C}$, $R^{14C}$, $R^{15C}$, $R^{16C}$, $R^{17C}$ and $R^{18C}$ are present (namely, $n^3$ is 2 or 3), it is permissible that at least one of a plurality of $R^{9C}$, $R^{10C}$, $R^{11C}$, $R^{12C}$, $R^{13C}$, $R^{14C}$, $R^{15C}$, $R^{16C}$, $R^{17C}$ and $R^{18C}$ is a dendron.

The dendron is preferably a group represented by the formula (D-A1), (D-A3), (D-B1) or (D-B3), more preferably a group represented by the formula (D-A1) or (D-B1), further preferably a group represented by the formula (D-A1).

$R^{9C}$, $R^{14C}$, $R^{15C}$ and $R^{18C}$ are preferably a hydrogen atom, an alkyl group, a cycloalkyl group, an aryl group, a monovalent heterocyclic group, an alkoxy group or a cycloalkoxy group, more preferably a hydrogen atom, an alkyl group or an aryl group, further preferably a hydrogen atom or an alkyl group, particularly preferably a hydrogen atom, and these groups each optionally have a substituent.

$R^{C11}$ to $R^{13C}$ are preferably a hydrogen atom, an alkyl group, a cycloalkyl group, an aryl group, a monovalent heterocyclic group, an alkoxy group, a cycloalkoxy group or a dendron, more preferably a hydrogen atom, an alkyl group, an aryl group, a monovalent heterocyclic group or a dendron, further preferably a hydrogen atom or an alkyl group, particularly preferably a hydrogen atom, and these groups each optionally have a substituent.

$R^{10C}$, $R^{16C}$ and $R^{17C}$ are preferably a hydrogen atom, an alkyl group, a cycloalkyl group, an aryl group, a monovalent heterocyclic group, an alkoxy group, a cycloalkoxy group or a dendron, more preferably a hydrogen atom, an alkyl group, an aryl group, a monovalent heterocyclic group or a dendron, further preferably a hydrogen atom or a dendron, and these groups each optionally have a substituent.

It is preferable that at least one selected from the group consisting of $R^{10C}$ to $R^{13C}$, $R^{16C}$ and $R^{17C}$ is a dendron, it is more preferable that $R^{16C}$ or $R^{17C}$ is a dendron, and it is further preferable that $R^{16C}$ is a dendron.

The phosphorescent compound represented by the formula (2-A2) includes, for example, phosphorescent compounds represented by the formula (2-A2-1) to the formula (2-A2-8).

TABLE 12

| formula | $M^1$ | $n^3$ | $R^{9C}$ to $R^{15C}$ | $R^{16C}$ | $R^{17C}$ | $R^{18C}$ | $n^4$ | $A^1$—$G^1$—$A^2$ |
|---|---|---|---|---|---|---|---|---|
| (2-A2-1) | Ir | 3 | H | formula (D-A-8) | H | H | 0 | — |
| (2-A2-2) | Ir | 3 | H | H | formula (D-A-8) | H | 0 | — |
| (2-A2-3) | Ir | 3 | H | formula (D-A-1) | H | H | 0 | — |
| (2-A2-4) | Ir | 3 | H | H | formula (D-A-1) | H | 0 | — |
| (2-A2-5) | Ir | 3 | H | formula (D-B-1) | H | H | 0 | — |

TABLE 12-continued

| formula | M¹ | n³ | $R^{9C}$ to $R^{15C}$ | $R^{16C}$ | $R^{17C}$ | $R^{18C}$ | n⁴ | A¹—G¹—A² |
|---|---|---|---|---|---|---|---|---|
| (2-A2-6) | Ir | 2 | H | formula (D-A-1) | H | H | 1 | 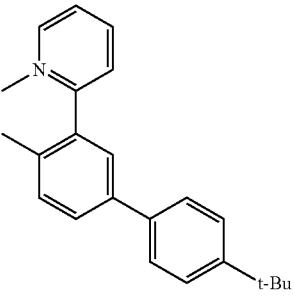 |
| (2-A2-7) | Ir | 1 | H | formula (D-A-1) | H | H | 2 | 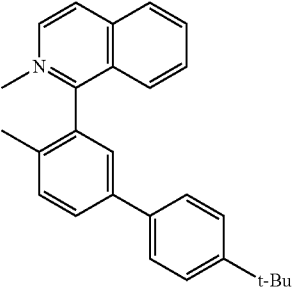 |
| (2-A2-8) | Pt | 2 | H | formula (D-A-1) | H | H | 0 | — |

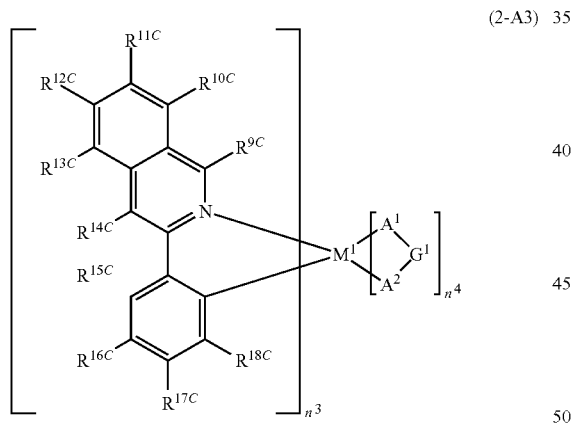

(2-A3)

[wherein, M¹, A¹-G¹-A², n³, n⁴, $R^{9C}$, $R^{10C}$, $R^{11C}$, $R^{12C}$, $R^{13C}$, $R^{14C}$, $R^{15C}$, $R^{16C}$, $R^{17C}$ and $R^{18C}$ represent the same meaning as described above.]

The phosphorescent compound represented by the formula (2-A3) includes, for example, phosphorescent compounds represented by the formula (2-A3-1) to the formula (2-A3-8).

TABLE 13

| formula | M¹ | n³ | $R^{9C}$ to $R^{15C}$ | $R^{16C}$ | $R^{17C}$ | $R^{18C}$ | n⁴ | A¹—G¹—A² |
|---|---|---|---|---|---|---|---|---|
| (2-A3-1) | Ir | 3 | H | formula (D-A-8) | H | H | 0 | — |

TABLE 13-continued

| formula | $M^1$ | $n^3$ | $R^{9C}$ to $R^{15C}$ | $R^{16C}$ | $R^{17C}$ | $R^{18C}$ | $n^4$ | $A^1$—$G^1$—$A^2$ |
|---|---|---|---|---|---|---|---|---|
| (2-A3-2) | Ir | 3 | H | H | formula (D-A-8) | H | 0 | — |
| (2-A3-3) | Ir | 3 | H | formula (D-A-1) | H | H | 0 | — |
| (2-A3-4) | Ir | 3 | H | H | formula (D-A-1) | H | 0 | — |
| (2-A3-5) | Ir | 3 | H | formula (D-B-1) | H | H | 0 | — |
| (2-A3-6) | Ir | 2 | H | formula (D-A-1) | H | H | 1 | (structure with pyridine, methyl, biphenyl-t-Bu) |
| (2-A3-7) | Ir | 1 | H | formula (D-A-1) | H | H | 2 | 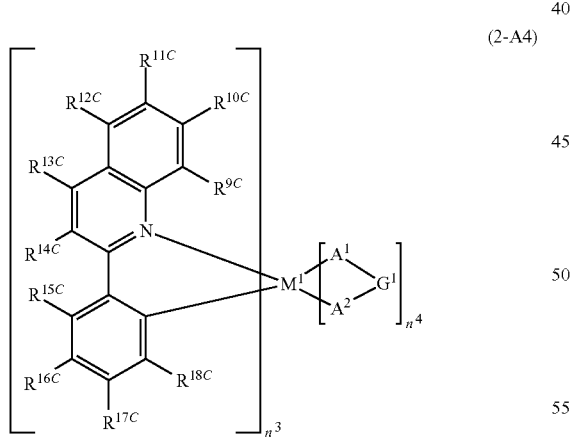 |
| (2-A3-8) | Pt | 2 | H | formula (D-A-1) | H | H | 0 | — |

(2-A4)

[wherein, $M^1$, $A^1$-$G^1$-$A^2$, $n^3$, $n^4$, $R^{9C}$, $R^{10C}$, $R^{11C}$, $R^{12C}$, $R^{13C}$, $R^{14C}$, $R^{15C}$, $R^{16C}$, $R^{17C}$ and $R^{18C}$ represent the same meaning as described above.]

The phosphorescent compound represented by the formula (2-A4) includes, for example, phosphorescent compounds represented by the formula (2-A4-1) to the formula (2-A4-8).

TABLE 14

| formula | $M^1$ | $n^3$ | $R^{9C}$ to $R^{15C}$ | $R^{16C}$ | $R^{17C}$ | $R^{18C}$ | $n^4$ | $A^1$—$G^1$—$A^2$ |
|---|---|---|---|---|---|---|---|---|
| (2-A4-1) | Ir | 3 | H | formula (D-A-8) | H | H | 0 | — |
| (2-A4-2) | Ir | 3 | H | H | formula (D-A-8) | H | 0 | — |
| (2-A4-3) | Ir | 3 | H | formula (D-A-1) | H | H | 0 | — |
| (2-A4-4) | Ir | 3 | H | H | formula (D-A-1) | H | 0 | — |
| (2-A4-5) | Ir | 3 | H | formula (D-B-1) | H | H | 0 | — |
| (2-A4-6) | Ir | 2 | H | formula (D-A-1) | H | H | 1 | 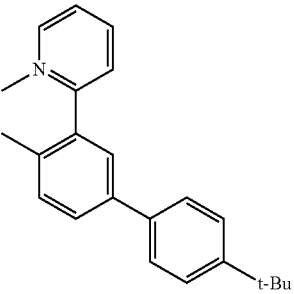 |
| (2-A4-7) | Ir | 1 | H | formula (D-A-1) | H | H | 2 | 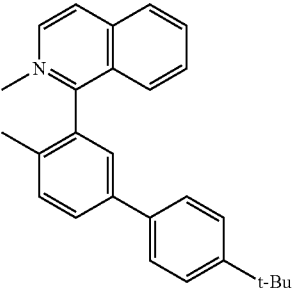 |
| (2-A4-8) | Pt | 2 | H | formula (D-A-1) | H | H | 0 | — |

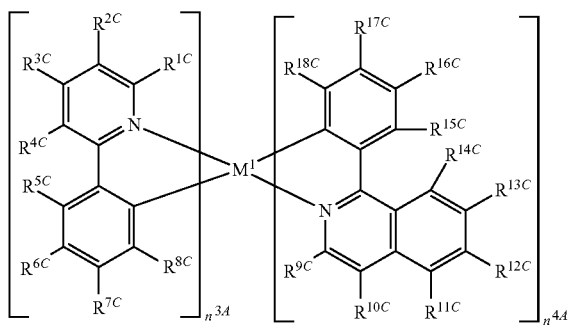

(2-A5)

[wherein, $M^1$, $A^1$-$G^1$-$A^2$, $R^{1C}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, $R^{12C}$, $R^{13C}$, $R^{14C}$, $R^{15C}$, $R^{16C}$, $R^{17C}$ and $R^{18C}$ represent the same meaning as described above.

$n^{3A}$ and $n^{4A}$ each independently represent an integer of 1 or more, and $n^{3A}+n^{4A}$ is 2 or 3. $n^{3A}+n^{4A}$ is 3 when $M^1$ is an iridium atom, while $n^{3A}+n^{4A}$ is 2 when $M^1$ is a platinum atom.]

The phosphorescent compound represented by the formula (2-A5) includes, for example, phosphorescent compounds represented by the formula (2-A5-1) to the formula (2-A5-10). In the formulae (2-A5-1) to (2-A5-10), $R^{1C}$, $R^{4C}$, $R^{5C}$, $R^{8C}$ to $R^{15C}$ and $R^{18C}$ in the formula (2-A5) represent a hydrogen atom.

TABLE 15

| formula | $M^1$ | $n^{3A}$ | $R^{2C}$ | $R^{3C}$ | $R^{6C}$ | $R^{7C}$ | $n^{3B}$ | $R^{16C}$ | $R^{17C}$ |
|---|---|---|---|---|---|---|---|---|---|
| (2-A5-1) | Ir | 2 | formula (D-A-14) | H | H | H | 1 | formula (D-A-1) | H |
| (2-A5-2) | Ir | 2 | H | formula (D-A-14) | H | H | 1 | H | formula (D-A-1) |

TABLE 15-continued

| formula | $M^1$ | $n^{3A}$ | $R^{2C}$ | $R^{3C}$ | $R^{6C}$ | $R^{7C}$ | $n^{3B}$ | $R^{16C}$ | $R^{17C}$ |
|---|---|---|---|---|---|---|---|---|---|
| (2-A5-3) | Ir | 2 | formula (D-A-14) | H | formula (D-A-1) | H | 1 | formula (D-A-1) | H |
| (2-A5-4) | Ir | 2 | H | formula (D-A-14) | H | formula (D-A-1) | 1 | formula (D-A-1) | H |
| (2-A5-5) | Ir | 2 | formula (D-A-14) | H | formula (D-A-9) | H | 1 | formula (D-A-1) | H |
| (2-A5-6) | Ir | 1 | formula (D-A-1) | H | H | H | 2 | formula (D-A-1) | H |
| (2-A5-7) | Ir | 2 | H | formula (D-A-1) | H | H | 1 | H | formula (D-A-1) |
| (2-A5-8) | Ir | 1 | formula (D-A-14) | H | H | H | 2 | formula (D-A-1) | H |
| (2-A5-9) | Pt | 2 | formula (D-A-14) | H | H | H | 1 | formula (D-A-1) | H |
| (2-A5-10) | Pt | 2 | formula (D-A-14) | H | formula (D-A-9) | H | 1 | formula (D-A-1) | H |

<Compound Represented by the Formula (H-1)>

The compound contained in the first composition of the present invention is a compound represented by the formula (H-1) (hereinafter, referred to also as "compound of the first composition".).

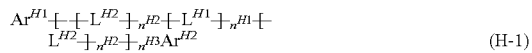
(H-1)

$Ar^{H1}$ and $Ar^{H2}$ are preferably a phenyl group, a fluorenyl group, a spirobifluorenyl group, a pyridyl group, a pyrimidinyl group, a triazinyl group, a quinolinyl group, an isoquinolinyl group, a thienyl group, a benzothienyl group, a dibenzothienyl group, a furyl group, a benzofuryl group, a dibenzofuryl group, a pyrrolyl group, an indolyl group, an azaindolyl group, a carbazolyl group, an azacarbazolyl group, a diazacarbazolyl group, a phenoxazinyl group or a phenothiazinyl group, more preferably a phenyl group, a spirobifluorenyl group, a pyridyl group, a pyrimidinyl group, a triazinyl group, a dibenzothienyl group, a dibenzofuryl group, a carbazolyl group or an azacarbazolyl group, further preferably a phenyl group, a pyridyl group, a carbazolyl group or an azacarbazolyl group, particularly preferably a group represented by the formula (TDA-1) or (TDA-3) described above, especially preferably a group represented by the formula (TDA-3) described above, and these groups each optionally have a substituent.

The substituent which $Ar^{H1}$ and $Ar^{H2}$ optionally have is preferably a halogen atom, an alkyl group, a cycloalkyl group, an alkoxy group, a cycloalkoxy group, an aryl group or a monovalent heterocyclic group, more preferably an alkyl group, a cycloalkyl group, an alkoxy group or cycloalkoxy group, further preferably an alkyl group or cycloalkyl group, and these groups each optionally further have a substituent.

$n^{H1}$ is preferably 1. $n^{H2}$ is preferably 0.

$n^{H3}$ is usually an integer of 0 to 10, preferably an integer of 0 to 5, further preferably an integer of 1 to 3, particularly preferably 1.

$n^{H11}$ is preferably an integer of 1 to 5, more preferably an integer of 1 to 3, further preferably 1.

$R^{H11}$ is preferably a hydrogen atom, an alkyl group, a cycloalkyl group, an aryl group or a monovalent heterocyclic group, more preferably a hydrogen atom, an alkyl group or a cycloalkyl groups, further preferably a hydrogen atom or an alkyl group, and these groups each optionally have a substituent.

$L^{H1}$ is preferably an arylene group or a divalent heterocyclic group.

$L^{H1}$ is preferably a group represented by the formula (A-1) to (A-3), the formula (A-8) to (A-10), the formula (AA-1) to (AA-6), the formula (AA-10) to (AA-21) or the formula (AA-24) to (AA-34), more preferably a group represented by the formula (A-1), the formula (A-2), the formula (A-8), the formula (A-9), the formula (AA-1) to (AA-4), the formula (AA-10) to (AA-15) or the formula (AA-29) to (AA-34), further preferably a group represented by the formula (A-1), the formula (A-2), the formula (A-8), the formula (A-9), the formula (AA-2), the formula (AA-4) or the formula (AA-10) to (AA-15), particularly preferably a group represented by the formula (A-1), the formula (A-2), the formula (A-8), the formula (AA-2), the formula (AA-4), the formula (AA-10), the formula (AA-12) or the formula (AA-14), especially preferably a group represented by the formula (A-1), the formula (A-2), the formula (AA-2), the formula (AA-4) or the formula (AA-14).

The substituent which $L^{H1}$ optionally has is preferably a halogen atom, an alkyl group, a cycloalkyl group, an alkoxy group, a cycloalkoxy group, an aryl group or a monovalent heterocyclic group, more preferably an alkyl group, an alkoxy group, an aryl group or a monovalent heterocyclic group, further preferably an alkyl group, an aryl group or a monovalent heterocyclic group, and these groups optionally further have a substituent.

$L^{H21}$ is preferably a single bond or an arylene group, more preferably a single bond, and this arylene group optionally has a substituent.

The definition and examples of the arylene group or the divalent heterocyclic group represented by $L^{H21}$ are the same as the definition and examples of the arylene group or the divalent heterocyclic group represented by $L^{H1}$.

$R^{H21}$ is preferably an aryl group or a monovalent heterocyclic group, and these groups each optionally have a substituent.

The definition and examples of the aryl group and the monovalent heterocyclic group represented by $R^{H21}$ are the same as the definition and examples of the aryl group and the monovalent heterocyclic group represented by $Ar^{H1}$ and $Ar^{H2}$.

The definition and examples of the substituent which $R^{H21}$ may optionally has are the same as the definition and examples of the substituent which $Ar^{H1}$ and $Ar^{H2}$ optionally have.

The compound represented by the formula (H-1) is preferably a compound represented by the formula (H-2).

(H-2)

[wherein, $Ar^{H1}$, $Ar^{H2}$, $n^{H3}$ and $L^{H1}$ represent the same meaning as described above.]
As the compound represented by the formula (H-1), compounds represented by the following formulae (H-101) to (H-118) are exemplified.
(H-101)
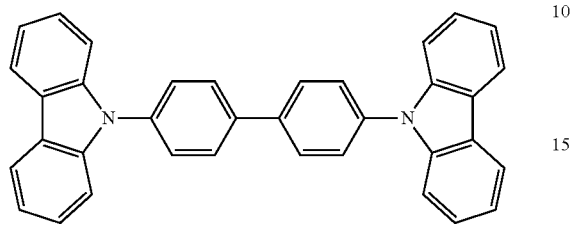
(H-102)
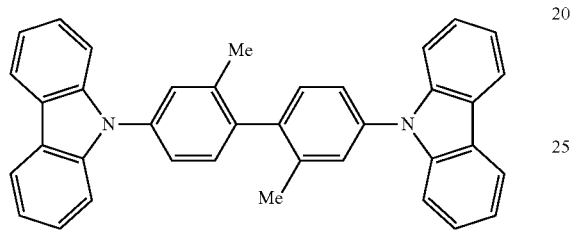
(H-103)
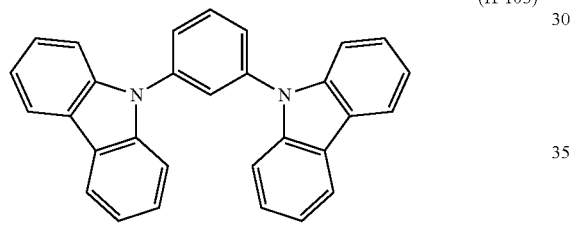
(H-104)
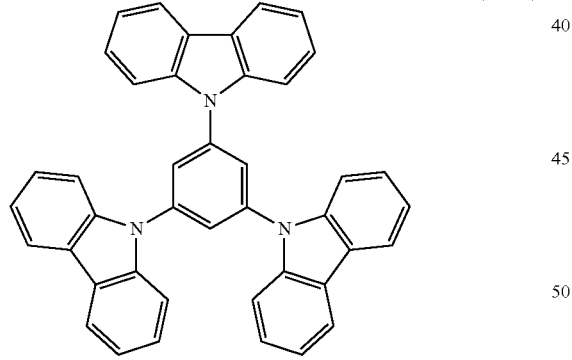
(H-105)
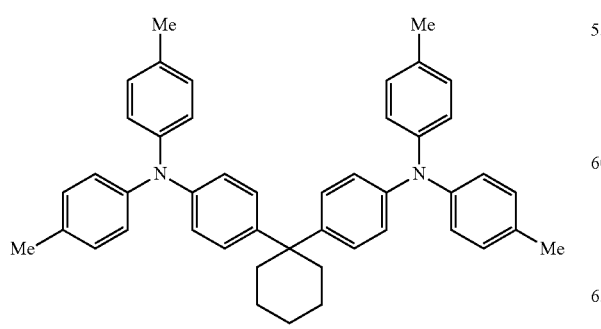
(H-106)
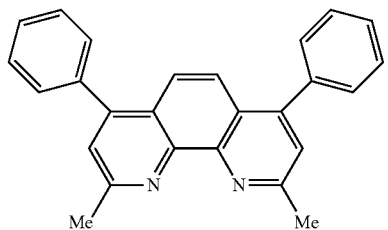
(H-107)
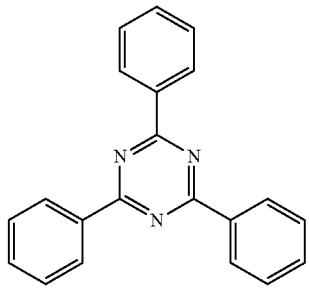
(H-108)
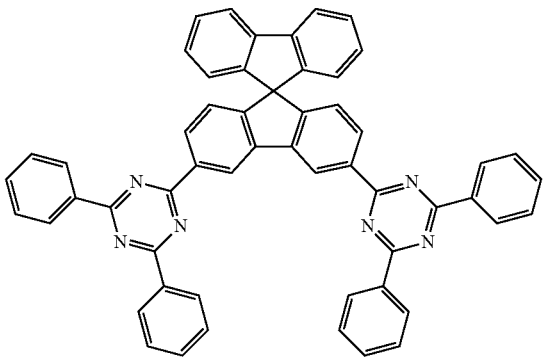
(H-109)
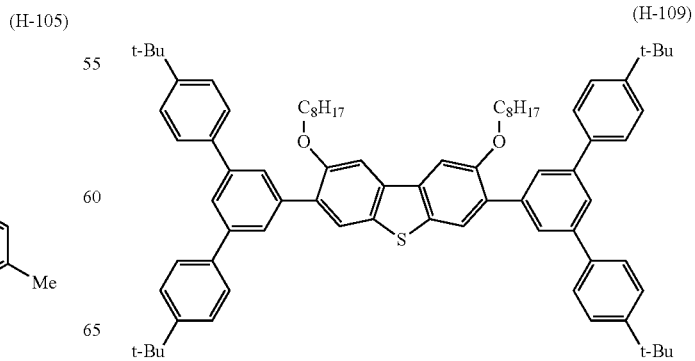

(H-110)
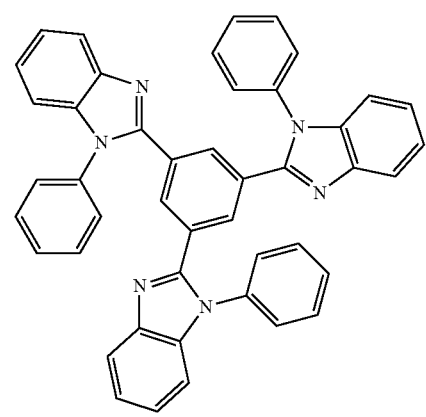
(H-111)
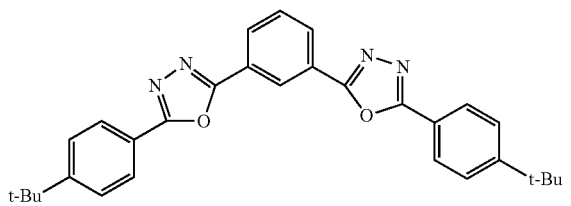
(H-112)
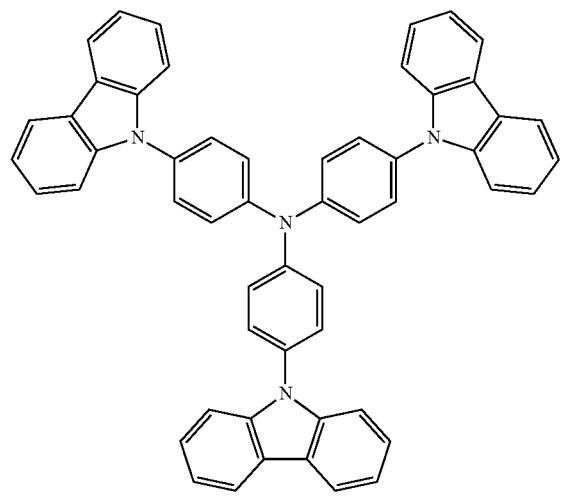
(H-113)
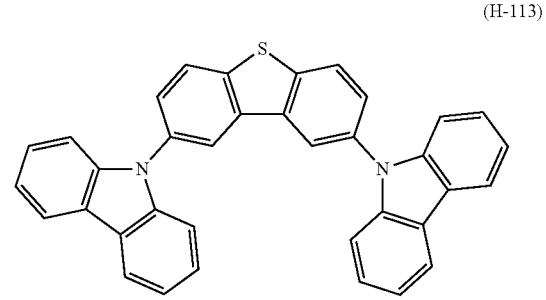
(H-114)
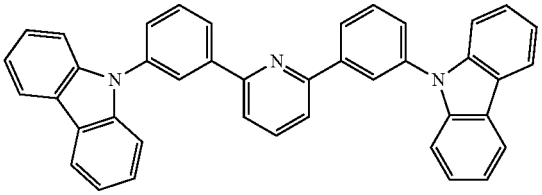
(H-115)
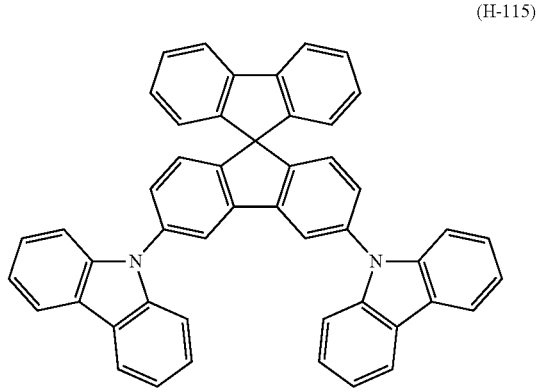
(H-116)
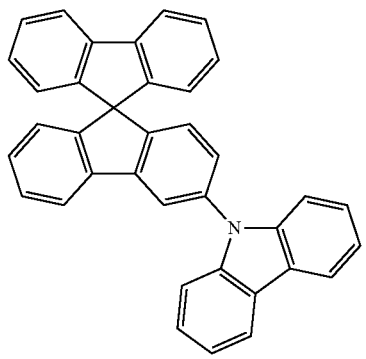
(H-117)
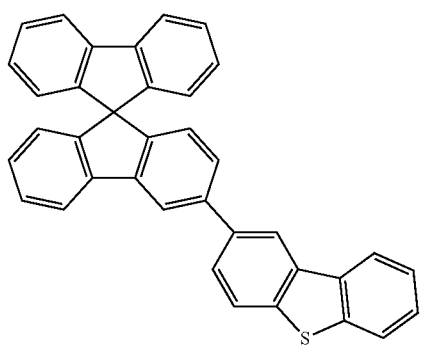

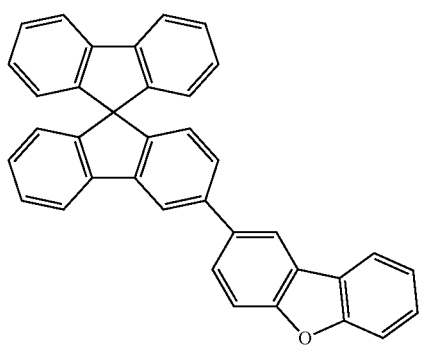
(H-118)

<Polymer Compound Comprising Constitutiol Unit Represented by the Formula (Y)>

The polymer compound contained in the second composition of the present invention is a polymer compound comprising a constitutional unit represented by the formula (Y) (hereinafter, referred to also as "polymer compound of the second composition".).

  (Y)

The arylene group represented by $Ar^{Y1}$ is more preferably a group represented by the formula (A-1), the formula (A-2), the formula (A-6) to (A-10), the formula (A-19) or the formula (A-20), further preferably a group represented by the formula (A-1), the formula (A-2), the formula (A-7), the formula (A-9) or the formula (A-19), and these groups each optionally have a substituent.

The divalent heterocyclic group represented by $Ar^{Y1}$ is more preferably a group represented by the formula (AA-1) to (AA-4), the formula (AA-10) to (AA-15), the formula (AA-18) to (AA-21), the formula (AA-33) or the formula (AA-34), further preferably a group represented by the formula (AA-4), the formula (AA-10), the formula (AA-12), the formula (AA-14) or the formula (AA-33), and these groups each optionally have a substituent.

The more preferable range and the further preferable range of the arylene group and the divalent heterocyclic group in the divalent group in which at least one arylene group and at least one divalent heterocyclic group are bonded directly to each other represented by $Ar^{Y1}$ are the same as the more preferable range and the further preferable range of the arylene group and the divalent heterocyclic group represented by $Ar^{Y1}$ described above, respectively.

"The divalent group in which at least one arylene group and at least one divalent heterocyclic group are bonded directly to each other" includes, for example, groups represented by the following formulae, and each of them optionally has a substituent.

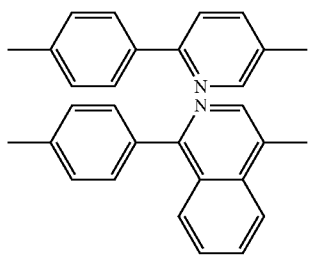

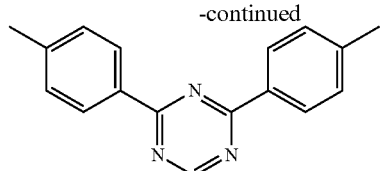

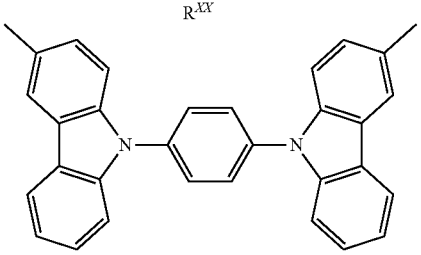

[wherein, $R^{XX}$ represents a hydrogen atom, an alkyl group, a cycloalkyl group, an aryl group or a monovalent heterocyclic group and these groups each optionally have a substituent.]

$R^{XX}$ is preferably an alkyl group, a cycloalkyl group or an aryl group, and these groups each optionally have a substituent.

The substituent which the group represented by $Ar^{Y1}$ optionally has is preferably an alkyl group, a cycloalkyl group or an aryl group, and these groups each optionally further have a substituent.

The constitutional unit represented by the formula (Y) includes, for example, constitutional units represented by the formulae (Y-1) to (Y-10), and from the standpoint of the external quantum efficiency of the light emitting device produced by using the second composition of the present invention preferable are constitutional units represented by the formula (Y-1), (Y-2) or (Y-3), from the standpoint of electron transportability of the polymer compound of the second composition preferable are constitutional units represented by the formulae (Y-4) to (Y-7), and from the standpoint of hole transportability of the polymer compound of the second composition preferable are constitutional units represented by the formulae (Y-8) to (Y-10).

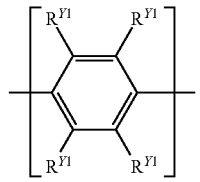  (Y-1)

[wherein, $R^{Y1}$ represents a hydrogen atom, an alkyl group, a cycloalkyl group, an alkoxy group, a cycloalkoxy group, an aryl group or a monovalent heterocyclic group, and these groups each optionally have a substituent. The plurality of $R^{Y1}$ may be the same or different, and adjacent groups $R^{Y1}$ may be combined together to form a ring together with the carbon atoms to which they are attached.]

$R^{Y1}$ is preferably a hydrogen atom, an alkyl group, a cycloalkyl group or an aryl group, and these groups each optionally have a substituent.

It is preferable that the constitutional unit represented by the formula (Y-1) is a constitutional unit represented by the formula (Y-1').

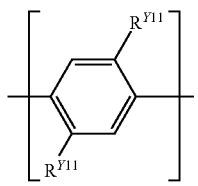
(Y-1')

[wherein, $R^{Y11}$ represents an alkyl group, a cycloalkyl group, an alkoxy group, a cycloalkoxy group, an aryl group or a monovalent heterocyclic group, and these groups each optionally have a substituent. The plurality of $R^{Y11}$ may be the same or different.]

$R^{Y11}$ is preferably an alkyl group, a cycloalkyl group or an aryl group, more preferably an alkyl group or a cycloalkyl group, and these groups each optionally have a substituent.

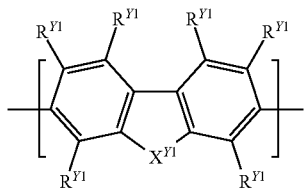
(Y-2)

[wherein, $R^{Y1}$ represents the same meaning as described above. $X^{Y1}$ represents a group represented by —C($R^{Y2}$)$_2$—, —C($R^{Y2}$)=C($R^{Y2}$)— or —C($R^{Y2}$)$_2$—C($R^{Y2}$)$_2$—. $R^{Y2}$ represents a hydrogen atom, an alkyl group, a cycloalkyl group, an alkoxy group, a cycloalkoxy group, an aryl group or a monovalent heterocyclic group and these groups each optionally have a substituent. The plurality of $R^{Y2}$ may be the same or different, and groups $R^{Y2}$ may be combined together to form a ring together with the carbon atoms to which they are attached.]

$R^{Y2}$ is preferably an alkyl group, a cycloalkyl group, an aryl group or a monovalent heterocyclic group, more preferably an alkyl group a cycloalkyl group or an aryl group, and these groups each optionally have a substituent.

Regarding the combination of two $R^{Y2}$s in the group represented by —C($R^{Y2}$)$_2$— in $X^{Y1}$, it is preferable that the both are an alkyl group or a cycloalkyl group, the both are an aryl group, the both are a monovalent heterocyclic group, or one is an alkyl group or a cycloalkyl group and the other is an aryl group or a monovalent heterocyclic group, it is more preferable that one is an alkyl group or cycloalkyl group and the other is an aryl group, and these groups each optionally have a substituent. The two groups $R^{Y2}$ may be combined together to form a ring together with the atoms to which they are attached, and when the groups $R^{Y2}$ form a ring, the group represented by —C($R^{Y2}$)$_2$— is preferably a group represented by the formula (Y-A1) to (Y-A5), more preferably a group represented by the formula (Y-A4), and these groups each optionally have a substituent.

(Y-A1)

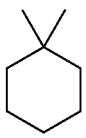
(Y-A2)

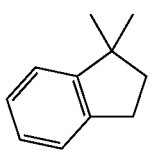
(Y-A3)

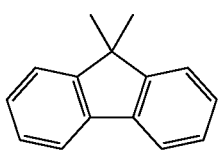
(Y-A4)

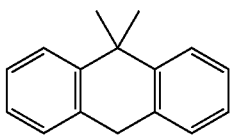
(Y-A5)

Regarding the combination of two $R^{Y2}$s in the group represented by —C($R^{Y2}$)=C($R^{Y2}$)— in $X^{Y1}$, it is preferable that the both are an alkyl group or cycloalkyl group, or one is an alkyl group or a cycloalkyl group and the other is an aryl group, and these groups each optionally have a substituent.

Four $R^{Y2}$s in the group represented by —C($R^{Y2}$)$_2$—C($R^{Y2}$)$_2$— in $X^{Y1}$ are preferably an alkyl group or a cycloalkyl group each optionally having a substituent. The plurality of $R^{Y2}$ may be combined together to form a ring together with the atoms to which they are attached, and when the groups $R^{Y2}$ form a ring, the group represented by —C($R^{Y2}$)$_2$—C($R^{Y2}$)$_2$— is preferably a group represented by the formula (Y-B1) to (Y-B5), more preferably a group represented by the formula (Y-B3), and these groups each optionally have a substituent.

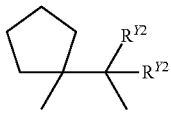
(Y-B1)

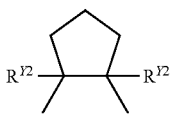
(Y-B2)

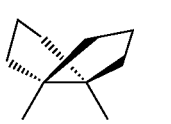
(Y-B3)

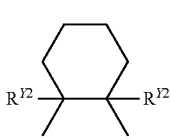
(Y-B4)

-continued (Y-B5)

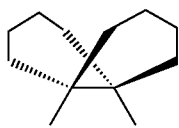

[wherein, $R^{Y2}$ represents the same meaning as described above.]

It is preferable that the constitutional unit represented by the formula (Y-2) is a constitutional unit represented by the formula (Y-2').

(Y-2')

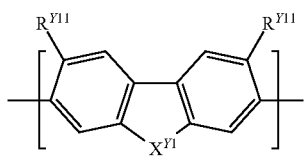

[wherein, $R^{Y11}$ and $X^{Y1}$ represent the same meaning as described above.]

(Y-3)

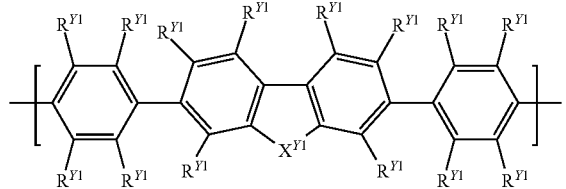

[wherein, $R^{Y1}$ and $X^{Y1}$ represent the same meaning as described above.]

It is preferable that the constitutional unit represented by the formula (Y-3) is a constitutional unit represented by the formula (Y-3').

(Y-3')

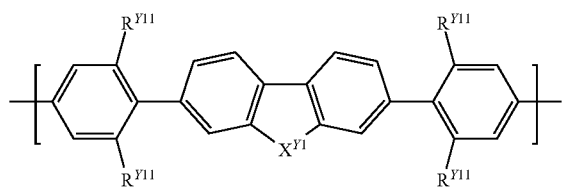

[wherein, $R^{Y11}$ and $X^{Y1}$ represent the same meaning as described above.]

(Y-4)

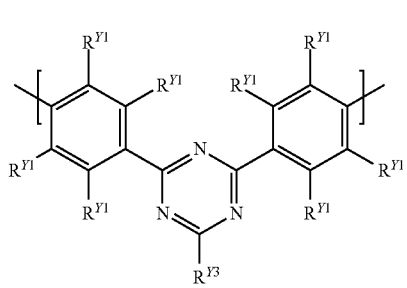

-continued (Y-5)

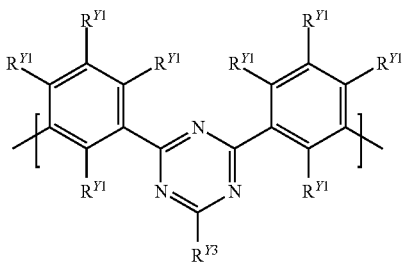

(Y-6)

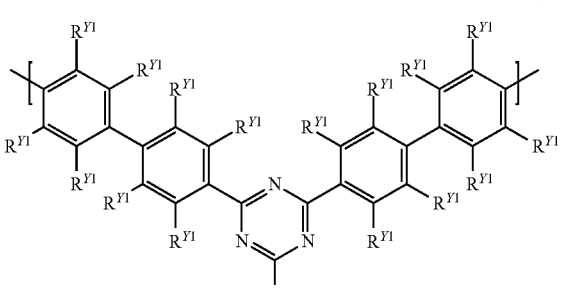

(Y-7)

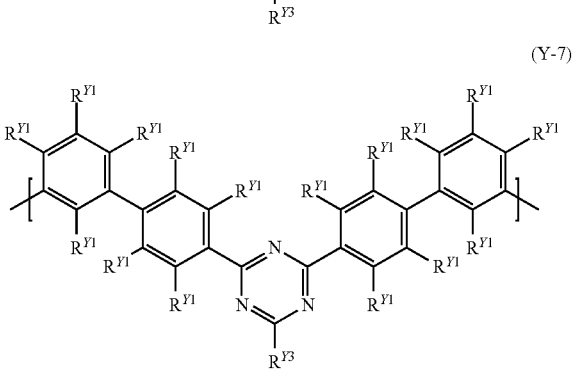

[wherein, $R^{Y1}$ represents the same meaning as described above. $R^{Y3}$ represents a hydrogen atom, an alkyl group, a cycloalkyl group, an alkoxy group, a cycloalkoxy group, an aryl group or a monovalent heterocyclic group and these groups each optionally have a substituent.]

$R^{Y3}$ is preferably an alkyl group, a cycloalkyl group, an alkoxy group, a cycloalkoxy group, an aryl group or a monovalent heterocyclic group, more preferably an aryl group, and these groups each optionally have a substituent.

It is preferable that the constitutional unit represented by the formula (Y-4) is a constitutional unit represented by the formula (Y-4'), and it is preferable that the constitutional unit represented by the formula (Y-6) is a constitutional unit represented by the formula (Y-6').

(Y-4')

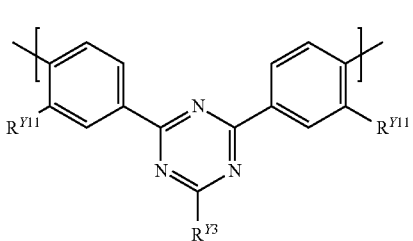

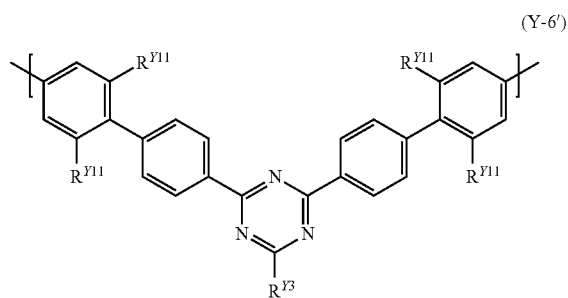
(Y-6')

[wherein, $R^{Y11}$ and $R^{Y3}$ represent the same meaning as described above.]

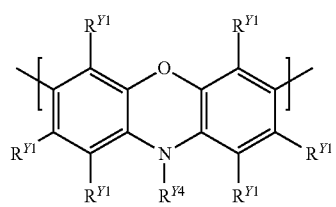
(Y-8)

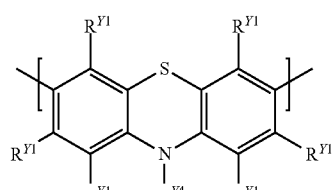
(Y-9)

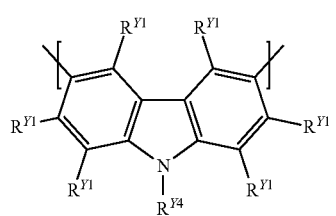
(Y-10)

[wherein, $R^{Y1}$ represents the same meaning as described above. $R^{Y4}$ represents a hydrogen atom, an alkyl group, a cycloalkyl group, an alkoxy group, a cycloalkoxy group, an aryl group or a monovalent heterocyclic group, and these groups each optionally have a substituent.]

$R^{Y4}$ is preferably an alkyl group, a cycloalkyl group, an alkoxy group, a cycloalkoxy group, an aryl group or a monovalent heterocyclic group, more preferably an aryl group, and these groups each optionally have a substituent.

The constitutional unit represented by the formula (Y) includes, for example, a constitutional unit composed of an arylene group represented by the formula (Y-101) to (Y-121), a constitutional unit composed of a divalent heterocyclic group represented by the formula (Y-201) to (Y-206), and a constitutional unit composed of a divalent group in which at least one arylene group and at least one divalent heterocyclic group are bonded directly to each other represented by the formula (Y-301) to (Y-304).

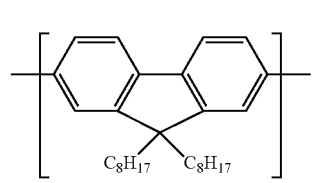
(Y-101)

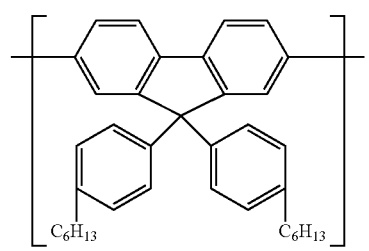
(Y-102)

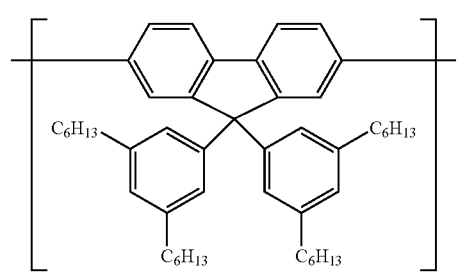
(Y-103)

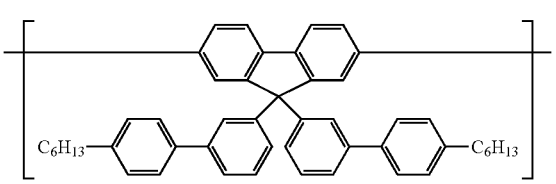
(Y-104)

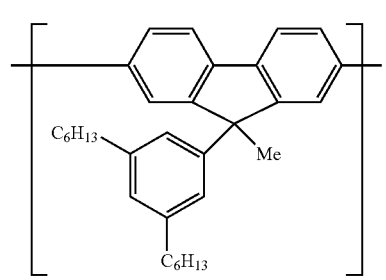
(Y-105)

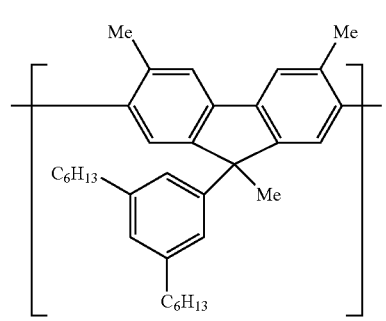
(Y-106)

(Y-107) 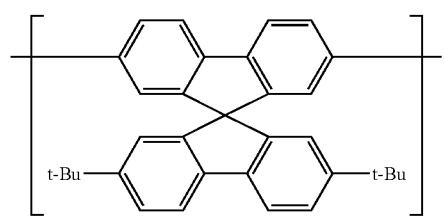
(Y-108) 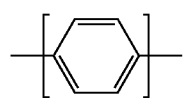
(Y-109) 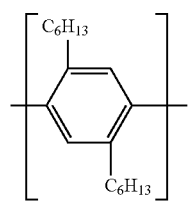
(Y-110) 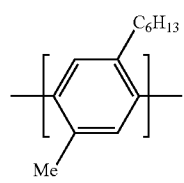
(Y-111) 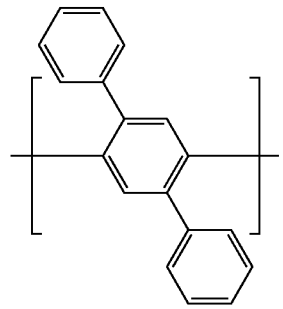
(Y-112) 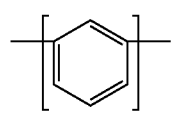
(Y-113) 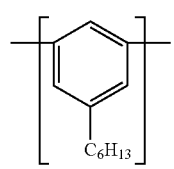
(Y-114) 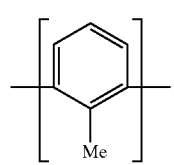
(Y-115) 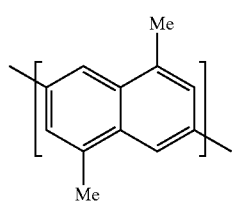
(Y-116) 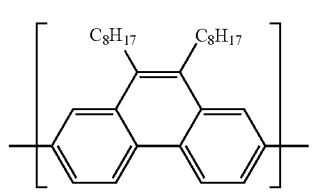
(Y-117) 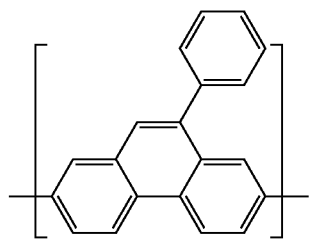
(Y-118) 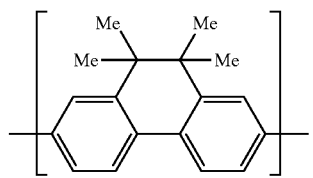
(Y-119) 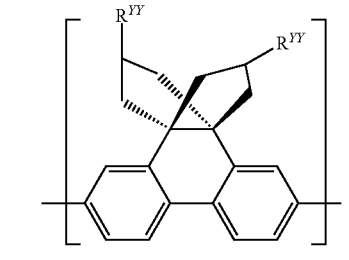
$R^{YY}=$ 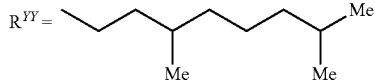
(Y-120) 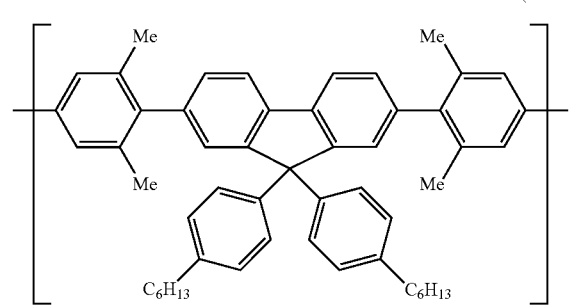

(Y-121) 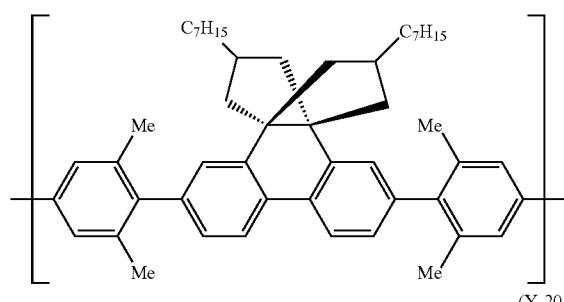
(Y-201) 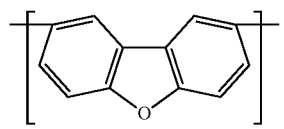
(Y-202) 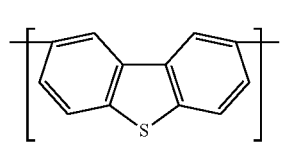
(Y-203) 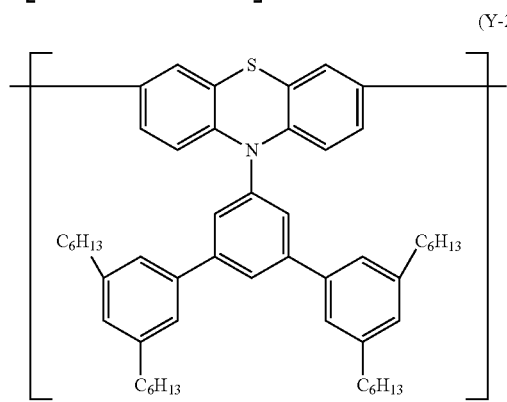
(Y-204) 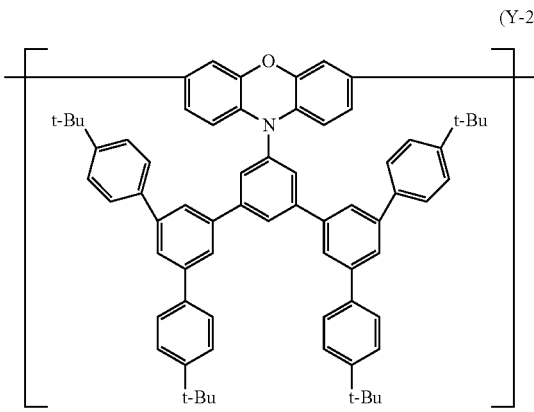
(Y-205) 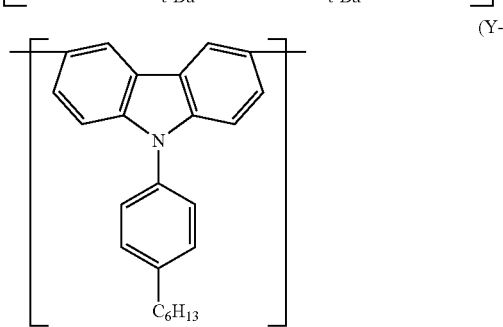
(Y-206) 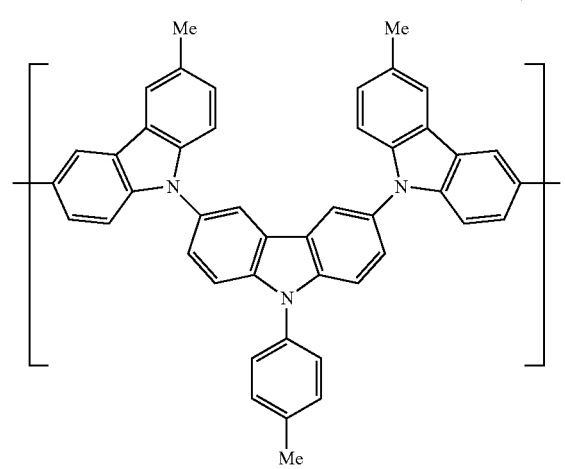
(Y-301) 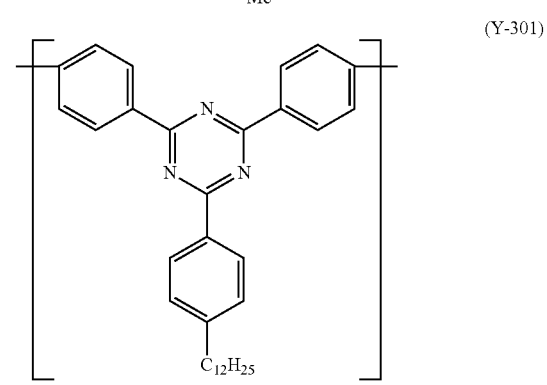
(Y-302) 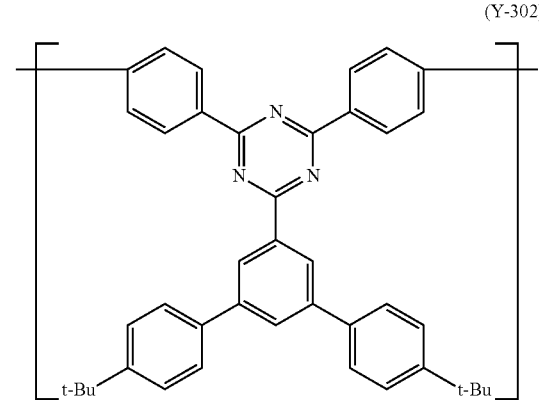
(Y-303) 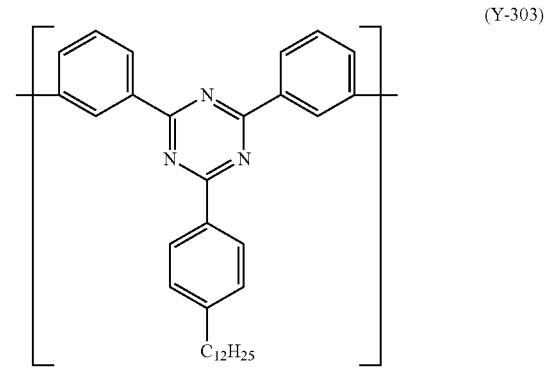

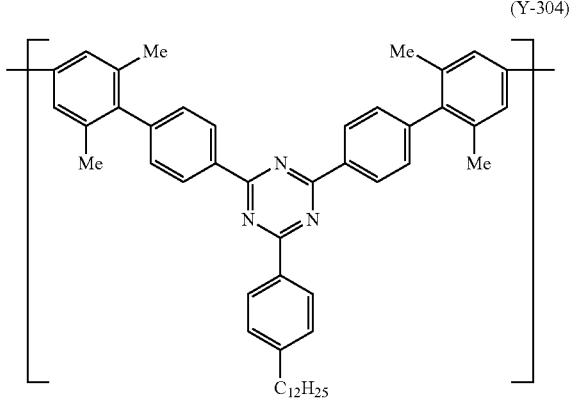

(Y-304)

The amount of the constitutional unit represented by the formula (Y) in which $Ar^{Y1}$ is an arylene group is preferably 0.5 to 90 mol %, more preferably 30 to 80 mol % with respect to the total amount of constitutional units contained in the polymer compound of the second composition, because the external quantum efficiency of a light emitting device produced by using the second composition of the present invention is excellent.

The amount of the constitutional unit represented by the formula (Y) in which $Ar^{Y1}$ is a divalent heterocyclic group or a divalent group in which at least one arylene group and at least one divalent heterocyclic group are bonded directly to each other is preferably 0.5 to 50 mol %, more preferably 3 to 20 mol % with respect to the total amount of constitutional units contained in the polymer compound of the second composition, because the charge transportability of a light emitting device produced by using the second composition of the present invention is excellent.

The constitutional unit represented by the formula (Y) may be contained only singly or two or more units thereof may be contained in the polymer compound of the second composition.

It is preferable that the polymer compound of the second composition further comprises a constitutional unit represented by the following formula (X), because hole transportability is excellent.

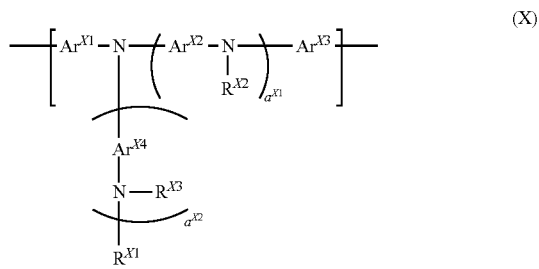

(X)

[wherein, $a^{X1}$ and $a^{X2}$ each independently represent an integer of 0 or more. $Ar^{X1}$ and $Ar^{X3}$ each independently represent an arylene group or a divalent heterocyclic group, and these groups each optionally have a substituent. $Ar^{X2}$ and $Ar^{X4}$ each independently represent an arylene group, a divalent heterocyclic group or a divalent group in which at least one arylene group and at least one divalent heterocyclic group are bonded directly to each other, and these groups each optionally have a substituent. $R^{X1}$, $R^{X2}$ and $R^{X3}$ each independently represent a hydrogen atom, an alkyl group, a cycloalkyl group, an aryl group or a monovalent heterocyclic group, and these groups each optionally have a substituent.]

$a^{X1}$ is preferably 2 or less, more preferably 1, because the external quantum efficiency of a light emitting device produced by using the second composition of the present invention is excellent.

$a^{X2}$ is preferably 2 or less, more preferably 0, because the external quantum efficiency of a light emitting device produced by using the second composition of the present invention is excellent.

$R^{X1}$, $R^{X2}$ and $R^{X3}$ are preferably an alkyl group, a cycloalkyl group, an aryl group or a monovalent heterocyclic group, more preferably an aryl group, and these groups each optionally have a substituent.

The arylene group represented by $Ar^{X1}$ and $Ar^{X3}$ is more preferably a group represented by the formula (A-1) or the formula (A-9), further preferably a group represented by the formula (A-1), and these groups each optionally have a substituent.

The divalent heterocyclic group represented by $Ar^{X1}$ and $Ar^{X3}$ is more preferably a group represented by the formula (AA-1), the formula (AA-2) or the formula (AA-7) to (AA-26), and these groups each optionally have a substituent.

$Ar^{X1}$ and $Ar^{X3}$ are preferably an arylene group optionally having a substituent.

The arylene group represented by $Ar^{X2}$ and $Ar^{X4}$ is more preferably a group represented by the formula (A-1), the formula (A-6), the formula (A-7), the formula (A-9) to (A-11) or the formula (A-19), and these groups each optionally have a substituent.

The more preferable range of the divalent heterocyclic group represented by $Ar^{X2}$ and $Ar^{X4}$ is the same as the more preferable range of the divalent heterocyclic group represented by $Ar^{X1}$ and $Ar^{X3}$.

The more preferable range and the further preferable range of the arylene group and the divalent heterocyclic group in the divalent group in which at least one arylene group and at least one divalent heterocyclic group are bonded directly to each other represented by $Ar^{X2}$ and $Ar^{X4}$ are the same as the more preferable range and the further preferable range of the arylene group and the divalent heterocyclic group represented by $Ar^{X1}$ and $Ar^{X3}$, respectively.

The divalent group in which at least one arylene group and at least one divalent heterocyclic group are bonded directly to each other represented by $Ar^{X2}$ and $Ar^{X4}$ includes the same groups as the divalent group in which at least one arylene group and at least one divalent heterocyclic group are bonded directly to each other represented by $Ar^{Y1}$ in the formula (Y).

$Ar^{X2}$ and $Ar^{X4}$ are preferably an arylene group optionally having a substituent.

The substituent which the group represented by $Ar^{X1}$ to $Ar^{X4}$ and $R^{X1}$ to $R^{X3}$ optionally has is preferably an alkyl group, a cycloalkyl group or an aryl group, and these groups each optionally further have a substituent.

The constitutional unit represented by the formula (X) is preferably a constitutional unit represented by the formula (X-1) to (X-7), more preferably a constitutional unit represented by the formula (X-1) to (X-6), further preferably a constitutional unit represented by the formula (X-3) to (X-6).

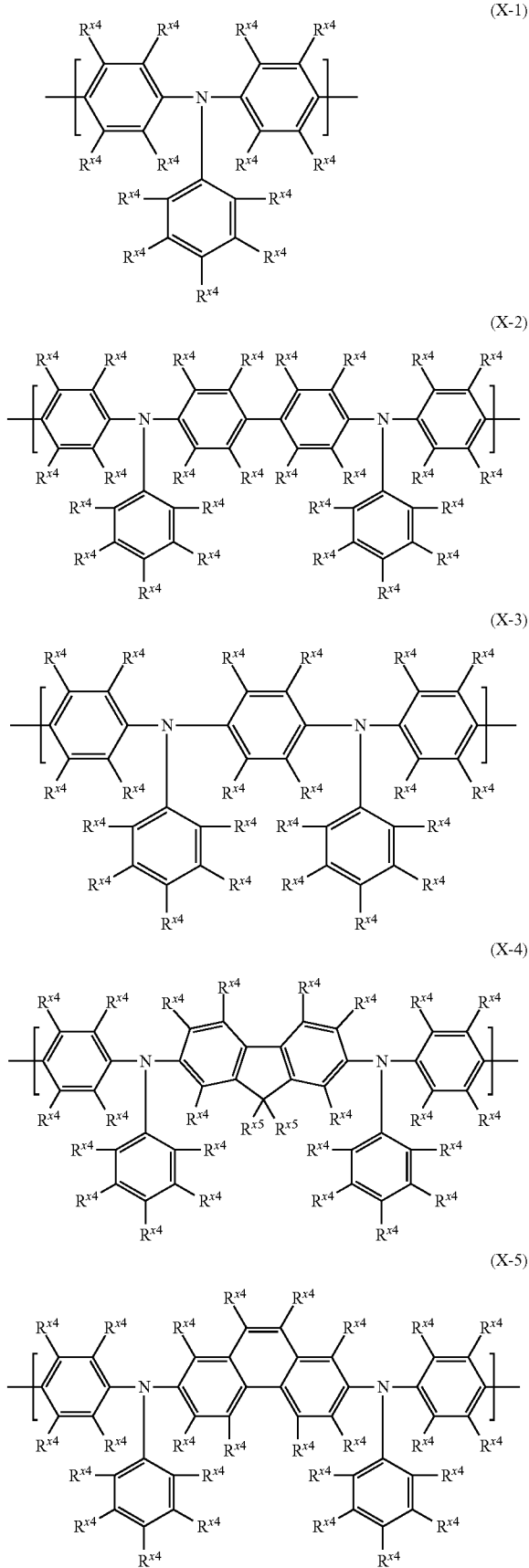

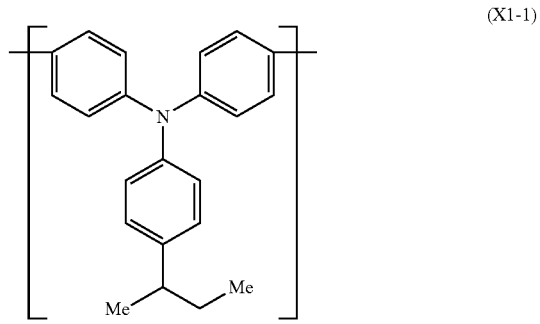

[wherein, $R^{X4}$ and $R^{X5}$ each independently represent a hydrogen atom, an alkyl group, a cycloalkyl group, an alkoxy group, a cycloalkoxy group, an aryl group, an aryloxy group, a halogen atom, a monovalent heterocyclic group or a cyano group, and these groups each optionally have a substituent. The plurality of $R^{X4}$ may be the same or different. The plurality of $R^{X5}$ may be the same or different, and adjacent groups $R^{X5}$ may be combined together to form a ring together with the carbon atoms to which they are attached.]

The amount of the constitutional unit represented by the formula (X) is preferably 0.1 to 50 mol %, more preferably 1 to 40 mol %, further preferably 5 to 30 mol % with respect to the total amount of constitutional units contained in the polymer compound of the second composition, because hole transportability is excellent.

The constitutional unit represented by the formula (X) includes, for example, constitutional units represented by the formulae (X1-1) to (X1-11), preferably constitutional units represented by the formulae (X1-3) to (X1-10).

-continued
(X1-2)
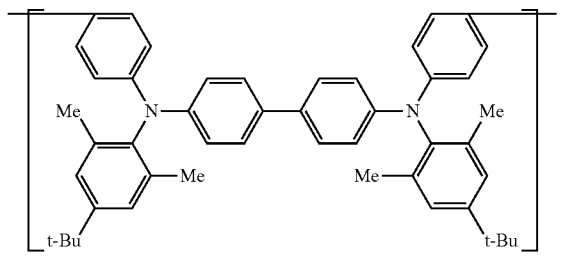
(X1-3)
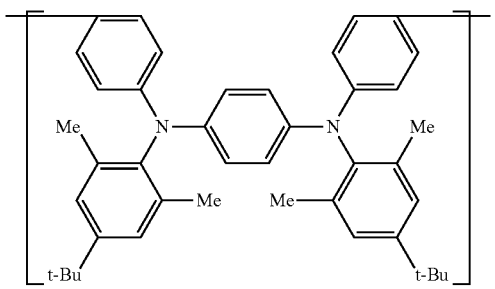
(X1-4)
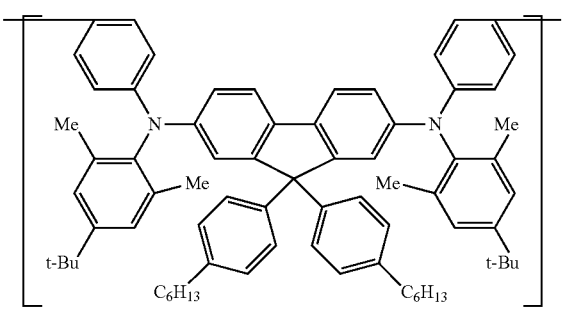
(X1-5)
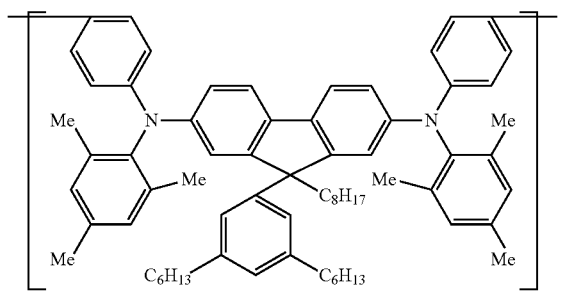
(X1-6)
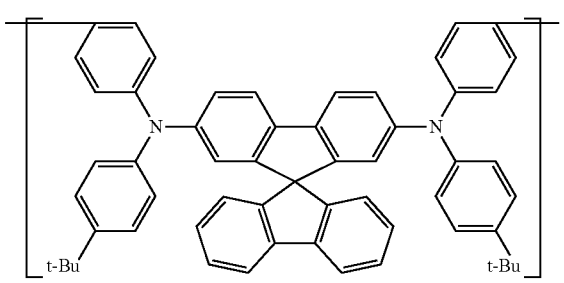
-continued
(X1-7)
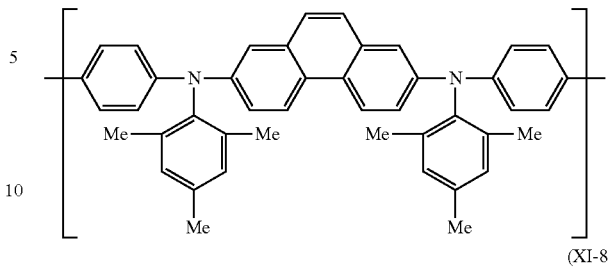
(XI-8)
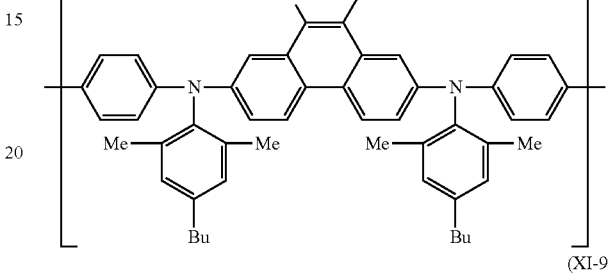
(XI-9)
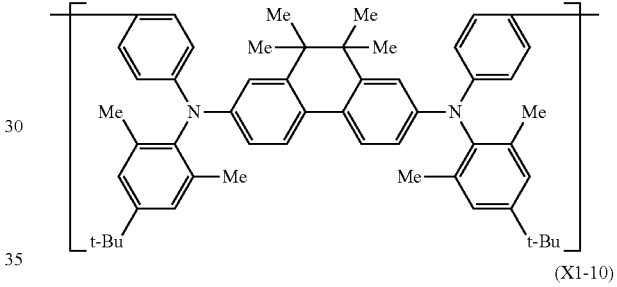
(X1-10)
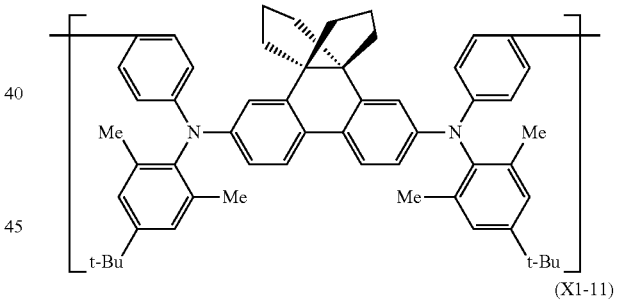
(X1-11)
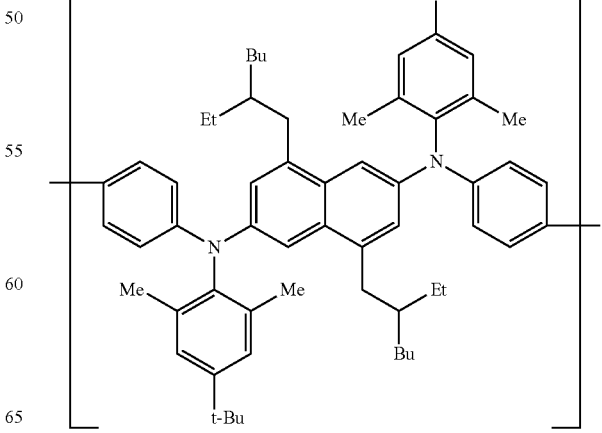

The constitutional unit represented by the formula (X) may be contained only singly or two or more units thereof may be contained in the polymer compound of the second composition.

Examples of the polymer compound of the second composition include polymer compounds (P-1) to (P-6) in the Table 16. "Other" constitutional unit denotes a constitutional unit other than the constitutional unit represented by the formula (Y) and the constitutional unit represented by the formula (X).

TABLE 16

| | constitutional unit and mole fraction thereof | | | | |
|---|---|---|---|---|---|
| | formula (Y) | | formula (X) | | |
| polymer compound | formulae (Y-1) to (Y-3) p | formulae (Y-4) to (Y-7) q | formulae (Y-8) to (Y-10) r | formulae (X-1) to (X-7) s | other t |
| (P-1) | 0.1 to 99.9 | 0.1 to 99.9 | 0 | 0 | 0 to 30 |
| (P-2) | 0.1 to 99.9 | 0 | 0.1 to 99.9 | 0 | 0 to 30 |
| (P-3) | 0.1 to 99.8 | 0.1 to 99.8 | 0 | 0.1 to 99.8 | 0 to 30 |
| (P-4) | 0.1 to 99.8 | 0.1 to 99.8 | 0.1 to 99.8 | 0 | 0 to 30 |
| (P-5) | 0.1 to 99.8 | 0 | 0.1 to 99.8 | 0.1 to 99.8 | 0 to 30 |
| (P-6) | 0.1 to 99.7 | 0.1 to 99.7 | 0.1 to 99.7 | 0.1 to 99.7 | 0 to 30 |

[In the table, p, q, r, s and t represent the mole fraction of each constitutional unit. p+q+r+s+t=100, and 100≥p+q+r+s≥70. Other constitutional unit denotes a constitutional unit other than the constitutional unit represented by the formula (Y) and the constitutional unit represented by the formula (X).]

The polymer compound of the second composition may be any of a block copolymer, a random copolymer, an alternating copolymer or a graft copolymer, and may also be another embodiment, and is preferably a copolymer produced by copolymerizing a plurality of raw material monomers.

<Production Method of Polymer Compound of the Second Composition>

The polymer compound of the second composition can be produced by using known polymerization methods described in Chem. Rev., vol. 109, pp. 897-1091 (2009) and the like, and the known polymerization methods include, for example, methods for causing polymerization by a coupling reaction using a transition metal catalyst such as the Suzuki reaction, the Yamamoto reaction, the Buchwald reaction, the Stille reaction, the Negishi reaction and the Kumada reaction.

In the above-described polymerization methods, the monomer charging method includes a method in which the total amount of monomers is charged in a lump into the reaction system, a method in which a part of monomers is charged and reacted, then, the remaining monomers are charged in a lump, continuously or in divided doses, a method in which monomers are charged continuously or in divided doses, and the like.

The transition metal catalyst includes a palladium catalyst and a nickel catalyst.

The post treatment of the polymerization reaction is conducted by using known methods, for example, a method in which water-soluble impurities are removed by liquid-separation, a method in which the reaction solution after the polymerization reaction is added to a lower alcohol such as methanol and the like, the deposited precipitate is filtrated, then, dried, and other methods, singly or in combination. When the purity of the polymer host is low, purification can be carried out by usual methods such as, for example, recrystallization, reprecipitation, continuous extraction using a Soxhlet extractor, column chromatography and the like.

<Composition>

The first composition of the present invention is a composition comprising a phosphorescent compound (B), two or more phosphorescent compounds (DGR) and a compound of the first composition.

The second composition of the present invention is a composition comprising a phosphorescent compound (B), two or more phosphorescent compounds (DGR) and a polymer compound of the second composition.

In the first and second compositions of the present invention, the phosphorescent compound (B) may be contained singly, or two or more of the phosphorescent compounds (B) may be contained.

In the first composition of the present invention, the compound of the first composition may be contained singly, or two or more of the compounds may be contained.

In the first composition of the present invention, the lowest excited triplet state ($T_1$) of the compound of the first composition is preferably at an energy level equivalent to or an energy level higher than $T_1$ of the phosphorescent compound (B), because a light emitting device produced by using the first composition of the present invention is excellent in external quantum efficiency.

In the first composition of the present invention, the compound of the first composition is preferably one showing solubility in a solvent which is capable of dissolving the phosphorescent compound (B) and the phosphorescent compound (DGR), because a light emitting device produced by using the first composition of the present invention can be fabricated by a solution application process.

In the second composition of the present invention, the polymer compound of the second composition may be contained singly, or two or more of the polymer compounds may be contained.

In the second composition of the present invention, the lowest excited triplet state ($T_1$) of the polymer compound of the second composition is preferably at an energy level equivalent to or an energy level higher than $T_1$ of the phosphorescent compound (B), because a light emitting device produced by using the second composition of the present invention is excellent in external quantum efficiency.

In the second composition of the present invention, the polymer compound of the second composition is preferably one showing solubility in a solvent which is capable of dissolving the phosphorescent compound (B) and the phosphorescent compound (DGR), because a light emitting device produced by using the second composition of the present invention can be fabricated by a solution application process.

In the first composition of the present invention, the sum of the content of the phosphorescent compound (B) and the content of the phosphorescent compound (DGR) is usually 0.1 to 99 parts by weight, preferably 1 to 90 parts by weight, more preferably 10 to 70 parts by weight, further preferably 20 to 50 parts by weight, when the sum of the contents of the phosphorescent compound (B), the phosphorescent compound (DGR) and the compound of the first composition is 100 parts by weight.

In the first composition of the present invention, the content of the phosphorescent compound (DGR) is preferably 0.01 to 50 parts by weight, more preferably 0.05 to 30 parts by weight, further preferably 0.1 to 10 parts by weight, particularly preferably 0.5 to 5 parts by weight, when the content of the phosphorescent compound (B) is 100 parts by weight.

In the second composition of the present invention, the sum of the content of the phosphorescent compound (B) and the content of the phosphorescent compound (DGR) is usually 0.1 to 99 parts by weight, preferably 1 to 90 parts by weight, more preferably 10 to 70 parts by weight, further preferably 20 to 50 parts by weight, when the sum of the contents of the phosphorescent compound (B), the phosphorescent compound (DGR) and the polymer compound of the second composition is 100 parts by weight.

In the second composition of the present invention, the content of the phosphorescent compound (DGR) is preferably 0.01 to 50 parts by weight, more preferably 0.05 to 30 parts by weight, further preferably 0.1 to 10 parts by weight, particularly preferably 0.5 to 5 parts by weight, when the content of the phosphorescent compound (B) is 100 parts by weight.

At least one of the two or more phosphorescent compounds (DGR) contained in the first and second compositions of the present invention is preferably a phosphorescent compound represented by the formula (2-A1) to (2-A5), more preferably a phosphorescent compound represented by the formula (2-A1), (2-A2) or (2-A5), further preferably a phosphorescent compound represented by the formula (2-A1), because a light emitting device produced by using the first or second composition of the present invention is excellent in external quantum efficiency.

The combination of the two phosphorescent compounds (DGR) contained in the first and second compositions of the present invention is preferably a combination of two selected from phosphorescent compounds represented by the formulae (2-A1) to (2-A5), more preferably a combination of two selected from phosphorescent compounds represented by the formulae (2-A1), (2-A2) and (2-A5), further preferably a combination of two of phosphorescent compounds represented by the formula (2-A1), a combination of a phosphorescent compound represented by the formula (2-A1) and a phosphorescent compound represented by the formula (2-A2) or a combination of a phosphorescent compound represented by the formula (2-A1) and a phosphorescent compound represented by the formula (2-A3).

When the content of one of the two phosphorescent compounds (DGR) contained in the first and second compositions of the present invention is 100 parts by weight, the content of the other compound is usually 1 to 10000 parts by weight, and preferably 5 to 2000 parts by weight, more preferably 10 to 1000 parts by weight, because a light emitting device produced by using the first or second composition of the present invention is excellent in color reproducibility.

In the first and second compositions of the present invention, emission color can be adjusted and emission color can also be adjusted to white, by controlling the ratio of the content of the phosphorescent compound (B) to the content of two or more phosphorescent compounds (DGR).

The emission color of a light emitting device can be confirmed by measuring the emission chromaticity of a light emitting device and determining the chromaticity coordinate thereof (CIE chromaticity coordinate). In white emission color, for example, X of the chromaticity coordinate is in the range of 0.25 to 0.55 and Y of the chromaticity coordinate is in the range of 0.25 to 0.55, and it is preferable that X of the chromaticity coordinate is in the range of 0.30 to 0.50 and Y of the chromaticity coordinate is in the range of 0.30 to 0.50.

The maximum peak wavelength of the emission spectrum of the phosphorescent compound (B) is preferably 400 nm to 490 nm, more preferably 420 nm to 480 nm, from the standpoint of the emission color (especially, white) of a light emitting device produced by using the first or second composition of the present invention.

The maximum peak wavelength of the emission spectrum of the phosphorescent compound (DGR) is preferably 500 nm to 680 nm, more preferably 505 nm to 630 nm, from the standpoint of the emission color (especially, white) of a light emitting device produced by using the first or second composition of the present invention.

It is preferable that the maximum peak wavelengths of the emission spectra of the two phosphorescent compounds (DGR) contained in the first and second compositions of the present invention are mutually different, from the standpoint of the emission color (especially, white) of a light emitting device produced by using the first or second composition of the present invention, and the difference thereof is preferably 10 to 200 nm, more preferably 20 to 180 nm, further preferably 40 to 125 nm.

When the maximum peak wavelengths of the light emission spectra of the two phosphorescent compounds (DGR) contained in the first and second compositions of the present invention are different, the phosphorescent compound (DGR) having a maximum peak wavelength of a light emission spectrum at shorter wavelength side has a maximum peak wavelength of a light emission spectrum of preferably 500 nm or more and less than 570 nm, more preferably 505 nm to 550 nm, from the standpoint of the emission color (especially, white) of a light emitting device produced by using the first or second composition of the present invention. The phosphorescent compound (DGR) having a maximum peak wavelength of a light emission spectrum at longer wavelength side has a maximum peak wavelength of a light emission spectrum of preferably 570 nm to 680 nm, more preferably 590 nm to 630 nm.

The total content of the two or more phosphorescent compounds (DGR) is preferably 0.01 to 50 parts by weight, more preferably 0.05 to 30 parts by weight, further preferably 0.1 to 10 parts by weight, particularly preferably 0.5 to 5 parts by weight, when the content of the phosphorescent compound (B) is 100 parts by weight, from the standpoint of the emission color (especially, white) of a light emitting device produced by using the first or second composition of the present invention.

When the maximum peak wavelengths of the light emission spectra of the two phosphorescent compounds (DGR) contained in the first and second compositions of the present invention are different, the content of the phosphorescent compound (DGR) having a maximum peak wavelength of a light emission spectrum at longer wavelength side is usually 1 to 10000 parts by weight, from the standpoint of the emission color (especially, white) of a light emitting device produced by using the first or second composition of the present invention, and it is preferably 5 to 1000 parts by weight, more preferably 10 to 200 parts by weight, because a light emitting device produced by using the first or second composition of the present invention is excellent in color reproducibility, when the content of the phosphorescent compound (DGR) having a maximum peak wavelength of a light emission spectrum at shorter wavelength side is 100 parts by weight.

The first and second compositions of the present invention may further comprises at least one material selected from the group consisting of a hole transporting material, a hole injection material, an electron transporting material, an electron injection material, a light emitting material (different from the phosphorescent compound (B) and the phosphorescent compound (DGR)), an antioxidant and a solvent.

The first and second compositions of the present invention comprising a solvent (hereinafter, referred to as "ink") are suitable for fabrication of a light emitting device using a printing method such as an inkjet print method and a nozzle print method.

The viscosity of the ink may be adjusted depending on the kind of the application method, and when a solution goes through a discharge apparatus such as in an inkjet printing method, the viscosity is preferably in the range of 1 to 20 mPa·s at 25° C. because clogging in discharging and curved aviation are unlikely.

As the solvent contained in the ink, those capable of dissolving or uniformly dispersing solid components in the ink are preferable. The solvent includes, for example, chlorine-based solvents such as 1,2-dichloroethane, 1,1,2-trichloroethane, chlorobenzene and o-dichlorobenzene; ether solvents such as THF, dioxane, anisole and 4-methylanisole; aromatic hydrocarbon solvents such as toluene, xylene, mesitylene, ethylbenzene, n-hexylbenzene and cyclohexylbenzene; aliphatic hydrocarbon solvents such as cyclohexane, methylcyclohexane, n-pentane, n-hexane, n-heptane, n-octane, n-nonane, n-decane, n-dodecane and bicyclohexyl; ketone solvents such as acetone, methylethylketone, cyclohexanone and acetophenone; ester solvents such as ethyl acetate, butyl acetate, ethylcellosolve acetate, methyl benzoate and phenyl acetate; polyhydric alcohol solvents such as ethylene glycol, glycerin and 1,2-hexanediol; alcohol solvents such as isopropylalcohol and cyclohexanol; sulfoxide solvents such as dimethyl sulfoxide; and amide solvents such as N-methyl-2-pyrrolidone and N,N-dimethylformamide. These solvents may be used singly, or two or more of them may be used in combination.

In the ink, the compounding amount of the solvent is usually 1000 to 100000 parts by weight, preferably 2000 to 20000 parts by weight when the sum of the phosphorescent compound (B), the phosphorescent compound (DGR) and the compound of the first composition contained in the first composition of the present invention is 100 parts by weight.

In the ink, the compounding amount of the solvent is usually 1000 to 100000 parts by weight, preferably 2000 to 20000 parts by weight when the sum of the phosphorescent compound (B), the phosphorescent compound (DGR) and the polymer compound of the second composition contained in the second composition of the present invention is 100 parts by weight.

[Hole Transporting Material]

The hole transporting material is classified into low molecular weight compounds and polymer compounds, and polymer compounds are preferable, and polymer compounds having a crosslinkable group are more preferable.

The polymer compound includes, for example, polyvinylcarbazole and derivatives thereof; polyarylene having an aromatic amine structure in the side chain or main chain and derivatives thereof. The polymer compound may also be a compound in which an electron accepting portion is linked. The electron accepting portion includes, for example, fullerene, tetrafluorotetracyanoquinodimethane, tetracyanoethylene, trinitrofluorenone and the like, preferably fullerene.

In the first composition of the present invention, the compounding amount of the hole transporting material is usually 1 to 400 parts by weight, preferably 5 to 150 parts by weight when the sum of the phosphorescent compound (B), the phosphorescent compound (DGR) and the compound of the first composition contained in the first composition of the present invention is 100 parts by weight.

In the second composition of the present invention, the compounding amount of the hole transporting material is usually 1 to 400 parts by weight, preferably 5 to 150 parts by weight when the sum of the phosphorescent compound (B), the phosphorescent compound (DGR) and the polymer compound of the second composition contained in the second composition of the present invention is 100 parts by weight.

The hole transporting material may be used singly, or two or more hole transporting materials may be used in combination.

[Electron Transporting Material]

The electron transporting material is classified into low molecular weight compounds and polymer compounds. The electron transporting material optionally has a crosslinkable group.

The low molecular weight compound includes, for example, a metal complex having 8-hydroxyquinoline as a ligand, oxadiazole, anthraquinodimethane, benzoquinone, naphthoquinone, anthraquinone, tetracyanoanthraquinodimethane, fluorenone, diphenyldicyanoethylene, diphenoquinone and derivatives thereof.

The polymer compound includes, for example, polyphenylene, polyfluorene and derivatives thereof. These polymer compounds may be doped with a metal.

In the first composition of the present invention, the compounding amount of the electron transporting material is usually 1 to 400 parts by weight, preferably 5 to 150 parts by weight when the sum of the phosphorescent compound (B), the phosphorescent compound (DGR) and the compound of the first composition contained in the first composition of the present invention is 100 parts by weight.

In the second composition of the present invention, the compounding amount of the electron transporting material is usually 1 to 400 parts by weight, preferably 5 to 150 parts by weight when the sum of the phosphorescent compound (B), the phosphorescent compound (DGR) and the polymer compound of the second composition contained in the second composition of the present invention is 100 parts by weight.

The electron transporting material may be used singly, or two or more electron transporting materials may be used in combination.

[Hole Injection Material and Electron Injection Material]

The hole injection material and the electron injection material are each classified into low molecular weight compounds and polymer compounds. The hole injection material and the electron injection material each optionally have a crosslinkable group.

The low molecular weight compound includes, for example, metal phthalocyanines such as copper phthalocyanine; carbon; oxides of metals such as molybdenum and tungsten; metal fluorides such as lithium fluoride, sodium fluoride, cesium fluoride and potassium fluoride.

The polymer compound includes, for example, polyaniline, polythiophene, polypyrrole, polyphenylenevinylene, polythienylenevinylene, polyquinoline and polyquinoxaline, and derivatives thereof; electrically conductive polymers such as a polymer comprising an aromatic amine structure in the main chain or side chain.

In the first composition of the present invention, the compounding amounts of the hole injection material and the electron injection material are each usually 1 to 400 parts by weight, preferably 5 to 150 parts by weight when the sum of the phosphorescent compound (B), the phosphorescent compound (DGR) and the compound of the first composition contained in the first composition of the present invention is 100 parts by weight.

In the second composition of the present invention, the compounding amounts of the hole injection material and the electron injection material are each usually 1 to 400 parts by weight, preferably 5 to 150 parts by weight when the sum of the phosphorescent compound (B), the phosphorescent compound (DGR) and the polymer compound of the second composition contained in the second composition of the present invention is 100 parts by weight.

The hole injection material and the electron injection material may each be used singly, or two or more of them may be used in combination.

[Ion Dope]

When the hole injection material or the electron injection material comprises an electrically conductive polymer, the electric conductivity of the electrically conductive polymer is preferably $1\times10^{-5}$ S/cm to $1\times10^3$ S/cm. For adjusting the electric conductivity of the electrically conductive polymer within such a range, the electrically conductive polymer can be doped with a suitable amount of ions.

The kind of the ion to be doped is an anion for a hole injection material and a cation for an electron injection material. The anion includes, for example, a polystyrenesulfonate ion, an alkylbenzenesulfonate ion and a camphorsulfonate ion. The cation includes, for example, a lithium ion, a sodium ion, a potassium ion and a tetrabutylammonium ion.

The ion to be doped may be used singly, or two or more ions to be doped may be used.

[Light Emitting Material]

The light emitting material (different from the phosphorescent compound (B) and the phosphorescent compound (DGR)) is classified into low molecular weight compounds and polymer compounds. The light emitting material optionally has a crosslinkable group.

The low molecular weight compound includes, for example, naphthalene and derivatives thereof, anthracene and derivatives thereof, perylene and derivatives thereof, and, triplet light emitting complexes having iridium, platinum or europium as the central metal.

The polymer compound includes, for example, polymer compounds comprising a phenylene group, a naphthalenediyl group, a fluorenediyl group, a phenanthrenediyl group, dihydrophenanthrenediyl group, a group represented by the formula (X), a carbazolediyl group, a phenoxazinediyl group, a phenothiazinediyl group, an anthracenediyl group, a pyrenediyl group and the like.

The light emitting material preferably comprises a triplet light emitting complex and a polymer compound.

The triplet light emitting complex includes, for example, metal complexes listed below.

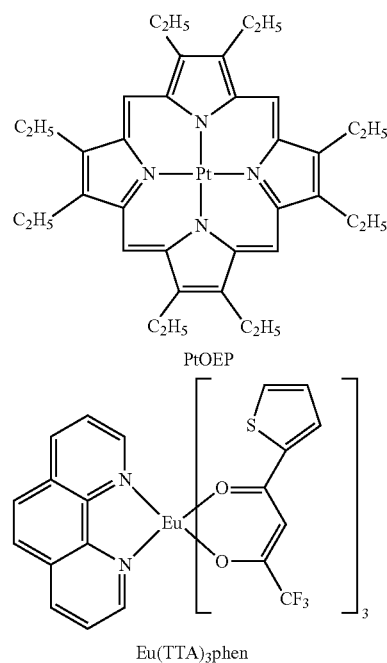

PtOEP

Eu(TTA)₃phen

In the first composition of the present invention, the compounding amount of the light emitting material is usually 0.1 to 400 parts by weight when the sum of the phosphorescent compound (B), the phosphorescent compound (DGR) and the compound of the first composition contained in the first composition of the present invention is 100 parts by weight.

In the second composition of the present invention, the compounding amount of the light emitting material is usually 0.1 to 400 parts by weight when the sum of the phosphorescent compound (B), the phosphorescent compound (DGR) and the polymer compound of the second composition contained in the second composition of the present invention is 100 parts by weight.

[Antioxidant]

The antioxidant may advantageously be one which is soluble in the same solvent as for the phosphorescent compound (B), the phosphorescent compound (DGR), and the compound of the first composition or the polymer compound of the second composition, and does not disturb light emission and charge transportation, and the examples thereof include phenol-based antioxidants and phosphorus-based antioxidants.

In the first composition of the present invention, the compounding amount of the antioxidant is usually 0.001 to 10 parts by weight when the sum of the phosphorescent compound (B), the phosphorescent compound (DGR) and the compound of the first composition contained in the first composition of the present invention is 100 parts by weight.

In the second composition of the present invention, the compounding amount of the antioxidant is usually 0.001 to 10 parts by weight when the sum of the phosphorescent compound (B), the phosphorescent compound (DGR) and the polymer compound of the second composition contained in the second composition of the present invention is 100 parts by weight.

The antioxidant may be used singly, or two or more antioxidants may be used in combination.

<Film>

The film comprises the first or second composition of the present invention.

The film includes also an insolubilized film obtained by insolubilizing a compound contained in the first or second composition of the present invention in a solvent by cross-linking. The insolubilized film is a film obtained by cross-linking a compound contained in the first or second composition of the present invention by an external stimulus such as heating, irradiation and the like. The insolubilized film can be suitably used for lamination of a light emitting device, because it is substantially insoluble in a solvent.

The temperature of heating for cross-linking the film is usually 25 to 300° C., and is preferably 50 to 250° C., more preferably 150 to 200° C., because external quantum efficiency is excellent.

The light used in irradiation for cross-linking the film is, for example, ultraviolet light, near ultraviolet light or visible light.

The film is suitable as a light emitting layer, a hole transporting layer or a hole injection layer in a light emitting device.

The ink can be fabricated by, for example, a spin coat method, a casting method, a micro gravure coat method, a gravure coat method, a bar coat method, a roll coat method, a wire bar coat method, a dip coat method, a spray coat method, a screen printing method, a flexo printing method, an offset printing method, an inkjet printing method, a capillary coat method or a nozzle coat method by using an ink.

The thickness of the film is usually 1 nm to 10 μm.

<Light Emitting Device>

The light emitting device of the present invention is a light emitting device produced by using the composition of the present invention (the first or second composition of the present invention), and may be a light emitting device comprising the first or second composition of the present invention as it is, or may also be a light emitting device comprising a cross-linked body obtained by intramolecular or intermolecular cross-linking, or by intramolecular and intermolecular cross-linking of a compound contained in the first or second composition of the present invention, and the light emitting device comprising the first or second composition of the present invention as it is preferable.

The constitution of the light emitting device of the present invention has, for example, electrodes consisting of an anode and a cathode, and a layer obtained by using the composition of the present invention disposed between the electrodes.

[Layer Constitution]

The layer obtained by using the composition of the present invention is usually at least one of a light emitting layer, a hole transporting layer, a hole injection layer, an electron transporting layer and an electron injection layer, and preferably is a light emitting layer. These layers comprise a light emitting material, a hole transporting material, a hole injection material, an electron transporting material and an electron injection material, respectively. These layers can be formed by dissolving a light emitting material, a hole transporting material, a hole injection material, an electron transporting material and an electron injection material, respectively, in the solvent described above to prepare inks and by adopting the same method as for film fabrication described above using the inks.

The light emitting device has a light emitting layer between an anode and a cathode. The light emitting device of the present invention preferably has at least one of a hole injection layer and a hole transporting layer between an anode and a light emitting layer from the standpoint of hole injectability and hole transportability, and preferably has at least one of an electron injection layer and an electron transporting layer between a cathode and a light emitting layer from the standpoint of electron injectability and electron transportability.

The materials of a hole transporting layer, an electron transporting layer, a light emitting layer, a hole injection layer and an electron injection layer include the hole transporting material, the electron transporting material, the light emitting material, the hole injection material and the electron injection material described above, respectively, in addition to the composition of the present invention.

When the light emitting device of the present invention has a hole transporting layer, the hole transporting material used for formation of the hole transporting layer is preferably a polymer compound (hereinafter, referred to also as "polymer compound of hole transporting layer") comprising a constitutional unit represented by the formula (X) described above and at least one constitutional unit selected from the group consisting of a constitutional unit represented by the formula (3) and a constitutional unit represented by the formula (4). The polymer compound of a hole transporting layer may further comprise a constitutional unit represented by the formula (Y) described above.

When the light emitting device of the present invention has a hole transporting layer obtained by using the polymer compound of a hole transporting layer, the a hole transporting layer may be a layer comprising the polymer compound of a hole transporting layer as it is, or may also be a layer comprising a cross-linked body obtained by intramolecular or intermolecular cross-linking or by intramolecular and intermolecular cross-linking of the polymer compound of a hole transporting layer, and the layer containing a cross-linked body of the polymer compound of a hole transporting layer is preferable.

The amount of the constitutional unit represented by the formula (X) described above is preferably 1 to 99 mol %, more preferably 10 to 80 mol %, further preferably 20 to 70 mol % with respect to the total amount of constitutional units contained in the polymer compound of a hole transporting layer, because the polymer compound of a hole transporting layer is excellent in hole transportability.

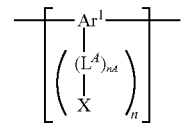

(3)

[wherein, nA represents an integer of 0 to 5, and n represents an integer of 1 to 4.

Ar¹ represents an aromatic hydrocarbon group or a heterocyclic group, and these groups each optionally have a substituent.

$L^A$ represents an alkylene group, a cycloalkylene group, an arylene group, a divalent heterocyclic group, a group represented by —NR'—, an oxygen atom or a sulfur atom, and these groups each optionally have a substituent. R' represents a hydrogen atom, an alkyl group, a cycloalkyl group, an aryl group or a monovalent heterocyclic group, and these groups each optionally have a substituent. When a plurality of $L^A$ are present, they may be the same or different.

X represents a crosslinkable group represented by any of the above-described formulae (B-1) to (B-17). When a plurality of X are present, they may be the same or different.]

nA is preferably an integer of 0 to 3, more preferably an integer of 0 to 2, because the light emitting device of the present invention is more excellent in external quantum efficiency.

n is preferably 1 or 2, more preferably 2, because the light emitting device of the present invention is more excellent in external quantum efficiency.

$Ar^1$ is preferably an aromatic hydrocarbon group which optionally has a substituent, because the light emitting device of the present invention is more excellent in external quantum efficiency.

The number of carbon atoms of the aromatic hydrocarbon group represented by $Ar^1$, not including the number of carbon atoms of a substituent, is usually 6 to 60, preferably 6 to 30, more preferably 6 to 18.

The arylene group portion obtained by removing n substituents of the aromatic hydrocarbon group represented by $Ar^1$ is preferably a group represented by the formula (A-1) to the formula (A-20), more preferably a group represented by the formula (A-1), the formula (A-2), the formula (A-6) to the formula (A-10), the formula (A-19) or the formula (A-20), further preferably a group represented by the formula (A-1), the formula (A-2), the formula (A-7), the formula (A-9) or the formula (A-19).

The number of carbon atoms of the heterocyclic group represented by $Ar^1$, not including the number of carbon atoms of a substituent, is usually 2 to 60, preferably 3 to 30, more preferably 4 to 18.

The divalent heterocyclic group portion obtained by removing n substituents of the heterocyclic group represented by $Ar^1$ is preferably a group represented by the formula (AA-1) to (AA-34).

The aromatic hydrocarbon group and the heterocyclic group represented by $Ar^1$ optionally have a substituent. The substituent which the aromatic hydrocarbon group and the heterocyclic group optionally have includes, for example, an alkyl group, a cycloalkyl group, an alkoxy group, a cycloalkoxy group, an aryl group, an aryloxy group, a halogen atom, a monovalent heterocyclic group and a cyano group.

The number of carbon atoms of the alkylene group represented by $L^A$, not including the number of carbon atoms of a substituent, is usually 1 to 20, preferably 1 to 15, more preferably 1 to 10. The number of carbon atoms of the cycloalkylene group represented by $L^A$, not including the number of carbon atoms of a substituent, is usually 3 to 20.

The alkylene group and the cycloalkylene group each optionally have a substituent, and examples thereof include a methylene group, an ethylene group, a propylene group, a butylene group, a hexylene group, a cyclohexylene group and an octylene group.

The alkylene group and the cycloalkylene group represented by $L^A$ each optionally have a substituent. The substituent which the alkylene group and the cycloalkylene group optionally have includes, for example, an alkyl group, a cycloalkyl group, an alkoxy group, a cycloalkoxy group, a halogen atom and a cyano group.

The arylene group represented by $L^A$ optionally has a substituent. The arylene group is preferably a phenylene group or a fluorenediyl group, more preferably a m-phenylene group, a p-phenylene group, a fluorene-2,7-diyl group or a fluorene-9,9-diyl group. The substituent which the arylene group optionally has includes, for example, an alkyl group, a cycloalkyl group, an alkoxy group, a cycloalkoxy group, an aryl group, an aryloxy group, a monovalent heterocyclic group, a halogen atom, a cyano group and a crosslinkable group selected from Group A of crosslinkable group.

The divalent heterocyclic group represented by $L^A$ is preferably a group represented by the formula (AA-1) to (AA-34).

$L^A$ is preferably an arylene group or an alkylene group, more preferably a phenylene group, a fluorenediyl group or an alkylene group having a number of carbon atoms of 1 to 10, because synthesis of the polymer compound of a hole transporting layer is easy, and these groups each optionally have a substituent.

The crosslinkable group represented by X is preferably a crosslinkable group represented by the formula (B-1) to (B-13), more preferably a crosslinkable group represented by the formula (B-1), (B-3) or (B-9) to (B-13), further preferably a crosslinkable group represented by the formula (B-1) or (B-9), because the polymer compound of a hole transporting layer is excellent in crosslinkability.

The amount of the constitutional unit represented by the formula (3) is preferably 1 to 90 mol %, more preferably 3 to 75 mol %, further preferably 5 to 60 mol % with respect to the total amount of constitutional units contained in the polymer compound of a hole transporting layer, because the polymer compound of a hole transporting layer is excellent in crosslinkability.

The constitutional unit represented by the formula (3) may be contained singly or two or more of the constitutional units may be contained in the polymer compound of a hole transporting layer.

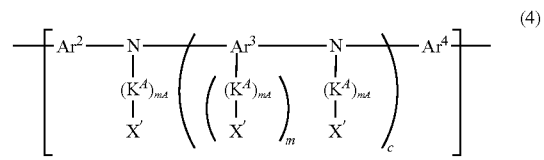

(4)

[wherein, mA represents an integer of 0 to 5, m represents an integer of 1 to 4, and c represents 0 or 1. When a plurality of mA are present, they may be the same or different.

$Ar^3$ represents an aromatic hydrocarbon group, a heterocyclic group, or a group in which at least one aromatic hydrocarbon ring and at least one heterocyclic ring are bonded directly to each other, and these groups each optionally have a substituent.

$Ar^2$ and $Ar^4$ each independently represent an arylene group or a divalent heterocyclic group, and these groups each optionally have a substituent.

Each of $Ar^2$, $Ar^3$ and $Ar^4$ may be bonded directly or via an oxygen atom or a sulfur atom to a group that is different from that group and that is attached to the nitrogen atom to which that group is attached, thereby forming a ring.

$K^A$ represents an alkylene group, a cycloalkylene group, an arylene group, a divalent heterocyclic group, a group represented by —NR"—, an oxygen atom or a sulfur atom, and these groups each optionally have a substituent. R" represents a hydrogen atom, an alkyl group, a cycloalkyl group, an aryl group or a monovalent heterocyclic group, and these groups each optionally have a substituent. When a plurality of $K^A$ are present, they may be the same or different.

X' represents a crosslinkable group represented by any of the above-described formulae (B-1) to (B-17), a hydrogen atom, an alkyl group, a cycloalkyl group, an aryl group or a monovalent heterocyclic group, and these groups each optionally have a substituent. At least one X' is a crosslinkable group represented by any of the above-described formulae (B-1) to (B-17).]

mA is preferably 0 to 2, more preferably 0 or 1, further preferably 0, because the light emitting device of the present invention is more excellent in external quantum efficiency.

m is preferably 1 or 2, more preferably 2, because the light emitting device of the present invention is more excellent in external quantum efficiency.

c is preferably 0, because synthesis of the polymer compound of a hole transporting layer is easy and the light emitting device of the present invention is more excellent in external quantum efficiency.

$Ar^3$ is preferably an aromatic hydrocarbon group which optionally has a substituent, because the light emitting device of the present invention is more excellent in external quantum efficiency.

The definition and examples of the arylene group portion obtained by removing m substituents of the aromatic hydrocarbon group represented by $Ar^3$ are the same as the definition and examples of the arylene group represented by $Ar^{X2}$ in the formula (X) described above.

The definition and examples of the divalent heterocyclic group portion obtained by removing m substituents of the heterocyclic group represented by $Ar^3$ are the same as the definition and examples of the divalent heterocyclic group portion represented by $Ar^{X2}$ in the formula (X) described above.

The definition and examples of the divalent group obtained by removing m substituents of the group obtained by directly bonding at least one aromatic hydrocarbon ring and at least one heterocyclic ring represented by $Ar^3$ are the same as the definition and examples of the divalent group obtained by directly bonding at least one arylene group and at least one divalent heterocyclic group represented by $Ar^{X2}$ in the formula (X) described above.

$Ar^2$ and $Ar^4$ are preferably an arylene group optionally having a substituent, because the light emitting device of the present invention is excellent in luminance life.

The definition and examples of the arylene group represented by $Ar^2$ and $Ar^4$ are the same as the definition and examples of the arylene group represented by $Ar^{X1}$ and $Ar^{X3}$ in the formula (X) described above.

The definition and examples of the divalent heterocyclic group represented by $Ar^2$ and $Ar^4$ are the same as the definition and examples of the divalent heterocyclic group represented by $Ar^{X1}$ and $Ar^{X3}$ in the formula (X) described above.

The group represented by $Ar^2$, $Ar^3$ and $Ar^4$ optionally has a substituent, and the substituent includes an alkyl group, a cycloalkyl group, an alkoxy group, a cycloalkoxy group, an aryl group, an aryloxy group, a halogen atom, a monovalent heterocyclic group and a cyano group.

The definition and examples of the alkylene group, the cycloalkylene group, the arylene group and the divalent heterocyclic group represented by $K^A$ are the same as the definition and examples of the alkylene group, the cycloalkylene group, the arylene group and the divalent heterocyclic group represented by $L^A$, respectively.

$K^A$ is preferably a phenylene group or an alkylene group having a number of carbon atoms of 1 to 10, because synthesis of the polymer compound of a hole transporting layer is easy, and these groups each optionally have a substituent.

The definition and examples of the crosslinkable group represented by X' are the same as the definition and examples of the crosslinkable group represented by X described above.

The amount of the constitutional unit represented by the formula (4) is preferably 1 to 90 mol %, more preferably 3 to 50 mol %, further preferably 5 to 20 mol %, with respect to the total amount of constitutional units contained in the polymer compound of a hole transporting layer, because the polymer compound of a hole transporting layer is excellent in crosslinkability.

The constitutional unit represented by the formula (4) may be contained singly or two or more of the constitutional units may be contained in the polymer compound of a hole transporting layer.

The constitutional unit represented by the formula (3) includes, for example, constitutional units represented by the formula (3-1) to the formula (3-30), and the constitutional unit represented by the formula (4) includes, for example, constitutional units represented by the formula (4-1) to the formula (4-9). Of them, preferable are constitutional units represented by the formula (3-1) to the formula (3-30), more preferable are constitutional units represented by the formula (3-1) to the formula (3-15), the formula (3-19), the formula (3-20), the formula (3-23), the formula (3-25) or the formula (3-30), further preferable are constitutional units represented by the formula (3-1) to the formula (3-13) or the formula (3-30), particularly preferable are constitutional units represented by the formula (3-1) to the formula (3-9) or the formula (3-30), because the polymer compound of a hole transporting layer is excellent in crosslinkability.

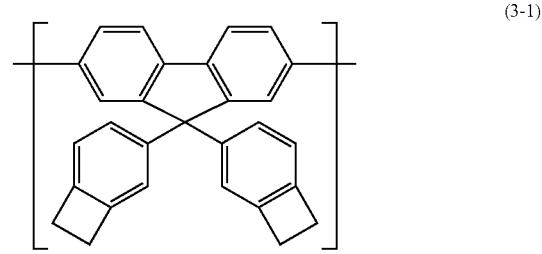

(3-1)

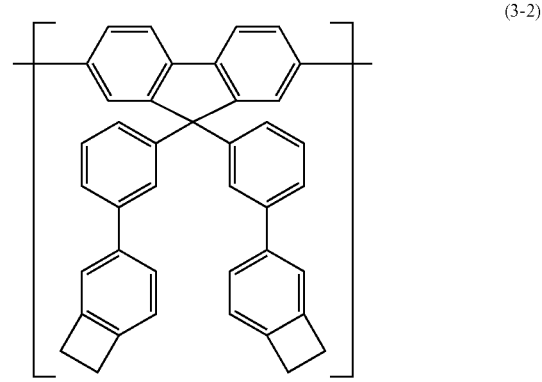

(3-2)

(3-3)
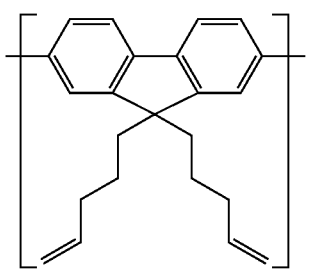
(3-7)
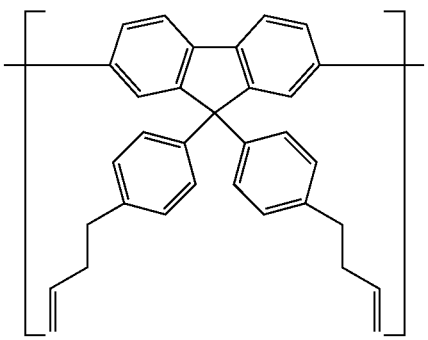
(3-4)
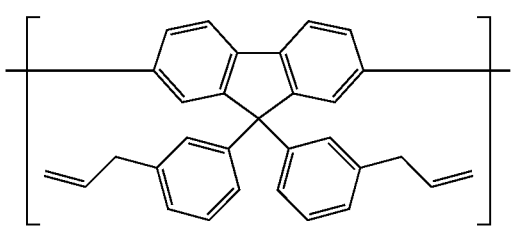
(3-8)
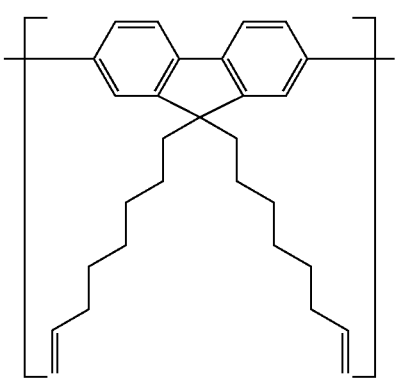
(3-5)
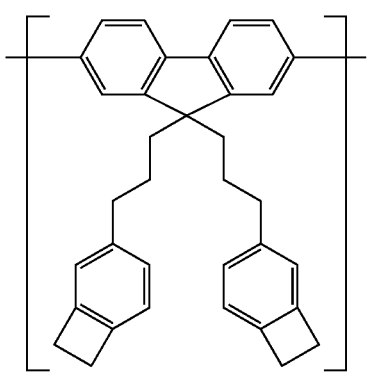
(3-9)
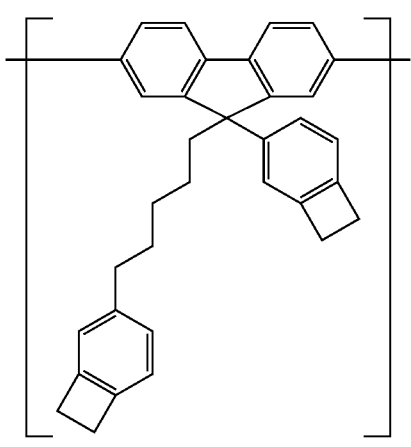
(3-6)
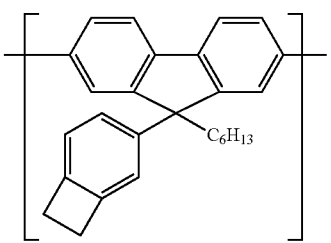
(3-10)

(3-11) 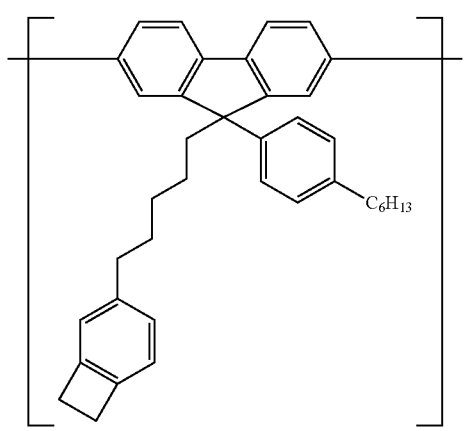
(3-12) 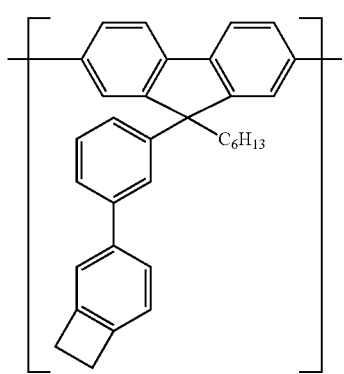
(3-13) 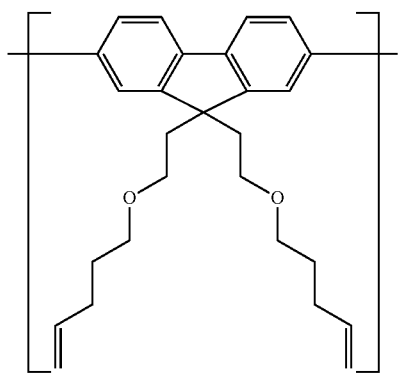
(3-14) 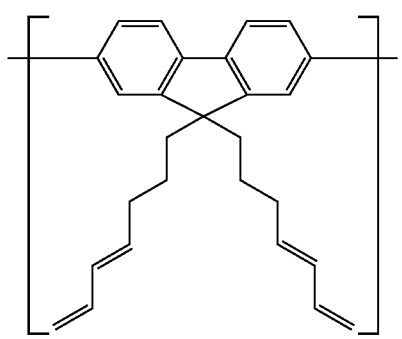
(3-15) 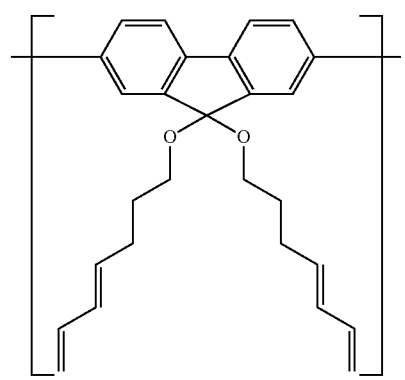
(3-16) 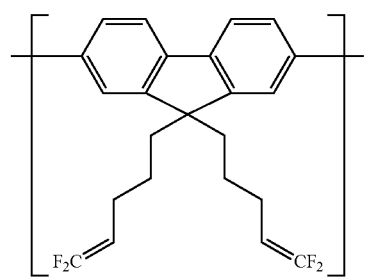
(3-17) 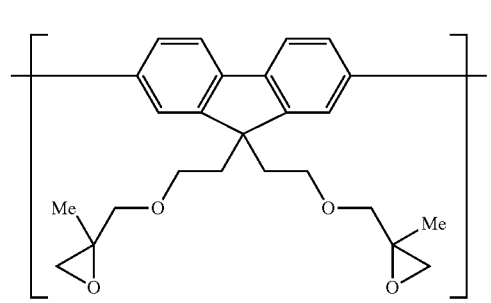
(3-18) 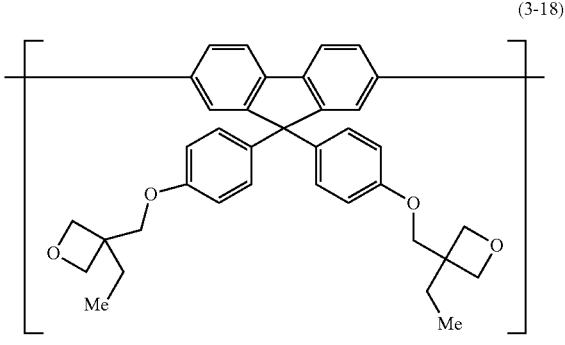

(3-19)
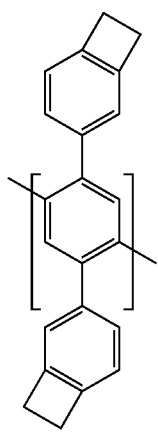
(3-20)
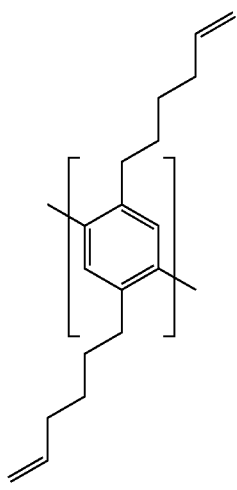
(3-21)
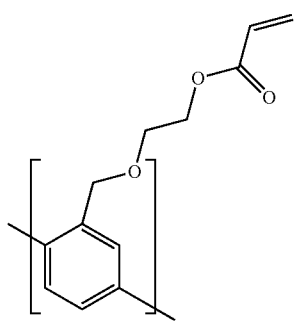
(3-22)
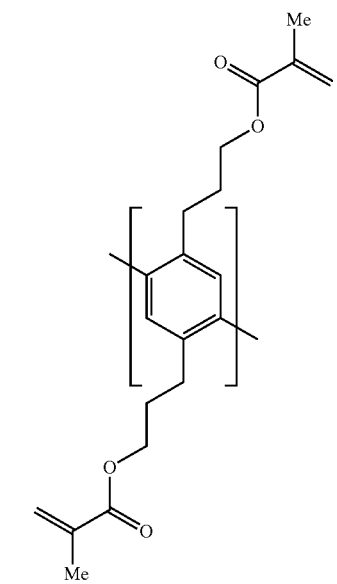
(3-23)
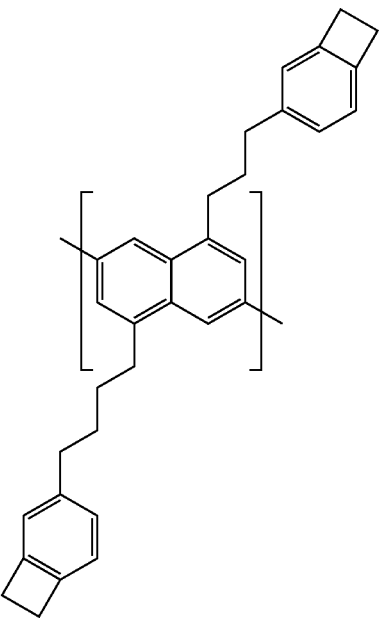

(3-24)
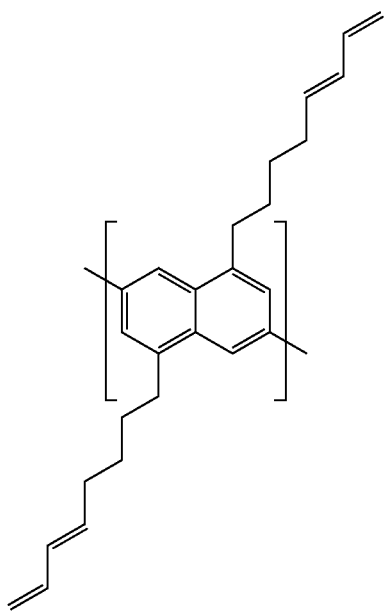
(3-25)
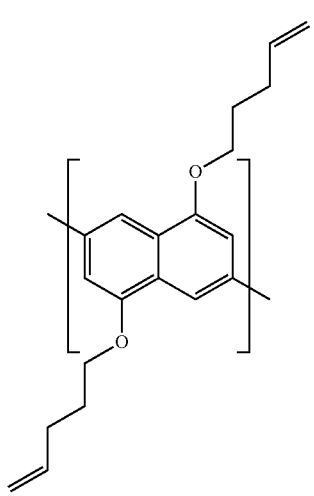
(3-26)
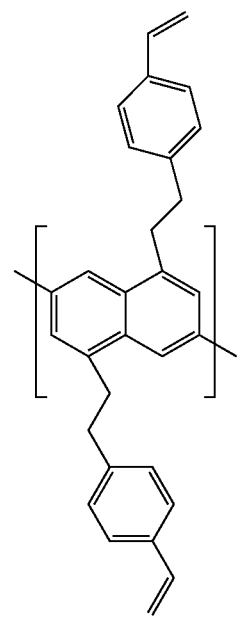
(3-27)
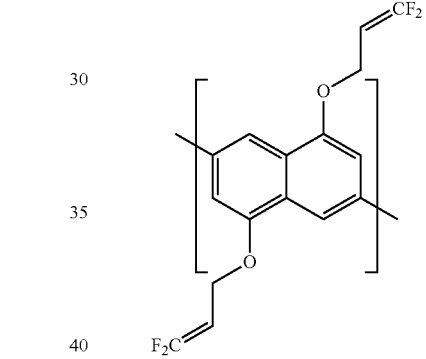
(3-28)
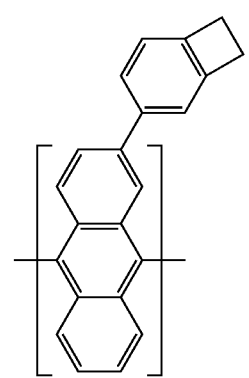
(3-29)
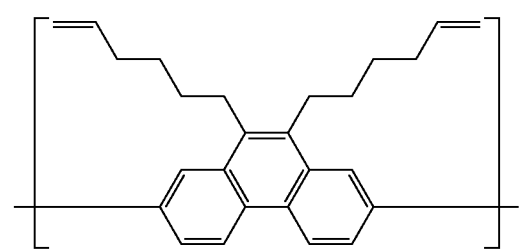

(3-30)
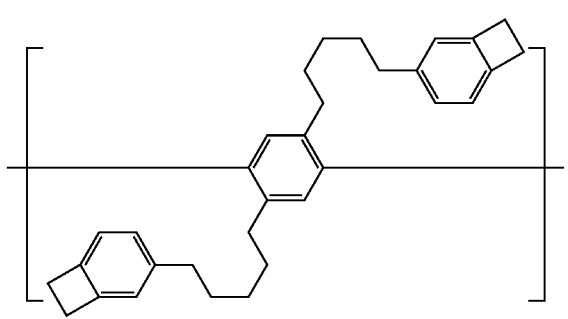
(4-1)
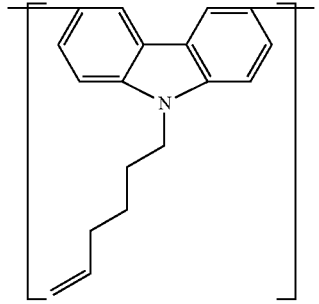
(4-2)
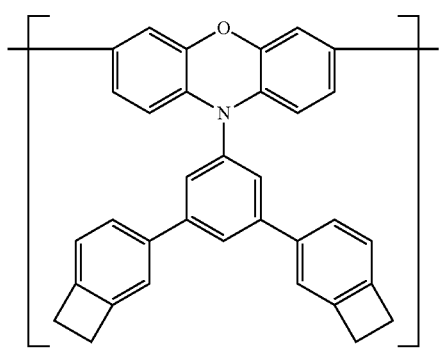
(4-3)
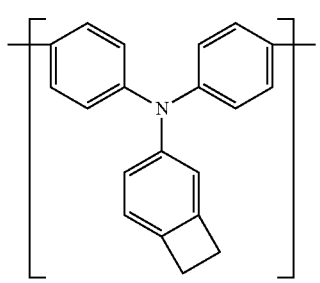
(4-4)
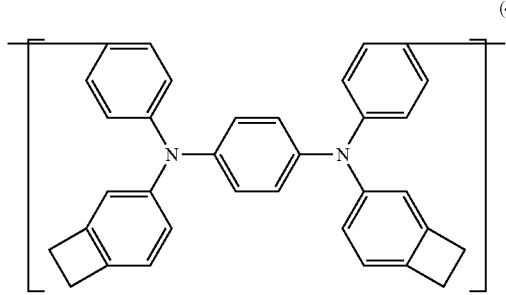
(4-5)
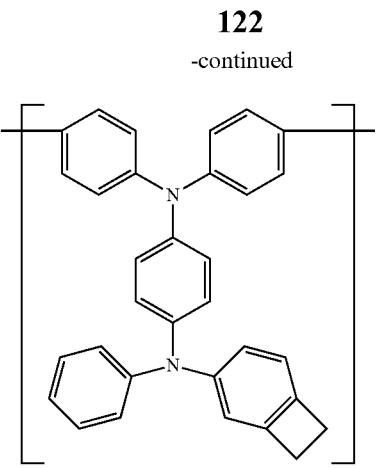
(4-6)
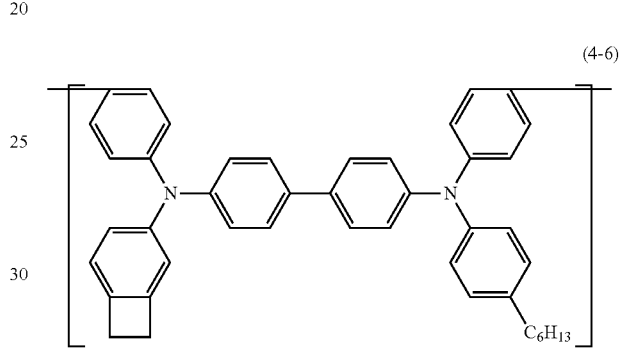
(4-7)
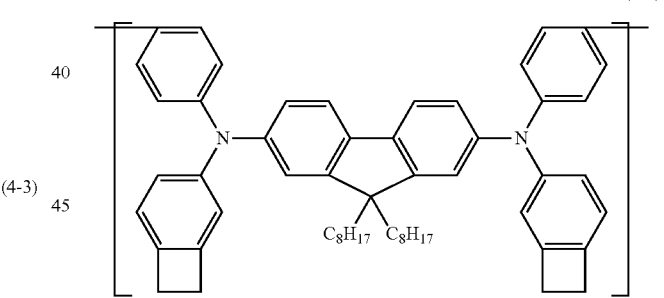
(4-8)
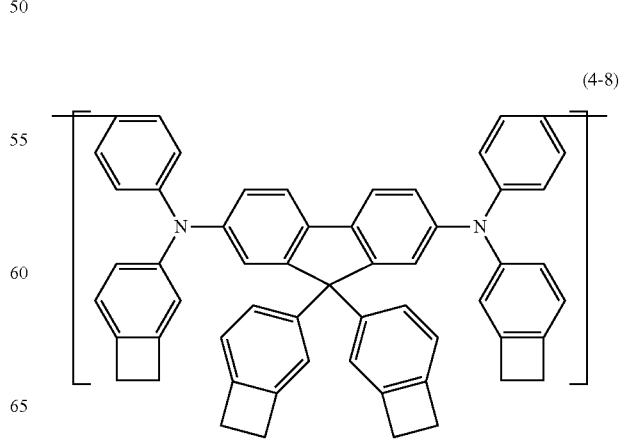

(4-9)

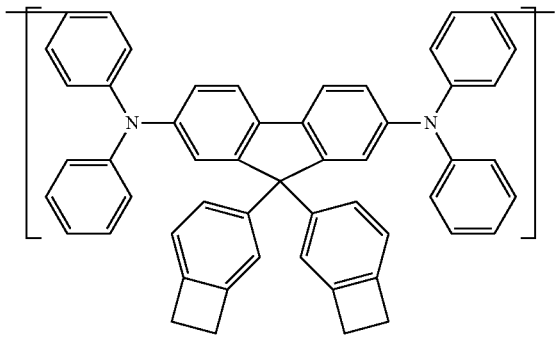

When the light emitting device of the present invention has an electron transporting layer, the electron transporting material used for formation of the electron transporting layer is preferably a polymer compound comprising at least one constitutional unit selected from the group consisting of a constitutional unit represented by the formula (ET-1) and a constitutional unit represented by the formula (ET-2) (hereinafter, referred to also as "polymer compound of electron transporting layer".).

When the light emitting device of the present invention has an electron transporting layer obtained by using the polymer compound of an electron transporting layer, the electron transporting layer may be a layer comprising the polymer compound of an electron transporting layer as it is, or may also be a layer comprising a cross-linked body obtained by intramolecular or intermolecular cross-linking or intramolecular and intermolecular cross-linking of the polymer compound of an electron transporting layer, and the layer comprising the polymer compound of an electron transporting layer as it is preferable.

(ET-1)

[wherein, nE1 represents an integer of 1 or more.

$Ar^{E1}$ represents an aromatic hydrocarbon group or a heterocyclic group, and these groups each optionally have a substituent other than $R^{E1}$.

$R^{E1}$ represents a group represented by the formula (ES-1). When a plurality of $R^{E1}$ are present, they may be the same or different.]

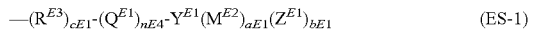
(ES-1)

[wherein, cE1 represents 0 or 1, nE4 represents an integer of 0 or more, aE1 represents an integer of 1 or more, and bE1 represents an integer of 0 or more.

$R^{E3}$ represents an arylene group or a divalent heterocyclic group, and these groups each optionally have a substituent.

$Q^{E1}$ represents an alkylene group, an arylene group, an oxygen atom or a sulfur atom, and these groups each optionally have a substituent. When a plurality of $Q^{E1}$ are present, they may be the same or different.

$Y^{E1}$ represents $-CO_2^-$, $-SO_3^-$, $-SO_2^-$ or $PO_3^{2-}$.

$M^{E2}$ represents a metal cation or an ammonium cation, and this ammonium cation optionally has a substituent. When a plurality of $M^{E2}$ are present, they may be the same or different.

$Z^{E1}$ represents $F^-$, $Cl^-$, $Br^-$, $I^-$, $OH^-$, $R^{E4}SO_3^-$, $R^{E4}COO^-$, $ClO^-$, $ClO_2^-$, $ClO_3^-$, $ClO_4^-$, $SCN^-$, $CN^-$, $NO_3^-$, $SO_4^{2-}$, $HSO_4^-$, $PO_4^{3-}$, $HPO_4^{2-}$, $H_2PO_4^-$, $BF_4^-$ or $PF_6^-$. $R^{E4}$ represents an alkyl group, a cycloalkyl group or an aryl group, and these groups each optionally have a substituent. When a plurality of $Z^{E1}$ are present, they may be the same or different.

aE1 and bE1 are selected so that the charge of the group represented by the formula (ES-1) is 0.]

nE1 is preferably an integer of 1 to 4, more preferably 1 or 2.

The aromatic hydrocarbon group or the heterocyclic group represented by $Ar^{E1}$ is preferably an atomic group remaining after removing from a 1,4-phenylene group, a 1,3-phenylene group, a 1,2-phenylene group, a 2,6-naphthalenediyl group, a 1,4-naphthalenediyl group, a 2,7-fluorenediyl group, a 3,6-fluorenediyl group, a 2,7-phenanthrenediyl group or a 2,7-carbazolediyl group nE1 hydrogen atoms bonding directly to atoms constituting the ring, and optionally has a substituent other than $R^{E1}$.

The substituent other than $R^{E1}$ which $Ar^{E1}$ optionally has includes a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group, a cycloalkynyl group, a carboxyl group, and a group represented by the formula (ES-3).

(ES-3)

[wherein, n', m' and nx represent an integer of 1 or more.]

cE1 is preferably 0 or 1, and nE4 is preferably an integer of 0 to 6.

$R^{E3}$ is preferably an arylene group.

$Q^{E1}$ is preferably an alkylene group, an arylene group or an oxygen atom.

$Y^{E1}$ is preferably $-CO_2^-$ or $SO_3^-$.

$M^{E2}$ is preferably $Li^+$, $Na^+$, $K^+$, $Cs^+$, $N(CH_3)_4^+$, $NH(CH_3)_3^+$, $NH_2(CH_3)_2^+$ or $N(C_2H_5)_4^+$.

$Z^{E1}$ is preferably $F^-$, $Cl^-$, $Br^-$, $I^-$, $OH^-$, $R^{E4}SO_3^-$ or $R^{E4}COO^-$.

The substituent which $R^{E3}$ optionally has includes an alkyl group, a cycloalkyl group, an aryl group, a monovalent heterocyclic group arid a group represented by the formula (ES-3). It is preferable that $R^{E3}$ has a group represented by the formula (ES-3) as a substituent, because the light emitting device of the present invention is more excellent in external quantum efficiency.

The group represented by the formula (ES-1) includes, for example, groups represented by the following formulae.

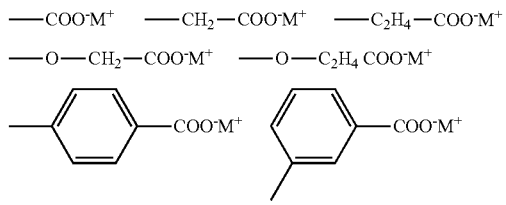

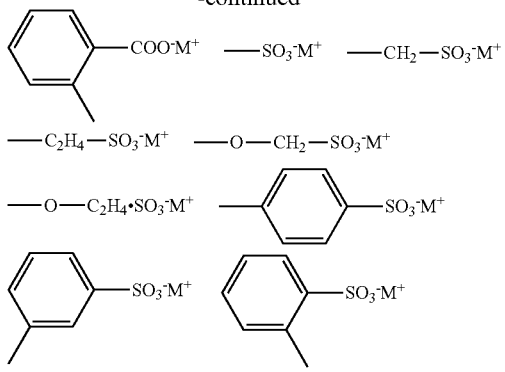

[wherein, M⁺ represents Li⁺, Na⁺, K⁺, Cs⁺, N(CH₃)₄⁺, NH(CH₃)₃⁺, NH₂(CH₃)₂⁺ or N(C₂H₅)₄⁺.]

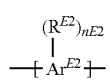 (ET-2)

[wherein, nE2 represents an integer of 1 or more.

$Ar^{E2}$ represents an aromatic hydrocarbon group or a heterocyclic group, and these groups each optionally have a substituent other than $R^{E2}$.

$R^{E2}$ represents a group represented by the formula (ES-2). When a plurality of $R^{E2}$ are present, they may be the same or different.]

—$(R^{E6})_{cE2}$-$(Q^{E2})_{nE6}$-$Y^{E2}(M^{E3})_{bE2}(Z^{E2})_{aE2}$ (ES-2)

[wherein, cE2 represents 0 or 1, nE6 represents an integer of 0 or more, bE2 represents an integer of 1 or more, and aE2 represents an integer of 0 or more.

$R^{E6}$ represents an arylene group or a divalent heterocyclic group, and these groups each optionally have a substituent.

$Q^{E2}$ represents an alkylene group, an arylene group, an oxygen atom or a sulfur atom, and these groups each optionally have a substituent. When a plurality of $Q^{E2}$ are present, they may be the same or different.

$Y^{E2}$ represents a carbocation, an ammonium cation, a phosphonyl cation or a sulfonyl cation.

$M^{E3}$ represents F⁻, Cl⁻, Br⁻, I⁻, OH⁻, $R^{E7}SO_3^-$, $R^{E7}COO^-$, ClO⁻, ClO₂⁻, ClO₃⁻, ClO₄⁻, SCN⁻, CN⁻, NO₃⁻, SO₄²⁻, HSO₄⁻, PO₄³⁻, HPO₄²⁻, H₂PO₄⁻, tetraphenyl borate, BF₄⁻ or PF₆⁻. $R^{E7}$ represents an alkyl group, a perfluoroalkyl group or an aryl group, and these groups each optionally have a substituent. When a plurality of $M^{E3}$ are present, they may be the same or different.

$Z^{E2}$ represents a metal ion or an ammonium ion, and this ammonium ion optionally has a substituent. When a plurality of $Z^{E2}$ are present, they may be the same or different.

aE2 and bE2 are selected so that the charge of the group represented by the formula (ES-2) is 0.]

nE2 is preferably an integer of 1 to 4, more preferably 1 or 2.

The aromatic hydrocarbon group or the heterocyclic group represented by $Ar^{E2}$ is preferably an atomic group remaining after removing from a 1,4-phenylene group, a 1,3-phenylene group, a 1,2-phenylene group, a 2,6-naphthalenediyl group, a 1,4-naphthalenediyl group, a 2,7-fluorenediyl group, a 3,6-fluorenediyl group, a 2,7-phenanthrenediyl group or a 2,7-carbazolediyl group nE2 hydrogen atoms bonding directly to atoms constituting the ring, and optionally has a substituent other than $R^{E2}$.

The substituent other than $R^{E2}$ which $Ar^{E2}$ optionally has is the same as the substituent other than $R^{E1}$ which $Ar^{E1}$ optionally has.

cE2 is preferably 0 or 1, and nE6 is preferably an integer of 0 to 6.

$R^{E6}$ is preferably an arylene group.

$Q^{E2}$ is preferably an alkylene group, an arylene group or an oxygen atom.

$Y^{E2}$ is preferably a carbocation or an ammonium cation.

$M^{E3}$ is preferably F⁻, Cl⁻, Br⁻, I⁻, tetraphenyl borate, $CF_3SO_3^-$ or $CH_3COO^-$.

$Z^{E2}$ is preferably Li⁺, Na⁺, K⁺, Cs⁺, N(CH₃)₄⁺, NH(CH₃)₃⁺, NH₂(CH₃)₂⁺ or N(C₂H₅)₄⁺.

The substituent which $R^{E6}$ optionally has includes an alkyl group, a cycloalkyl group, an aryl group, a monovalent heterocyclic group and a group represented by the formula (ES-3). It is preferable that $R^{E6}$ has a group represented by the formula (ES-3) as a substituent, because the light emitting device of the present invention is more excellent in external quantum efficiency.

The group represented by the formula (ES-2) includes, for example, groups represented by the following formulae.

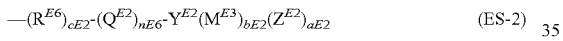
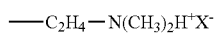
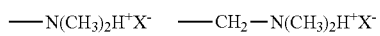
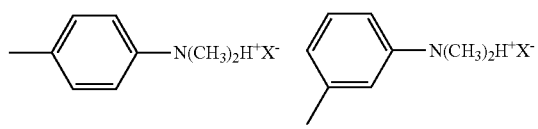
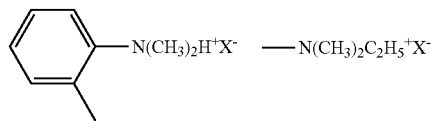
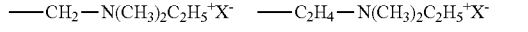
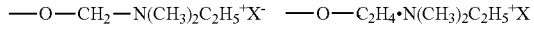
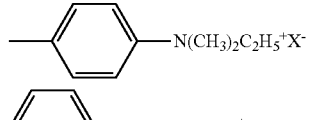
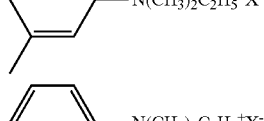

[wherein, X⁻ represents F⁻, Cl⁻, Br⁻, I⁻, tetraphenyl borate, $CF_3SO_3^-$ or $CH_3COO^-$.]

The constitutional unit represented by the formula (ET-1) and the formula (ET-2) includes, for example, constitutional units represented by the formula (ET-31) to the formula (ET-34) described below.

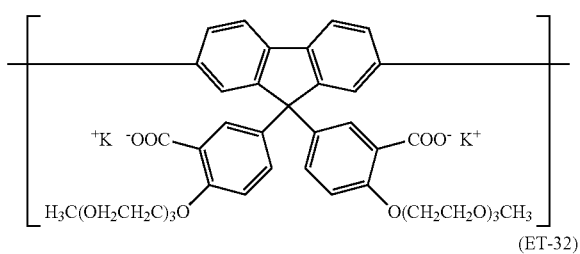

(ET-31)

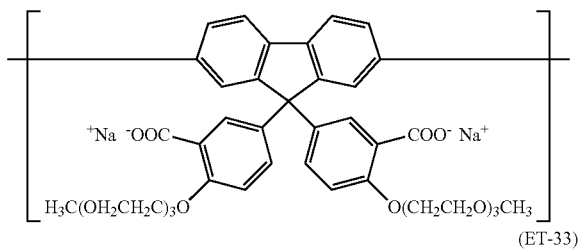

(ET-32)

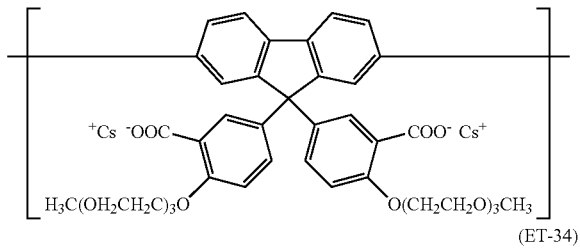

(ET-33)

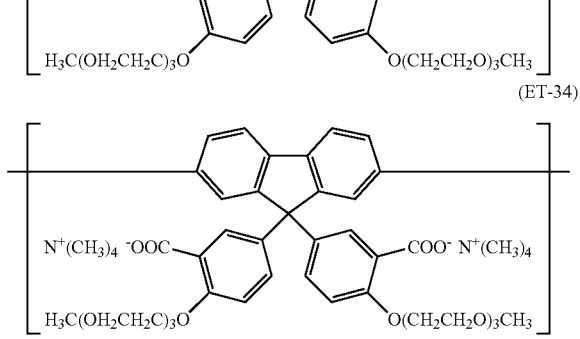

(ET-34)

When the material of a hole transporting layer, the material of an electron transporting layer and the material of a light emitting layer are dissolvable in a solvent used in forming layers adjacent to a hole transporting layer, an electron transporting layer and a light emitting layer, respectively, in fabrication of a light emitting device, it is preferable that the materials have a crosslinkable group for avoiding dissolution of the materials in the solvent. After forming each layer using the material having a crosslinkable group, the crosslinkable group can be cross-linked to insolubilize the layer.

The method of forming a layer such as a light emitting layer, a hole transporting layer, an electron transporting layer, a hole injection layer and an electron injection layer in the light emitting device of the present invention includes, for example, a method of vacuum vapor deposition from a powder and a method by film formation from solution or melted state when a low molecular weight compound is used, and, for example, a method by film formation from solution or melted state when a polymer compound is used.

The order, the number and the thickness of layers to be laminated are regulated in view of external quantum efficiency and luminance life.

[Substrate/Electrode]

The substrate in the light emitting device may advantageously be a substrate on which an electrode can be formed and which does not chemically change in forming an organic layer, and is a substrate made of a material such as, for example, glass, plastic and silicon. In the case of an opaque substrate, it is preferable that an electrode most remote from the substrate is transparent or semi-transparent.

The material of the anode includes, for example, electrically conductive metal oxides and semi-transparent metals, preferably, indium oxide, zinc oxide and tin oxide; electrically conductive compounds such as indium.tin.oxide (ITO) and indium.zinc.oxide; a composite of silver, palladium and copper (APC); NESA, gold, platinum, silver and copper.

The material of the cathode includes, for example, metals such as lithium, sodium, potassium, rubidium, cesium, beryllium, magnesium, calcium, strontium, barium, aluminum, zinc and indium; alloys composed of two or more of them; alloys composed of one or more of them and at least one of silver, copper, manganese, titanium, cobalt, nickel, tungsten and tin; and graphite and graphite intercalation compounds. The alloy includes, for example, a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy.

The anode and the cathode may each take a lamination structure composed of two or more layers.

[Use]

For producing planar light emission by using a light emitting device, a planar anode and a planar cathode are disposed so as to overlap with each other. Patterned light emission can be produced by a method of placing a mask with a patterned window on the surface of a planer light emitting device, a method of forming an extremely thick layer intended to be a non-light emitting, thereby having the layer essentially no-light emitting or a method of forming an anode, a cathode or both electrodes in a patterned shape. By forming a pattern with any of these methods and disposing certain electrodes so as to switch ON/OFF independently, a segment type display capable of displaying numbers and letters and the like is provided. For producing a dot matrix display, both an anode and a cathode are formed in a stripe shape and disposed so as to cross with each other. Partial color display and multi-color display are made possible by a method of printing separately certain polymer compounds showing different emission or a method of using a color filter or a fluorescence conversion filter. The dot matrix display can be passively driven, or actively driven combined with TFT and the like. These displays can be used in computers, television sets, portable terminals and the like. The planar light emitting device can be suitably used as a planer light source for backlight of a liquid crystal display or as a planar light source for illumination. If a flexible substrate is used, it can be used also as a curved light source and a curved display.

EXAMPLES

The present invention will be illustrated further in detail by examples below, but the present invention is not limited to these examples.

In the present examples, the polystyrene-equivalent number average molecular weight (Mn) and the polystyrene-equivalent weight average molecular weight (Mw) of a polymer compound were measured by size exclusion chromatography (SEC) (manufactured by Shimadzu Corp., trade name: LC-10Avp). SEC measurement conditions are as described below.

[Measurement Condition]

The polymer compound to be measured was dissolved in tetrahydrofuran at a concentration of about 0.05 wt %, and 10 µL of the solution was injected into SEC. As the mobile phase of SEC, tetrahydrofuran was used and allowed to flow at a flow rate of 2.0 mL/min. As the column, PLgel MIXED-B (manufactured by Polymer Laboratories) was used. As the detector, UV-VIS detector (manufactured by Shimadzu Corp., trade name: SPD-10Avp) was used.

Measurement of LC-MS was carried out according to the following method.

A measurement sample was dissolved in chloroform or tetrahydrofuran so as to give a concentration of about 2 mg/mL, and about 1 µL of the solution was injected into LC-MS (manufactured by Agilent Technologies, tradename: 1100LCMSD). As the mobile phase of LC-MS, acetonitrile and tetrahydrofuran were used while changing the ratio thereof and allowed to flow at a flow rate of 0.2 mL/min. As the column, L-column 2 ODS (3 µm) (manufactured by Chemicals Evaluation and Research Institute, internal diameter: 2.1 mm, length: 100 mm, particle size: 3 µm) was used.

Measurement of NMR was carried out according to the following method.

5 to 10 mg of a measurement sample was dissolved in about 0.5 mL of deuterated chloroform ($CDCl_3$), deuterated tetrahydrofuran (THF-$d_8$), deuterated dimethyl sulfoxide (DMSO-$d_6$) or deuterated methylene chloride ($CD_2Cl_2$), and measurement was performed using an NMR apparatus (manufactured by Agilent, trade name: INOVA 300 or MERCURY 400VX).

As the index of the purity of a compound, a value of the high performance liquid chromatography (HPLC) area percentage was used. This value is a value in high performance liquid chromatography (HPLC, manufactured by Shimadzu Corp., trade name: LC-20A) at 254 nm, unless otherwise stated. In this operation, the compound to be measured was dissolved in tetrahydrofuran or chloroform so as to give a concentration of 0.01 to 0.2 wt %, and depending on the concentration, 1 to 10 µL of the solution was injected into HPLC. As the mobile phase of HPLC, acetonitrile and tetrahydrofuran were used and allowed to flow at a flow rate of 1 mL/min as gradient analysis of acetonitrile/tetrahydrofuran=100/0 to 0/100 (volume ratio). As the column, Kaseisorb LC ODS 2000 (manufactured by Tokyo Chemical Industry Co., Ltd.) or an ODS column having an equivalent performance was used. As the detector, a photo diode array detector (manufactured by Shimadzu Corp., trade name: SPD-M20A) was used.

In the present examples, the emission spectrum maximum peak wavelength of a phosphorescent compound was measured by a spectrophotometer (manufactured by JASCO Corporation, FP-6500) at room temperature. A phosphorescent compound was dissolved in xylene at a concentration of about $0.8 \times 10^{-4}$ wt % and the resultant xylene solution was used as a sample. As the excitation light, UV light having a wavelength of 325 nm was used.

Synthesis Example 1

Synthesis of Compound B1

The compound B1 was synthesized according to a method described in JP-A No. 2013-147450.

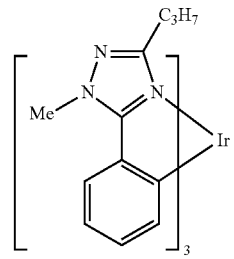

Compound B1

The compound B1 had an emission spectrum the maximum peak wavelength of which was 450 nm.

Synthesis Example 2

Synthesis of Compound B2

The compound B2 was synthesized according to a method described in JP-A No. 2012-36381.

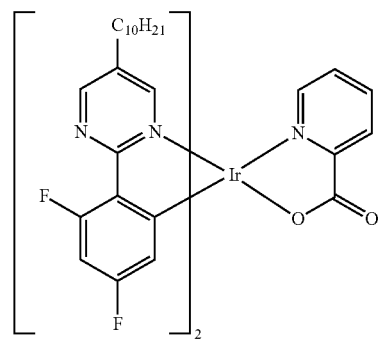

Compound B2

The compound B2 had an emission spectrum the maximum peak wavelength of which was 472 nm.

Synthesis Example 3

Synthesis of Compound B3

The compound B3 was synthesized according to a method described in International Publication WO2006/121811.

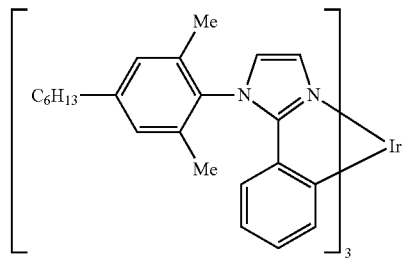

Compound B3

The compound B3 had an emission spectrum the maximum peak wavelength of which was 469 nm.

Synthesis Example 4

Synthesis of Compound B4

The compound B4 was synthesized according to a method described in International Publication WO2006/121811 and JP-A No. 2013-048190.

Compound B4

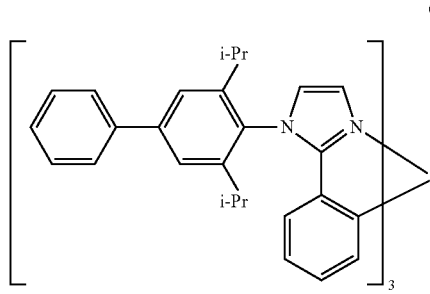

The compound B4 had an emission spectrum the maximum peak wavelength of which was 471 nm.

Synthesis Example 5

Synthesis of Compound G1

The compound G1 was synthesized according to a method described in JP-A No. 2013-237789.

Compound G1

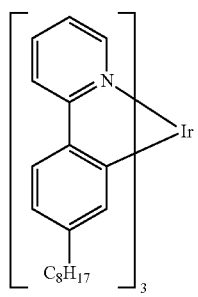

The compound G1 had an emission spectrum the maximum peak wavelength of which was 508 nm.

Synthesis Example 6

Synthesis of Compound G2

The compound G2 was synthesized according to a method described in JP-A No. 2006-188673.

Compound G2

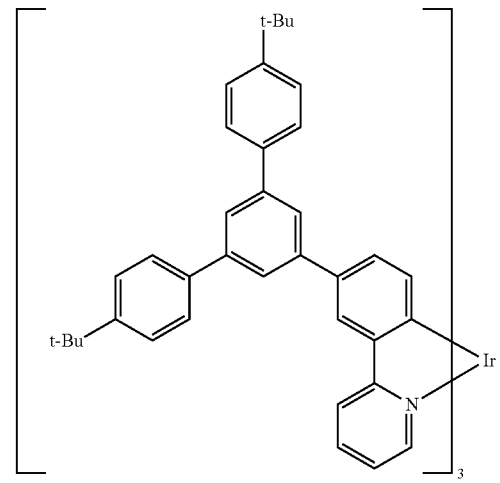

The compound G2 had an emission spectrum the maximum peak wavelength of which was 514 nm.

Synthesis Example 7

Synthesis of Compound S1

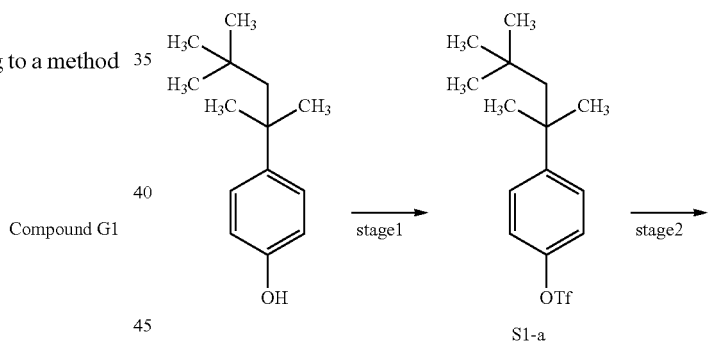

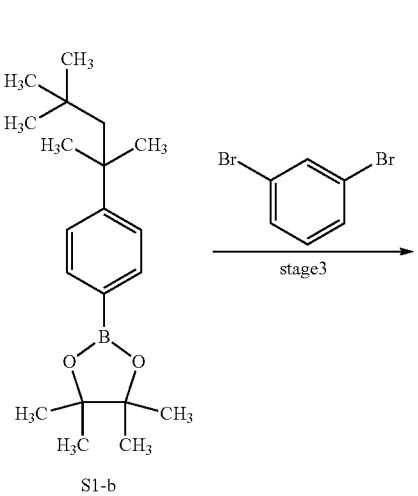

-continued

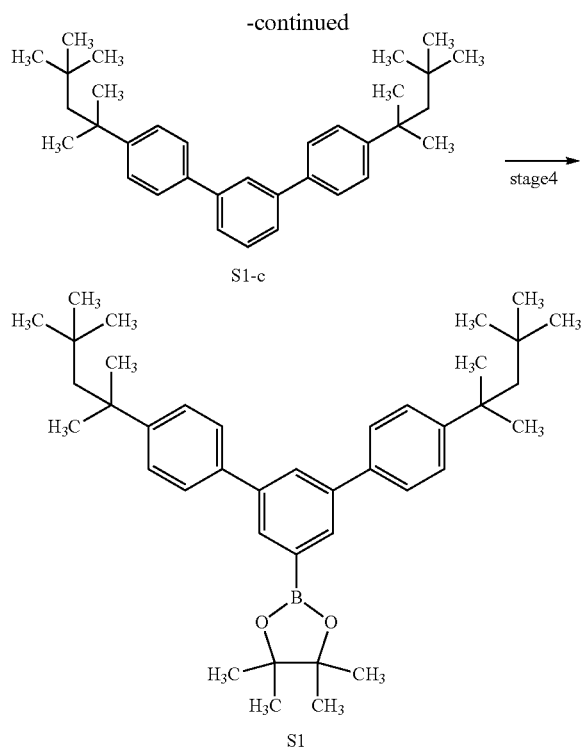

<Stage 1>

The atmosphere in a reaction vessel was turned into a nitrogen gas stream, then, 4-tert-octylphenol (250.00 g, 1.21 mol, manufactured by Aldrich), N,N-dimethyl-4-aminopyridine (177.64 g, 1.45 mol) and dichloromethane (3100 mL) were added, and this mixture was cooled down to 5° C. with ice. Thereafter, trifluoromethanesulfonic anhydride (376.06 g, 1.33 mol) was dropped into this over a period of 45 minutes. After completion of dropping, the mixture was stirred for 30 minutes under ice cool, then, returned to room temperature and further stirred for 1.5 hours. To the resultant reaction mixture was added hexane (3100 mL), and this reaction mixture was filtrated using 410 g of silica gel, and further, the silica gel was washed with a mixed solvent (2.5 L) of hexane/dichloromethane (1/1 (by volume)). The resultant filtrate and the wash solution were concentrated, to obtain a compound S1-a (410.94 g, 1.21 mol, LC purity: 99.7%) as a colorless oil.

<Stage 2>

The atmosphere in a reaction vessel was turned into a nitrogen gas stream, then, the compound S1-a (410.94 g, 1.21 mol), bis(pinacolato)diboron (338.47 g, 1.33 mol), potassium acetate (237.83 g, 2.42 mol), 1,4-dioxane (2600 mL), palladium acetate (4.08 g, 0.018 mol) and tricyclohexylphosphine (10.19 g, 0.036 mol) were added, and the mixture was refluxed for 2 hours. After cooling down to room temperature, the resultant reaction mixture was filtrated and the filtrate was collected, and further, the filtrated substance was washed with 1,4-dioxane (2.5 L), and the resultant filtrate and the wash solution were concentrated. The resultant residue was dissolved into a mixed solvent of hexane/dichloromethane (1/1 (by volume)), and the solution was filtrated using 770 g silica gel, and further, the silica gel was washed with a mixed solvent (2.5 L) of hexane/dichloromethane (1/1 (by volume)). The resultant filtrate and the wash solution were concentrated, and to the resultant residue was added methanol (1500 mL), and the mixture was ultrasonically cleaned for 30 minutes. Thereafter, this was filtrated to obtain a compound S1-b (274.27 g). The filtrate and the wash solution were concentrated, and methanol was added, and the mixture was ultrasonically cleaned and filtrated, and such an operation was repeated, to obtain a compound S1-b (14.29 g). The total yielded amount of the resultant compound S1-b was 288.56 g.

<Stage 3>

The atmosphere in a reaction vessel was turned into a nitrogen gas stream, then, 1,3-dibromobenzene (102.48 g, 0.434 mol), the compound S1-b (288.56 g, 0.912 mol), toluene (2100 mL), a 20 wt % tetraethyl ammonium hydroxide aqueous solution (962.38 g, 1.31 mol) and bis(triphenylphosphine)palladium(II) dichloride (3.04 g, 0.004 mol) were added, and the mixture was refluxed for 7 hours. After cooling down to room temperature, the aqueous layer and the organic layer were separated, and the organic layer was collected. To this aqueous layer was added toluene (1 L), and the organic layer was further extracted. The resultant organic layers were combined, and this mixture was washed with a mixed aqueous solution of distilled water/saturated saline (1.5 L/1.5 L). The resultant organic layer was filtrated through 400 g silica gel, and further, the silica gel was washed with toluene (2 L). The resultant solution was concentrated, and the resultant residue was dissolved in hexane. This solution was purified by silica gel column chromatography. Impurities were eluted with a developing solvent hexane, then, developed with a mixed solvent of hexane/dichloromethane (10/1 (by volume)). The each resultant fraction was concentrated under reduced pressure to remove the solvent, obtaining a colorless crystalline compound S1-c (154.08 g, LC purity: 99.1%) and a coarse compound S1-c (38.64 g, LC purity: 83%). This coarse compound S1-c was column-purified again under the same developing conditions, and the solvent was distilled off under reduced pressure, to obtain a compound S1-c (28.4 g, LC purity: 99.6%). The total yielded amount the resultant compound S1-c was 182.48 g (0.40 mol).

<Stage 4>

The atmosphere in a reaction vessel was turned into a nitrogen gas stream, then, the compound S1-c (182.48 g, 0.401 mol), bis(pinacolato)diboron (112.09 g, 0.441 mol), 4,4'-di-tert-butyl-2,2'-dipyridyl (3.23 g, 0.012 mol), cyclohexane (2000 mL) and bis(1,5-cyclooctadiene)di-μ-methoxydiiridium(I) (3.99 g, 0.006 mol) were added, and the mixture was refluxed for 2 hours. After cooling with air down to room temperature, silica gel (220 g) was added over a period of 20 minutes while stirring the resultant reaction mixture. The resultant suspension was filtrated through 440 g of silica gel, and further, the silica gel was washed with dichloromethane (2 L), and the solution was concentrated. To the resultant residue were added methanol (1100 mL) and dichloromethane (110 mL), and the mixture was refluxed for 1 hour. After cooling down to room temperature, this was filtrated. The resultant filtrated substance was washed with methanol (500 mL), and the resultant solid was dried, to obtain a compound S1 (220.85 g, 0.380 mol).

$^1$H-NMR (CDCl$_3$, 300 MHz): δ (ppm)=8.00 (d, J=1.8 Hz, 2H), 7.92 (t, J=1.9 Hz, 1H), 7.60 (d, J=8.5 Hz, 4H), 7.44 (t, J=8.5 Hz, 4H), 1.78 (s, 4H), 1.41 (s, 12H), 1.37 (s, 12H), 0.75 (s, 18H).

Synthesis Example 8

Synthesis of Compound G3

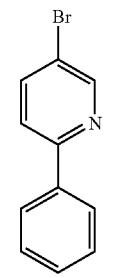

Compound G3a

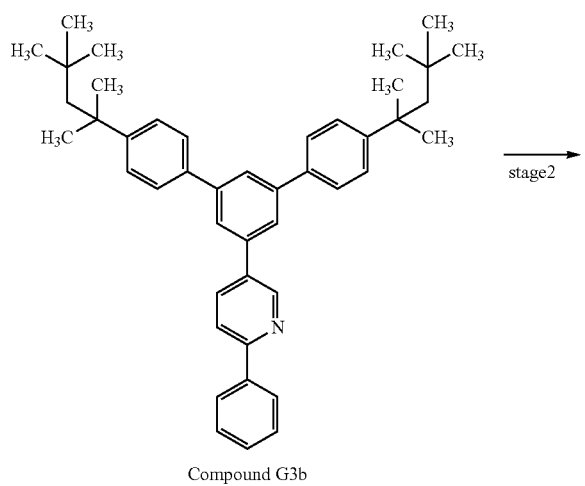

Compound G3b

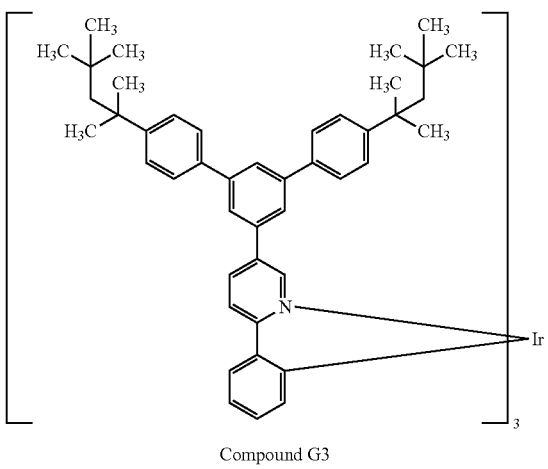

Compound G3

<Stage 1>

The atmosphere in a reaction vessel was turned into an argon gas atmosphere, then, a compound G3a (36.17 g) synthesized according to a method described in JP-A No. 2008-179617, the compound S1 (94.20 g), toluene (1545 mL), a 20 wt % tetraethyl ammonium hydroxide aqueous solution (341.28 g) and tetrakis(triphenylphosphine)palladium(0) (8.927 g) were added, and the mixture was stirred for 4 hours at 80° C. After cooling down to room temperature, to the resultant reaction solution was added water (1545 mL), and the organic layer was extracted. The resultant organic layer was washed with water (1545 mL) twice, and with saline (1545 mL) once. The resultant organic layer was filtrated using 188 g of silica gel. The resultant filtrate was concentrated under reduced pressure. To the resultant residue were added toluene (235 g) and methanol (1174 g), and the mixture was heated at 60° C. for 30 minutes. Thereafter, this was cooled down to 5° C. by an ice bath, to cause deposition of a solid. The resultant solid was filtrated, and washed with cold methanol. The resultant solid was dried under reduced pressure, to obtain a compound G3b (82.0 g) represented by the above-described formula.

<Stage 2>

The atmosphere in a reaction vessel was turned into a nitrogen gas atmosphere, then, iridium chloride trihydrate (11.51 g) and ion-exchange water (114 mL) were added, and these were dissolved by heating at 50° C. Into another reaction vessel having a nitrogen gas atmosphere were added the compound G3b (43.80 g), 2-ethoxyethanol (792 mL) and ion-exchange water (57 mL), and the mixture was stirred for 1 hour with heating at 100° C. Thereafter, into this solution, an iridium chloride aqueous solution (total amount) prepared previously was dropped slowly. After completion of dropping, the mixture was stirred for 15 hours at 120° C. After cooling down to room temperature, to the resultant reaction mixture was added methanol (207 g), and the mixture was filtrated. The resultant solid was washed with methanol (207 g) four times, and with hexane (115 g) once. The resultant solid was dried under reduced pressure, to obtain an intermediate G3 (42.88 g).

The atmosphere in a reaction vessel was turned into a nitrogen gas atmosphere, then, the intermediate G3 (7.61 g), the compound G3b (16.05 g), silver trifluoromethanesulfonate (1.63 g) and diethylene glycol dimethyl ether (79 mL) were added, and the mixture was stirred for 16 hours at 160° C. After cooling down to room temperature, to the resultant reaction mixture was added methanol (304 mL), and the generated precipitate was filtrated. The resultant precipitate was purified by silica gel column chromatography (a mixed solvent of hexane/toluene=4/6.5 (by volume)), and the solvent was removed under reduced pressure. The resultant residue (8.05 g) was dissolved in dichloromethane (80 mL), and to this solution was added methanol (80 mL). The generated precipitate was collected by filtration, and this was dried under reduced pressure, to obtain a compound G3 (6.25 g).

$^1$H-NMR (CD$_2$Cl$_2$, 300 MHz): δ (ppm)=8.09 (m, 3H), 8.01 (s, 6H), 7.84 (m, 3H), 7.72 (d, 3H), 7.57 (m, 6H), 7.42 (d, 12H), 7.19 (d, 12H), 7.03 (d, 3H), 6.96-6.86 (m, 6H), 1.65 (s, 12H), 1.24 (s, 36H), 0.63 (s, 54H).

The compound G3 had an emission spectrum the maximum peak wavelength of which was 545 nm.

137
Synthesis Example 9
Synthesis of Compound S2
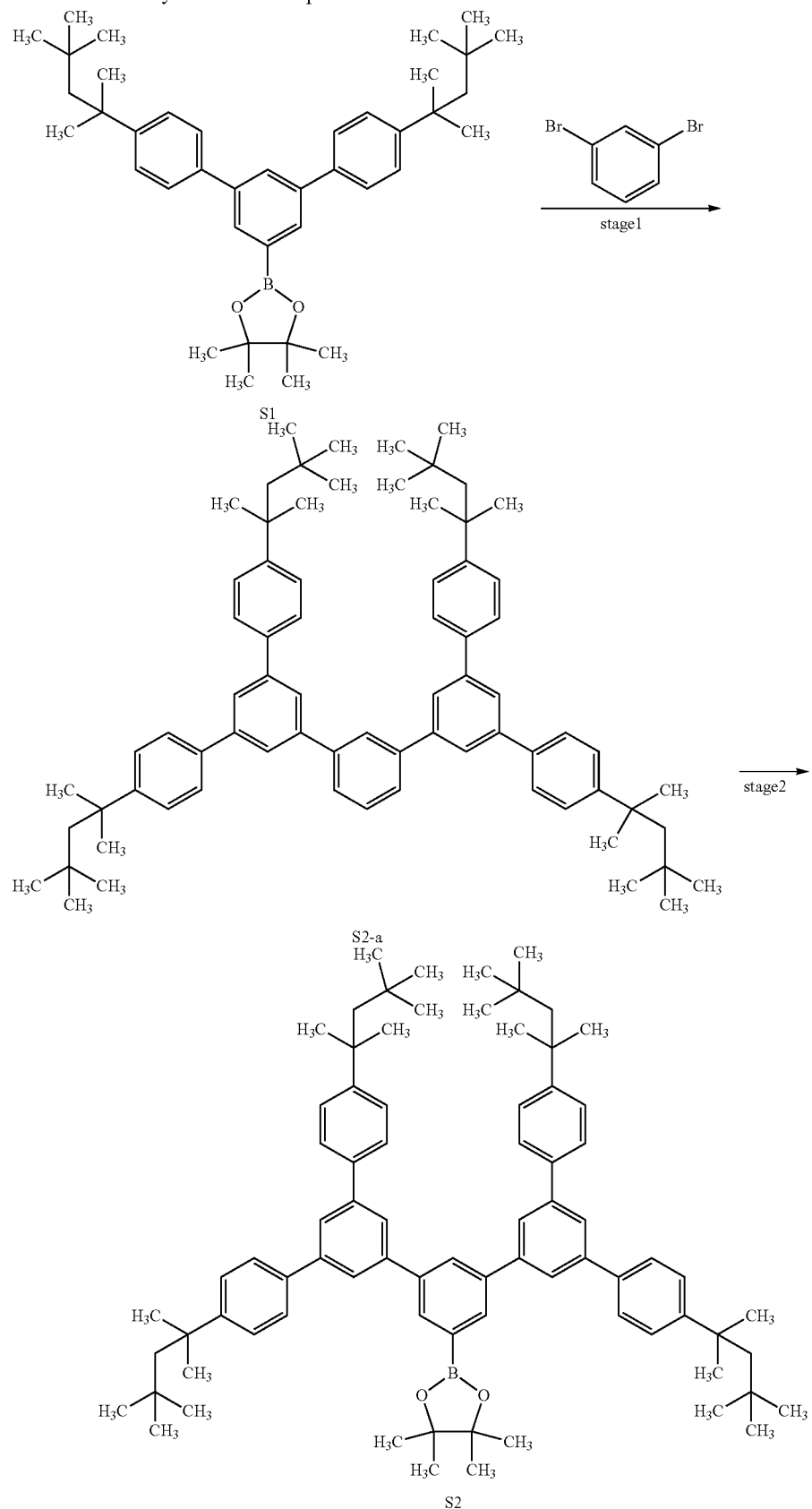

<Stage 1>

The atmosphere in a reaction vessel was turned into a nitrogen gas stream, then, the compound S1 (91.49 g), m-dibromobenzene (17.70 g) and toluene (478 mL) were added, and the mixture was bubbled with a nitrogen gas for 20 minutes. Thereafter, to this were added a 20 wt % tetraethylammonium hydroxide aqueous solution (166 mL) and bis(triphenylphosphine)palladium(II) dichloride (0.26 g), and the mixture was refluxed for 6.5 hours. After cooling down to room temperature, the organic layer was separated from the resultant reaction solution, and this organic layer was washed with water (300 mL) and saturated saline (300 mL) in this order. The resultant organic layer was dried over sodium sulfate, then, the solvent was distilled off under reduced pressure. The resultant residue was dissolved into a mixed solvent of hexane/chloroform (20/1 (by volume)), and the solution was purified by silica gel column chromatography, and concentrated under reduced pressure, to remove the solvent. To the resultant residue were added methanol (845 mL) and chloroform (56 mL), and the mixture was refluxed for 30 minutes. The resultant solution was cooled to obtain a precipitate which was then filtrated and dried, to obtain a compound S2-a (74.40 g).

<Stage 2>

The atmosphere in a reaction vessel was turned into a nitrogen gas stream, then, the compound S2-a (74.40 g), bis(pinacolato)diboron (21.13 g), 4,4'-di-tert-butyl-2,2'-dipyridyl (609 mg), cyclohexane (734 mL) and bis(1,5-cyclooctadiene)di-μ-methoxydiiridium(I) (752 mg) were added, and the mixture was refluxed for 8 hours. After cooling with air down to room temperature, then, to the resultant reaction solution was added silica gel (83.93 g), and it was purified by silica gel column chromatography (developing solvent: a mixed solvent of dichloromethane/acetonitrile (100/1 (by volume))). Thereafter, the solvent was distilled off under reduced pressure, and the resultant residue was dissolved in toluene (420 mL), and this solution was heated at 50° C. Thereafter, acetonitrile (839 mL) was dropped into this, and the deposited solid was filtrated. The resultant solid was refluxed in a mixed solvent of hexane/acetonitrile (1/1 (by volume)) for 30 minutes, then, cooled down to room temperature and the precipitate was collected by filtration, and dried, to obtain a compound S2 (68.53 g).

$^1$H-NMR (CDCl$_3$, 300 MHz): δ (ppm)=8.14 (d, J=1.8 Hz, 2H), 8.09 (m, 1H), 7.85 (d, J=1.6 Hz, 4H), 7.82 (m, 2H), 7.64 (d, J=8.5 Hz, 8H), 7.48 (d, J=8.5 Hz, 8H), 1.79 (s, 8H), 1.42 (s, 24H), 1.39 (s, 12H), 0.77 (s, 36H).

Synthesis Example 10

Synthesis of Compound G4

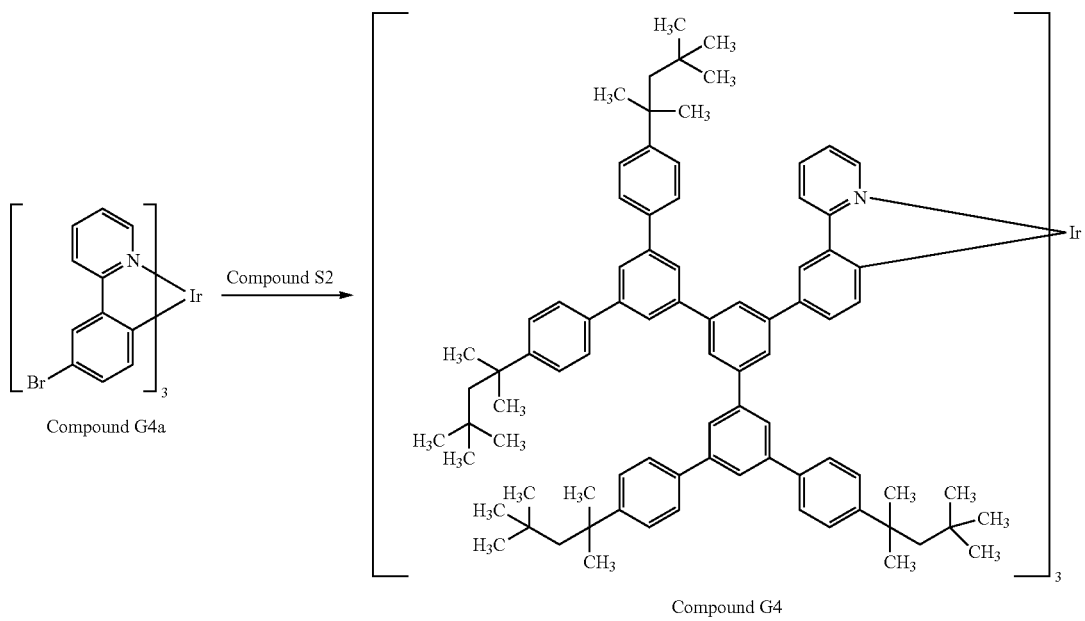

The atmosphere in a reaction vessel was turned into a nitrogen gas stream, then, a compound G4a (8.00 g) synthesized according to a method described in JP-A No. 2004-531485, the compound S2 (39.83 g) and tetrahydrofuran (640 mL) were added, and the mixture was bubbled with nitrogen for 20 minutes. Thereafter, to this were added a 20 wt % tetraethylammonium hydroxide aqueous solution (13.22 g) and tetrakis(triphenylphosphine)palladium(0) (1.244 g), and the mixture was refluxed for 41 hours. After cooling down to room temperature, to the resultant reaction solution were added water (1500 mL) and toluene (1500 mL) and the organic layer was separated, and the resultant organic layer was washed with water (1500 mL) three times. The resultant organic layer was dried over sodium sulfate, then, concentrated. The resultant residue was dissolved in a mixed solvent of toluene/hexane ((20/1 (by volume)), purified by silica gel column chromatography, and the solvent was removed under reduced pressure. The resultant residue was dissolved in toluene (350 mL), and this was heated at 50° C. Into the resultant solution, acetonitrile (700 mL) was dropped, to cause deposition of a solid. The resultant solid was filtrated, and washed with methanol (100 mL). To the resultant solid were added hexane (350 mL) and acetonitrile (350 mL), and this was refluxed for 30 minutes. After cooling down to room temperature, the resultant solid was filtrated, and washed with acetonitrile (100 mL). The resultant solid was dried under reduced pressure, to obtain a compound G4 (31.29 g) represented by the above-described formula.

$^1$H-NMR (CD$_2$Cl$_2$, 300 MHz): δ (ppm)=8.16-8.13 (m, 6H), 8.04 (m, 6H), 7.99 (m, 3H), 7.95 (s, 12H), 7.86 (m, 6H), 7.76-7.65 (m, 30H), 7.47 (d, 24H), 7.37 (d, 3H), 7.15 (d, 3H), 7.05-7.00 (m, 3H), 1.77 (s, 24H), 1.37 (s, 72H), 0.72 (s, 108H).

The compound G4 had an emission spectrum the maximum peak wavelength of which was 514 nm.

Synthesis Example 11

Synthesis of Compound R1

The compound R1 was synthesized according to a method described in International Publication WO2002/44189.

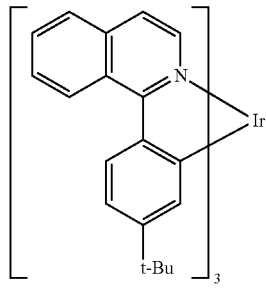

Compound R1

The compound R1 had an emission spectrum the maximum peak wavelength of which was 617 nm.

Synthesis Example 12

Synthesis of Compound R2

The compound R2 was synthesized according to a method described in JP-A No. 2006-188673.

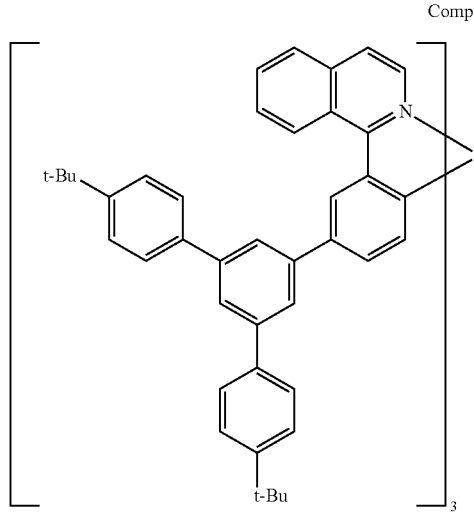

Compound R2

The compound R2 had an emission spectrum the maximum peak wavelength of which was 619 nm.

Synthesis Example 13

Synthesis of Compound R3

The compound R3 was synthesized according to a method described in JP-A No. 2011-105701.

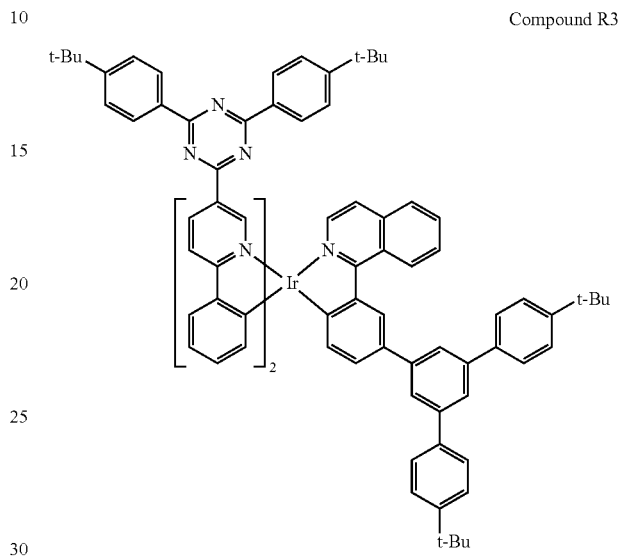

Compound R3

The compound R3 had an emission spectrum the maximum peak wavelength of which was 611 nm.

Synthesis Example 14

Synthesis of Compound R4

The compound R4 was synthesized according to a method described in JP-A No. 2008-179617.

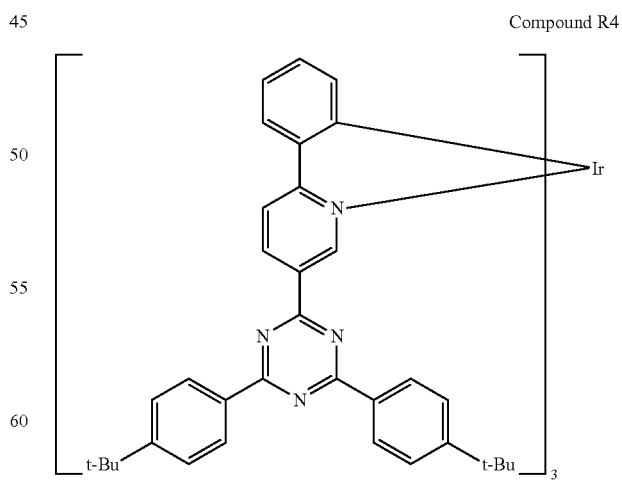

Compound R4

The compound R4 had an emission spectrum the maximum peak wavelength of which was 594 nm.

Synthesis Example 15
Synthesis of Compound R5
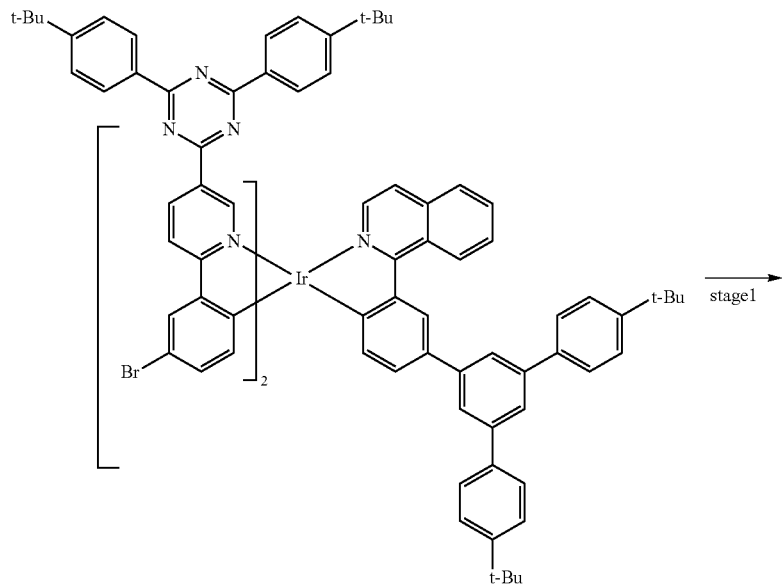
Compound R5a
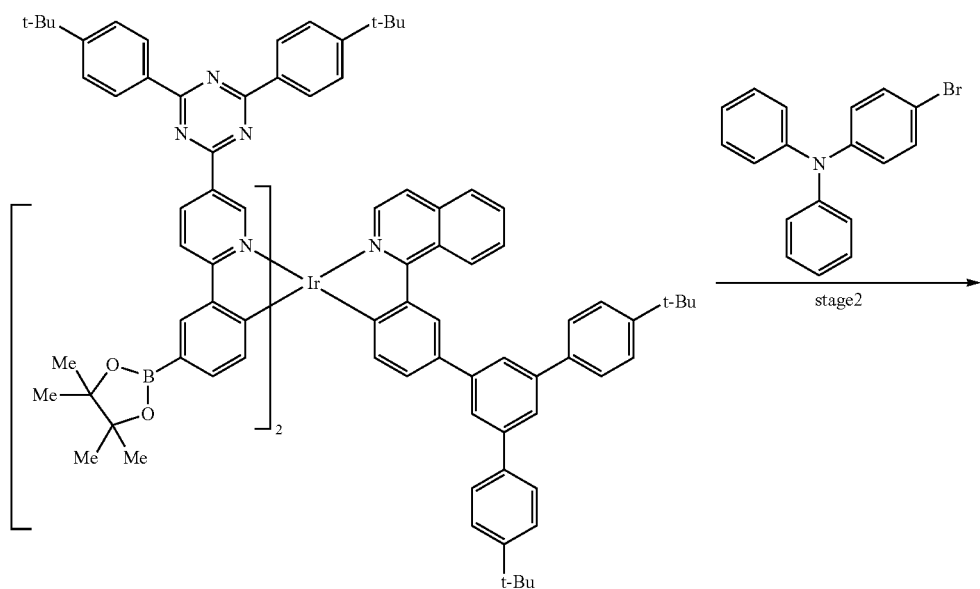
Compound R5b -continued

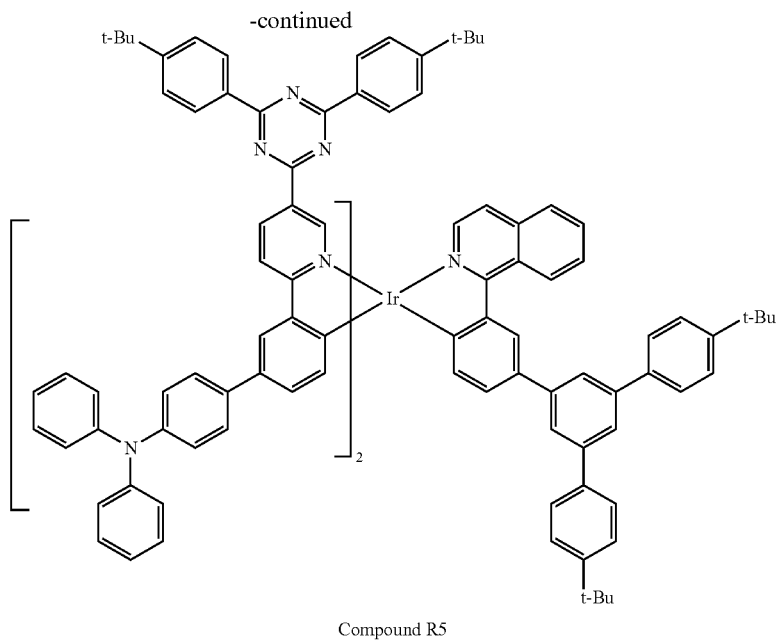

Compound R5

<Stage 1>

The atmosphere in a light-shielded reaction vessel was turned into an argon gas atmosphere, then, a compound R5a (381 mg) synthesized according to a method described in JP-A No. 2011-105701, bis(pinacolato)diboron (157 mg, 0.62 mmol), [1,1'-bis(diphenylphosphino)ferrocene]palladium(II) dichloride dichloromethane adduct ($PdCl_2$ (dppf)·$CH_2Cl_2$, 20 mg, 0.024 mmol), potassium acetate (118 mg, 1.2 mmol) and tetrahydrofuran (13 mL) were added, and the mixture was stirred for 11 hours under reflux with heating. Thereafter, the mixture was cooled down to room temperature, toluene (10 mL) was added and the mixture was concentrated under reduced pressure to distill off the solvent, obtaining a solid. The resultant solid was purified by silica gel column chromatography (hexane/toluene), to obtain a fraction containing the intended substance. The resultant fraction was concentrated, and the resultant solid was washed with methanol, then, dried under reduced pressure at 50° C. overnight, to obtain a compound R5b (187 mg) as a red solid. The yield was 47%. The resultant compound R5b showed a HPLC area percentage value (detection wavelength: UV 254 nm) of 99.9% or more.

MALDI-TOF/MS (positive): m/z=1984 [M]$^+$ $^1$H-NMR (300 MHz, $CDCl_3$): δ (ppm)=9.25 (s, 1H), 9.09 (m, 3H), 8.89 (d, 1H), 8.53 (s, 1H), 8.36 (m, 5H), 8.27 (m, 7H), 7.86 (m, 1H), 7.81 (d, 1H), 7.76 (s, 2H), 7.64 (m, 7H), 7.42 (m, 13H), 7.14-7.30 (m, 4H), 7.07 (t, 2H), 1.38 (s, 18H), 1.35 (s, 30H), 1.31 (s, 12H), 1.24 (s, 18H).

<Stage 2>

The atmosphere in a light-shielded reaction vessel was turned into an argon gas atmosphere, then, the compound R5b (140 mg), 4-bromotriphenylamine (51 mg), tetrakis(triphenylphosphine)palladium(0) (5.6 mg), tetrahydrofuran (9 mL) and a 20 wt % tetraethylammonium hydroxide aqueous solution (258 mg) were added, and the mixture was stirred for 8 hours under reflux with heating. Thereafter, the mixture was cooled down to room temperature, toluene (10 mL) was added and the mixture was concentrated under reduced pressure to distill off the solvent, obtaining a solid. The resultant solid was purified by silica gel column chromatography (hexane/toluene), to obtain a fraction containing the intended substance. The resultant fraction was concentrated, and the resultant solid was purified again by silica gel column chromatography (hexane/chloroform), to obtain a fraction containing the intended substance. The resultant fraction was concentrated, and the resultant solid was washed with methanol, then, dried under reduced pressure at 50° C. overnight, to obtain the intended compound R5 (130 mg) as a red solid. The yield was 84%. The resultant compound R5 showed a HPLC area percentage value (detection wavelength: UV 254 nm) of 99.0% or more.

MALDI-TOF/MS (positive): m/z=2219 [M]$^+$ $^1$H-NMR (600 MHz, THF-$d_8$): δ (ppm)=9.49 (s, 1H), 9.33 (s, 1H), 9.26 (d, 1H), 9.23 (m, 1H), 9.03 (d, 1H), 8.70 (s, 1H), 8.60 (d, 1H), 8.56 (d, 1H), 8.43 (d, 4H), 8.39 (d, 4H), 8.22 (s, 1H), 8.19 (s, 1H), 8.08 (m, 1H), 8.07 (d, 1H), 7.85 (s, 2H), 7.73 (m, 3H), 7.69 (d, 1H), 7.66 (d, 4H), 7.60 (d, 2H), 7.58 (d, 2H), 7.51 (m, 8H), 7.47 (d, 4H), 7.32 (d, 1H), 7.24 (m, 10H), 7.15 (m, 3H), 7.09 (m, 12H), 6.98 (m, 4H), 1.42 (s, 18H), 1.36 (s, 18H), 1.27 (s, 18H).

The compound R5 had an emission spectrum the maximum peak wavelength of which was 615 nm.

Synthesis Example 16

Synthesis of Compound MC2

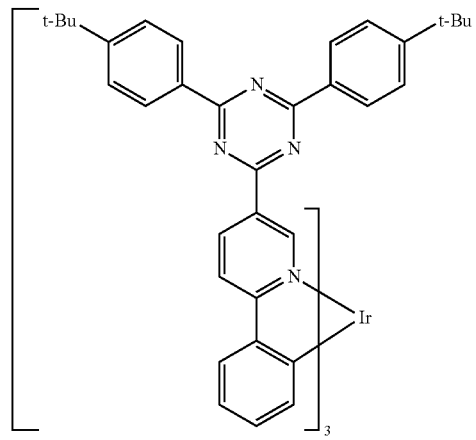

MC1

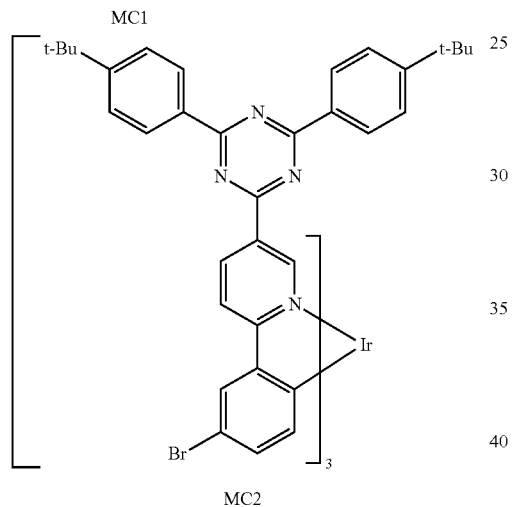

MC2

The atmosphere in a light-shielded reaction vessel was turned into a nitrogen gas atmosphere, then, a compound MC1 (38 g, 22.6 mmol) synthesized according to a method described in JP-A No. 2008-179617, N-bromosuccinimide (12.1 g, 68 mmol) and chloroform (1800 mL) were added, and the mixture was stirred for 24 hours at room temperature. The resultant reaction mixture was allowed to pass through a filtering apparatus paved with silica gel, to remove solid components. The resultant filtrate was concentrated under reduced pressure to distill off the solvent, obtaining a solid. The resultant solid was purified by silica gel column chromatography (chloroform/hexane=1/3), to obtain a fraction containing the intended substance. The resultant fraction was concentrated, and purified by performing recrystallization (dichloromethane/hexane) three times, and dried under reduced pressure at 50° C. overnight, to obtain a compound MC2 (22.1 g) as a red solid. The yield was 51%. The resultant compound MC2 showed a HPLC area percentage value (detection wavelength: UV 254 nm) of 99.4%.

LC/MS (APCI-posi): m/z=1920 [M+H]$^+$ $^1$H-NMR (300 MHz/CD$_2$Cl$_2$): δ (ppm=) 9.31 (d, 3H), 9.26 (dd, 3H), 8.38 (d, 12H), 8.22 (d, 3H), 7.96 (d, 3H), 7.43 (d, 12H), 7.00 (dd, 3H), 6.82 (d, 3H), 1.23 (s, 18H).

Synthesis Example 17

Synthesis of Compound R6

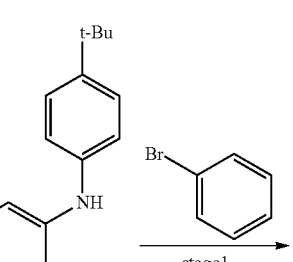 stage1

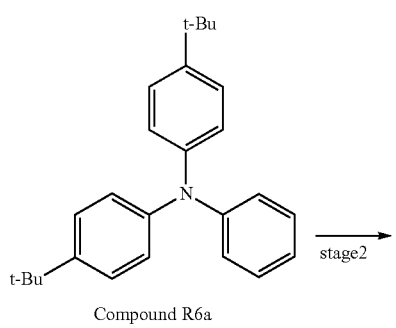

Compound R6a stage2

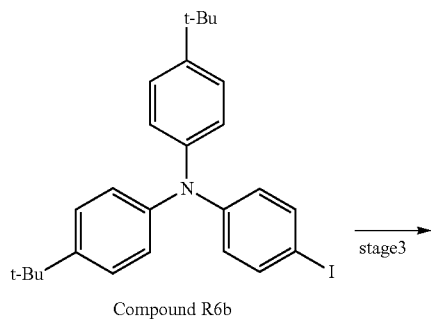

Compound R6b stage3

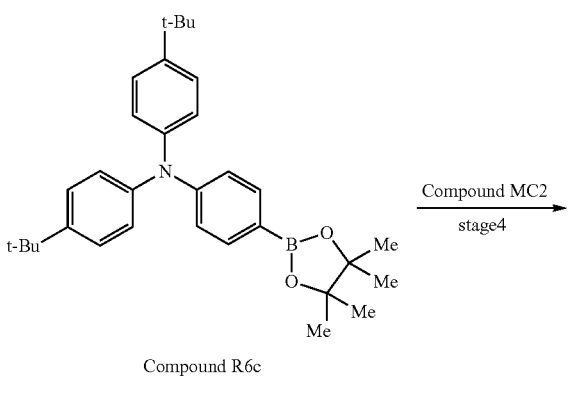

Compound R6c stage4 Compound MC2

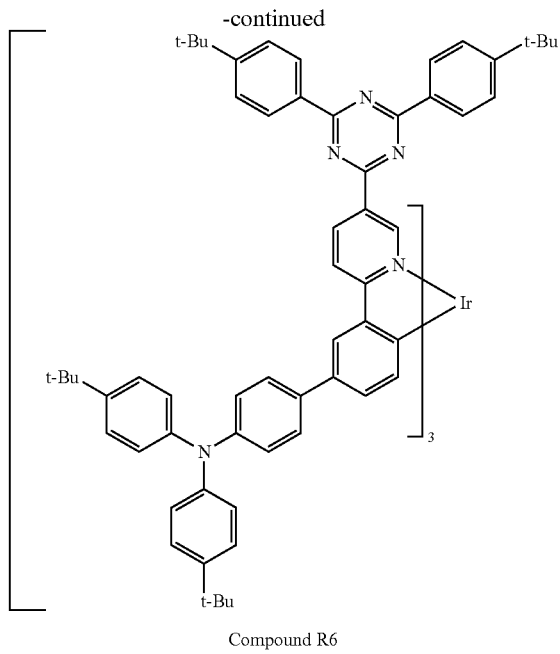

Compound R6

<Stage 1>

The atmosphere in a reaction vessel was turned into an argon gas atmosphere, then, bis(4-tert-butylphenyl)amine (98.5 g), tris(dibenzylideneacetone)dipalladium(0) (3.21 g), tri-tert-butylphosphine tetrafluoroborate salt (4.06 g), sodium-tert-butoxide (67.3 g) and toluene (665 mL) were added, and the mixture was heated at 80° C. while stirring. Thereafter, into this, bromobenzene (57.1 g) dissolved in toluene (55 mL) was dropped, and the mixture was stirred for 4 hours at 85° C. The resultant reaction mixture was diluted with toluene (680 mL), then, hot-filtrated, to remove a solid. To the resultant filtrate were added activated white earth (35 g) and activated alumina (35 g), and the mixture was stirred for 1.5 hours at 90° C., then, hot-filtrated, to remove a solid. The resultant filtrate was concentrated under reduced pressure, to remove the solvent, obtaining a solid. The resultant solid was purified by performing recrystallization (hexane/ethanol) twice, and dried under reduced pressure at 50° C. overnight, to obtain the intended compound R6a (99 g) as a solid. The yield was 79%. The resultant compound R6a showed a HPLC area percentage value (detection wavelength: UV 254 nm) of 99.9% or more.

<Stage 2>

The atmosphere in a light-shielded reaction vessel was turned into an argon gas atmosphere, then, the compound R6a (71.5 g), N-iodosuccinimide (49.5 g) and N,N-dimethylformamide (800 mL) were added, and the mixture was heated at 30° C. while stirring. Thereafter, into this, trifluoroacetic acid (11.4 g) was dropped, and the mixture was stirred for 4 hours at 50° C. Thereafter, the mixture was cooled using an ice bath, and ion-exchange water (800 mL) and a 10% sodium chloride aqueous solution (200 mL) were dropped, to obtain a solid. The resultant solid was dissolved in toluene (1 L), then, the solution was washed twice using ion-exchange water (800 mL), to obtain an organic layer. The resultant organic layer was dried over anhydrous sodium sulfate, then, concentrated under reduced pressure to distill off the solvent, obtaining a solid. The resultant solid was dried under reduced pressure at 50° C. overnight, then, purified by performing recrystallization (chloroform/methanol), and dried under reduced pressure at 50° C. overnight, to obtain the intended compound R6b (64 g) as a solid. The yield was 87%. The resultant compound R6b showed a HPLC area percentage value (detection wavelength: UV 254 nm) of 99.4%.

<Stage 3>

The atmosphere in a light-shielded reaction vessel was turned into a nitrogen gas atmosphere, then, the compound R6b (7.5 g) and tetrahydrofuran (80 mL) were added. Thereafter, into this, isopropylmagnesium chloride (2 mol/L, 15 mL) dissolved in tetrahydrofuran was dropped, and the mixture was stirred for 1 hour at room temperature. Thereafter, the mixture was cooled using an ice bath, and 2-isopropoxy-4,4,5,5-tetramethyl-1,3,2-dioxaborolane (6.4 mL) was added, and the mixture was stirred for 5 minutes. Thereafter, the ice bath was removed, and the mixture was stirred for 3 hours while raising temperature slowly up to room temperature. Thereafter, the mixture was cooled again using an ice bath, then, the mixture was extracted using a mixed solvent of ethyl acetate (90 mL) and toluene (30 mL), and the resultant organic layer was washed with 15 wt % saline (50 mL) twice, to obtain an organic layer. The resultant organic layer was dried over anhydrous sodium sulfate, then, concentrated under reduced pressure to distill off the solvent, obtaining a solid. The resultant solid was purified by performing recrystallization (chloroform/methanol) twice, and dried under reduced pressure at 50° C. overnight, to obtain the intended compound R6c (5.5 g) as a white solid. The yield was 74%. The resultant compound R6c showed a HPLC area percentage value (detection wavelength: UV 254 nm) of 99.5% or more.

TLC/MS (DART positive): m/z=484 [M+H]$^+$

<Stage 4>

The atmosphere in a light-shielded reaction vessel was turned into a nitrogen gas atmosphere, then, the compound MC2 (5.0 g), the compound R6c (4.4 g), tetrakis(triphenylphosphine)palladium(0) (360 mg), a 20 wt % tetraethylammonium hydroxide aqueous solution (20 mL) and tetrahydrofuran (210 mL) were added, and the mixture was stirred for 24 hours under reflux with heating. Thereafter, the mixture was cooled down to room temperature, and toluene (400 mL) and ion-exchange water (400 mL) were added and extraction was performed, to obtain an organic layer. The resultant organic layer was washed with ion-exchange water twice, and with 5 wt % saline once, to obtain an organic layer. The resultant organic layer was dried over anhydrous sodium sulfate, then, concentrated under reduced pressure to distill off the solvent, obtaining a solid. The resultant solid was purified by performing recrystallization (toluene/isopropanol), and dried under reduced pressure at 50° C. overnight, to obtain a compound R6 (3.9 g) as a red solid. The yield was 55%. The resultant compound R6 showed a HPLC area percentage value (detection wavelength: UV 254 nm) of 99.5% or more.

$^1$H-NMR (300 MHz/CD$_2$Cl$_2$): δ (ppm)=9.41 (d, 3H), 9.21 (dd, 3H), 8.39 (d, 12H), 8.26 (d, 3H), 7.96 (s, 3H), 7.45 to 7.38 (m, 18H), 7.27 (dd, 12H), 7.23 to 7.16 (m, 6H), 6.96 (d, 18H), 1.30 (s, 54H), 1.22 (s, 54H).

LC/MS (APCI positive): m/z=2751 [M+H]$^+$

The compound R6 had an emission spectrum the maximum peak wavelength of which was 619 nm.

Synthesis Example 18

Synthesis of Polymer Compound HP-1

A nitrogen gas atmosphere was prepared in a reaction vessel, then, a mixture of a compound M0 (2.4290 g)

synthesized according to a method described in JP-A No. 2010-189630, a compound M1 (2.4940 g) synthesized according to a method described in International Publication WO2013/191088, a compound M2 (1.2936 g) synthesized according to a method described in International Publication WO2013/191088 and toluene (94 ml) was heated at about 80° C., then, bis[tris(2-methoxyphenyl)phosphine]palladium dichloride (8.56 mg) and a 20 wt % tetraethylammonium hydroxide aqueous solution (17.2 g) were added, and the mixture was stirred for about 9 hours under argon gas reflux.

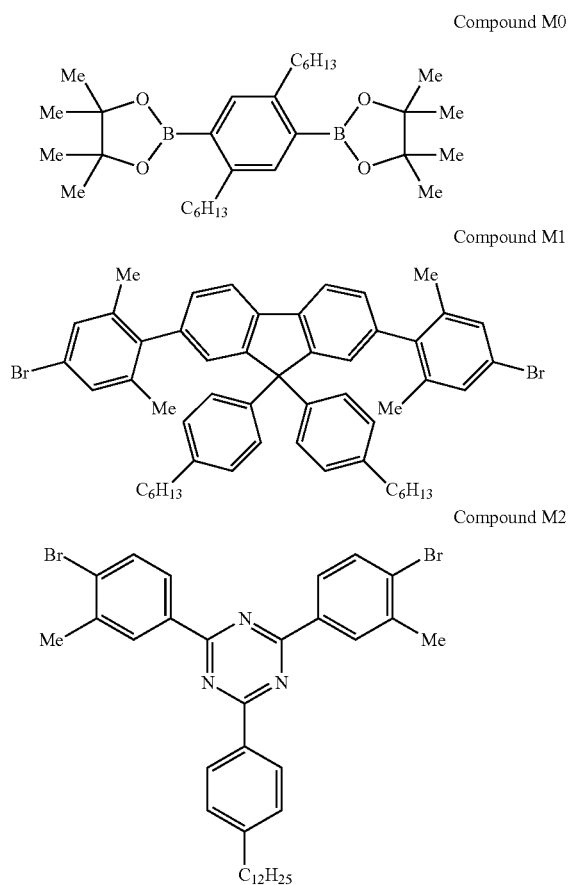

Thereafter, phenylboronic acid (0.1201 g), bis[tris(2-methoxyphenyl)phosphine]palladium dichloride (4.30 mg) and a 20 wt % tetraethylammonium hydroxide aqueous solution (17.2 g) were added, and further, the mixture was stirred for about 14 hours under argon gas reflux. Thereafter, a solution prepared by dissolving sodium N,N-diethyldithiocarbamate trihydrate (1.37 g) in ion exchanged water (26 ml) was added, and the mixture was stirred for about 2 hours while heating at 85° C. The resultant organic layer was washed with 3.6 wt % hydrochloric acid twice, with 2.5 wt % ammonia water twice and with ion exchanged water six times, in series. The resultant organic layer was dropped into methanol to cause precipitation, and the precipitate was isolated by filtration, and dried, to obtain a solid. The resultant solid was dissolved in toluene, and the solution was allowed to pass through a silica gel column and an alumina column through which toluene had passed previously. The resultant solution was dropped into methanol to cause precipitation, and the filtrate was isolated by filtration, and dried, to obtain a polymer compound HP-1 (3.769 g). The polystyrene-equivalent number-average molecular weight (Mn) and weight-average molecular weight (Mw) of the polymer compound HP-1 were Mn=$8.2\times10^4$ and Mw=$2.4\times10^5$.

The polymer compound HP-1 is a copolymer constituted of a constitutional unit derived from a compound M0, a constitutional unit derived from a compound M1 and a constitutional unit derived from a compound M2 at a molar ratio of 50:30:20, according to theoretical values calculated from the amounts of charged raw materials.

Synthesis Example 19

Synthesis of Polymer Compound HP-2

The polymer compound HP-2 was synthesized according to a method described in International Publication WO2013/191088, using a compound M0 synthesized according to a method described in JP-A No. 2010-189630, a compound M1 synthesized according to a method described in International Publication WO2013/191088 and a compound M3 synthesized according to a method described in International Publication WO2013/191088.

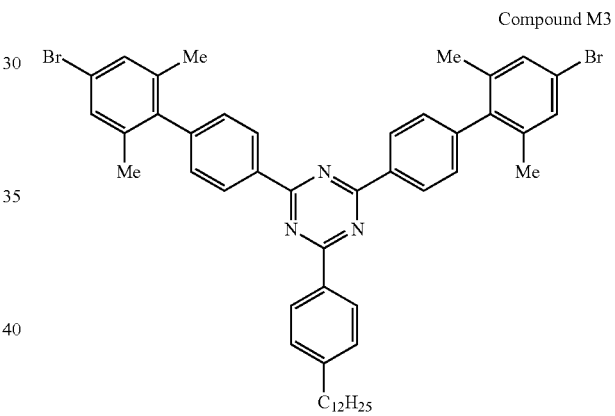

The polystyrene-equivalent number-average molecular weight (Mn) and weight-average molecular weight (Mw) of the polymer compound HP-2 were Mn=$9.8\times10^4$ and Mw=$2.7\times10^5$.

The polymer compound HP-2 is a copolymer constituted of a constitutional unit derived from a compound M0, a constitutional unit derived from a compound M1 and a constitutional unit derived from a compound M3 at a molar ratio of 50:26:24, according to theoretical values calculated from the amounts of charged raw materials.

Synthesis Example 20

Synthesis of Polymer Compound HP-3

The polymer compound HP-3 was synthesized according to a method described in JP-A No. 2012-36381, using a compound M0, a compound M11 synthesized according to a method described in JP-A No. 2012-36381 and a compound M12 synthesized according to a method described in JP-A No. 2012-36381.

Compound M11

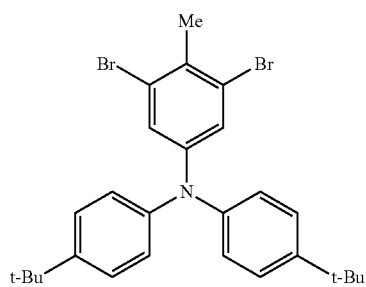

Compound M4

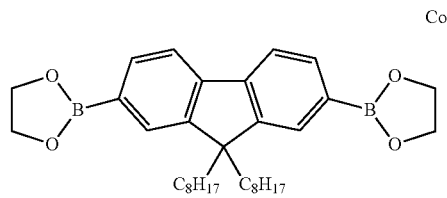

Compound M12

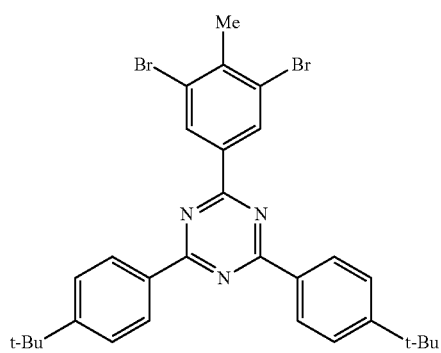

Compound M5

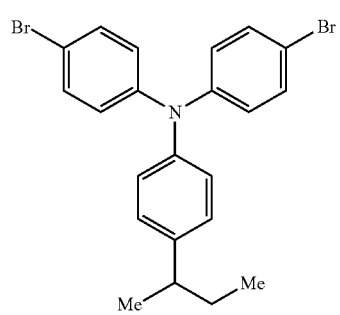

The polystyrene-equivalent number-average molecular weight (Mn) and weight-average molecular weight (Mw) of the polymer compound HP-3 were Mn=$3.4\times10^4$ and Mw=$1.2\times10^5$.

The polymer compound HP-3 is a copolymer constituted of a constitutional unit derived from a compound M0, a constitutional unit derived from a compound M1 and a constitutional unit derived from a compound M3 at a molar ratio of 50:20:30, according to theoretical values calculated from the amounts of charged raw materials.

Synthesis Example 21

Synthesis of Polymer Compound HP-4

The polymer compound HP-4 was synthesized according to a method described in International Publication WO2013/191088, using a compound M0 and a compound M1.

The polystyrene-equivalent number-average molecular weight (Mn) and weight-average molecular weight (Mw) of the polymer compound HP-4 were Mn=$9.7\times10^4$ and Mw=$2.9\times10^5$.

The polymer compound HP-4 is a copolymer constituted of a constitutional unit derived from a compound M0 and a constitutional unit derived from a compound M1 at a molar ratio of 50:50, according to theoretical values calculated from the amounts of charged raw materials.

Synthesis Example 22

Synthesis of Polymer Compound HTL-1

The polymer compound HTL-1 was synthesized according to a method described in International Publication WO2011/049241, using a compound M4 synthesized according to a method described in International Publication WO2002/045184, a compound M5 synthesized according to a method described in International Publication WO2002/045184 and a compound M6 synthesized according to a method described in International Publication WO2011/049241.

Compound M6

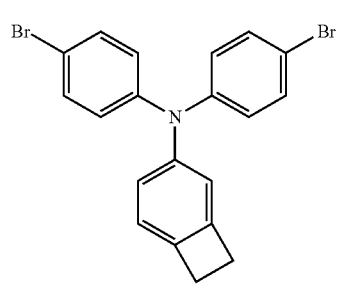

The polystyrene-equivalent number-average molecular weight and weight-average molecular weight of the polymer compound HTL-1 were Mn=$8.9\times10^4$ and Mw=$4.2\times10^5$, respectively.

The polymer compound HTL-1 is a copolymer constituted of a constitutional unit derived from a compound M4, a constitutional unit derived from a compound M5 and a constitutional unit derived from a compound M6 at a molar ratio of 50:42.5:7.5, according to theoretical values calculated from the amounts of charged raw materials.

Synthesis Example 23

Synthesis of Polymer Compound HTL-2

The polymer compound HTL-2 was synthesized according to a method described in JP-A No. 2011-174062, using a compound M7 synthesized according to a method described in JP-A No. 2011-174062, a compound M8 synthesized according to a method described in International Publication WO2002/045184, a compound M9 synthesized according to a method described in International Publication WO2005/049546 and a compound M10 synthesized according to a method described in JP-A No. 2008-106241.

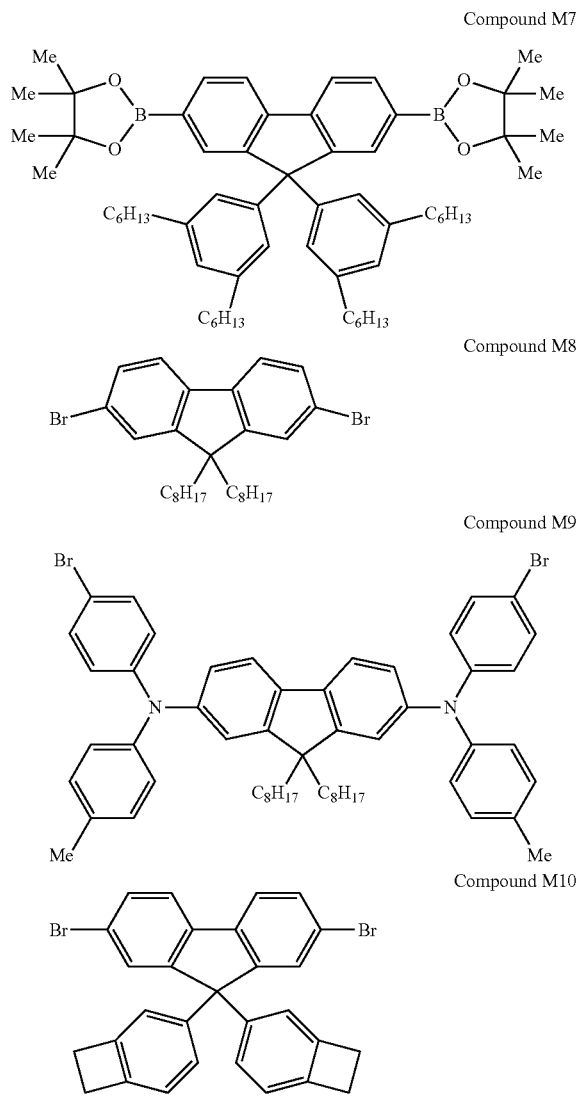

Compound M7

Compound M8

Compound M9

Compound M10

The polystyrene-equivalent number-average molecular weight and weight-average molecular weight of the polymer compound HTL-2 were $Mn=7.8\times10^4$ and $Mw=2.6\times10^5$, respectively.

The polymer compound HTL-2 is a copolymer constituted of a constitutional unit derived from a compound M7, a constitutional unit derived from a compound M8, a constitutional unit derived from a compound M9 and a constitutional unit derived from a compound M10 at a molar ratio of 50:12.5:30:7.5, according to theoretical values calculated from the amounts of charged raw materials.

Synthesis Example 24

Synthesis of Polymer Compound HTL-3

The polymer compound HTL-3 was synthesized according to a method described in JP-A No. 2012-36381, using a compound M4 and a compound M5.

The polystyrene-equivalent number-average molecular weight and weight-average molecular weight of the polymer compound HTL-3 were $Mn=8.1\times10^4$ and $Mw=3.4\times10^5$, respectively.

The polymer compound HTL-3 is a copolymer constituted of a constitutional unit derived from a compound M4 and a constitutional unit derived from a compound M5 at a molar ratio of 50:50, according to theoretical values calculated from the amounts of charged raw materials.

Synthesis Example 25

Synthesis of Compound Ma3

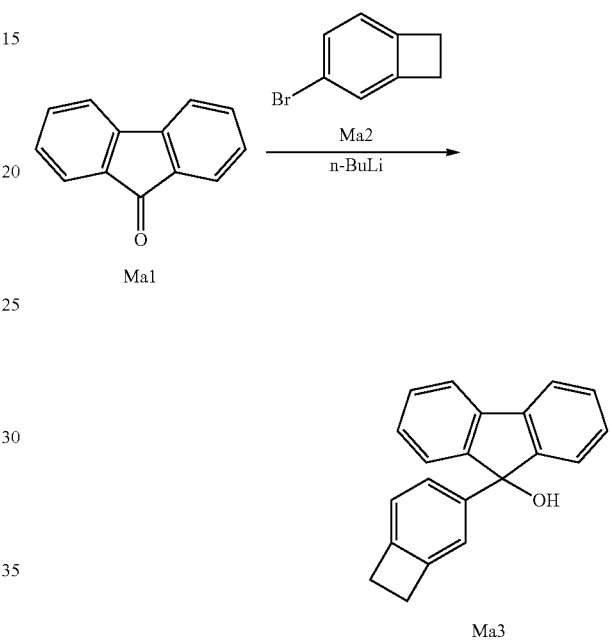

A gas in a flask equipped with a stirrer was purged with a nitrogen gas, then, a compound Ma2 (64.6 g) and tetrahydrofuran (615 mL) were added, and the mixture was cooled down to −70° C. Into this, a n-butyllithium hexane solution (1.6 M, 218 mL) was dropped over a period of 1 hour, then, the mixture was stirred at −70° C. for 2 hours. To this, a compound Ma1 (42.1 g) was added in several batches, then, the mixture was stirred at −70° C. for 2 hours. Into this, methanol (40 mL) was dropped over a period of 1 hour, then, the mixture was heated up to room temperature. Thereafter, the solvent was distilled off by concentrating under reduced pressure, and toluene and water were added. Thereafter, an aqueous layer was separated and the resultant organic layer was further washed with water. The resultant organic layer was concentrated under reduced pressure, and the resultant residue was purified by using a silica gel column (developing solvent: a mixed solvent of hexane and ethyl acetate), thereby obtaining 71 g of a compound Ma3 as a colorless oil. The resultant compound Ma3 had an HPLC area percentage value (UV: 254 nm) of 97.5%. This operation was repeated, thereby obtaining a necessary amount of the compound Ma3.

$^1$H-NMR (CDCl$_3$, 300 MHz): δ (ppm): 2.43 (1H, s), 3.07-3.13 (4H, m), 6.95 (1H, d), 7.07 (1H, s), 7.18-7.28 (3H, m), 7.28-7.40 (4H, m), 7.66 (2H, s).

Synthesis Example 26

Synthesis of Compound Ma4

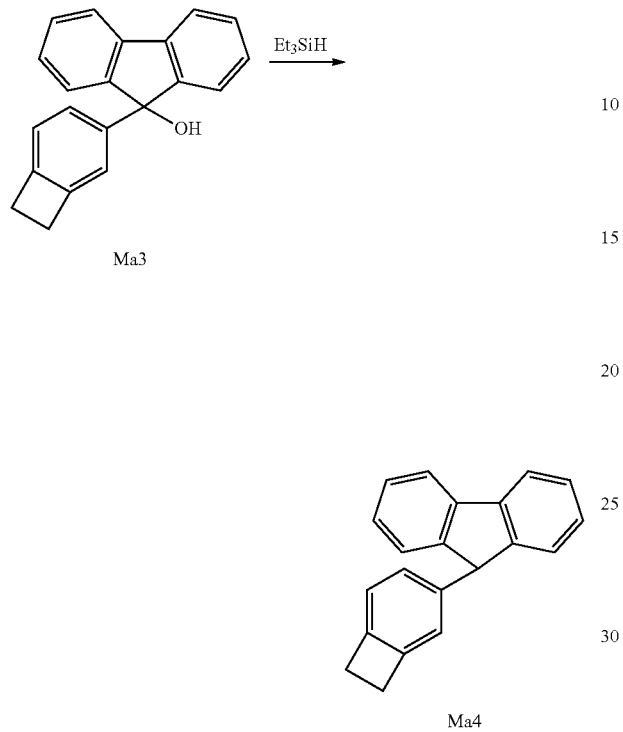

A gas in a flask equipped with a stirrer was purged with a nitrogen gas, then, the compound Ma3 (72.3 g), toluene (723 mL) and triethylsilane (118.0 g) were added, and the mixture was heated up to 70° C. Into this, methanesulfonic acid (97.7 g) was dropped over a period of 1.5 hours, then, the mixture was stirred at 70° C. for 0.5 hours. Thereafter, the mixture was cooled down to room temperature, and toluene (1 L) and water (1 L) were added, then, an aqueous layer was separated. The resultant organic layer was washed with water, a 5 wt % sodium hydrogen carbonate aqueous solution and water in this order. The resultant organic layer was concentrated under reduced pressure, and the resultant coarse product was recrystallized from a mixed solvent of toluene and ethanol, thereby obtaining 51.8 g of a compound Ma4 as a white solid. The resultant compound Ma4 had an HPLC area percentage value (UV: 254 nm) of 99.5% or more. This operation was repeated, thereby obtaining a necessary amount of the compound Ma4.

$^1$H-NMR (CDCl$_3$, 300 MHz): δ (ppm): 3.03-3.14 (4H, m), 4.99 (1H, s), 6.68 (1H, s), 6.92-7.01 (2H, m), 7.20-7.28 (2H, m), 7.29-7.38 (4H, m), 7.78 (2H, d).

Synthesis Example 27

Synthesis of Compound Mb3

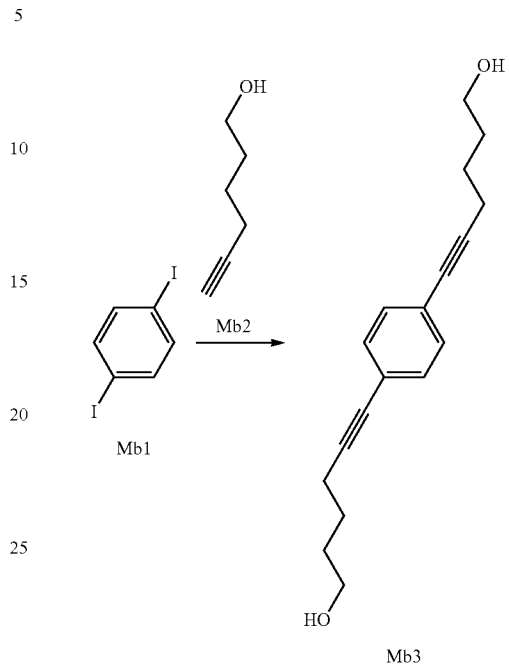

A gas in a flask equipped with a stirrer was purged with a nitrogen gas, then, a compound Mb1 (185.0 g), a compound Mb2 (121.1 g), CuI (3.2 g), dichloromethane (185 mL) and triethylamine (2.59 L) were added, and the mixture was heated up to the reflux temperature. Thereafter, the mixture was stirred at the reflux temperature for 0.5 hours, and cooled down to room temperature. To this was added dichloromethane (1.85 L), then, the mixture was filtrated through a filter paved with celite. To the resultant filtrate was added a 10 wt % sodium hydrogen carbonate aqueous solution, then, an aqueous layer was separated. The resultant organic layer was washed with water twice, washed with a saturated NaCl aqueous solution, then, magnesium sulfate was added. The resultant mixture was filtrated, and the resultant filtrate was concentrated under reduced pressure. The resultant residue was purified by using a silica gel column (developing solvent: a mixed solvent of chloroform and ethyl acetate), thereby obtaining a coarse product. The resultant coarse product was dissolved in ethanol (1.4 L), then, activated carbon (5 g) was added, and the mixture was filtrated. The resultant filtrate was concentrated under reduced pressure, and the resultant residue was recrystallized from hexane, thereby obtaining 99.0 g of a compound Mb3 as a white solid. The resultant compound Mb3 had an HPLC area percentage value (UV: 254 nm) of 99.5% or more. This operation was repeated, thereby obtaining a necessary amount of the compound Mb3.

$^1$H-NMR (DMSO-d6, 300 MHz): δ (ppm): 1.52-1.55 (8H, m), 2.42 (4H, t), 3.38-3.44 (4H, m), 4.39-4.43 (2H, m), 7.31 (4H, s).

Synthesis Example 28

Synthesis of Compound Mb4

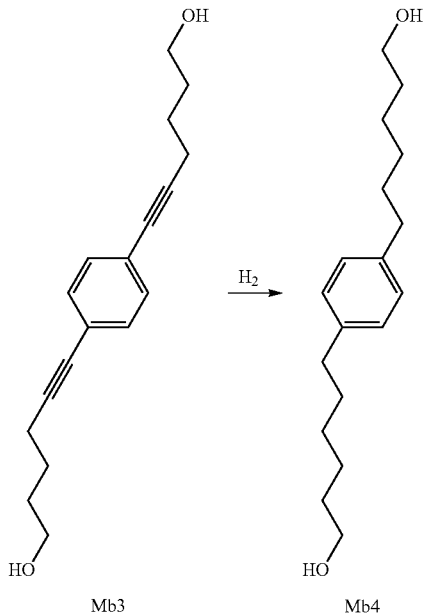 [SMILES: OCCCCC#Cc1ccc(C#CCCCCO)cc1 ; "H2" ; OCCCCCCc1ccc(CCCCCCO)cc1]

A gas in a flask equipped with a stirrer was purged with a nitrogen gas, then, the compound Mb3 (110.0 g), ethanol (1.65 L) and palladium/carbon (Pd weight: 10%) (11.0 g) were added, and the mixture was heated up to 30° C. Thereafter, a gas in the flask was purged with a hydrogen gas. Thereafter, the mixture was stirred at 30° C. for 3 hours while feeding a hydrogen gas into the flask. Thereafter, a gas in the flask was purged with a nitrogen gas. The resultant mixture was filtrated, and the resultant filtrate was concentrated under reduced pressure. The resultant residue was purified by using a silica gel column (developing solvent: a mixed solvent of chloroform and ethyl acetate), thereby obtaining a coarse product. The resultant coarse product was recrystallized from hexane, thereby obtaining 93.4 g of a compound Mb4 as a white solid. The resultant compound Mb4 had an HPLC area percentage value (UV: 254 nm) of 98.3%.

$^1$H-NMR (CDCl$_3$, 300 MHz): δ (ppm): 1.30-1.40 (8H, m), 1.55-1.65 (8H, m), 2.58 (4H, t), 3.64 (4H, t), 7.09 (4H, s).

$^{13}$C-NMR (CDCl$_3$, 75 MHz): δ (ppm): 25.53, 28.99, 31.39, 32.62, 35.37, 62.90, 128.18, 139.85.

Synthesis Example 29

Synthesis of Compound Mb5

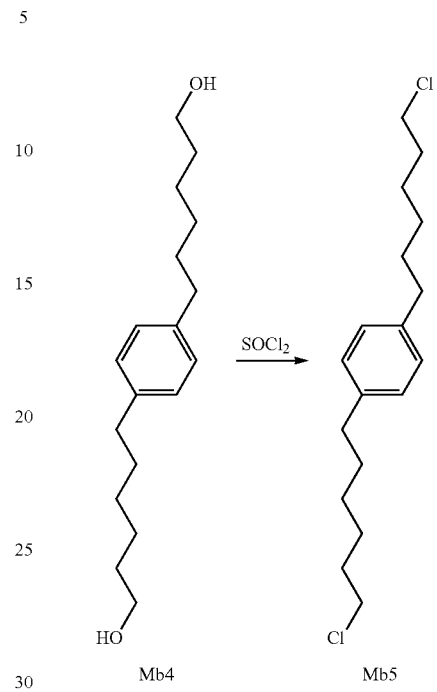

A gas in a flask equipped with a stirrer was purged with a nitrogen gas, then, the compound Mb4 (61.0 g), pyridine (0.9 g) and toluene (732 mL) were added, and the mixture was heated up to 60° C. Into this, thionyl chloride (91.4 g) was dropped over a period of 1.5 hours, then, the mixture was stirred at 60° C. for 5 hours. The resultant mixture was cooled down to room temperature, then, concentrated under reduced pressure. The resultant residue was purified by using a silica gel column (developing solvent: a mixed solvent of hexane and ethyl acetate), thereby obtaining 64.3 g of a compound Mb5 as a colorless oil. The resultant compound Mb5 had an HPLC area percentage value (UV: 254 nm) of 97.2%.

$^1$H-NMR (CDCl$_3$, 300 MHz): δ (ppm): 1.35-1.40 (4H, m), 1.41-1.50 (4H, m), 1.60-1.68 (4H, m), 1.75-1.82 (4H, m), 2.60 (4H, t), 3.55 (4H, t), 7.11 (4H, s).

Synthesis Example 30

Synthesis of Compound Mb6

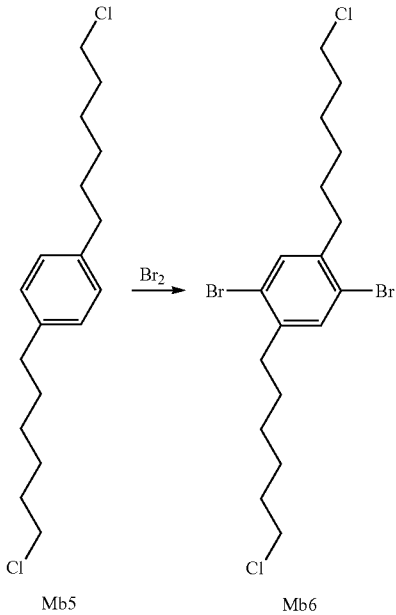

Synthesis Example 31

Synthesis of Compound Mb7

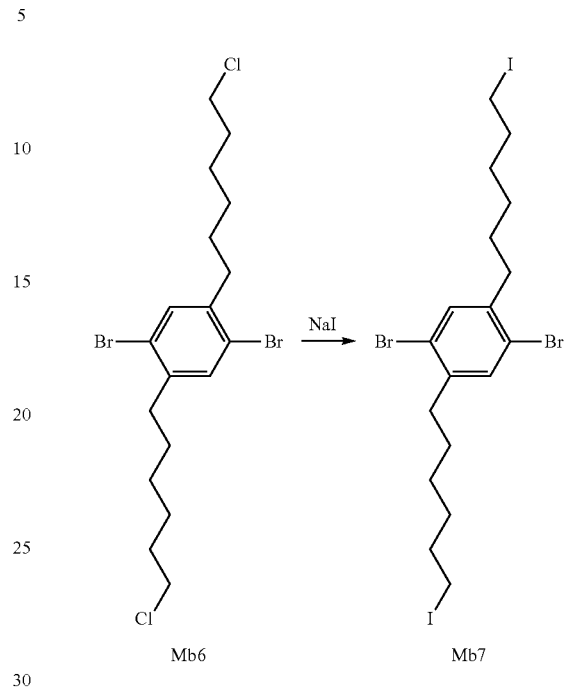

A gas in a flask equipped with a stirrer was purged with a nitrogen gas, then, the compound Mb5 (42.0 g), an iron powder (1.7 g), iodine (0.3 g) and dichloromethane (800 mL) were added. Thereafter, the whole flask was light-shielded, and cooled at 0 to 5° C. Into this, a mixed liquid of bromine (44.7 g) and dichloromethane (200 mL) was dropped over a period of 1 hour, then, the mixture was stirred at 0 to 5° C. overnight. The resultant mixed liquid was added to water (1.2 L) cooled at 0 to 5° C., then, an organic layer was separated. The resultant organic layer was washed with a 10 wt % sodium thiosulfate aqueous solution, and further, washed with a saturated sodium chloride aqueous solution and water in this order. To the resultant organic layer was added sodium sulfate, then, the mixture was filtrated, and the resultant filtrate was concentrated under reduced pressure. The resultant residue was purified by using a silica gel column (developing solvent; hexane), thereby obtaining a coarse product. The resultant coarse product was recrystallized from hexane, thereby obtaining 47.0 g of a compound Mb6 as a white solid. The resultant compound Mb6 had an HPLC area percentage value (UV: 254 nm) of 98.3%.

$^1$H-NMR (CDCl$_3$, 300 MHz): δ (ppm): 1.38-1.45 (4H, m), 1.47-1.55 (4H, m), 1.57-1.67 (4H, m), 1.77-1.84 (4H, m), 2.66 (4H, t), 3.55 (4H, t), 7.36 (2H, s).

A gas in a flask equipped with a stirrer was purged with a nitrogen gas, then, sodium iodide (152.1 g) and acetone (600 mL) were added, and the mixture was stirred at room temperature for 0.5 hours. To this was added Mb6 (40.0 g), then, the mixture was heated up to the reflux temperature, and stirred at the reflux temperature for 24 hours. Thereafter, the mixture was cooled down to room temperature, and the resultant mixed liquid was added to water (1.2 L). The deposited solid was separated by filtration, then, washed with water, thereby obtaining a coarse product. The resultant coarse product was recrystallized from a mixed liquid of toluene and methanol, thereby obtaining 46.0 g of a compound Mb7 as a white solid. The resultant compound Mb7 had an HPLC area percentage value (UV: 254 nm) of 99.4%. This operation was repeated, thereby obtaining a necessary amount of the compound Mb7.

$^1$H-NMR (CDCl$_3$, 300 MHz): δ (ppm): 1.35-1.50 (8H, m), 1.57-1.65 (4H, m), 1.80-1.89 (4H, m), 2.65 (4H, t), 3.20 (4H, t), 7.36 (2H, s).

Synthesis Example 32

Synthesis of Compound Mb8

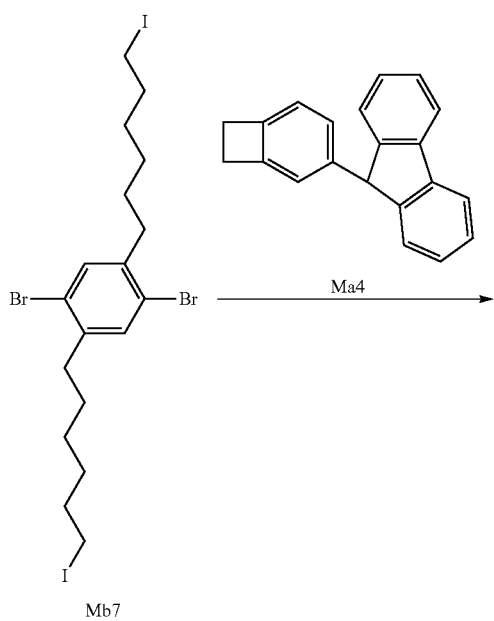

A gas in a flask equipped with a stirrer was purged with a nitrogen gas, then, sodium hydride (60 wt %, dispersed in liquid paraffin) (9.4 g), tetrahydrofuran (110 mL) and the compound Mb7 (63.2 g) were added. To this, a compound Ma4 (55.0 g) was added in several batches, then, the mixture was stirred for 12 hours. To this were added toluene (440 mL) and water (220 mL), then, an aqueous layer was separated. The resultant organic layer was washed with water, then, magnesium sulfate was added. The resultant mixed liquid was filtrated, and the resultant filtrate was concentrated under reduced pressure, thereby obtaining a coarse product. The resultant coarse product was purified by using a silica gel column (developing solvent: a mixed solvent of hexane and toluene). Thereafter, the product was recrystallized from heptane, thereby obtaining 84.1 g of a compound Mb8 as a white solid. The resultant compound Mb8 had an HPLC area percentage value (UV: 254 nm) of 99.5% or more.

$^1$H-NMR (CDCl$_3$, 300 MHz): δ (ppm): 0.70-0.76 (4H, m), 1.10-1.21 (8H, m), 1.32-1.44 (4H, m), 2.39-2.58 (8H, m), 3.00-3.12 (8H, m), 6.82-6.94 (4H, m), 7.00-7.05 (2H, m), 7.17-7.28 (10H, m), 7.30-7.38 (4H, m), 7.71-7.77 (4H, m).

Synthesis Example 33

Synthesis of Compound M13

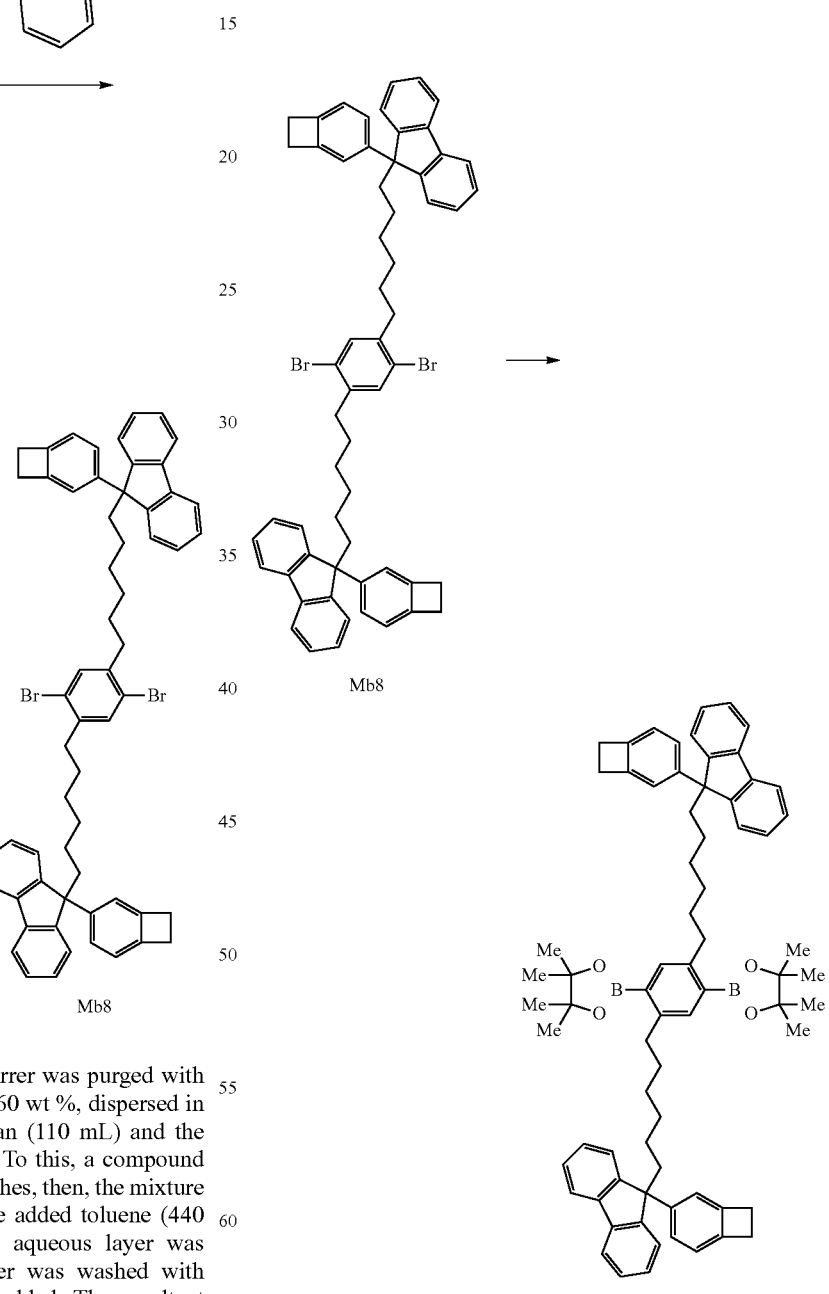

A gas in a flask equipped with a stirrer was purged with a nitrogen gas, then, the compound Mb8 (84.0 g), [1,1'-bis (diphenylphosphino)ferrocene]palladium(II) dichloride dichloromethane adduct ($PdCl_2$ (dppf).$CH_2Cl_2$, 2.2 g), bispinacolatodiboron (63.3 g), potassium acetate (52.8 g) and cyclopentyl methyl ether (840 mL) were added, and the mixture was heated up to the reflux temperature, then, stirred at the reflux temperature for 5 hours. Thereafter, the mixture was cooled down to room temperature, and toluene (500 mL) and water (300 mL) were added, then, an aqueous layer was separated. The resultant organic layer was washed with water, then, activated carbon (18.5 g) was added. The resultant mixed liquid was filtrated, and the resultant filtrate was concentrated under reduced pressure, thereby obtaining a coarse product. The resultant coarse product was purified by using a silica gel column (developing solvent: a mixed solvent of hexane and toluene). Thereafter, an operation of recrystallizing from a mixed liquid of toluene and acetonitrile was repeated, thereby obtaining 45.8 g of a compound MM1 as a white solid. The resultant compound M13 had an HPLC area percentage value (UV: 254 nm) of 99.4%.

$^1$H-NMR ($CDCl_3$, 300 MHz): δ (ppm): 0.70-0.76 (4H, m), 1.24-1.40 (36H, m), 2.39-2.48 (4H, m), 2.66-2.75 (4H, m), 3.00-3.10 (8H, m), 6.76-6.90 (4H, m), 7.00-7.05 (2H, m), 7.19-7.30 (8H, m), 7.30-7.36 (4H, m), 7.43 (2H, s), 7.72 (4H, d).

Synthesis Example 34

Synthesis of Polymer Compound HTL-4

Compound M14

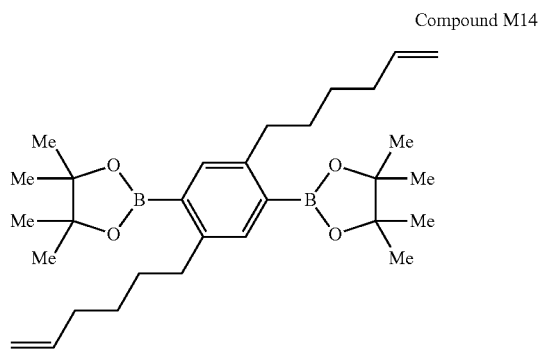 [SMILES: C=CCCCCc1cc(B2OC(C)(C)C(C)(C)O2)c(CCCCC=C)cc1B1OC(C)(C)C(C)(C)O1]

(Step 1) An inert gas atmosphere was prepared in a reaction vessel, then, a compound M13 (0.923 g), a compound M14 (0.0496 g) synthesized according to a method described in International Publication WO2013/146806, a compound M9 (0.917 g), dichlorobis(tris-o-methoxyphenylphosphine)palladium (1.76 mg) and toluene (34 ml) were added, and the mixture was heated at 105° C.

(Step 2) Into the reaction liquid, a 20 wt % tetraethylammonium hydroxide aqueous solution (6.7 ml) was dropped, and the mixture was refluxed for 6 hours.

(Step 3) After the reaction, to this were added phenylboronic acid (48.8 mg) and dichlorobis(tris-o-methoxyphenylphosphine)palladium (0.88 mg), and the mixture was refluxed for 14.5 hours.

(Step 4) Thereafter, to this was added a sodium diethyldithiacarbamate aqueous solution, and the mixture was stirred at 80° C. for 2 hours. After cooling, the resultant reaction liquid was washed with water twice, with a 3 wt % acetic acid aqueous solution twice and with water twice, and the resultant solution was dropped into methanol, to cause precipitation. The resultant precipitate was dissolved in toluene, and purified by passing through an alumina column and a silica gel column in this order. The resultant solution was dropped into methanol, and the mixture was stirred, then, the resultant precipitate was isolated by filtration, and dried, to obtain 1.23 g of a polymer compound HTL-4.

The polymer compound HTL-4 had a polystyrene-equivalent number-average molecular weight of $2.3 \times 10^4$ and a polystyrene-equivalent weight-average molecular weight of $1.2 \times 10^5$.

The polymer compound HTL-4 is a copolymer constituted of a constitutional unit derived from a compound M13, a constitutional unit derived from a compound M14 and a constitutional unit derived from a compound M9 at a molar ratio of 45:5:50, according to theoretical values calculated from the amounts of charged raw materials.

Synthesis Example 35

Synthesis of Polymer Compound ETL-1

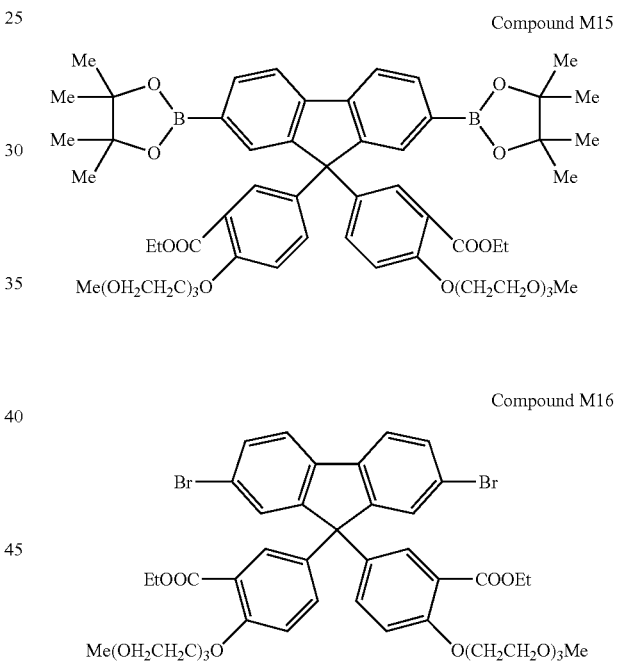

Compound M15

Compound M16

(Synthesis of Polymer Compound ETL-1a)

The polymer compound ETL-1a was synthesized according to a method described in JP-A No. 2012-33845, using a compound M15 synthesized according to a method described in JP-A No. 2012-33845 and a compound M16 synthesized according to a method described in JP-A No. 2012-33845.

The polymer compound ETL-1a had a Mn of $5.2 \times 10^4$.

The polymer compound ETL-1a is a copolymer constituted of a constitutional unit derived from a compound M15 and a constitutional unit derived from a compound M16 at a molar ratio of 50:50, according to theoretical values calculated from the amounts of charged raw materials.

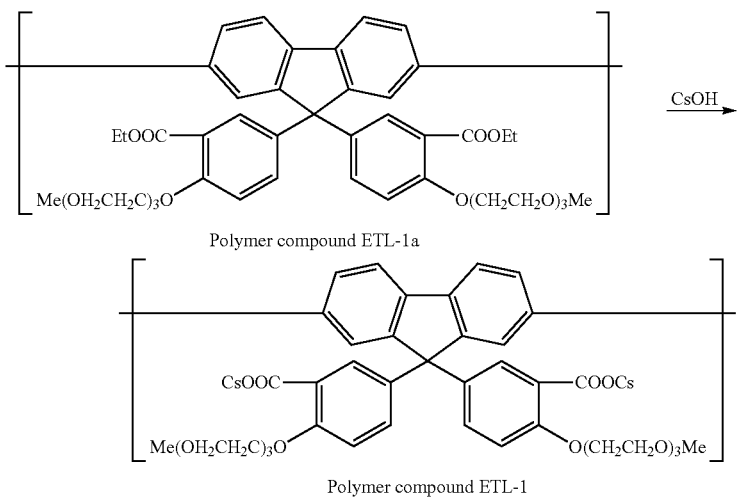

Polymer compound ETL-1a

Polymer compound ETL-1

(Synthesis of Polymer Compound ETL-1a)

An inert gas atmosphere was prepared in a reaction vessel, then, a polymer compound ETL-1a (200 mg), tetrahydrofuran (20 ml) and ethanol (20 ml) were added, and the mixture was heated at 55° C. To this was added cesium hydroxide (200 mg) dissolved in water (2 ml), and the mixture was stirred at 55° C. for 6 hours. Thereafter, the mixture was cooled down to room temperature, then, concentrated under reduced pressure, to obtain a solid. The resultant solid was washed with water, then, dried under reduced pressure, to obtain a polymer compound ETL-1 (150 mg, pale yellow solid). It was confirmed that a signal derived from an ethyl group of an ethyl ester portion of a polymer compound ETL-1a disappeared completely, by the NMR spectrum of the resultant polymer compound ETL-1.

Example D1

Fabrication and Evaluation of Light Emitting Device D1

(Fabrication of Light Emitting Device D1)
(Formation of Anode and Hole Injection Layer)

An ITO film with a thickness of 45 nm was attached to a glass substrate by a sputtering method, to form an anode. On the anode, a polythiophene.sulfonic acid type hole injection agent AQ-1200 (manufactured by Plextronics) was spin-coated to form a film with a thickness of 50 nm, and the film was heated on a hot plate at 170° C. for 15 minutes under an air atmosphere, to form a hole injection layer.

(Formation of Hole Transporting Layer)

A polymer compound HTL-1 was dissolved at a concentration of 0.6 wt % in xylene. The resultant xylene solution was spin-coated on the hole injection layer to form a film with a thickness of 20 nm, and the film was heated on a hot plate at 180° C. for 60 minutes under a nitrogen gas atmosphere to form a hole transporting layer.

(Formation of Light Emitting Layer)

A polymer compound HP-1, a compound B1, a compound G2 and a compound R2 (polymer compound HP-1/compound B1/compound G2/compound R2=59 wt %/40 wt %/0.6 wt %/0.4 wt %) were dissolved at a concentration of 1.2 wt % in xylene. The resultant xylene solution was spin-coated on the hole transporting layer to form a film with a thickness of 60 nm, and the film was heated at 130° C. for 10 minutes under a nitrogen gas atmosphere to form a light emitting layer.

(Formation of Cathode)

The substrate carrying the light emitting layer formed thereon was placed in a vapor deposition machine, and the pressure was reduced to $1.0 \times 10^{-4}$ Pa or less, then, as a cathode, sodium fluoride was vapor-deposited with a thickness of about 4 nm on the light emitting layer, then, aluminum was vapor-deposited with a thickness of about 80 nm on the sodium fluoride layer. After vapor deposition, sealing was performed using a glass substrate, to fabricate a light emitting device D1.

(Evaluation of Light Emitting Device)

Voltage was applied to the light emitting device D1, to observe EL emission. The external quantum efficiency at 50 cd/m² was 14.2%, and the CIE chromaticity coordinate (x, y) was (0.35, 0.52). The external quantum efficiency at 1000 cd/m² was 11.6%, and the CIE chromaticity coordinate (x, y) was (0.35, 0.52).

Comparative Example CD3

Fabrication and Evaluation of Light Emitting Device CD3

A light emitting device CD3 was fabricated in the same manner as in Example D1, excepting that a polymer compound HP-1, a compound B1, a compound G1 and a compound R1 (polymer compound HP-1/compound B1/compound G1/compound R1=59 wt %/40 wt %/0.6 wt %/0.4 wt %) were used instead of the polymer compound HP-1, the compound B1, the compound G2 and the compound R2 (polymer compound HP-1/compound B1/compound G2/compound R2=59 wt %/40 wt %/0.6 wt %/0.4 wt %) in Example D1.

Voltage was applied to the light emitting device CD3, to observe EL emission. The external quantum efficiency at 50 cd/m² was 12.9%, and the CIE chromaticity coordinate (x, y) was (0.36, 0.52).

Comparative Example CD4

Fabrication and Evaluation of Light Emitting Device CD4

A light emitting device CD4 was fabricated in the same manner as in Example D1, excepting that a polymer compound HTL-3, and, a polymer compound HP-3, a compound B2, a compound G1 and a compound R2 (polymer compound HP-3/compound B2/compound G1/compound R2=59 wt %/40 wt %/0.6 wt %/0.4 wt %) were used instead of the polymer compound HTL-1, and, the polymer compound HP-1, the compound B1, the compound G2 and the compound R2 (polymer compound HP-1/compound B1/compound G2/compound R2=59 wt %/40 wt %/0.6 wt %/0.4 wt %) in Example D1.

Voltage was applied to the light emitting device CD4, to observe EL emission. The external quantum efficiency at 50 cd/m$^2$ was 1.6%, and the CIE chromaticity coordinate (x, y) was (0.28, 0.59).

TABLE 17

| | light emitting device | hole transporting layer | light emitting layer composition | composition ratio (wt %) | external quantum efficiency (%) (50 cd/m$^2$) |
|---|---|---|---|---|---|
| Example D1 | D1 | HTL-1 | HP-1/B1/G2/R2 | 59/40/0.6/0.4 | 14.2 |
| Comparative Example CD3 | CD3 | HTL-1 | HP-1/B1/G1/R1 | 59/40/0.6/0.4 | 12.9 |
| Comparative Example CD4 | CD4 | HTL-3 | HP-3/B2/G1/R2 | 59/40/0.6/0.4 | 1.6 |

Example D2

Fabrication and Evaluation of Light Emitting Device D2

(Fabrication of Light Emitting Device D2)
(Formation of Anode and Hole Injection Layer)

An ITO film with a thickness of 45 nm was attached to a glass substrate by a sputtering method, to form an anode. On the anode, a polythiophene.sulfonic acid type hole injection agent AQ-1200 (manufactured by Plextronics) was spin-coated to form a film with a thickness of 35 nm, and the film was heated on a hot plate at 170° C. for 15 minutes under an air atmosphere, to form a hole injection layer.

(Formation of Hole Transporting Layer)

Poly(9-vinylcarbazole) (polymer compound PVK) (manufactured by Sigma-Aldrich, weight-average molecular weight: about 1.1×10$^6$, powdery) was dissolved at a concentration of 0.6 wt % in chlorobenzene. The resultant chlorobenzene solution was spin-coated on the hole injection layer to form a film with a thickness of 20 nm, and the film was heated on a hot plate at 180° C. for 60 minutes under a nitrogen gas atmosphere to form a hole transporting layer.

(Formation of Light Emitting Layer)

A polymer compound HP-2, a compound B1, a compound G3 and a compound R2 (polymer compound HP-2/compound B1/compound G3/compound R2=59 wt %/40 wt %/0.6 wt %/0.4 wt %) were dissolved at a concentration of 1.8 wt % in xylene. The resultant xylene solution was spin-coated on the hole transporting layer to form a film with a thickness of 75 nm, and the film was heated at 130° C. for 10 minutes under a nitrogen gas atmosphere to form a light emitting layer.

(Formation of Cathode)

The substrate carrying the light emitting layer formed thereon was placed in a vapor deposition machine, and the pressure was reduced to 1.0×10$^{-4}$ Pa or less, then, as a cathode, sodium fluoride was vapor-deposited with a thickness of about 4 nm on the light emitting layer, then, aluminum was vapor-deposited with a thickness of about 80 nm on the sodium fluoride layer. After vapor deposition, sealing was performed using a glass substrate, to fabricate a light emitting device D3.

(Evaluation of Light Emitting Device)

Voltage was applied to the light emitting device D2, to observe EL emission. The external quantum efficiency at 50 cd/m$^2$ was 16.5%, and the CIE chromaticity coordinate (x, y) was (0.41, 0.45). The external quantum efficiency at 1000 cd/m$^2$ was 15.0%, and the CIE chromaticity coordinate (x, y) was (0.41, 0.45).

Example D3

Fabrication and Evaluation of Light Emitting Device D3

A light emitting device D3 was fabricated in the same manner as in Example D2, excepting that a polymer compound HP-2, a compound B1, a compound G3 and a compound R3 (polymer compound HP-2/compound B1/compound G3/compound R3=59 wt %/40 wt %/0.6 wt %/0.4 wt %) were used instead of the polymer compound HP-2, the compound B1, the compound G3 and the compound R2 (polymer compound HP-2/compound B1/compound G3/compound R2=59 wt %/40 wt %/0.6 wt %/0.4 wt %) in Example D2.

Voltage was applied to the light emitting device D3, to observe EL emission. The external quantum efficiency at 50 cd/m$^2$ was 17.1%, and the CIE chromaticity coordinate (x, y) was (0.54, 0.40). The external quantum efficiency at 1000 cd/m$^2$ was 15.6%, and the CIE chromaticity coordinate (x, y) was (0.49, 0.42).

Example D4

Fabrication and Evaluation of Light Emitting Device D4

A light emitting device D4 was fabricated in the same manner as in Example D2, excepting that a polymer compound HP-2, a compound B1, a compound G3 and a compound R4 (polymer compound HP-2/compound B1/compound G3/compound R4=59 wt %/40 wt %/0.6 wt %/0.4 wt %) were used instead of the polymer compound HP-2, the compound B1, the compound G3 and the compound R2 (polymer compound HP-2/compound B1/compound G3/compound R2=59 wt %/40 wt %/0.6 wt %/0.4 wt %) in Example D2.

Voltage was applied to the light emitting device D4, to observe EL emission. The external quantum efficiency at 50 cd/m$^2$ was 19.5%, and the CIE chromaticity coordinate (x, y) was (0.55, 0.42). The external quantum efficiency at 1000 cd/m$^2$ was 17.7%, and the CIE chromaticity coordinate (x, y) was (0.51, 0.44).

Example D5

Fabrication and Evaluation of Light Emitting Device D5

A light emitting device D5 was fabricated in the same manner as in Example D2, excepting that a polymer compound HP-2, a compound B1, a compound G3 and a compound R5 (polymer compound HP-2/compound B1/compound G3/compound R5=59 wt %/40 wt %/0.6 wt %/0.4 wt %) were used instead of the polymer compound HP-2, the compound B1, the compound G3 and the compound R2 (polymer compound HP-2/compound B1/compound G3/compound R2=59 wt %/40 wt %/0.6 wt %/0.4 wt %) in Example D2.

Voltage was applied to the light emitting device D5, to observe EL emission. The external quantum efficiency at 50 cd/m$^2$ was 15.0%, and the CIE chromaticity coordinate (x, y) was (0.54, 0.40). The external quantum efficiency at 1000 cd/m$^2$ was 14.2%, and the CIE chromaticity coordinate (x, y) was (0.47, 0.42).

Example D6

Fabrication and Evaluation of Light Emitting Device D6

A light emitting device D6 was fabricated in the same manner as in Example D2, excepting that a polymer compound HP-2, a compound B1, a compound G3 and a compound R6 (polymer compound HP-2/compound B1/compound G3/compound R6=59 wt %/40 wt %/0.6 wt %/0.4 wt %) were used instead of the polymer compound HP-2, the compound B1, the compound G3 and the compound R2 (polymer compound HP-2/compound B1/compound G3/compound R2=59 wt %/40 wt %/0.6 wt %/0.4 wt %) in Example D2.

Voltage was applied to the light emitting device D6, to observe EL emission. The external quantum efficiency at 50 cd/m$^2$ was 14.8%, and the CIE chromaticity coordinate (x, y) was (0.54, 0.40). The external quantum efficiency at 1000 cd/m$^2$ was 13.8%, and the CIE chromaticity coordinate (x, y) was (0.48, 0.42).

Example D7

Fabrication and Evaluation of Light Emitting Device D7

A light emitting device D7 was fabricated in the same manner as in Example D2, excepting that a polymer compound HP-2, a compound B1, a compound G3 and a compound R6 (polymer compound HP-2/compound B1/compound G3/compound R6=59.2 wt %/40 wt %/0.6 wt %/0.2 wt %) were used instead of the polymer compound HP-2, the compound B1, the compound G3 and the compound R2 (polymer compound HP-2/compound B1/compound G3/compound R2=59 wt %/40 wt %/0.6 wt %/0.4 wt %) in Example D2.

Voltage was applied to the light emitting device D7, to observe EL emission. The external quantum efficiency at 50 cd/m$^2$ was 17.4%, and the CIE chromaticity coordinate (x, y) was (0.46, 0.44). The external quantum efficiency at 1000 cd/m$^2$ was 16.3%, and the CIE chromaticity coordinate (x, y) was (0.41, 0.45).

Example D8

Fabrication and Evaluation of Light Emitting Device D8

A light emitting device D8 was fabricated in the same manner as in Example D2, excepting that a polymer compound HP-2, a compound B1, a compound G3 and a compound R6 (polymer compound HP-2/compound B1/compound G3/compound R6=59.1 wt %/40 wt %/0.6 wt %/0.3 wt %) were used instead of the polymer compound HP-2, the compound B1, the compound G3 and the compound R2 (polymer compound HP-2/compound B1/compound G3/compound R2=59 wt %/40 wt %/0.6 wt %/0.4 wt %) in Example D2.

Voltage was applied to the light emitting device D8, to observe EL emission. The external quantum efficiency at 50 cd/m$^2$ was 16.3%, and the CIE chromaticity coordinate (x, y) was (0.51, 0.42). The external quantum efficiency at 1000 cd/m$^2$ was 15.4%, and the CIE chromaticity coordinate (x, y) was (0.46, 0.44).

Example D9

Fabrication and Evaluation of Light Emitting Device D9

A light emitting device D9 was fabricated in the same manner as in Example D2, excepting that a polymer compound HP-2, a compound B1, a compound G2 and a compound R2 (polymer compound HP-2/compound B1/compound G2/compound R2=59 wt %/40 wt %/0.6 wt %/0.4 wt %) were used instead of the polymer compound HP-2, the compound B1, the compound G3 and the compound R2 (polymer compound HP-2/compound B1/compound G3/compound R2=59 wt %/40 wt %/0.6 wt %/0.4 wt %) in Example D2.

Voltage was applied to the light emitting device D9, to observe EL emission. The external quantum efficiency at 50 cd/m$^2$ was 14.8%, and the CIE chromaticity coordinate (x, y) was (0.34, 0.45). The external quantum efficiency at 1000 cd/m$^2$ was 13.2%, and the CIE chromaticity coordinate (x, y) was (0.33, 0.44).

Example D11

Fabrication and Evaluation of Light Emitting Device D11

A light emitting device D11 was fabricated in the same manner as in Example D2, excepting that a polymer compound HP-2, a compound B1, a compound G4 and a compound R2 (polymer compound HP-2/compound B1/compound G4/compound R2=59 wt %/40 wt %/0.6 wt %/0.4 wt %) were used instead of the polymer compound HP-2, the compound B1, the compound G3 and the compound R2 (polymer compound HP-2/compound B1/compound G3/compound R2=59 wt %/40 wt %/0.6 wt %/0.4 wt %) in Example D2.

Voltage was applied to the light emitting device D11, to observe EL emission. The external quantum efficiency at 50 cd/m$^2$ was 15.8%, and the CIE chromaticity coordinate (x, y) was (0.22, 0.36). The external quantum efficiency at 1000 cd/m$^2$ was 13.7%, and the CIE chromaticity coordinate (x, y) was (0.21, 0.36).

Comparative Example CD1

Fabrication and Evaluation of Light Emitting Device CD1

A light emitting device CD1 was fabricated in the same manner as in Example D2, excepting that a polymer compound HP-2, a compound B2, a compound G1 and a compound R2 (polymer compound HP-2/compound B2/compound G1/compound R2=59 wt %/40 wt %/0.6 wt %/0.4 wt %) were used instead of the polymer compound HP-2, the compound B1, the compound G3 and the compound R2 (polymer compound HP-2/compound B1/compound G3/compound R2=59 wt %/40 wt %/0.6 wt %/0.4 wt %) in Example D2.

Voltage was applied to the light emitting device CD1, to observe EL emission. The external quantum efficiency at 50 cd/m$^2$ was 1.5%, and the CIE chromaticity coordinate (x, y) was (0.30, 0.53). Voltage was applied up to 12 V, however, 1000 cd/m$^2$ was not attained.

agent AQ-1200 (manufactured by Plextronics) was spin-coated to form a film with a thickness of 35 nm, and the film was heated on a hot plate at 170° C. for 15 minutes under an air atmosphere, to form a hole injection layer.
(Formation of Hole Transporting Layer)

A polymer compound HTL-2 was dissolved at a concentration of 0.6 wt % in xylene. The resultant xylene solution was spin-coated on the hole injection layer to form a film with a thickness of 20 nm, and the film was heated on a hot plate at 180° C. for 60 minutes under a nitrogen gas atmosphere to form a hole transporting layer.
(Formation of Light Emitting Layer)

A polymer compound HP-2, a compound B1, a compound G2 and a compound R4 (polymer compound HP-2/compound B1/compound G2/compound R4=59 wt %/40 wt %/0.6 wt %/0.4 wt %) were dissolved at a concentration of 1.2 wt % in chlorobenzene. The resultant chlorobenzene solution was spin-coated on the hole transporting layer to form a film with a thickness of 60 nm, and the film was heated at 130° C. for 10 minutes under a nitrogen gas atmosphere to form a light emitting layer.
(Formation of Cathode)

The substrate carrying the light emitting layer formed thereon was placed in a vapor deposition machine, and the pressure was reduced to 1.0×10$^{-4}$ Pa or less, then, as a cathode, sodium fluoride was vapor-deposited with a thickness of about 4 nm on the light emitting layer, then, aluminum was vapor-deposited with a thickness of about 80 nm on the sodium fluoride layer. After vapor deposition,

TABLE 18

| | light emitting device | hole transporting layer | light emitting layer composition | composition ratio (wt %) | external quantum efficiency (%) (50 cd/m$^2$) |
|---|---|---|---|---|---|
| Example D2 | D2 | PVK | HP-2/B1/G3/R2 | 59/40/0.6/0.4 | 16.5 |
| Example D3 | D3 | PVK | HP-2/B1/G3/R3 | 59/40/0.6/0.4 | 17.1 |
| Example D4 | D4 | PVK | HP-2/B1/G3/R4 | 59/40/0.6/0.4 | 19.5 |
| Example D5 | D5 | PVK | HP-2/B1/G3/R5 | 59/40/0.6/0.4 | 15.0 |
| Example D6 | D6 | PVK | HP-2/B1/G3/R6 | 59/40/0.6/0.4 | 14.8 |
| Example D7 | D7 | PVK | HP-2/B1/G3/R6 | 59.2/40/0.6/0.2 | 17.4 |
| Example D8 | D8 | PVK | HP-2/B1/G3/R6 | 59.1/40/0.6/0.3 | 16.3 |
| Example D9 | D9 | PVK | HP-2/B1/G2/R2 | 59/40/0.6/0.4 | 14.8 |
| Example D11 | D11 | PVK | HP-2/B1/G4/R2 | 59/40/0.6/0.4 | 15.8 |
| Comparative Example CD1 | CD1 | PVK | HP-2/B2/G1/R2 | 59/40/0.6/0.4 | 1.5 |

Example D10

Fabrication and Evaluation of Light Emitting Device D10

(Fabrication of Light Emitting Device D10)
(Formation of Anode and Hole Injection Layer)

An ITO film with a thickness of 45 nm was attached to a glass substrate by a sputtering method, to form an anode. On the anode, a polythiophene.sulfonic acid type hole injection sealing was performed using a glass substrate, to fabricate a light emitting device D10.
(Evaluation of Light Emitting Device)

Voltage was applied to the light emitting device D10, to observe EL emission. The external quantum efficiency at 50 cd/m$^2$ was 14.6%, and the CIE chromaticity coordinate (x, y) was (0.56, 0.41). The external quantum efficiency at 1000 cd/m$^2$ was 12.6%, and the CIE chromaticity coordinate (x, y) was (0.50, 0.44).

Comparative Example CD2

Fabrication and Evaluation of Light Emitting Device CD2

A light emitting device CD2 was fabricated in the same manner as in Example D10, excepting that poly(9-vinylcarbazole) (polymer compound PVK) (manufactured by Sigma-Aldrich, weight-average molecular weight: about $1.1 \times 10^6$, powdery), a compound B1, a compound G2 and a compound R4 (polymer compound PVK/compound B1/compound G2/compound R4=59 wt %/40 wt %/0.6 wt %/0.4 wt %) were used instead of the polymer compound HP-2, the compound B1, the compound G2 and the compound R4 (polymer compound HP-2/compound B1/compound G2/compound R4=59 wt %/40 wt %/0.6 wt %/0.4 wt %) in Example D10.

Voltage was applied to the light emitting device CD2, to observe EL emission. The external quantum efficiency at 50 cd/m² was 1.3%, and the CIE chromaticity coordinate (x, y) was (0.48, 0.42). The external quantum efficiency at 1000 cd/m² was 2.5%, and the CIE chromaticity coordinate (x, y) was (0.44, 0.42).

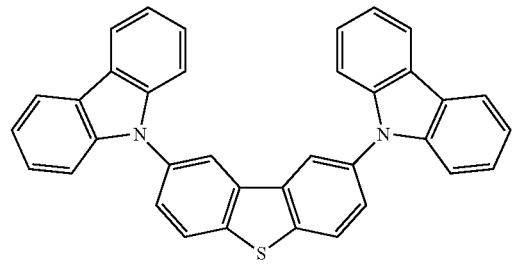 [SMILES: c1ccc2c(c1)c1ccccc1n2-c1ccc2sc3ccc(-n4c5ccccc5c5ccccc54)cc3c2c1]

Low Molecular Weight Compound HM-1

(Formation of Electron Transporting Layer)

A polymer compound ETL-1 was dissolved at a concentration of 0.25 wt % in 2,2,3,3,4,4,5,5-octafluoro-1-pentanol.

TABLE 19

| | light emitting device | hole transporting layer | light emitting layer composition | composition ratio (wt %) | external quantum efficiency (%) (50 cd/m²) |
|---|---|---|---|---|---|
| Example D10 | D10 | HTL-2 | HP-2/B1/G2/R4 | 59/40/0.6/0.4 | 14.6 |
| Comparative Example CD2 | CD2 | HTL-2 | PVK/1/G2/R4 | 59/40/0.6/0.4 | 1.3 |

Example D12

Fabrication and Evaluation of Light Emitting Device D12

(Fabrication of Light Emitting Device D12)
(Formation of Anode and Hole Injection Layer)

An ITO film with a thickness of 45 nm was attached to a glass substrate by a sputtering method, to form an anode. On the anode, a polythiophene.sulfonic acid type hole injection agent AQ-1200 (manufactured by Plextronics) was spin-coated to form a film with a thickness of 35 nm, and the film was heated on a hot plate at 170° C. for 15 minutes under an air atmosphere, to form a hole injection layer.

(Formation of Hole Transporting Layer)

A polymer compound HTL-4 was dissolved at a concentration of 0.7 wt % in xylene. The resultant xylene solution was spin-coated on the hole injection layer to form a film with a thickness of 20 nm, and the film was heated on a hot plate at 180° C. for 60 minutes under a nitrogen gas atmosphere to form a hole transporting layer.

(Formation of Light Emitting Layer)

A low molecular weight compound HM-1 (manufactured by Luminescence Technology), a compound B3, a compound G2 and a compound R2 (low molecular weight compound HM-1/compound B3/compound G2/compound R2=73.9 wt %/25 wt %/1 wt %/0.1 wt %) were dissolved at a concentration of 2.0 wt % in toluene. The resultant toluene solution was spin-coated on the hole transporting layer to form a film with a thickness of 60 nm, and the film was heated at 130° C. for 10 minutes under a nitrogen gas atmosphere to form a light emitting layer.

The resultant 2,2,3,3,4,4,5,5-octafluoro-1-pentanol solution was spin-coated on the light emitting layer to form a film with a thickness of 10 nm, and the film was heated at 130° C. for 10 minutes under a nitrogen gas atmosphere to form an electron transporting layer.

(Formation of Cathode)

The substrate carrying the electron transporting layer formed thereon was placed in a vapor deposition machine, and the pressure was reduced to $1.0 \times 10^{-4}$ Pa or less, then, as a cathode, sodium fluoride was vapor-deposited with a thickness of about 4 nm on the light emitting layer, then, aluminum was vapor-deposited with a thickness of about 80 nm on the sodium fluoride layer. After vapor deposition, sealing was performed using a glass substrate, to fabricate a light emitting device D12.

(Evaluation of Light Emitting Device)

Voltage was applied to the light emitting device D12, to observe EL emission. The external quantum efficiency at 5000 cd/m² was 3.6%, and the CIE chromaticity coordinate (x, y) was (0.26, 0.48). The electric current value was set so that the initial luminance was 5000 cd/m², then, the device was driven at constant current, and the time until when the luminance reached 70% of the initial luminance was measured, to find a time of 12.5 hours.

Example D13

Fabrication and Evaluation of Light Emitting Device D13

A light emitting device D13 was fabricated in the same manner as in Example D12, excepting that a low molecular weight compound HM-1, a compound B3, a compound G2 and a compound R4 (low molecular weight compound HM-1/compound B3/compound G2/compound R4=73.9 wt %/25 wt %/1 wt %/0.1 wt %) were used instead of the low molecular weight compound HM-1, the compound B3, the compound G2 and the compound R2 (low molecular weight compound HM-1/compound B3/compound G2/compound R2=73.9 wt %/25 wt %/1 wt %/0.1 wt %) in Example D12.

Voltage was applied to the light emitting device D13, to observe EL emission. The external quantum efficiency at 5000 cd/m$^2$ was 4.4%, and the CIE chromaticity coordinate (x, y) was (0.31, 0.50). The electric current value was set so that the initial luminance was 5000 cd/m$^2$, then, the device was driven at constant current, and the time until when the luminance reached 70% of the initial luminance was measured, to find a time of 14.9 hours.

Example D14

Fabrication and Evaluation of Light Emitting Device D14

A light emitting device D14 was fabricated in the same manner as in Example D12, excepting that a low molecular weight compound HM-1, a compound B4, a compound G2 and a compound R2 (low molecular weight compound HM-1/compound B4/compound G2/compound R2=73.9 wt %/25 wt %/1 wt %/0.1 wt %) were used instead of the low molecular weight compound HM-1, the compound B3, the compound G2 and the compound R2 (low molecular weight compound HM-1/compound B3/compound G2/compound R2=73.9 wt %/25 wt %/1 wt %/0.1 wt %) in Example D12.

Voltage was applied to the light emitting device D14, to observe EL emission. The external quantum efficiency at 5000 cd/m$^2$ was 7.0%, and the CIE chromaticity coordinate (x, y) was (0.26, 0.48). The electric current value was set so that the initial luminance was 5000 cd/m$^2$, then, the device was driven at constant current, and the time until when the luminance reached 70% of the initial luminance was measured, to find a time of 11.1 hours.

Comparative Example CD5

Fabrication and Evaluation of Light Emitting Device CD5

A light emitting device CD5 was fabricated in the same manner as in Example D12, excepting that a low molecular weight compound HM-1, a compound B3, a compound G1 and a compound R1 (low molecular weight compound HM-1/compound B3/compound G1/compound R1=73.9 wt %/25 wt %/1 wt %/0.1 wt %) were used instead of the low molecular weight compound HM-1, the compound B3, then compound G2 and the compound R2 (low molecular weight compound HM-1/compound B3/compound G2/compound R2=73.9 wt %/25 wt %/1 wt %/0.1 wt %) in Example D12.

Voltage was applied to the light emitting device CD5, to observe EL emission. The external quantum efficiency at 5000 cd/m$^2$ was 3.2%, and the CIE chromaticity coordinate (x, y) was (0.28, 0.50). The electric current value was set so that the initial luminance was 5000 cd/m$^2$, then, the device was driven at constant current, and the time until when the luminance reached 70% of the initial luminance was measured, to find a time of 9.4 hours.

TABLE 20

| | light emitting device | hole transporting layer | light emitting layer composition | composition ratio (wt %) | external quantum efficiency (%) (5000 cd/m$^2$) |
|---|---|---|---|---|---|
| Example D12 | D12 | HTL-4 | HM1/B3/G2/R2 | 73.9/25/1/0.1 | 3.6 |
| Example D13 | D13 | HTL-4 | HM1/B3/G2/R4 | 73.9/25/1/0.1 | 4.4 |
| Example D14 | D14 | HTL-4 | HM1/B4/G2/R2 | 73.9/25/1/0.1 | 7.0 |
| Comparative Example CD5 | CD5 | HTL-4 | HM1/B3/G1/R1 | 73.9/25/1/0.1 | 3.2 |

Example D15

Fabrication and Evaluation of Light Emitting Device D15

(Fabrication of Light Emitting Device D15)
(Formation of Anode and Hole Injection Layer)

An ITO film with a thickness of 45 nm was attached to a glass substrate by a sputtering method, to form an anode. On the anode, a polythiophene.sulfonic acid type hole injection agent AQ-1200 (manufactured by Plextronics) was spin-coated to form a film with a thickness of 35 nm, and the film was heated on a hot plate at 170° C. for 15 minutes under an air atmosphere, to form a hole injection layer.

(Formation of Hole Transporting Layer)

Poly(9-vinylcarbazole) (polymer compound PVK) (manufactured by Sigma-Aldrich, weight-average molecular weight: about 1.1×10$^6$, powdery) was dissolved at a concentration of 0.6 wt % in chlorobenzene. The resultant chlorobenzene solution was spin-coated on the hole injection layer to form a film with a thickness of 20 nm, and the film was heated on a hot plate at 180° C. for 60 minutes under a nitrogen gas atmosphere to form a hole transporting layer.

(Formation of Light Emitting Layer)

A low molecular weight compound HM-1, a compound B3, a compound G2 and a compound R2 (low molecular weight compound HM-1/compound B3/compound G2/compound R2=73.9 wt %/25 wt %/1 wt %/0.1 wt %) were dissolved at a concentration of 2.0 wt % in toluene. The resultant toluene solution was spin-coated on the hole transporting layer to form a film with a thickness of 60 nm, and the film was heated at 130° C. for 10 minutes under a nitrogen gas atmosphere to form a light emitting layer.

Voltage was applied to the light emitting device CD6, to observe EL emission. The external quantum efficiency at 5000 cd/m² was 4.6%, and the CIE chromaticity coordinate (x, y) was (0.25, 0.49). The electric current value was set so that the initial luminance was 5000 cd/m², then, the device was driven at constant current, and the time until when the luminance reached 70% of the initial luminance was measured, to find a time of 0.51 hours.

TABLE 21

| light emitting device | hole transporting layer | light emitting layer composition | composition ratio (wt %) | external quantum efficiency (%) (5000 cd/m²) |
|---|---|---|---|---|
| Example D15 | D15 | PVK | HM1/B3/G2/R2 | 73.9/25/1/0.1 | 5.4 |
| Comparative Example CD6 | CD6 | PVK | HM1/B3/G1/R1 | 73.9/25/1/0.1 | 4.6 |

(Formation of Electron Transporting Layer)

A polymer compound ETL-1 was dissolved at a concentration of 0.25 wt % in 2,2,3,3,4,4,5,5-octafluoro-1-pentanol. The resultant 2,2,3,3,4,4,5,5-octafluoro-1-pentanol solution was spin-coated on the light emitting layer to form a film with a thickness of 10 nm, and the film was heated at 130° C. for 10 minutes under a nitrogen gas atmosphere to form an electron transporting layer.

(Formation of Cathode)

The substrate carrying the electron transporting layer formed thereon was placed in a vapor deposition machine, and the pressure was reduced to $1.0 \times 10^{-4}$ Pa or less, then, as a cathode, sodium fluoride was vapor-deposited with a thickness of about 4 nm on the light emitting layer, then, aluminum was vapor-deposited with a thickness of about 80 nm on the sodium fluoride layer. After vapor deposition, sealing was performed using a glass substrate, to fabricate a light emitting device D15.

(Evaluation of Light Emitting Device)

Voltage was applied to the light emitting device D15, to observe EL emission. The external quantum efficiency at 5000 cd/m² was 5.4%, and the CIE chromaticity coordinate (x, y) was (0.24, 0.47). The electric current value was set so that the initial luminance was 5000 cd/m², then, the device was driven at constant current, and the time until when the luminance reached 70% of the initial luminance was measured, to find a time of 0.69 hours.

Example CD6

Fabrication and Evaluation of Light Emitting Device CD6

A light emitting device CD6 was fabricated in the same manner as in Example D15, excepting that a low molecular weight compound HM-1, a compound B3, a compound G1 and a compound R1 (low molecular weight compound HM-1/compound B3/compound G1/compound R1=73.9 wt %/25 wt %/1 wt %/0.1 wt %) were used instead of the low molecular weight compound HM-1, the compound B3, the compound G2 and the compound R2 (low molecular weight compound HM-1/compound B3/compound G2/compound R2=73.9 wt %/25 wt %/1 wt %/0.1 wt %) in Example D15.

Example D16

Fabrication and Evaluation of Light Emitting Device D16

(Fabrication of Light Emitting Device D16)
(Formation of Anode and Hole Injection Layer)

An ITO film with a thickness of 45 nm was attached to a glass substrate by a sputtering method, to form an anode. On the anode, a polythiophene.sulfonic acid type hole injection agent AQ-1200 (manufactured by Plextronics) was spin-coated to form a film with a thickness of 35 nm, and the film was heated on a hot plate at 170° C. for 15 minutes under an air atmosphere, to form a hole injection layer.

(Formation of Hole Transporting Layer)

A polymer compound HTL-2 was dissolved at a concentration of 0.7 wt % in xylene. The resultant xylene solution was spin-coated on the hole injection layer to form a film with a thickness of 20 nm, and the film was heated on a hot plate at 180° C. for 60 minutes under a nitrogen gas atmosphere to form a hole transporting layer.

(Formation of Light Emitting Layer)

A polymer compound HP-4, a compound B3, a compound G3 and a compound R2 (polymer compound HP-4/compound B3/compound G3/compound R2=59 wt %/40 wt %/0.6 wt %/0.4 wt %) were dissolved at a concentration of 1.8 wt % in xylene. The resultant xylene solution was spin-coated on the hole transporting layer to form a film with a thickness of 75 nm, and the film was heated at 130° C. for 10 minutes under a nitrogen gas atmosphere to form a light emitting layer.

(Formation of Electron Transporting Layer)

A polymer compound ETL-1 was dissolved at a concentration of 0.25 wt % in 2,2,3,3,4,4,5,5-octafluoro-1-pentanol. The resultant 2,2,3,3,4,4,5,5-octafluoro-1-pentanol solution was spin-coated on the light emitting layer to form a film with a thickness of 10 nm, and the film was heated at 130° C. for 10 minutes under a nitrogen gas atmosphere to form an electron transporting layer.

(Formation of Cathode)

The substrate carrying the electron transporting layer formed thereon was placed in a vapor deposition machine, and the pressure was reduced to $1.0 \times 10^{-4}$ Pa or less, then, as a cathode, sodium fluoride was vapor-deposited with a thickness of about 4 nm on the light emitting layer, then, aluminum was vapor-deposited with a thickness of about 80 nm on the sodium fluoride layer. After vapor deposition, sealing was performed using a glass substrate, to fabricate a light emitting device D16.

(Evaluation of Light Emitting Device)

Voltage was applied to the light emitting device D16, to observe EL emission. The external quantum efficiency at 100 cd/m² was 5.9%, and the CIE chromaticity coordinate (x, y) was (0.30, 0.47).

Comparative Example CD7

Fabrication and Evaluation of Light Emitting Device CD7

A light emitting device CD7 was fabricated in the same manner as in Example D16, excepting that a polymer compound HP-4, a compound B3, a compound G1 and a compound R1 (polymer compound HP-4/compound B3/compound G1/compound R1=59 wt %/40 wt %/0.6 wt %/0.4 wt %) were used instead of the polymer compound HP-4, the compound B3, the compound G3 and the compound R2 (polymer compound HP-4/compound B3/compound G3/compound R2=59 wt %/40 wt %/0.6 wt %/0.4 wt %) in Example D16.

Voltage was applied to the light emitting device CD7, to observe EL emission. The external quantum efficiency at 100 cd/m² was 4.7%, and the CIE chromaticity coordinate (x, y) was (0.28, 0.49).

TABLE 22

| | light emitting device | hole transporting layer | light emitting layer composition | composition ratio (wt %) | external quantum efficiency (%) (100 cd/m²) |
|---|---|---|---|---|---|
| Example D16 | D16 | HTL-2 | HP-4/B3/G3/R2 | 59/40/0.6/0.4 | 5.9 |
| Comparative Example CD7 | CD7 | HTL-2 | HP-4/B3/G1/R1 | 59/40/0.6/0.4 | 4.7 |

The invention claimed is:

1. A composition comprising
a phosphorescent compound (B) having an emission spectrum whose maximum peak wavelength is from 380 nm to less than 495 nm and having no dendron represented by the formula (D-A) or (D-B), wherein the emission spectrum is obtained by measuring the PL spectrum of a dilute solution comprising the phosphorescent compound (B) and an organic solvent at room temperature,
two or more phosphorescent compounds (DGR) having an emission spectrum whose maximum peak wavelength is from 495 nm to less than 750 nm and having a dendron represented by the formula (D-A) or (D-B'), wherein the emission spectrum is obtained by measuring the PL spectrum of a dilute solution comprising the phosphorescent compound (DGR) and an organic solvent at room temperature, and
a compound represented by the formula (H-1), wherein the phosphorescent compound (B) is a phosphorescent compound represented by the formula (1'),
each of the two or more phosphorescent compounds (DGR) is a phosphorescent compound represented by the formula (2), and at least one of the two or more phosphorescent compounds (DGR) is a phosphorescent further compound represented by the formula (2-A1), (2-A2), (2-A3), or (2-A4), and
a ratio of the content of the two or more phosphorescent compounds (DGR) to the content of the phosphorescent compound (B) is 0.1 to 10 parts by weight to 100 parts by weight:

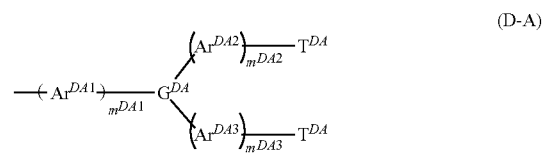

(D-A)

wherein
$m^{DA1}$, $m^{DA2}$ and $m^{DA3}$ each independently represent an integer of 0 or more,
$G^{DA}$ represents a nitrogen atom, an aromatic hydrocarbon group or a heterocyclic group and these groups each optionally have a substituent,
$Ar^{DA1}$, $Ar^{DA2}$ and $Ar^{DA3}$ each independently represent an arylene group or a divalent heterocyclic group and these groups each optionally have a substituent, and when a plurality of $Ar^{DA1}$, $Ar^{DA2}$ and $Ar^{DA3}$ are present, they may be the same or different at each occurrence, and $T^{DA}$ represents an aryl group or a monovalent heterocyclic group and these groups each optionally have a substituent, and the plurality of $T^{DA}$ may be the same or different:

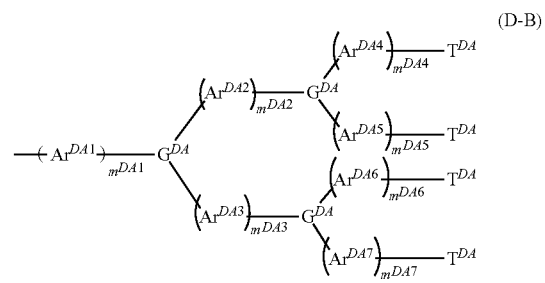

(D-B)

wherein
$m^{DA4}$, $m^{DA5}$, $m^{DA6}$ and $m^{DA7}$ each independently represent an integer of 0 or more, the plurality of $G^{DA}$ may be the same or different, $Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group and these groups each optionally have a substituent, and when a plurality of $Ar^{DA1}$, $Ar^{DA2}$, $Ar^{DA3}$, $Ar^{DA4}$, $Ar^{DA5}$, $Ar^{DA6}$ and $Ar^{DA7}$ are present, they may be the same or different at each occurrence;

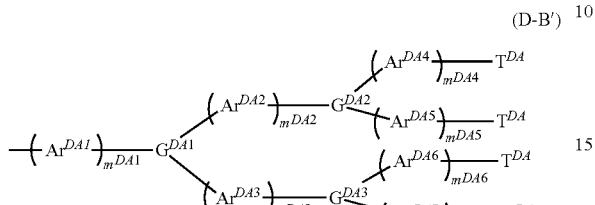

(D-B')

wherein $G^{DA1}$, $G^{DA2}$ and $G^{DA3}$ each independently represent a nitrogen atom, anaromatic hydrocarbon group or a heterocyclic group and these groups each optionally have a substituent, and $m^{DA2}$ is an integer of 1 or more when $G^{DA1}$ and $G^{DA2}$ are each a nitrogen atom, $m^{DA3}$ is an integer of 1 or more when $G^{DA1}$ and $G^{DA3}$ are each a nitrogen atom;

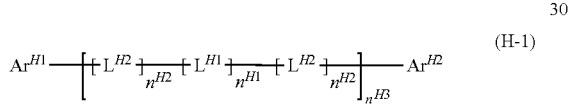

(H-1)

wherein $Ar^{H1}$ and $Ar^{H2}$ each independently represent an aryl group or a monovalent heterocyclic group and these groups each optionally have a substituent, $n^{H1}$ represents 1, $n^{H2}$ represents 0 or 1, and a plurality of $n^{H2}$ may be the same or different, $n^{H3}$ represents 1, $L^{H1}$ represents a divalent heterocyclic group represented by the formula (AA-10), (AA-11), (AA-12), (AA-13), (AA-14), (AA-15), (AA-33) or (AA-34), $L^{H2}$ represents a group represented by -N(-$L^{H21}$- $R^{H21}$)-, and when a plurality of $L^{H2}$ are present, they may be the same or different, and $L^{H21}$ represents a single bond, an arylene group or a divalent heterocyclic group and these groups each optionally have a substituent, and $R^{H21}$ represents a hydrogen atom, an alkyl group, a cycloalkyl group, an aryl group or a monovalent heterocyclic group and these groups each optionally have a substituent:

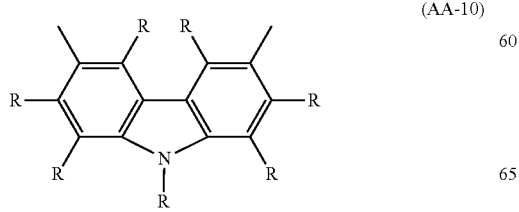

(AA-10)

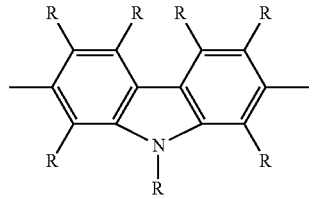

(AA-11)

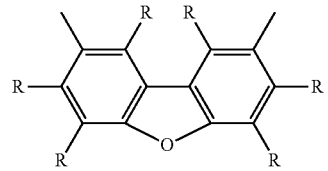

(AA-12)

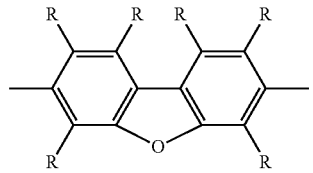

(AA-13)

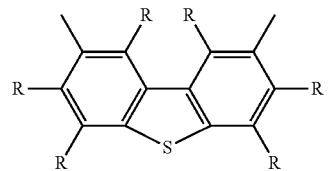

(AA-14)

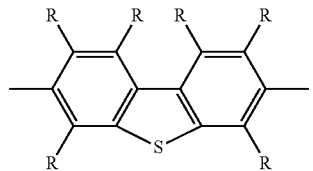

(AA-15)

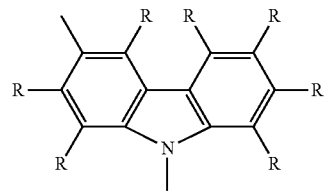

(AA-33)

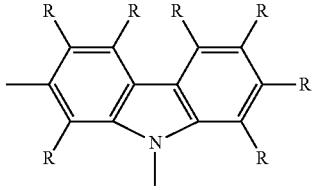

(AA-34)

wherein R represents a hydrogen atom, an alkyl group, a cycloalkyl group, an aryl group or a monovalent heterocyclic group, and a plurality of R may be the same or different:

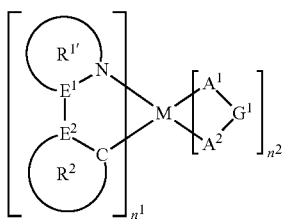

(1')

wherein
M represents a ruthenium atom, a rhodium atom, a palladium atom, an iridium atom or a platinum atom,
$n^1$ represents an integer of 1 or more, $n^2$ represents an integer of 0 or more, and $n^1+n^2$ is 2 or 3, and $n^1+n^2$ is 3 when M is a ruthenium atom, a rhodium atom or an iridium atom, while $n^1+n^2$ is 2 when M is a palladium atom or a platinum atom,
$E^1$ and $E^2$ each independently represent a carbon atom or a nitrogen atom, and at least one of $E^1$ and $E^2$ is a carbon atom,
the ring $R^{1'}$ represents a diazole ring and this diazole ring optionally has a substituent, and when a plurality of substituents are present, they may be the same or different and may form a ring together with atoms to which they are attached, and when a plurality of the rings $R^{1'}$ are present, they may be the same or different,
the ring $R^2$ represents a 5-membered or 6-membered aromatic hydrocarbon ring or a 5-membered or 6-membered aromatic heterocyclic ring and these rings each optionally have a substituent, and when a plurality of substituents are present, they may be the same or different and may form a ring together with atoms to which they are attached, and when a plurality of the rings $R^2$ are present, they may be the same or different, and $E^2$ is a carbon atom when the ring $R^2$ is a 6-membered aromatic heterocyclic ring,
the substituent which the ring $R^{1'}$ optionally has and the substituent which the ring $R^2$ optionally has may form a ring together with atoms to which they are attached, and
$A^1$-$G^1$-$A^2$ represents an anionic bidentate ligand, $A^1$ and $A^2$ each independently represent a carbon atom, an oxygen atom or a nitrogen atom and together may constitute a ring, $G^1$ represents a single bond or an atomic group constituting the bidentate ligand together with $A^1$ and $A^2$, and when a plurality of $A^1$-$G^1$-$A^2$ are present, they may be the same or different:

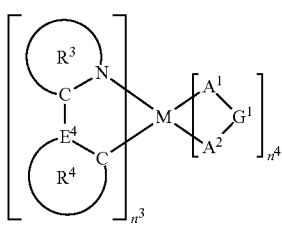

(2)

wherein
M represents a ruthenium atom, a rhodium atom, a palladium atom, an iridium atom or a platinum atom,
$n^3$ represents an integer of 1 or more, $n^4$ represents an integer of 0 or more, and $n^3+n^4$ is 2 or 3, and $n^3+n^4$ is 3 when M is a ruthenium atom, a rhodium atom or an iridium atom, while $n^3+n^4$ is 2 when M is a palladium atom or a platinum atom,
$E^4$ represents a carbon atom or a nitrogen atom,
the ring $R^3$ represents a 6-membered aromatic heterocyclic ring and this ring optionally has a substituent, and when a plurality of substituents are present, they may be the same or different and may form a ring together with atoms to which they are attached, and when a plurality of the rings $R^3$ are present, they may be the same or different,
the ring $R^4$ represents a 5-membered or 6-membered aromatic hydrocarbon ring or a 5-membered or 6-membered aromatic heterocyclic ring and these rings each optionally have a substituent and when a plurality of substituents are present, they may be the same or different and may form a ring together with atoms to which they are attached, and when a plurality of the rings $R^4$ are present, they may be the same or different, and $E^4$ is a carbon atom when the ring $R^4$ is a 6-membered aromatic heterocyclic ring,
the substituent which the ring $R^3$ optionally has and the substituent which the ring $R^4$ optionally has may form a ring together with atoms to which they are attached,
at least one ring selected from the group consisting of the ring $R^3$ and the ring $R^4$ has a dendron represented by the formula (D-A) or (D-B'), and
$A^1$-$G^1$-$A^2$ represents an anionic bidentate ligand, $A^1$ and $A^2$ each independently represent a carbon atom, an oxygen atom or a nitrogen atom and together may constitute a ring, $G^1$ represents a single bond or an atomic group constituting the bidentate ligand together with $A^1$ and $A^2$, and when a plurality of $A^1$-$G^1$-$A^2$ are present, they may be the same or different:

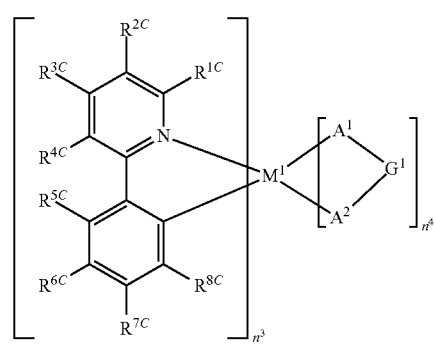

(2-A1)

wherein
$M^1$ represents an iridium atom or a platinum atom,
$A^1$-$G^1$-$A^2$, $n^3$ and $n^4$ represent the same meaning as described above,
$R^{1C}$, $R^{2C}$, $R^{3C}$, $R^{4C}$, $R^{5C}$, $R^{6C}$, $R^{7C}$ $R^{8C}$ each independently represent a hydrogen atom, an alkyl group, a cycloalkyl group, an alkoxy group, a cycloalkoxy group, an aryl group, an aryloxy group, a monovalent heterocyclic group, a halogen atom or a dendron represented by the formula (D-A) or (D-B') and these groups each optionally have a substituent, and when a plurality of $R^{1C}$, $R^{2C}$, $R^{3C}$, $R^{4C}$, $R^{5C}$, $R^{6C}$, $R^{7C}$ and $R^{8C}$ are present they may be the same or different at each occurrence, and $R^{1C}$, and $R^{2C}$, $R^{2C}$ and $R^{3C}$, $R^{3C}$ and $R^{4C}$, $R^{4C}$ and $R^{5C}$ and $R^{6C}$, $R^{6C}$ and $R^{7C}$, and $R^{7C}$ and $R^{8C}$ each may be combined together to form a ring together with the carbon atoms to which they are attached, and at least one selected from the group consisting of $R^{1C}$, $R^{2C}$, $R^{3C}R^{4C}$, $R^{5C}$, $R^{6C}$, $R^{7C}$ and $R^{8C}$ is a dendron represented by the formula (D-A) wherein $G^{DA}$ is a group represented by the formula (GDA-14) or a dendron represented by the formula (D-B') wherein $G^{DA1}$ is a group represented by the formula (GDA-14):

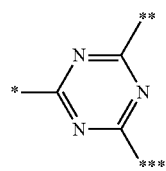

(GDA-14)

wherein * represents a linkage to $Ar^{DA1}$,  represents a linkage to $Ar^{DA2}$, and * represents a linkage to $Ar^{DA3}$:

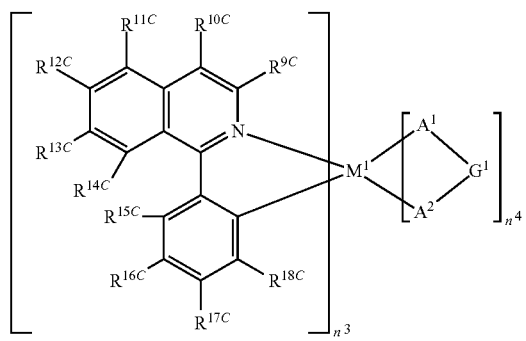

(2-A2)

wherein $M^1$, $A^1$-$G^1$-$A^2$, $n^3$ and $n^4$ represent the same meaning as described above, $R^{9C}$, $R^{10C}$, $R^{11C}$, $R^{12C}$, $R^{13C}$, $R^{14C}$, $R^{15C}$, $R^{16C}$, $R^{17C}$ and $R^{18C}$ each independently represent a hydrogen atom, an alkyl group, a cycloalkyl group, an alkoxy group, a cycloalkoxy group, an aryl group, an aryloxy group, a monovalent heterocyclic group, a halogen atom or a dendron represented by the formula (D-A) or (D-B') and these groups each optionally have a substituent, and when a plurality of $R^{9C}$, $R^{10C}$, $R^{11C}$, $R^{12C}$, $R^{13C}$, $R^{14C}$, $R^{15C}$, $R^{16C}$, $R^{17C}$ and $R^{18C}$ are present, they may be the same or different at each occurrence, and $R^{9C}$ and $R^{10C}$, $R^{11C}$, and $R^{11C}$ and $R^{12C}$, $R^{12C}$ and $R^{13C}$, $R^{13C}$ and $R^{14C}$, $R^{14C}$ and $R^{15C}$, $R^{15C}$ and $R^{16C}$, $R^{16C}$ and $R^{17C}$ and $R^{18C}$ each may be combined together to form a ring together with the carbon atoms to which they are attached, and at least one selected from the group consisting of $R^{9C}$, $R^{10C}$, $R^{11C}$ $R^{12C}$, $R^{13C}$, $R^{14C}$, $R^{15C}$, $R^{16C}$, $R^{17C}$ and $R^{18C}$ is a dendron represented by the formula (D- A) or (D-B'):

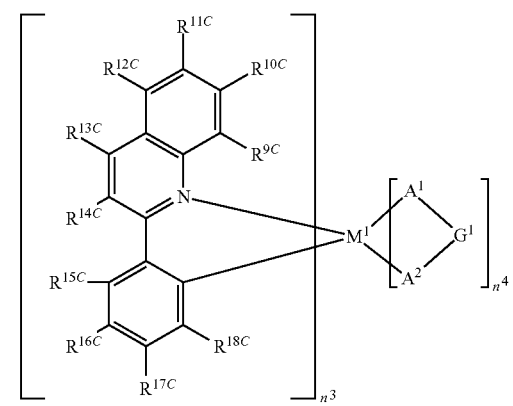

(2-A3)

wherein $M^1$, $A^1$-$G^1$-$A^2$, $n^3$, $n^4$, $R^{9C}$, $R^{10C}$, $R^{11C}R^{12C}$, $R^{13C}$, $R^{14C}$, $R^{15C}$, $R^{16C}$, $R^{17C}$ and $R^{18C}$ represent the same meaning as described above:

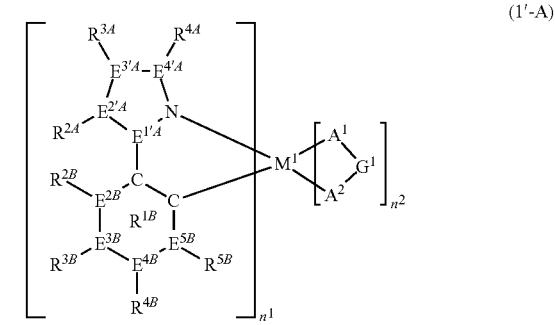

(2-A4)

wherein $M^1$, $A^1$-$G^1$-$A^2$, $n^3$, $n^4$, $R^{9C}$, $R^{10C}$, $R^{11C}$, $R^{12C}$, $R^{13C}$, $R^{14C}$, $R^{15C}$, $R^{16C}$, $R^{17C}$ and $R^{18C}$ represent the same meaning as described above .

2. The composition according to claim 1, wherein the phosphorescent compound (B) represented by the formula (1') is a phosphorescent compound represented by the formula (1'-A):

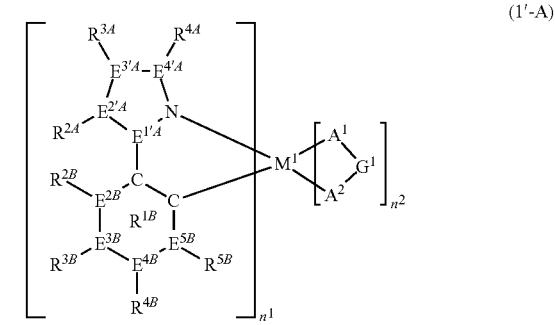

(1'-A)

wherein n¹, n² and A¹-G¹-A² represent the same meaning as described above,

M¹ represents an iridium atom or a platinum atom, one selected from the group consisting of $E^{1'A}$, $E^{2'A}$, $E^{3'A}$ and $E^{4'A}$ represents a nitrogen atom, the remaining three represent a carbon atom, and two selected from the group consisting of $E^{2B}$, $E^{3B}$, $E^{4B}$ and $E^{5B}$ represent a nitrogen atom or a carbon atom, the remaining two represent a carbon atom, and when a plurality of $E^{1'A}$, $E^{2'A}$, $E^{3'A}$, $E^{4'A}$, $E^{2B}$,$E^{3B}$,$E^{4B}$ and $E^{5B}$ are present, they may be the same or different at each occurrence, and $R^{2A}$ may be either present or not present when $E^{2'A}$ is a nitrogen atom, $R^{3A}$ may be either present or not present when $E^{3'A}$ is a nitrogen atom, $R^{4A}$ may be either present or not present when $E^{4'A}$ is a nitrogen atom, and $R^{2B}$ is not present when $E^{2B}$ is a nitrogen atom, $R^{3B}$ is not present when $E^{3B}$ is a nitrogen atom, $R^{4B}$ is not present when $E^{4B}$ is a nitrogen atom, $R^{5B}$ is not present when $E^{5B}$ is a nitrogen atom, $R^{2A}$, $R^{3A}$, $R^{4A}$, $R^{2B}$, $R^{3B}$, $R^{4B}$ and $R^{5B}$ each independently represent a hydrogen atom, an alkyl group, a cycloalkyl group, an alkoxy group, a cycloalkoxy group, an aryl group, an aryloxy group, a monovalent heterocyclic group or a halogen atom and these groups each optionally have a substituent, and when a plurality of $R^{2A}$, $R^{3A}$, $R^{4A}$, $R^{2B}$, $R^{3B}$, $R^{4B}$ and $R^{5B}$ are present, they may be the same or different at each occurrence, and $R^{2A}$ and $R^{3A}$, $R^{3A}$ and $R^{4A}$, $R^{2A}$ and $R^{2B}$, $R^{2B}$ and $R^{3B}$, $R^{3B}$ and $R^{4B}$, and $R^{4B}$ and $R^{5B}$ each may form a ring together with the atoms to which they are attached, the ring $R^{1'A}$ represents a diazole ring, and the ring $R^{1B}$ represents a benzene ring wherein $E^{2B}$, $E^{3B}$, $E^{4B}$, and $E^{5B}$ are each a carbon atom, a pyridine ring wherein one selected from the group consisting of $E^{2B}$, $E^{3B}$, $E^{4B}$, and $E^{5B}$ is a nitrogen atom, and the remaining three are each a carbon atom, or a pyrimidine ring wherein $E^{2B}$ and $E^{4B}$ are each a nitrogen atom and $E^{3B}$ and $E^{5B}$ are each a carbon atom, or $E^{3B}$ and $E^{5B}$ are each a nitrogen atom and $E^{2B}$ and $E^{4B}$ are each a carbon atom.

3. The composition according to claim 2, wherein the phosphorescent compound (B) represented by the formula (1'-A) is a phosphorescent compound represented by the formula (1-A3) or (1-A4):

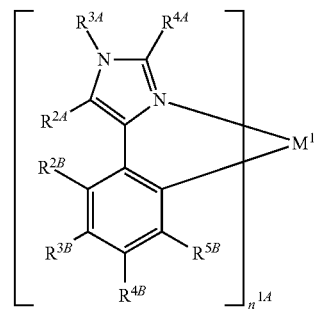

(1-A3)

(1-A4)

wherein

M¹, $R^{2A}$, $R^{3A}$, $R^{4A}$, $R^{2B}$, $R^{3B}$, $R^{4B}$ $R^{5B}$ represent the same meaning as described above, and $n^{1A}$ represents an integer of 2 or 3, and $n^{1A}$ is 3 when M¹ is an iridium atom, while $n^{1A}$ is 2 when M¹ is a platinum atom.

4. The composition according to claim 1, wherein the compound represented by the formula (H-1) is a compound represented by the formula (H-2):

$$Ar^{H1}\text{---}[L^{H1}]_{n^{H3}}Ar^{H2} \quad (H-2)$$

wherein $Ar^{H1}$, $Ar^{H2}$, $n^{H3}$ and $L^{H1}$ represent the same meaning as described above.

5. The composition according to claim 1, wherein for any compound (DGR) of formula (2) that is not further represented by formula (2-A1), (2-A2), (2-A3), or (2-A4), the ring R³ is a pyridine ring optionally having a substituent, a diazabenzene ring optionally having a substituent, a quinoline fused ring optionally having a substituent or an isoquinoline fused ring optionally having a substituent.

6. The composition according to claim 1, wherein for any compound (DGR) of formula (2) that is not further represented by formula (2-A1), (2-A2), (2-A3), or (2-A4), the ring R⁴ is a benzene ring optionally having a substituent, a naphthalene fused ring optionally having a substituent, a fluorene fused ring optionally having a substituent, a phenanthrene fused ring optionally having a substituent, a pyridine ring optionally having a substituent, a diazabenzene ring optionally having a substituent, a pyrrole ring optionally having a substituent, a furan ring optionally having a substituent or a thiophene ring optionally having a substituent.

7. The composition according to claim 6, wherein the ring R⁴ is a benzene ring optionally having a substituent.

8. The composition according to claim 1, wherein the dendron group represented by the formula (D-A) is a group represented by the formula (D-A1), (D-A2) or (D-A3), provided at least one dendron in any compound represented by formula (2-A1) is a group represented by (D-A3):

(D-A1)

(D-A2)

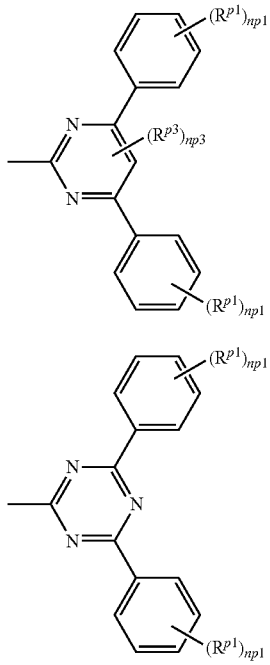

(D-A3)

wherein
$R^{p1}$, $R^{p2}$ and $R^{p3}$ each independently represent an alkyl group, a cycloalkyl group, an alkoxy group, a cycloalkoxy group or a halogen atom, and when a plurality of $R^{p1}$ and $R^{p2}$ are present, they may be the same or different at each occurrence, and np1 represents an integer of 0 to 5, np2 represents an integer of 0 to 3, np3 represents 0 or 1, and the plurality of np1 may be the same or different.

9. The composition according to claim 1, wherein the dendron represented by the formula (D-B') is a group represented by the formula (D-B1), (D-B2) or (D-B3), provided at least one dendron in any compound represented by formula (2-A1) is a group represented by (D-B3):

(D-B1)

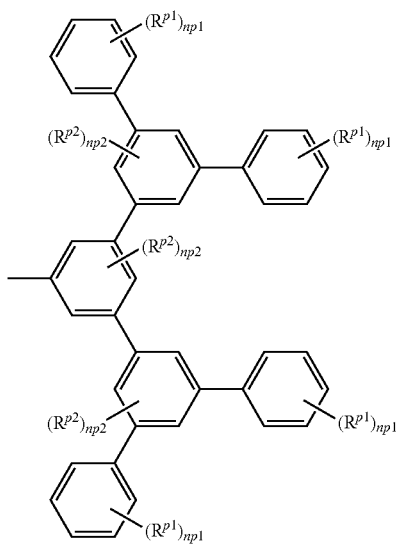

(D-B2)

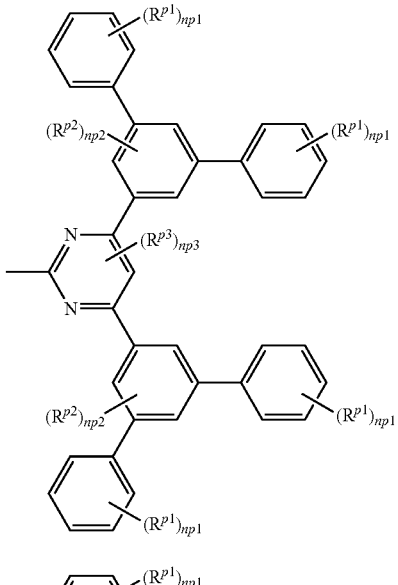

(D-B3)

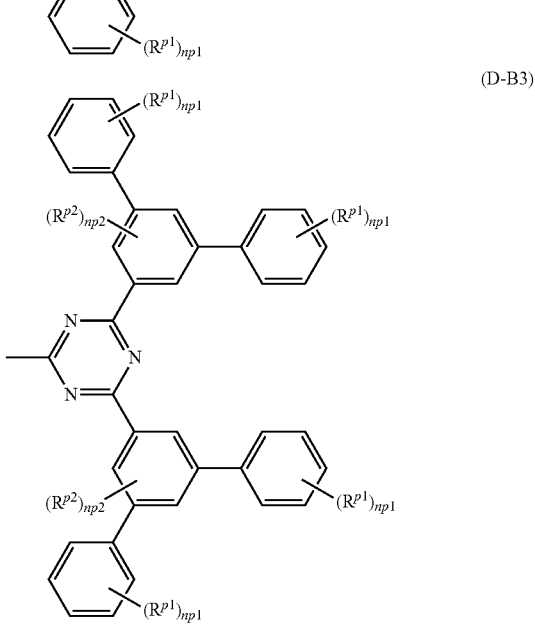

wherein
$R^{p1}$, $R^{p2}$ and $R^{p3}$ each independently represent an alkyl group, a cycloalkyl group, an alkoxy group, a cycloalkoxy group or a halogen atom, and when a plurality of $R^{p1}$ and $R^{p2}$ are present, they may be the same or different at each occurrence, and np1 represents an integer of 0 to 5, np2 represents an integer of 0 to 3, np3 represents 0 or 1, and when a plurality of np1 and np2 are present, they may be the same or different at each occurrence.

10. The composition according to claim 1, further comprising at least one material selected from the group consisting of a hole transporting material, an electron transporting material, a light emitting material, an antioxidant and a solvent.

11. A light emitting device comprising the composition according to claim 1.

12. The composition according to claim 1, wherein the phosphorescent compound represented by the formula (2-A1) or (2-A2) is a phosphorescent compound represented by the formula (2-A5):

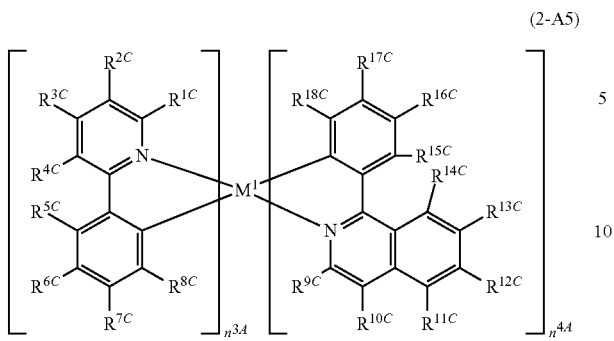

(2-A5)

wherein $M^1$ represents the same meaning as described above, $n^{3A}$ and $n^{4A}$ each independently represent an integer of 1 or more, and $n^{3A}+n^{4A}$ is 2 or 3, and $n^{3A}+n^{4A}$ is 3 when $M^1$ is an iridium atom, while $n^{3A}+n^{4A}$ is 2 when $M^1$ is a platinum atom, $R^{1C}$, $R^{2C}$, $R^{3C}$, $R^{4C}$, $R^{5C}$, $R^{6C}$, $R^{7C}$, $R^{8C}$, $R^{9C}$, $R^{10C}$, $R^{11C}$, $R^{12C}$, $R^{13C}$, $R^{14C}$, $R^{15C}$, $R^{16C}$, $R^{17C}$ and $R^{18C}$ each independently represent a hydrogen atom, an alkyl group, a cycloalkyl group, an alkoxy group, a cycloalkoxy group, an aryl group, an aryloxy group, a monovalent heterocyclic group, a halogen atom or a dendron represented by the formula (D-A) or (D-B') and these groups each optionally have a substituent, and when a plurality of $R^{1C}$, $R^{2C}$, $R^{3C}$ $R^{4C}$, $R^{5C}$, $R^{6C}$, $R^{7C}$, $R^{8C}$, $R^{9C}$, $R^{10C}$, $R^{11C}$, $R^{12C}$ $R^{13C}$, $R^{14C}$, $R^{15C}$, $R^{16C}$, $R^{17C}$ and $R^{18C}$ are present, they may be the same or different at each occurrence, and $R^{1C}$ and $R^{2C}$, $R^{2C}$ and $R^{3C}$, $R^{3C}$ and $R^{4C}$, $R^{4C}$ and $R^{5C}$, $R^{5C}$ and $R^{R6}$, $R^{6C}$ and $R^{7C}$, $R^{7C}$ and $R^{8C}$, $R^{9C}$ and $R^{10C}$, $R^{10C}$ and $R^{11C}$, $R^{11C}$ and $R^{12C}$, $R^{12C}$ and $R^{13C}$, $R^{13C}$ and $R^{14C}$, $R^{14C}$ and $R^{15C}$, $R^{15C}$ and $R^{16C}$, $R^{16C}$ and $R^{17C}$, and $R^{17C}$ and $R^{18C}$ each may be combined together to form a ring together with the carbon atoms to which they are attached, and at least one selected from the group consisting of $R^{1C}$, $R^{2C}$, $R^{3C}$, $R^{4C}$, $R^{5C}$, $R^{6C}$, $R^{7C}$ and $R^{8C}$, is a dendron represented by the formula (D-A) wherein $G^{DA}$ is a group represented by the formula (GDA-14) or a dendron represented by the formula (D-B') wherein $G^{DA1}$ is a group represented by the formula (GDA-14), or at least one selected from the group consisting of $R^{9C}$, $R^{10C}$, $R^{11C}$, $R^{12C}$, $R^{13C}$, $R^{14C}$, $R^{15C}$, $R^{16C}$, $R^{17C}$ and $R^{18C}$ is a dendron represented by the formula (D-A) or (D-B').

* * * * *